(12) United States Patent
Kato et al.

(10) Patent No.: US 6,391,595 B1
(45) Date of Patent: May 21, 2002

(54) TRANSFERASE AND AMYLASE, PROCESS FOR PRODUCING THE ENZYMES, USE THEREOF, AND GENE CODING FOR THE SAME

(75) Inventors: Masaru Kato; Yutaka Miura, both of Takasaki (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/298,924

(22) Filed: Apr. 26, 1999

Related U.S. Application Data

(62) Division of application No. 08/750,569, filed as application No. PCT/JP95/01189 on Jun. 14, 1995.

(30) Foreign Application Priority Data

| Jun. 15, 1994 | (JP) | 6-133354 |
| Aug. 18, 1994 | (JP) | 6-194223 |
| Oct. 31, 1994 | (JP) | 6-290334 |
| Nov. 21, 1994 | (JP) | 6-286917 |
| Nov. 21, 1994 | (JP) | 6-311185 |
| Apr. 21, 1995 | (JP) | 7-120673 |

(51) Int. Cl.⁷ .......... C12P 19/12; C12P 19/34; C12P 19/18; C12N 9/00; C12N 9/12

(52) U.S. Cl. ............ 435/100; 435/91.53; 435/97; 435/183; 435/194; 435/200

(58) Field of Search .................. 435/183, 194, 435/200, 97, 100

(56) References Cited

U.S. PATENT DOCUMENTS

| 5,455,168 A | * 10/1995 | Maruta et al. ........... 435/201 |
| 5,576,303 A | * 11/1996 | Shibuya et al. .......... 514/53 |
| 5,681,826 A | * 10/1997 | Shibuya et al. .......... 514/54 |

FOREIGN PATENT DOCUMENTS

| EP | 0 606 753 | * 12/1993 |
| EP | 0 619 951 | * 10/1994 |
| EP | 0 628 630 | * 12/1994 |
| EP | 0 670 327 | * 9/1995 |
| EP | 0 671 470 | * 9/1995 |
| EP | 0 674 005 | * 9/1995 |
| EP | 0 686 866 | * 12/1995 |
| EP | 0 688 867 | * 12/1995 |
| EP | 0 690 130 | * 1/1996 |
| EP | 0 690 131 | * 1/1996 |
| EP | 0 691 344 | * 1/1996 |
| EP | 0 691 407 | * 1/1996 |
| EP | 0 697 461 | * 2/1996 |
| EP | 0 709 461 | * 5/1996 |
| EP | 727485 A1 | * 8/1996 |
| JP | 63-500562 | * 3/1988 |
| JP | 63-129990 | * 6/1988 |
| JP | 6-62869 | * 3/1994 |
| WO | WO 95/34642 | * 12/1995 |

OTHER PUBLICATIONS

Lama(b) et al. Biotechnol. Forum. Europe, 1991, vol.8(4):201–203.*
Lama et al. Starch conversion with immobilized thermophilic archaebacterium *S.sulfotaricus* 1990.*
Lama et al.; "Thermostable Amylolytic Activity From *Sulfolobus Solfataricus*"; Biotech. Forum Eur.; vol. 8, No. 4; Apr. 1991; pp. 201–203; XP000562901.
Lama et al.; "Starch Conversion With Immobilized Thermophilic Archaebacterium *Sulfolobus Solfataricus*"; Biotechnology Letters; vol. 12, No. 6; pp. 431–432; XP000562604.
L. Lama et al., "Starch Conversion with Immobilized Thermophilic Archaebacterium *Sulfolobus Solfatarius*" Biotechnology Letters, vol. 12, No. 6, (1990), pp. 431–432.
L. Lama et al., "Thermostable Amylolytic from *Sulfolobus solfataricus*", Biotech. Forum. Eur., vol. 8, No. 4, (1991), pp. 201–203.
B. Nicolaus et al., "Trehalose in Archaebacteria", System. Appl. Microbiol., 10:215–217 (1988).

* cited by examiner

*Primary Examiner*—Ponnathapu Achutamurthy
*Assistant Examiner*—Manjunath N. Rao
(74) *Attorney, Agent, or Firm*—Foley & Lardner

(57) ABSTRACT

The invention provides a novel transferase that acts on a saccharide, as a substrate, composed of at least three sugar units wherein at least three glucose residues on the reducing end are linked α-1,4 so as to transfer the α-1,4 lingages to a α-1,α-1 linkages; a process for producing the transferase; a gene coding for the same; and a process for producing an oligosaccharide by using the same. Also provided are a novel amylase that has a principal activity of acting on a saccharide, as a substrate, composed of at least three sugar units wherein at least three sugar units on the reducing end side are glucose units and the linkage between the first and the second glucose units is α-1,α-1 while the linkage between the second and the third glucose units is α-1,4 so as to liberate α,α-trehalose by hydrolyzing the α-1,4 linkage and another activity of hydrolyzing the α-1,4 linkage within the molecular chain of the substrate and that liberates disaccharides and/or monosaccharides as the principal final products; a process for producing the amylase; a gene coding for the same; and a process for producing α,α-trehalose by using a combination of the transferase and the amylase.

38 Claims, 44 Drawing Sheets

SUBSTRATE: MALTOPENTAOSE

SUBSTRATE: AMYLOSE DP17

SUBSTRATE: SOLUBLE STARCH

BEFORE ADDITION OF CRUDE ENZYME EXTRACT

AFTER ADDITION OF CRUDE ENZYME EXTRACT

```
  1'                                           MASPGSNHGYDVIDHSRIND
                                               *.***.*****.***.**.
  1"  MIIGTYRLQLNKKFTFYDIIENLDYFKELGVSHLYLSPILKARPGSTHGYDVVDHSEINE

21'  ELGGEKEYRRLIETAHTIGLGIIQDIVPNHMAVNSLNWRLMDVLKMGKKSKYYTYFDFFP
      *****...  .*..*.. **.************.  ******.** *.****.***  .
 61"  ELGGEEGCFKLVKEAKSRGLEIIQDIVPNHMAVHHTNWRLMDLLKSWKNSKYYNYFDHY-

81'  EDDKIRLPILGEDLDTVISKGLLKIVKDGDEY---------FLEYFKWKLPLTE---VG
      .**** ****...******.***.*..**..**         .*...*.   ...
.120" DDDKIILPILEDELDTVIDKGLIKLQKDNIEYRGLILPINDEGVEFLKRINCFDNSCLKK

128'  NDIYDTLQKQNYTLMSWKNP-PSYRRFFDVNTLIGVNVEKDHVFQESHSKILDLDVDGYR
      .** . * * * ..**. *.*****.**.**.*.**.*.**.***.  *.* *** *
180"  EDIKKLLLIQYYQLTYWKKGYPNYRRFFAVNDLIAVRVELDEVFRESHEIIAKLPVDGLR

187'  IDHIDGLYDPEKYINDLRSII-KNKIIIVEKILGFQEELK--LNSDGTTGYDFLNYSNLL
      ********.*..*...**  .. ..*** *****...*.*.   .************ *.*
240"  IDHIDGLYNPKEYLDKLRQLVGNDKIIYVEKILSINEKLRDDWKVDGTTGYDFLNYVNML

244'  F--NFNQEIMDSIYENFTAEKISISESIKKIKAQIIDELFSYEVKRLASQLGISYDILRD
      .  . ...* ....**** .. **.*.* .. *  . ...**. ...**.. *...** * *
300"  LVDGSGEEELTKFYENFIGRKINIDELIIQSKKLVANQLFKGDIERLSKLLNVNYDYLVD

302'  YLSCIDVYRTYANQIVKECDKTNEIEEATK-RNPEAYTKLQQYMPAVYAKAYEDTFLFRY
      .*.*.. ****   ..  ..* ....* .. ..  .*******..**.**** ** *
360"  FLACMKKYRTY--LPYEDINGIRECDKEGKLKDEKGIMRLQQYMPAIFAKGYEDTTLFIY

361'  NRLISINEVGSDLRYYKISPDQFHVFNQKRRGKITLNATSTHDTKFSEDVRMKISVLSEF
      *****.********...*..**.**.*..*..*.* ************ .******.
418"  NRLISLNEVGSDLRRFSLSIKDFHNFNLSRVNTISMNTLSTHDTKFSEDVRARISVLSEI

421'  PEEWKNKVEEWHSIINPKVSRNDEYRYYQVLVGSFYEGFSNDFKERIKQHMIKSVREAKI
      *.**...* ** ....*....*****.**.**** **** * *****.****..****.
478"  PKEWEERVIYWHDLLRPNIDKNDEYRFYQTLVGS-YEGF--DNKERIKNHMIKVIREAKV

481'  NTSWRNQNKEYENRVMELVEETFTNKDFIKSFMKFESKIRRIGMIKSLSLVALKIMSAGI
      .*.* *.* ***.*. ......*.*.*..* ..**.** .  * .*** .*...*.*.
535"  HTTWENPNIEYEKKVLGFIDEVFENSNFRNDFENFEKKIVYFGYMKSLIATTLRFLSPGV

541'  PDFYQGTEIWRYLLTDPDNRVPVDFKKLHEILEKSKKFEKNMLESMDDGRIKMYLTYKLL
      **.*****.**.********.*******.*  ......** ..* *.** . ***
595"  PDIYQGTEVWRFLLTDPDNRMPVDFKKLKELL---NNLTEKNLE-LSDPRVKMLYVKKLL

601'  SLRKQLAEDFLKGEYKGLDLEEGLCGFIRFNKILVIIKTKGSVNYKLKLEEGAIYTDVLT
      **.   ..  ..** . ** *.*.*..... . .* *.. . .* .
651"  QLRR----EYSLNDYKPLPF-----GFQR-GKVAVLFSPIVTREVKEKISIRQKSVDWIR

661'  GEEIKK-EVQINELPRILVRM
      .***.. * ...**
701"  NEEISSGEYNLSELIGKHKVVILTEKRE
```

FIG. 31

```
 816'                      ATGGCTTCGCCAGGAAGTA-ACCATGGGTACGATGTAA
                           *  ****  **  *  *  ****  ****  *  ***   **    **    *
 455" AAGGCTAGACCAGGGAGCACTCACGGCTACG--ATGTAGTAGATCAT-AGTGAAATTAAT

853' TAGATCATTCAAGGATAAACGATGAAC-TTGGAGGAG---AGAAAGAATACAGGAGATTA
       **    *    ****  **   *   *  ***   *   **    **  ***     *  **  ***
 512" GAGGAATTAGGAGGAGAAGAGGGGTGCTTTAAACTAGTTAAGGAAGCTAAGAGTAGAGGT

909' ATAGAGACAGCTCATACTATTGGATTAGGTATTAT-ACAGGACATAGTACCAAAT-CACA
       ****  *     **    ***   *    *   *  **   *  *  ****   ***  **   *   * *
 572" TTAGAAATCATACAAGATATAGTGCCAAATCACATGGCGGTACATCATACTAATTGGAGA

967' TGGCTGTAAATTCTCTA-AATTGG-CGACTAATGGATGTATTAAAAATGGGTAAAAAGAG
             **   *    *   *   *   ****    **  **   *  **       ***    **      *   *
 632" CTTATGGATCTGTTAAAGAGTTGGAAGAATAGTAAATACTATAACTATT-TTGATCACTA

1025' TAAATATTATACGTACTTTGACTTTTTCCCAGAAGATGA-TAAGATACGATTACCCATAT
                 *   **  *  *  *      *    *  *    **  **  **    **    *****   **     *  **
 691" CGATGATGACAAGATAATCCTCCCAATACTTGAGGACGAGTTGGATACCGTT--ATAGAT

1084' TAGGAGAAGATTTAGATACAG--TGATAAGTAAAGGTTTATTAAAGATAGTAAAAGATGG
             ***      ***   *  *****    ****    *   **   *    *   *  *   **    *   **    *
 749" AAGGGATTGATAAAACTACAGAAGGATAATATAGAGTACAG-AGGGCTTATATTACCTAT

1142' AGATGAATATTTCCTAGAATATTTCAAATGGA--AACT--TCCTCTAACAGAGGTTGGAA
         *  ****    *         *  ****    **  ***  ***    **   *      ***    *  ***   **
 808" AAATGATGAAGGAGTTGAATTCTTGAAAAGGATTAATTGCTTTGATAATTCATGTTTAAA

1198' -----ATGATATATACGACACTTTACAAAAACAGAATTATACCCTAATGTCTTGGAA---
            *  ******  *    *     **    **  ***   *****       ****   *   *****
 868" GAAAGAGGATATAAAGAAATTACTATTAATACAATATTATCAGCTAACTTACTGGAAGAA

1250' AAATCCTCCTAGCTATAGACGATTCTTCGATGTTAATACTTTAATAGGAGTAAATGTCGA
        *    *   ***  *  ******    ****   ****   **  ***    ***  *****    **  *    **  **
 928" AGGTTATCCAAACTATAGGAGATTTTTCGCAGTAAATGATTTGATAGCTGTTAGGGTAGA

1310' AAAAGATCACGTATTTCAAGAGTCCCATTCAAAGATCTTAGATTTAGATGTTGATGGCTA
       *      ***   *  ******   **********     *    **      *    **     *****  **   *
 988" ATTGGATGAAGTATTTAGAGAGTCCCATGAGATAATTGCTAAGCTACCAGTTGACGGTTT

1370' TAGAATTGATCATATTGATGGATTATATGATCCTGAGAAATATATTAATGACCT--GA-G
        ********   **   *   ******  *****  *  ***  **  *  ***    *    **  **   **
1048" AAGAATTGACCACATAGATGGACTATATAACCCTAAGGAGTATTTAGATAAGCTAAGACA

1427' GTCAATAATTAAAAATAAAATAATTATTGTAGAAAAAATTCTGGGATTTCAGGAGGAATT
       **  *  **        **   ****  *****         *****  **   **    *  *    *  ***  ****
1108" GTTAGTAGGAAATGATAAGATAATATACGTAGAGAAGATATTGTCAATCAACGAGAAATT

1487' AA------AATTAAATTCAGATGGAACTACAGGATATGACTTCTTAAATTACTCCAACTT
       **           *  *    **   ******   *****   ********   **  ***     **   *
1168" AAGAGATGATTGGAAAGTAGATGGGACTACTGGATATGATTTCTTGAACTACGTTAATAT

1541' ACTGTT--TA-ATTTTAATCAAGA-GA-TAATGGAC-AGTATATATGAGAATTTCACAGC
        **  **   **  **     *   *       **  **    *  *   **  *      *  *************    *
1228" GCTATTAGTAGATGGAAGTGGTGAGGAGGAGTTAACTAAGTTTTATGAGAATTTCATTGG

1595' GGAGAAAATATCTATAAGTGAAAGTATAAAGAAAATAAAAGCGCAAATAATTGATGAGCT
       ******       ****   **    ****    ***    ***      *   *      **  **  *
1288" AAGGAAAATCAATATAGACGAGTTAATAATACAAAGTAAAAAATTAGTTGCAAATCAGTT

1655' ATTTAGTTATGAAGTTAAAAGATTAGCATCACAACTAGGAATTAGCTACGATATATTGAG
       *****     ***    ********         ***              ***     ***  ******  ****   **
1348" ATTTAAAGGTGACATTGAAAGATTAAGCAAGTTACTGAACGTTAATTACGAT-TATTTAG

1715' -AGATTACCTTTCTTGTATAGATGTGTACAGAACTTATGCTAATCAGAT-TGTAAAAGAG
        *****   **  *  ******   *       *****  ******  *  *  **  **    *   ***    *
1407" TAGATTTTCTAGCATGTATGAAAAAATACAGGACTTAT--TTACCATATGAGGATATTAA
```

FIG. 32A

```
1773' TGTGATAAGACCAATGAGATAGAGGAAGCAACCAAAAGAAATCCAGAGGCTTATACTAAA
      *  *****  **** **** **** *  **    ** * **  * ***    *    * *
1465" CGGAATAAG-GGAATGCGATA-AGGAGGGAAAGTTAAAAGATGAAAAGGGAATCATGAGA

1833' TTACAACAATATATGCCAGCAGTATACGCTAAAGCTTATGAAGATACTTTCCTCTTTAGA
      * ********* ********* * * ****** *  ***** ******  ****** *
1523" CTCCAACAATACATGCCAGCAATCTTCGCTAAGGGCTATGAGGATACTACCCTCTTCATC

1893' TACAATAGATTAATATCCATAAATGAGGTTGGAAGCGATTTACGATATTATAAGATATCG
      ************* *** ** ******** *****  ** ** *  ****** *  **
1583" TACAATAGATTAATTTCCCTTAACGAGGTTGGGAGCGACCTAAGA-AGATTCAGTTTAAG

1953' CCT-GATCAGTTTCATGTATTTAATCAAAAACGAAGAGGAAAAATCACACTAAATGCCAC
      * *  * ******  ***** *  **  **  *  *   ** ** *  ** **   *
1642" CATCAAAGACTTTCATAACTTTAACCTAAGCAGAGTAAATACCATATCAATGAACACTCT

2012' TAGCACACATGACTAAGTTTAGTGAAGATGTAAGGATGAAAATAAGTGTATTAAGTGA
      * *** *********** ** ******** ** **   * ****  *** ** * ***
1702" TTCCACTCATGATACTAAATTCAGTGAAGACGTTAGAGCTAGAATATCAGTACTATCTGA

2072' ATTTCCTGAAGAATGGAAAAATAAGGTCGAGGAATGGCATAGTATCATAAATCCAAAGGT
      * **  * ** *** * * *  ***    ******  * * * **  *****  *
1762" GATACCAAAGGAGTGGGAGGAGAGGGTAATATACTGGCATGATTTGTTAAGGCCAAATAT

2132' ATCAAGAAATGATGAATATAGATATTATCAGGTTTTAGTGGGAAGTTTTTATGAGGGATT
      * *** ***** ******* ******    * ********  *** ********
1822" TGATAAAAACGATGAGTATAGATTTTATCAAACACTTGTGGGAAG---TTACGAGGGATT

2192' CTCTAATGATTTTAAGGAGAGAATAAAGCAACATATGATAAAAAGTGTCAGAGAAGCTAA
      ***  ************ *** **  *****  **            * **********
1879" ----T--GATAATAAGGAGAGAATTAAGAACCACATGATTAAGGTCATAAGAGAAGCTAA

2252' GATAAATACCTCATGGAGAAATCAAAATAAAGAATATGAAAATAGAGTAATGGAATTAGT
      * ** ****  * ***  ***** **** *** ********  *  *** *** **  *
1933" GGTACATACAACGTGGGAAAATCCTAATATAGAGTATGAAAAGAAGGTTCTGGGTTTCAT

2312' GGAAGAAACTTTTACCAATAAGGATTTCATTAAAAGTTTCATGAAATTTGAAAGTAAGAT
      ** ***   **   ** *  **** *   *  ***  ** ******* ** **  ** **
1993" AGATGAAGTGTTCGAGAACAGTAATTTTAGAAATGATTTTGAAAATTTTGAAAAGAAAAT

2372' AAGAAGGATAGGGATGATTAAGAGCTTATCCTTGGTCGCATTAAAAATTATGTCAGCCGG
      *     * **     ** **   ***  *      ** ** *    *  * **   ****
2053" AGTTTATTTCGGTTATATGAAATCATTAATCGCAACGACACTTAGGTTCCTTTCGCCCGG

2432' TATACCTGATTTTTTATCAGGGAACAGAAATATGGCGATATTTACTTACAGATCCAGATAA
      * ****  ***  *******  ****  *** ** *********  * ****** ********
2113" TGTACCAGATATTTATCAAGGAACTGAAGTTTGGAGATTCTTACTTACAGACCCAGATAA

2492' CAGAGTCCCAGTGGATTTTAAGAAATTACACGAAATATTAGAAAAATCCAAAAAATTTGA
      ****  *  ********  ******  ** * *** ***** *  *    **        *
2173" CAGAATGCCGGTGGATTTCAAGAAACTAAAGGAATTATTAAATAATTTGACTGAAAAGAA

2552' AAAAAATATGTTAGAGTCTATGGAC--GATGGAAGA-ATTAAGATGTATTTAACATATAA
      * *  *  *** *  * * *     ***  *  ****** * *  ***  * * * *  *
2233" CTTAGAACTCTCAGATCCAAGAGTCAAAATGTTATATGTTAAGAAAT-TGCTACAGCTTA

2609' GCTTTTATCCCTAAGAAAACAGTTGGCTGAGGATTTTTTAAAGGGCGAGTATAAGGG---
      *    *   ** *  ****  **    * *    **          ***     *  ***
2292" GAAGAGAGTACTCACTAAACGATT--ATAAACCATTGCCCTTTTGGCTTCCAAAGGGGAAA

2656' ATTAGATCTAGAAGAAGGACTATGTGGGTTTA-TTAGGTTTAACAAAATTTTGGTAATAA
      * **** *     *        ** * **    ** *  *  ** ** **  * **  **
2350" AGTAGCTGTCCTTTTCTCACCAATAGTGACTAGGGAGGTTAAAGAGAAAATTAGT-ATAA

2725' TAAAAACCAAGGGAAGTGTTAATTACAAACTGAAACTTGAAGAGGGAGCAATTTACACAG
      ***  ***    * *   *    ** * **   ***  * *  **     **  ***
2409" GGCAAA-AAAGCGTTGATTGGATCAGAAATGAGGAAATTAGTAGTGGAGAAT----ACAA

2785' ATGTATTGACAGGAGAAGAAATTAAAAAAGAGGTACAGATTAATGAGCTACCTAGGATAC
      *  * ***    **   * **  ***   *  * ** *  **   ***
2464" TTTAAGTGAGTTGATTGGGAAGCATAAAGTCGTTATA-TTAACTGAAAAAAGGGAG
```

FIG. 32B

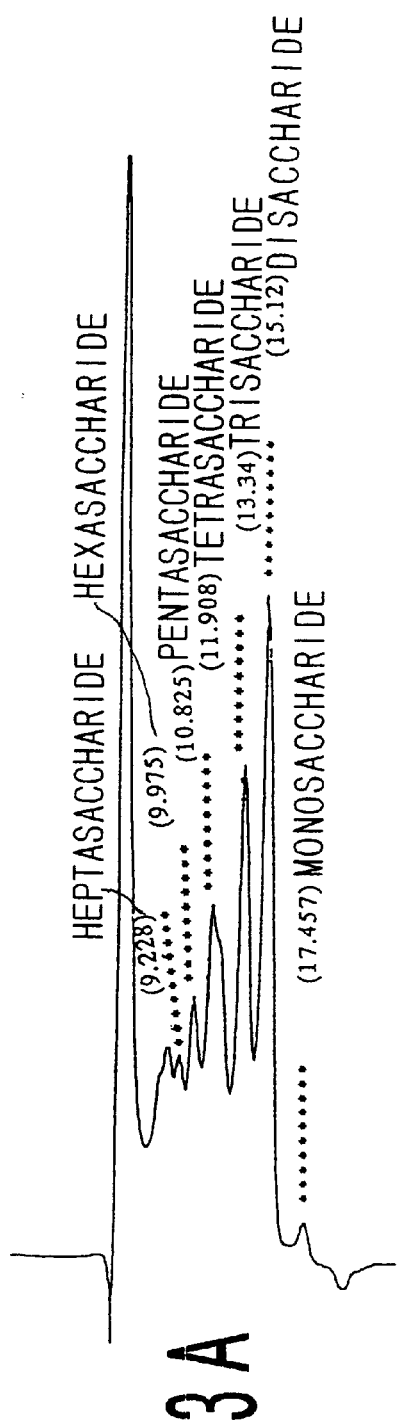
FIG. 33A  IN THE PRESENCE OF THE ENZYME
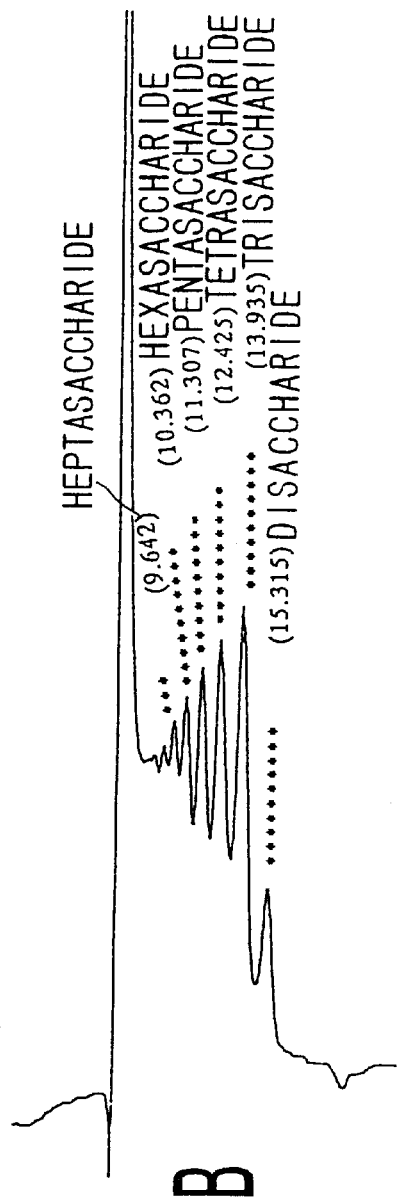
FIG. 33B  CONTROL

```
  1' MFSFGGNIEKNKGIFKLWAPYVNSVKLK-LSKKLIPMEKNDEGFFEVEIDDIEENLTYSY
     .*. .*. *. **.***** .***** *.* *  **....*.......... . *.*
  1" TFAYKIDGNEVIFTLWAPYQKSVKLKVLEKGLYEMERDEKGYFTITLNNVKVRDRYKY

60' IIEDKREIPDPASRYQPLGVHDKSQLIRTDYQILDLGKVKIEDLIIYELHVGTFSQEGNF
     ...* .************ ***. **.*... .. . . .* *******.***** ..**.*
 59" VLDDASEIPDPASRYQPEGVHGPSQIIQESKEFNNETFLKKEDLIIYEIHVGTFTPEGTF

120' KGVIEKLDYLKDLGITGIELMPVAQFPGNRDWGYDGVFLYAVQNTYGGPWELAKLVNEAH
     .*** *********** .**.**..*****.********.******.**** .. ***.***
119" EGVIRKLDYLKDLGITAIEIMPIAQFPGKRDWGYDGVYLYAVQNSYGGPEGFRKLVDEAH

180' KRGIAVILDVVYNHIGPEGNYLLGLGPYFSDRYKTPWGLTFNFDDRGCDQVRKFILENVE
     *.* .********* ******.. ****** .************* ..*.**********
179" KKGLGVILDVVYNHVGPEGNYMVKLGPYFSQKYKTPWGLTFNFDDAESDEVRKFILENVE

240' YWFKTFKIDGLRLDAVHAIFDNSPKHILQEIAEKAHQLGKFVIAESDLNDPKIV--KDDC
     **.*....**.********.*.******.***. .*. ...**********..* *..*
239" YWIKEYNVDGFRLDAVHAIIDTSPKHILEEIADVVHKYNRIVIAESDLNDPRVVNPKEKC

298' GYKIDAQWVDDFHHAVHAFITKEKDYYYQDFGRIEDIEKTFKDVFVYDGKYSRYRGRTHG
     **.************..**..* *.. ** ***...** *..************..* .***
299" GYNIDAQWVDDFHHSIHAYLTGERQGYYTDFGNLDDIVKSYKDVFVYDGKYSNFRRKTHG

358' APVGDLPPRKFVVFIQNHDQVGNRGNGERLSILTDKTTYLMAATLYILSPYIPLIFMGEE
     .***.*   .***.************.***. *.*...* .**.** ****** .******
359" EPVGELDGCNFVVYIQNHDQVGNRGKGERIIKLVDRESYKIAAALYLLSPYIPMIFMGEE

418' YYETNPFFFFSDFSDPVLIKGVREGRLKENNQMIDPQSEEAFLKSKLSWKIDEEVLDYYK
     * *.***.*******. **.****** ***.* .***.*.* **********....**
419" YGEENPFYFFSDFSDSKLIQGVREGRKKENGQDTDPQDESTFNASKLSWKIDEEIFSFYK

478' QLINIRKRYN-NCKRVKEVRREGNCITLIMEKIGIIASFDDIVINSKITGNLLIGI--GF
     **..** . .*.* .* ...*  ...  . *.. *.*.*.**.. .*
479" ILIKMRKELSIACDRRVNVVNGENWLIIKGREYFSLYVFSKSSIEVKYSGTLLLSSNNSF

535' PKKLKKDELIKVNRGVGVYQLE
     *........ ..* ..*.*
539" PQHIEEGK-YEFDKGFALYKL
```

FIG. 40

```
1176' ATGTTTTCGTTCGGTGGAAATATTGAAAAAAATAAAGGTATCTTTAAGTTATGGGCACCT
      ****  * *    ** ** **     ****  * *  *******  *************
 642" ACGTTTGCTTATAAAATAGATGGAAATGAGGTAATCTTTACCTTATGGGCACCT

1236' TATGTTAATAGTGTTAAGCTGAA-GTT--AAGCAAAAAACTTATTCCAATGGAAAAAAAC
      ***   **  **  *****  **  **  ***    *     ********  *  * *
 696" TATCAAAAGAGCGTTAAACTAAAGGTTCTAGAGAAGGGACTTTACGAAATGGAAAGAGAT

1293' GATGAGGGATTTTTCGAAGTAGAAATAGACGATATCGAGGAAAATTTAACCTATTCTTAT
      **  *  ** *    ***      *      **  ** *    *** *     *  *** **
 756" GAAAAAGGTTACTTCACCATTACCTTAAACAACGTAAAGGTTAGAGATAGGTATAAATAC

1353' ATTATAGAAGATAAGAGAGAGATACCTGATCCCGCATCACGATATCAACCTTTAGGAGTT
      ** **** ***   ** **  ****.  ***** *****    **** *****    *** **
 816" GTTTTAGATGATGCTAGTGAAATACCAGATCCAGCATCCAGATACCAACCAGAAGGTGTA

1413' CATGACAAATCACAACTTATAAGAACAGATTATCAGATTCTTGACCTTGGAAAAGTAAAA
      ****    ******  *****    *  *  *    ** *       **              *  **
 876" CATGGGCCTTCACAAATTATACAAGAAAGTAAAGAGTTCAACAACGAGACTTTTCTGAAG

1473' ATAGAAGATCTAATAATATATGAACTCCACGTTGGTACTTTTTCCCAAGAAGGAAATTTC
      *  *** **    *  ******  ****** **  *****    *  *  *** ****  **
 936" AAAGAGGACTTGATAATTTATGAAATACACGTGGGGACTTTCACTCCAGAGGGAACGTTT

1533' AAAGGAGTAATAGAAAAGTTAGATTACCTCAAGGATCTAGGAATCACAGGAATTGAACTG
      * ***** **   **   ** *  *  *** ***   *****   **  *    *** ***  *
 996" GAGGGAGTGATAAGGAAACTTGACTACTTAAAGGATTTGGGAATTACGGCAATAGAGATA

1593 ATGCCTGTGGCACAATTTCCAGGGAATAGAGATTGGGGATACGATGGTGTTTTTCTATAC
     *****  *  **  ********  ***** **  *********  **  ***** ****  *  ****
1056" ATGCCAATAGCTCAATTTCCTGGGAAAAGGGATTGGGGTTATGATGGAGTTTATTTATAT

1653' GCAGTTCAAAATACTTATGGCGGACCATGGGAATTGGCTAAGCTAGTAAACGAGGCACAT
      *****  ** **  *****  ** **  ***    *  **   ***  ****   *  ** ** **
1116" GCAGTACAGAACTCTTACGGAGGGCCAGAAGGTTTTAGAAAGTTAGTTGATGAAGCGCAC

1713' AAAAGGGGAATAGCCGTAATTTTGGATGTTGTATATAATCATATAGGTCCTGAGGGAAAT
      ** *  ***  **  *** ***  ***** **   ** **  *  *  ***  ** ********
1176" AAGAAAGGTTTAGGAGTTATTTTAGACGTAGTATACAACCACGTTGGACCAGAGGGAAAC

1773' TACCTTTTAGGATTAGGTCCTTATTTTTCAGACAGATATAAAACTCCATGGGGATTAACA
      **  *  *    *** **  **  ***** ***  * *  * ***  *****  *************
1236" TATATGGTTAAATTGGGGCCATATTTCTCACAGAAATACAAAACGCCATGGGGATTAACC

1833' TTTAATTTTGATGATAGGGGATGTGATCAAGTTAGAAAATTCATTTTAGAAAATGTCGAG
      *****  ***** ***   * * * *** *  ****** **  *****  ********  ** ***
1296" TTTAACTTTGACGATGCTGAAAGCGATGAGGTTAGGAAGTTCATCTTAGAAAACGTTGAG

1893' TATTGGTTTAAGACCTTTAAAATCGATGGTCTGAGACTGGATGCAGTTCATGCAATTTTT
      ** ***  *****  *  ****  * ******  *  ******  ***************  **
1356" TACTGGATTAAGGAATATAACGTTGATGGGTTTAGATTAGATGCGGTTCATGCAATTATT

1953' GATAATTCGCCTAAGCATATCCTCCAAGAGATAGCTGAAAAAGCCCATCAATTAGGAAAA
      ** * ***  ********  ***  *  * **  *********    *  *** * *          *
1416" GACACTTCTCCTAAGCACATCTTGGAGGAAATAGCTGACGTTGTGCATAAGTATAATAGG

2013' TTTGTTATTGCTGAAAGTGATTTAAATGATCCAAAAATAG-TAA-----AAGATGATTGT
      ****  **  **  ***************  ***** *  *  *  *  ***      * **   * ***
1476" ATTGTCATAGCCGAAAGTGATTTAAACGATCCTAGAGTCGTTAATCCCAAGGAAAAGTGT

2067' GGATATAAAATAGATGCTCAATGGGTTGACGATTTCCACCACGCAGTTCATGCATTCATA
      ********  **  ************************  **  **** ** * * **
1536" GGATATAATATTGATGCTCAATGGGTTGACGATTTCCATCATTCTATTCACGCTTACTTA

2127' ACAAAAGAAAAGATTATTATTACCAGGATTTTGGAAGGATAGAAGATATAGAGAAAACT
      **    ** **  *      *****   ****** **    *  ** *******   *** *
1596" ACTGGTGAGAGGCAAGGCTATTATACGGATTTCGGTAACCTTGACGATATAGTTAAATCG
```

FIG. 41A

```
2187' TTTAAAGATGTTTTTGTTTATGATGGAAAGTATTCTAGATACAGAGGAAGAACTCATGGT
      *  ***  **  *****  **  *********  *****  **  *   *   ***  ***  ******  **
1656" TATAAGGACGTTTTCGTATATGATGGTAAGTACTCCAATTTTAGAAGAAAAACTCACGGA

2247' GCTCCTGTAGGTGATCTTCCACCACGTAAATTTGTAGTCTTCATACAAAATCACGATCAA
      *  **  **  *****  **         *  **  **  *****  *  ******************
1716" GAACCAGTTGGTGAACTAGACGGATGCAATTTCGTAGTTTATATACAAAATCACGATCAA

2307' GTAGGAAATAGAGGAAATGGGGAAAGACTTTCCATATTAACCGATAAAACGACATACCTT
      **  ***********  **  **  ******  *     *  ****  *****     *   ***
1776" GTCGGAAATAGAGGCAAAGGTGAAAGAATAATTAAATTAGTCGATAGGGAAAGCTACAAG

2367' ATGGCAGCCACACTATATATACTCTCACCGTATATACCGCTAATATTTATGGGCGAGGAA
      **  **  **   *  **  **   *   **  **  *****  **   *  **  **  *****  ******
1836" ATCGCTGCAGCCCTTTACCTTCTTTCCCCCTATATTCCAATGATTTTCATGGGAGAGGAA

2427' TATTATGAGACGAATCCTTTTTTTCTTCTTCTCTGATTTCTCAGATCCCGTATTAATTAAG
      **    ****    *****  ****    *******  ******  *    *  **    *
1896" TACGGTGAGGAAAATCCCTTTTATTTCTTTTCTGATTTTTCAGATTCAAAACTGATACAA

2487' GGTGTTAGAGAAGGTAGACTAAAGGAAAATAATCAAATGATAGATCCACAATCTGAGGAA
      *****  **  *****  ***  *********   ***    *  **  ***  ***    *
1956" GGTGTAAGGGAAGGGAGAAAAAAGGAAAACGGGCAAGATACTGACCCTCAAGATGAATCA

2547' GCGTTCTTAAAGAGT--AAACTTTCATGGAAAATTGATGAGGAAGTTTTAGATTATTATA
      *  ****  *   *  *****   *****  *****  ******  *  **      *  ***  *
2016" AC--TTTTAACGCTTCCAAACTGAGTTGGAAGATTGACGAGGAAATCTTTTCATTTTACA

2605' AACAACTGATAAATATCAGAAA-GAGAT-ATAATA-ATTGTAAAAGGGTAAAGGAAGTTA
      *      *  *****  **  *****  ***  *  *     ***      ***  *  ***   *        *  **
2074" AGATTTTAATAAAAATGAGAAAGGAGTTGAGCATAGCGTGTGATAGGAGAGTAAACGTCG

2662' GGAGAGAAGGGAACTGTATTACTTTGATCATGGAAAAAATAGGAATAATTGCATCGTTTG
      **  *  *   *  **  **    *  *    *  *   *  *  ****   *  *  *    *   ***
2134" TGAATGGCGAAAATTGGTTGATCATCAAGG-GAAGAGAATACTTTTCACTCTACGTTTTC

2722' ATGATATTGT-AATTAATTCTAAAATTACAGGTAATTTACTTATAGGCATAGGATTTCCG
      *  **  *   ***  *    ***     *  **  *  *******  *    *   *       *  *
2193" TCTAAATCATCTATTGAAGTTAAGTACAGTGGAACTTTACTTTTGTCCTCAAATAATTCA

2781' AAAAAATTGAAAAAAGATGAA--TTAAT-TAAGGTTAACAGAGGTGTTGGGGTATATCAA
      *  *  *    **  ***    *  ***  *  **  **  *   *   **  ***  ******  **
2253" TTCCCTCAGCATATTGAAGAAGGTAAATATGAGTTTGATAAGGGATTTGCTTTATATAAA

2838' TTAGAA
         *
2313" CTT
```

FIG. 41B

SEQUENCE LISTING (1) GENERAL INFORMATION:

(iii) NUMBER OF SEQUENCES: 58

(2) INFORMATION FOR SEQ ID NO: 1:

(i) SEQUENCE CHARACTERISTICS:
      (A) LENGTH: 2578 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 335..2518

(xi) SEQUENCE DESCRIPTION: SEQ ID NO: 1:

```
GCATGCCATT AAAAGATGTA ACATTTTACA CTCCAGACGG TAAGGAGGTT G ATGAGAAAG      60

CATGGAATTC CCCAACGCAA ACTGTTATTT TCGTGTTAGA GGGGAGCGTA A TGGATGAGA    120

TTAACATCTA TGGAGAGAGA ATTGCGGATG ATTCATTCTT GATAATTCTT A ACGCAAATC    180

CCAATAACGT AAAAGTGAAG TTCCCAAAGG GTAAATGGGA ACTAGTTGTT G GTTCTTATT    240

TGAGAGAGAT AAAACCAGAA GAAAGAATTG TAGAAGGTGA GAAGGAATTG G AAATTGAGG    300

GAAGAACAGC ATTAGTTTAT AGGAGGACAG AACT ATG ATA ATA GGC ACA TAT         352
                                    Met Ile Ile Gly Thr Tyr
                                     1               5

AGG CTG CAA CTC AAT AAG AAA TTC ACT TTT T AC GAT ATA ATA GAA AAT      400
Arg Leu Gln Leu Asn Lys Lys Phe Thr Phe T yr Asp Ile Ile Glu Asn
             10                  15                  20

TTG GAT TAT TTT AAA GAA TTA GGA GTA TCA C AC CTA TAT CTA TCT CCA      448
Leu Asp Tyr Phe Lys Glu Leu Gly Val Ser H is Leu Tyr Leu Ser Pro
         25                  30                  35

ATA CTT AAG GCT AGA CCA GGG AGC ACT CAC G GC TAC GAT GTA GTA GAT      496
Ile Leu Lys Ala Arg Pro Gly Ser Thr His G ly Tyr Asp Val Val Asp
     40                  45                  50

CAT AGT GAA ATT AAT GAG GAA TTA GGA GGA G AA GAG GGG TGC TTT AAA      544
His Ser Glu Ile Asn Glu Glu Leu Gly Gly G lu Glu Gly Cys Phe Lys
 55                  60                  65                  70

CTA GTT AAG GAA GCT AAG AGT AGA GGT TTA G AA ATC ATA CAA GAT ATA      592
Leu Val Lys Glu Ala Lys Ser Arg Gly Leu G lu Ile Ile Gln Asp Ile
                 75                  80                  85

GTG CCA AAT CAC ATG GCG GTA CAT CAT ACT A AT TGG AGA CTT ATG GAT      640
Val Pro Asn His Met Ala Val His His Thr A sn Trp Arg Leu Met Asp
             90                  95                 100

CTG TTA AAG AGT TGG AAG AAT AGT AAA TAC T AT AAC TAT TTT GAT CAC      688
Leu Leu Lys Ser Trp Lys Asn Ser Lys Tyr T yr Asn Tyr Phe Asp His
         105                 110                 115

TAC GAT GAT GAC AAG ATA ATC CTC CCA ATA C TT GAG GAC GAG TTG GAT      736
Tyr Asp Asp Asp Lys Ile Ile Leu Pro Ile L eu Glu Asp Glu Leu Asp
     120                 125                 130

ACC GTT ATA GAT AAG GGA TTG ATA AAA CTA C AG AAG GAT AAT ATA GAG      784
Thr Val Ile Asp Lys Gly Leu Ile Lys Leu G ln Lys Asp Asn Ile Glu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 135 |     |     |     |     | 140 |     |     |     |     | 145 |     |     |     |     | 150 |      |
| TAC | AGA | GGG | CTT | ATA | TTA | CCT | ATA | AAT | GAT | G AA | GGA | GTT | GAA | TTC | TTG | 832  |
| Tyr | Arg | Gly | Leu | Ile | Leu | Pro | Ile | Asn | Asp | G lu | Gly | Val | Glu | Phe | Leu |      |
|     |     |     |     |     | 155 |     |     |     |     | 160 |     |     |     |     | 165 |      |
| AAA | AGG | ATT | AAT | TGC | TTT | GAT | AAT | TCA | TGT | T TA | AAG | AAA | GAG | GAT | ATA | 880  |
| Lys | Arg | Ile | Asn | Cys | Phe | Asp | Asn | Ser | Cys | L eu | Lys | Lys | Glu | Asp | Ile |      |
|     |     |     |     |     | 170 |     |     |     |     | 175 |     |     |     |     | 180 |      |
| AAG | AAA | TTA | CTA | TTA | ATA | CAA | TAT | TAT | CAG | C TA | ACT | TAC | TGG | AAG | AAA | 928  |
| Lys | Lys | Leu | Leu | Leu | Ile | Gln | Tyr | Tyr | Gln | L eu | Thr | Tyr | Trp | Lys | Lys |      |
|     |     |     |     |     | 185 |     |     |     |     | 190 |     |     |     |     | 195 |      |
| GGT | TAT | CCA | AAC | TAT | AGG | AGA | TTT | TTC | GCA | G TA | AAT | GAT | TTG | ATA | GCT | 976  |
| Gly | Tyr | Pro | Asn | Tyr | Arg | Arg | Phe | Phe | Ala | V al | Asn | Asp | Leu | Ile | Ala |      |
|     |     |     |     |     | 200 |     |     |     |     | 205 |     |     |     |     | 210 |      |
| GTT | AGG | GTA | GAA | TTG | GAT | GAA | GTA | TTT | AGA | G AG | TCC | CAT | GAG | ATA | ATT | 1024 |
| Val | Arg | Val | Glu | Leu | Asp | Glu | Val | Phe | Arg | G lu | Ser | His | Glu | Ile | Ile |      |
| 215 |     |     |     |     | 220 |     |     |     |     | 225 |     |     |     |     | 230 |      |
| GCT | AAG | CTA | CCA | GTT | GAC | GGT | TTA | AGA | ATT | G AC | CAC | ATA | GAT | GGA | CTA | 1072 |
| Ala | Lys | Leu | Pro | Val | Asp | Gly | Leu | Arg | Ile | A sp | His | Ile | Asp | Gly | Leu |      |
|     |     |     |     |     | 235 |     |     |     |     | 240 |     |     |     |     | 245 |      |
| TAT | AAC | CCT | AAG | GAG | TAT | TTA | GAT | AAG | CTA | A GA | CAG | TTA | GTA | GGA | AAT | 1120 |
| Tyr | Asn | Pro | Lys | Glu | Tyr | Leu | Asp | Lys | Leu | A rg | Gln | Leu | Val | Gly | Asn |      |
|     |     |     |     |     | 250 |     |     |     |     | 255 |     |     |     |     | 260 |      |
| GAT | AAG | ATA | ATA | TAC | GTA | GAG | AAG | ATA | TTG | T CA | ATC | AAC | GAG | AAA | TTA | 1168 |
| Asp | Lys | Ile | Ile | Tyr | Val | Glu | Lys | Ile | Leu | S er | Ile | Asn | Glu | Lys | Leu |      |
|     |     |     |     |     | 265 |     |     |     |     | 270 |     |     |     |     | 275 |      |
| AGA | GAT | GAT | TGG | AAA | GTA | GAT | GGG | ACT | ACT | G GA | TAT | GAT | TTC | TTG | AAC | 1216 |
| Arg | Asp | Asp | Trp | Lys | Val | Asp | Gly | Thr | Thr | G ly | Tyr | Asp | Phe | Leu | Asn |      |
|     |     |     |     |     | 280 |     |     |     |     | 285 |     |     |     |     | 290 |      |
| TAC | GTT | AAT | ATG | CTA | TTA | GTA | GAT | GGA | AGT | G GT | GAG | GAG | GAG | TTA | ACT | 1264 |
| Tyr | Val | Asn | Met | Leu | Leu | Val | Asp | Gly | Ser | G ly | Glu | Glu | Glu | Leu | Thr |      |
| 295 |     |     |     |     | 300 |     |     |     |     | 305 |     |     |     |     | 310 |      |
| AAG | TTT | TAT | GAG | AAT | TTC | ATT | GGA | AGG | AAA | A TC | AAT | ATA | GAC | GAG | TTA | 1312 |
| Lys | Phe | Tyr | Glu | Asn | Phe | Ile | Gly | Arg | Lys | I le | Asn | Ile | Asp | Glu | Leu |      |
|     |     |     |     |     | 315 |     |     |     |     | 320 |     |     |     |     | 325 |      |
| ATA | ATA | CAA | AGT | AAA | AAA | TTA | GTT | GCA | AAT | C AG | TTA | TTT | AAA | GGT | GAC | 1360 |
| Ile | Ile | Gln | Ser | Lys | Lys | Leu | Val | Ala | Asn | G ln | Leu | Phe | Lys | Gly | Asp |      |
|     |     |     |     |     | 330 |     |     |     |     | 335 |     |     |     |     | 340 |      |
| ATT | GAA | AGA | TTA | AGC | AAG | TTA | CTG | AAC | GTT | A AT | TAC | GAT | TAT | TTA | GTA | 1408 |
| Ile | Glu | Arg | Leu | Ser | Lys | Leu | Leu | Asn | Val | A sn | Tyr | Asp | Tyr | Leu | Val |      |
|     |     |     |     |     | 345 |     |     |     |     | 350 |     |     |     |     | 355 |      |
| GAT | TTT | CTA | GCA | TGT | ATG | AAA | AAA | TAC | AGG | A CT | TAT | TTA | CCA | TAT | GAG | 1456 |
| Asp | Phe | Leu | Ala | Cys | Met | Lys | Lys | Tyr | Arg | T hr | Tyr | Leu | Pro | Tyr | Glu |      |
|     |     |     |     |     | 360 |     |     |     |     | 365 |     |     |     |     | 370 |      |
| GAT | ATT | AAC | GGA | ATA | AGG | GAA | TGC | GAT | AAG | G AG | GGA | AAG | TTA | AAA | GAT | 1504 |
| Asp | Ile | Asn | Gly | Ile | Arg | Glu | Cys | Asp | Lys | G lu | Gly | Lys | Leu | Lys | Asp |      |
| 375 |     |     |     |     | 380 |     |     |     |     | 385 |     |     |     |     | 390 |      |
| GAA | AAG | GGA | ATC | ATG | AGA | CTC | CAA | CAA | TAC | A TG | CCA | GCA | ATC | TTC | GCT | 1552 |
| Glu | Lys | Gly | Ile | Met | Arg | Leu | Gln | Gln | Tyr | M et | Pro | Ala | Ile | Phe | Ala |      |
|     |     |     |     |     | 395 |     |     |     |     | 400 |     |     |     |     | 405 |      |
| AAG | GGC | TAT | GAG | GAT | ACT | ACC | CTC | TTC | ATC | T AC | AAT | AGA | TTA | ATT | TCC | 1600 |
| Lys | Gly | Tyr | Glu | Asp | Thr | Thr | Leu | Phe | Ile | T yr | Asn | Arg | Leu | Ile | Ser |      |
|     |     |     |     |     | 410 |     |     |     |     | 415 |     |     |     |     | 420 |      |
| CTT | AAC | GAG | GTT | GGG | AGC | GAC | CTA | AGA | AGA | T TC | AGT | TTA | AGC | ATC | AAA | 1648 |
| Leu | Asn | Glu | Val | Gly | Ser | Asp | Leu | Arg | Arg | P he | Ser | Leu | Ser | Ile | Lys |      |
|     |     |     |     |     | 425 |     |     |     |     | 430 |     |     |     |     | 435 |      |
| GAC | TTT | CAT | AAC | TTT | AAC | CTA | AGC | AGA | GTA | A AT | ACC | ATA | TCA | ATG | AAC | 1696 |
| Asp | Phe | His | Asn | Phe | Asn | Leu | Ser | Arg | Val | A sn | Thr | Ile | Ser | Met | Asn |      |
|     |     |     |     |     | 440 |     |     |     |     | 445 |     |     |     |     | 450 |      |
| ACT | CTT | TCC | ACT | CAT | GAT | ACT | AAA | TTC | AGT | G AA | GAC | GTT | AGA | GCT | AGA | 1744 |

```
Thr Leu Ser Thr His Asp Thr Lys Phe Ser Glu Asp Val Arg Ala Arg
455                 460                 465                 470

ATA TCA GTA CTA TCT GAG ATA CCA AAG GAG TGG GAG GAG AGG GTA ATA      1792
Ile Ser Val Leu Ser Glu Ile Pro Lys Glu Trp Glu Glu Arg Val Ile
                475                 480                 485

TAC TGG CAT GAT TTG TTA AGG CCA AAT ATT GAT AAA AAC GAT GAG TAT      1840
Tyr Trp His Asp Leu Leu Arg Pro Asn Ile Asp Lys Asn Asp Glu Tyr
                490                 495                 500

AGA TTT TAT CAA ACA CTT GTG GGA AGT TAC GAG GGA TTT GAT AAT AAG      1888
Arg Phe Tyr Gln Thr Leu Val Gly Ser Tyr Glu Gly Phe Asp Asn Lys
                505                 510                 515

GAG AGA ATT AAG AAC CAC ATG ATT AAG GTC ATA AGA GAA GCT AAG GTA      1936
Glu Arg Ile Lys Asn His Met Ile Lys Val Ile Arg Glu Ala Lys Val
                520                 525                 530

CAT ACA ACG TGG GAA AAT CCT AAT ATA GAG TAT GAA AAG AAG GTT CTG      1984
His Thr Thr Trp Glu Asn Pro Asn Ile Glu Tyr Glu Lys Lys Val Leu
535                 540                 545                 550

GGT TTC ATA GAT GAA GTG TTC GAG AAC AGT AAT TTT AGA AAT GAT TTT      2032
Gly Phe Ile Asp Glu Val Phe Glu Asn Ser Asn Phe Arg Asn Asp Phe
                555                 560                 565

GAA AAT TTT GAA AAG AAA ATA GTT TAT TTC GGT TAT ATG AAA TCA TTA      2080
Glu Asn Phe Glu Lys Lys Ile Val Tyr Phe Gly Tyr Met Lys Ser Leu
                570                 575                 580

ATC GCA ACG ACA CTT AGG TTC CTT TCG CCC GGT GTA CCA GAT ATT TAT      2128
Ile Ala Thr Thr Leu Arg Phe Leu Ser Pro Gly Val Pro Asp Ile Tyr
                585                 590                 595

CAA GGA ACT GAA GTT TGG AGA TTC TTA CTT ACA GAC CCA GAT AAC AGA      2176
Gln Gly Thr Glu Val Trp Arg Phe Leu Leu Thr Asp Pro Asp Asn Arg
                600                 605                 610

ATG CCG GTG GAT TTC AAG AAA CTA AAG GAA TTA TTA AAT AAT TTG ACT      2224
Met Pro Val Asp Phe Lys Lys Leu Lys Glu Leu Leu Asn Asn Leu Thr
615                 620                 625                 630

GAA AAG AAC TTA GAA CTC TCA GAT CCA AGA GTC AAA ATG TTA TAT GTT      2272
Glu Lys Asn Leu Glu Leu Ser Asp Pro Arg Val Lys Met Leu Tyr Val
                635                 640                 645

AAG AAA TTG CTA CAG CTT AGA AGA GAG TAC TCA CTA AAC GAT TAT AAA      2320
Lys Lys Leu Leu Gln Leu Arg Arg Glu Tyr Ser Leu Asn Asp Tyr Lys
                650                 655                 660

CCA TTG CCC TTT GGC TTC CAA AGG GGA AAA GTA GCT GTC CTT TTC TCA      2368
Pro Leu Pro Phe Gly Phe Gln Arg Gly Lys Val Ala Val Leu Phe Ser
                665                 670                 675

CCA ATA GTG ACT AGG GAG GTT AAA GAG AAA ATT AGT ATA AGG CAA AAA      2416
Pro Ile Val Thr Arg Glu Val Lys Glu Lys Ile Ser Ile Arg Gln Lys
                680                 685                 690

AGC GTT GAT TGG ATC AGA AAT GAG GAA ATT AGT AGT GGA GAA TAC AAT      2464
Ser Val Asp Trp Ile Arg Asn Glu Glu Ile Ser Ser Gly Glu Tyr Asn
695                 700                 705                 710

TTA AGT GAG TTG ATT GGG AAG CAT AAA GTC GTT ATA TTA ACT GAA AAA      2512
Leu Ser Glu Leu Ile Gly Lys His Lys Val Val Ile Leu Thr Glu Lys
                715                 720                 725

AGG GAG TGAACTACCT ACATAGATTT ATTCTTGAAC TACTCTGGTC AGAAATGTAT      2568
Arg Glu

TACGCAGATC                                                            2578
```

(2) INFORMATION FOR SEQ ID NO: 2:

(i) SEQUENCE CHARACTERISTICS:
        (A) LENGTH: 728 amino acids
        (B) TYPE: amino acid
        (D) TOPOLOGY: linear (ii) MOLECULE TYPE: protein (xi) SEQUENCE DESCRIPTION: SEQ ID NO: 2:

Met Ile Ile Gly Thr Tyr Arg Leu Gln Leu Asn Lys Lys Phe Thr Phe
 1               5                  10                  15

Tyr Asp Ile Ile Glu Asn Leu Asp Tyr Phe Lys Glu Leu Gly Val Ser
                 20                  25                  30

His Leu Tyr Leu Ser Pro Ile Leu Lys Ala Arg Pro Gly Ser Thr His
         35                  40                  45

Gly Tyr Asp Val Val Asp His Ser Glu Ile Asn Glu Leu Gly Gly
     50                  55                  60

Glu Glu Gly Cys Phe Lys Leu Val Lys Glu Ala Lys Ser Arg Gly Leu
 65                  70                  75                  80

Glu Ile Ile Gln Asp Ile Val Pro Asn His Met Ala Val His His Thr
                 85                  90                  95

Asn Trp Arg Leu Met Asp Leu Leu Lys Ser Trp Lys Asn Ser Lys Tyr
                100                 105                 110

Tyr Asn Tyr Phe Asp His Tyr Asp Asp Lys Ile Ile Leu Pro Ile
             115                 120                 125

Leu Glu Asp Glu Leu Asp Thr Val Ile Asp Lys Gly Leu Ile Lys Leu
130                 135                 140

Gln Lys Asp Asn Ile Glu Tyr Arg Gly Leu Ile Leu Pro Ile Asn Asp
145                 150                 155                 160

Glu Gly Val Glu Phe Leu Lys Arg Ile Asn Cys Phe Asp Asn Ser Cys
                165                 170                 175

Leu Lys Lys Glu Asp Ile Lys Lys Leu Leu Leu Ile Gln Tyr Tyr Gln
                180                 185                 190

Leu Thr Tyr Trp Lys Lys Gly Tyr Pro Asn Tyr Arg Arg Phe Phe Ala
         195                 200                 205

Val Asn Asp Leu Ile Ala Val Arg Val Glu Leu Asp Glu Val Phe Arg
         210                 215                 220

Glu Ser His Glu Ile Ile Ala Lys Leu Pro Val Asp Gly Leu Arg Ile
225                 230                 235                 240

Asp His Ile Asp Gly Leu Tyr Asn Pro Lys Glu Tyr Leu Asp Lys Leu
                245                 250                 255

Arg Gln Leu Val Gly Asn Asp Lys Ile Ile Tyr Val Glu Lys Ile Leu
                260                 265                 270

Ser Ile Asn Glu Lys Leu Arg Asp Asp Trp Lys Val Asp Gly Thr Thr
        275                 280                 285

Gly Tyr Asp Phe Leu Asn Tyr Val Asn Met Leu Leu Val Asp Gly Ser
    290                 295                 300

Gly Glu Glu Glu Leu Thr Lys Phe Tyr Glu Asn Phe Ile Gly Arg Lys
305                 310                 315                 320

Ile Asn Ile Asp Glu Leu Ile Ile Gln Ser Lys Lys Leu Val Ala Asn
                325                 330                 335

Gln Leu Phe Lys Gly Asp Ile Glu Arg Leu Ser Lys Leu Leu Asn Val
            340                 345                 350

Asn Tyr Asp Tyr Leu Val Asp Phe Leu Ala Cys Met Lys Lys Tyr Arg
            355                 360                 365

Thr Tyr Leu Pro Tyr Glu Asp Ile Asn Gly Ile Arg Glu Cys Asp Lys
        370                 375                 380

Glu Gly Lys Leu Lys Asp Glu Lys Gly Ile Met Arg Leu Gln Gln Tyr
385                 390                 395                 400

```
Met Pro Ala Ile Phe Ala Lys Gly Tyr Glu Asp Thr Thr Leu Phe Ile
                405                 410                 415

Tyr Asn Arg Leu Ile Ser Leu Asn Glu Val Gly Ser Asp Leu Arg Arg
            420                 425                 430

Phe Ser Leu Ser Ile Lys Asp Phe His Asn Phe Asn Leu Ser Arg Val
        435                 440                 445

Asn Thr Ile Ser Met Asn Thr Leu Ser Thr His Asp Thr Lys Phe Ser
    450                 455                 460

Glu Asp Val Arg Ala Arg Ile Ser Val Leu Ser Glu Ile Pro Lys Glu
465                 470                 475                 480

Trp Glu Glu Arg Val Ile Tyr Trp His Asp Leu Leu Arg Pro Asn Ile
                485                 490                 495

Asp Lys Asn Asp Glu Tyr Arg Phe Tyr Gln Thr Leu Val Gly Ser Tyr
            500                 505                 510

Glu Gly Phe Asp Asn Lys Glu Arg Ile Lys Asn His Met Ile Lys Val
        515                 520                 525

Ile Arg Glu Ala Lys Val His Thr Thr Trp Glu Asn Pro Asn Ile Glu
    530                 535                 540

Tyr Glu Lys Lys Val Leu Gly Phe Ile Asp Glu Val Phe Glu Asn Ser
545                 550                 555                 560

Asn Phe Arg Asn Asp Phe Glu Asn Phe Glu Lys Ile Val Tyr Phe
                565                 570                 575

Gly Tyr Met Lys Ser Leu Ile Ala Thr Thr Leu Arg Phe Leu Ser Pro
            580                 585                 590

Gly Val Pro Asp Ile Tyr Gln Gly Thr Glu Val Trp Arg Phe Leu Leu
        595                 600                 605

Thr Asp Pro Asp Asn Arg Met Pro Val Asp Phe Lys Lys Leu Lys Glu
    610                 615                 620

Leu Leu Asn Asn Leu Thr Glu Lys Asn Leu Glu Leu Ser Asp Pro Arg
625                 630                 635                 640

Val Lys Met Leu Tyr Val Lys Lys Leu Leu Gln Leu Arg Arg Glu Tyr
                645                 650                 655

Ser Leu Asn Asp Tyr Lys Pro Leu Pro Phe Gly Phe Gln Arg Gly Lys
            660                 665                 670

Val Ala Val Leu Phe Ser Pro Ile Val Thr Arg Glu Val Lys Glu Lys
        675                 680                 685

Ile Ser Ile Arg Gln Lys Ser Val Asp Trp Ile Arg Asn Glu Glu Ile
    690                 695                 700

Ser Ser Gly Glu Tyr Asn Leu Ser Glu Leu Ile Gly Lys His Lys Val
705                 710                 715                 720

Val Ile Leu Thr Glu Lys Arg Glu
                725

(2) INFORMATION FOR SEQ ID NO: 3:

(i) SEQUENCE CHARACTERISTICS:
        (A) LENGTH: 3467 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 816..2855

(ix) FEATURE:
        (A) NAME/KEY: mat_ peptide
```

-continued (B) LOCATION: 816..2855

(xi) SEQUENCE DESCRIPTION: SEQ ID NO: 3:

```
GCTAATAAAC TGAACAATGA GGACGGAATG AATGAAAATT ATAGCTGGAA T TGTGGAGTA      60

GAAGGAGAAA CTAACGATTC TAATATTCTT TATTGTAGAG AAAAACAAAG A AGAAATTTT     120

GTAATAACAT TATTTGTTAG CCAAGGTATA CCAATGATCT TAGGGGGAGA C GAAATAGGA     180

AGAACACAAA AAGGCAACAA TAATGCTTTT TGTCAGGATA ATGAGACAAG T TGGTATGAT     240

TGGAACCTTG ATGAAAATCG TGTAAGGTTT CATGATTTTG TGAGGAGACT T ACCAATTTT     300

TATAAAGCTC ATCCGATATT TAGGAGGGCT AGATATTTTC AGGGTAAGAA G TTACACGGT     360

TCCCCATTAA AGGATGTGAC GTGGCTAAAA CCTGACGGCA ATGAAGTTGA T GATTCAGTG     420

TGGAAATCTC CAACAAATCA TATTATTTAT ATATTAGAGG GAAGTGCTAT C GATGAAATA     480

AATTATAATG GAGAAAGGAT AGCTGACGAC ACTTTTCTAA TTATTTTGAA T GGAGCAAGT     540

ACTAATCTTA AGATAAAAGT ACCTCATGGA AAATGGGAGT TAGTGTTACA T CCTTATCCA     600

CATGAGCCAT CTAACGATAA AAAGATAATA GAAAACAACA AAGAAGTAGA A ATAGATGGA     660

AAGACTGCAC TAATTTACAG GAGGATAGAG TTCCAGTGAT ATCAGCAACC T ACAGATTAC     720

AGTTAAATAA GAATTTTAAT TTTGGTGACG TAATCGATAA CCTATGGTAT T TTAAGGATT     780

TAGGAGTTTC CCATCTCTAC CTCTCTCCTG TCTTA ATG GCT TCG CCA GGA AGT         833
                                   Met Ala Ser Pro Gly Ser
                                     1               5
```

```
AAC CAT GGG TAC GAT GTA ATA GAT CAT TCA A GG ATA AAC GAT GAA CTT       881
Asn His Gly Tyr Asp Val Ile Asp His Ser A rg Ile Asn Asp Glu Leu
             10                  15                      20

GGA GGA GAG AAA GAA TAC AGG AGA TTA ATA G AG ACA GCT CAT ACT ATT       929
Gly Gly Glu Lys Glu Tyr Arg Arg Leu Ile G lu Thr Ala His Thr Ile
     25                  30                      35

GGA TTA GGT ATT ATA CAG GAC ATA GTA CCA A AT CAC ATG GCT GTA AAT       977
Gly Leu Gly Ile Ile Gln Asp Ile Val Pro A sn His Met Ala Val Asn
 40                  45                      50

TCT CTA AAT TGG CGA CTA ATG GAT GTA TTA A AA ATG GGT AAA AAG AGT      1025
Ser Leu Asn Trp Arg Leu Met Asp Val Leu L ys Met Gly Lys Lys Ser
 55                  60                      65                  70

AAA TAT TAT ACG TAC TTT GAC TTT TTC CCA G AA GAT GAT AAG ATA CGA      1073
Lys Tyr Tyr Thr Tyr Phe Asp Phe Phe Pro G lu Asp Asp Lys Ile Arg
             75                  80                      85

TTA CCC ATA TTA GGA GAA GAT TTA GAT ACA G TG ATA AGT AAA GGT TTA      1121
Leu Pro Ile Leu Gly Glu Asp Leu Asp Thr V al Ile Ser Lys Gly Leu
     90                  95                     100

TTA AAG ATA GTA AAA GAT GGA GAT GAA TAT T TC CTA GAA TAT TTC AAA      1169
Leu Lys Ile Val Lys Asp Gly Asp Glu Tyr P he Leu Glu Tyr Phe Lys
105                 110                     115

TGG AAA CTT CCT CTA ACA GAG GTT GGA AAT G AT ATA TAC GAC ACT TTA      1217
Trp Lys Leu Pro Leu Thr Glu Val Gly Asn A sp Ile Tyr Asp Thr Leu
     120                 125                     130

CAA AAA CAG AAT TAT ACC CTA ATG TCT TGG A AA AAT CCT CCT AGC TAT      1265
Gln Lys Gln Asn Tyr Thr Leu Met Ser Trp L ys Asn Pro Pro Ser Tyr
135                 140                     145                 150

AGA CGA TTC TTC GAT GTT AAT ACT TTA ATA G GA GTA AAT GTC GAA AAA      1313
Arg Arg Phe Phe Asp Val Asn Thr Leu Ile G ly Val Asn Val Glu Lys
             155                 160                     165

GAT CAC GTA TTT CAA GAG TCC CAT TCA AAG A TC TTA GAT TTA GAT GTT      1361
Asp His Val Phe Gln Glu Ser His Ser Lys I le Leu Asp Leu Asp Val
     170                 175                     180

GAT GGC TAT AGA ATT GAT CAT ATT GAT GGA T TA TAT GAT CCT GAG AAA      1409
```

```
                    -continued

Asp Gly Tyr Arg Ile Asp His Ile Asp Gly L eu Tyr Asp Pro Glu Lys
            185                 190                  195

TAT ATT AAT GAC CTG AGG TCA ATA ATT AAA A AT AAA ATA ATT ATT GTA      1457
Tyr Ile Asn Asp Leu Arg Ser Ile Ile Lys A sn Lys Ile Ile Ile Val
200                      205                 210

GAA AAA ATT CTG GGA TTT CAG GAG GAA TTA A AA TTA AAT TCA GAT GGA      1505
Glu Lys Ile Leu Gly Phe Gln Glu Glu Leu L ys Leu Asn Ser Asp Gly
215                      220                 225                 230

ACT ACA GGA TAT GAC TTC TTA AAT TAC TCC A AC TTA CTG TTT AAT TTT      1553
Thr Thr Gly Tyr Asp Phe Leu Asn Tyr Ser A sn Leu Leu Phe Asn Phe
                     235                 240                 245

AAT CAA GAG ATA ATG GAC AGT ATA TAT GAG A AT TTC ACA GCG GAG AAA      1601
Asn Gln Glu Ile Met Asp Ser Ile Tyr Glu A sn Phe Thr Ala Glu Lys
                 250                 255                 260

ATA TCT ATA AGT GAA AGT ATA AAG AAA ATA A AA GCG CAA ATA ATT GAT      1649
Ile Ser Ile Ser Glu Ser Ile Lys Lys Ile L ys Ala Gln Ile Ile Asp
             265                 270                 275

GAG CTA TTT AGT TAT GAA GTT AAA AGA TTA G CA TCA CAA CTA GGA ATT      1697
Glu Leu Phe Ser Tyr Glu Val Lys Arg Leu A la Ser Gln Leu Gly Ile
         280                 285                 290

AGC TAC GAT ATA TTG AGA GAT TAC CTT TCT T GT ATA GAT GTG TAC AGA      1745
Ser Tyr Asp Ile Leu Arg Asp Tyr Leu Ser C ys Ile Asp Val Tyr Arg
295                 300                 305                 310

ACT TAT GCT AAT CAG ATT GTA AAA GAG TGT G AT AAG ACC AAT GAG ATA      1793
Thr Tyr Ala Asn Gln Ile Val Lys Glu Cys A sp Lys Thr Asn Glu Ile
                315                 320                 325

GAG GAA GCA ACC AAA AGA AAT CCA GAG GCT T AT ACT AAA TTA CAA CAA      1841
Glu Glu Ala Thr Lys Arg Asn Pro Glu Ala T yr Thr Lys Leu Gln Gln
            330                 335                 340

TAT ATG CCA GCA GTA TAC GCT AAA GCT TAT G AA GAT ACT TTC CTC TTT      1889
Tyr Met Pro Ala Val Tyr Ala Lys Ala Tyr G lu Asp Thr Phe Leu Phe
        345                 350                 355

AGA TAC AAT AGA TTA ATA TCC ATA AAT GAG G TT GGA AGC GAT TTA CGA      1937
Arg Tyr Asn Arg Leu Ile Ser Ile Asn Glu V al Gly Ser Asp Leu Arg
    360                 365                 370

TAT TAT AAG ATA TCG CCT GAT CAG TTT CAT G TA TTT AAT CAA AAA CGA      1985
Tyr Tyr Lys Ile Ser Pro Asp Gln Phe His V al Phe Asn Gln Lys Arg
375                 380                 385                 390

AGA GGA AAA ATC ACA CTA AAT GCC ACT AGC A CA CAT GAT ACT AAG TTT      2033
Arg Gly Lys Ile Thr Leu Asn Ala Thr Ser T hr His Asp Thr Lys Phe
                395                 400                 405

AGT GAA GAT GTA AGG ATG AAA ATA AGT GTA T TA AGT GAA TTT CCT GAA      2081
Ser Glu Asp Val Arg Met Lys Ile Ser Val L eu Ser Glu Phe Pro Glu
            410                 415                 420

GAA TGG AAA AAT AAG GTC GAG GAA TGG CAT A GT ATC ATA AAT CCA AAG      2129
Glu Trp Lys Asn Lys Val Glu Glu Trp His S er Ile Ile Asn Pro Lys
        425                 430                 435

GTA TCA AGA AAT GAT GAA TAT AGA TAT TAT C AG GTT TTA GTG GGA AGT      2177
Val Ser Arg Asn Asp Glu Tyr Arg Tyr Tyr G ln Val Leu Val Gly Ser
    440                 445                 450

TTT TAT GAG GGA TTC TCT AAT GAT TTT AAG G AG AGA ATA AAG CAA CAT      2225
Phe Tyr Glu Gly Phe Ser Asn Asp Phe Lys G lu Arg Ile Lys Gln His
455                 460                 465                 470

ATG ATA AAA AGT GTC AGA GAA GCT AAG ATA A AT ACC TCA TGG AGA AAT      2273
Met Ile Lys Ser Val Arg Glu Ala Lys Ile A sn Thr Ser Trp Arg Asn
                475                 480                 485

CAA AAT AAA GAA TAT GAA AAT AGA GTA ATG G AA TTA GTG GAA GAA ACT      2321
Gln Asn Lys Glu Tyr Glu Asn Arg Val Met G lu Leu Val Glu Glu Thr
            490                 495                 500
```

| | |
|---|---|
| TTT ACC AAT AAG GAT TTC ATT AAA AGT TTC A TG AAA TTT GAA AGT AAG<br>Phe Thr Asn Lys Asp Phe Ile Lys Ser Phe M et Lys Phe Glu Ser Lys<br>     505                       510                   515 | 2369 |
| ATA AGA AGG ATA GGG ATG ATT AAG AGC TTA T CC TTG GTC GCA TTA AAA<br>Ile Arg Arg Ile Gly Met Ile Lys Ser Leu S er Leu Val Ala Leu Lys<br>520                          525                     530 | 2417 |
| ATT ATG TCA GCC GGT ATA CCT GAT TTT TAT C AG GGA ACA GAA ATA TGG<br>Ile Met Ser Ala Gly Ile Pro Asp Phe Tyr G ln Gly Thr Glu Ile Trp<br>535                     540                   545                   550 | 2465 |
| CGA TAT TTA CTT ACA GAT CCA GAT AAC AGA G TC CCA GTG GAT TTT AAG<br>Arg Tyr Leu Leu Thr Asp Pro Asp Asn Arg V al Pro Val Asp Phe Lys<br>                555                       560                   565 | 2513 |
| AAA TTA CAC GAA ATA TTA GAA AAA TCC AAA A AA TTT GAA AAA AAT ATG<br>Lys Leu His Glu Ile Leu Glu Lys Ser Lys L ys Phe Glu Lys Asn Met<br>     570                       575                   580 | 2561 |
| TTA GAG TCT ATG GAC GAT GGA AGA ATT AAG A TG TAT TTA ACA TAT AAG<br>Leu Glu Ser Met Asp Asp Gly Arg Ile Lys M et Tyr Leu Thr Tyr Lys<br>585                     590                   595 | 2609 |
| CTT TTA TCC CTA AGA AAA CAG TTG GCT GAG G AT TTT TTA AAG GGC GAG<br>Leu Leu Ser Leu Arg Lys Gln Leu Ala Glu A sp Phe Leu Lys Gly Glu<br>     600                       605                   610 | 2657 |
| TAT AAG GGA TTA GAT CTA GAA GAA GGA CTA T GT GGG TTT ATT AGG TTT<br>Tyr Lys Gly Leu Asp Leu Glu Glu Gly Leu C ys Gly Phe Ile Arg Phe<br>615                     620                   625                   630 | 2705 |
| AAC AAA ATT TTG GTA ATA ATA AAA ACC AAG G GA AGT GTT AAT TAC AAA<br>Asn Lys Ile Leu Val Ile Ile Lys Thr Lys G ly Ser Val Asn Tyr Lys<br>                635                       640                   645 | 2753 |
| CTG AAA CTT GAA GAG GGA GCA ATT TAC ACA G AT GTA TTG ACA GGA GAA<br>Leu Lys Leu Glu Glu Gly Ala Ile Tyr Thr A sp Val Leu Thr Gly Glu<br>     650                       655                   660 | 2801 |
| GAA ATT AAA AAA GAG GTA CAG ATT AAT GAG C TA CCT AGG ATA CTA GTT<br>Glu Ile Lys Lys Glu Val Gln Ile Asn Glu L eu Pro Arg Ile Leu Val<br>665                     670                   675 | 2849 |
| AGA ATG TAAGTTATAA TAATCCGATT TTTATGTGAC AAGATTACG C TTACGAAAA<br>Arg Met<br>     680 | 2905 |
| GGACTGTTAA ATCAACTTTT ATGTGAATTA TGAAACGTAA ATTATAAGTT T CCTGAGGAT | 2965 |
| AAACATATAT ATCTCTATCT CTCATTGATA TCACATGAGT ATTAGATTAA G GGGAAGTAA | 3025 |
| TTCTTACGGA CATTCAGGCT GGTTTACAGT ATACTGTAGA ATATGTAATA G GAAAATAAG | 3085 |
| AATAGGAACG GACTTAGTCT ACAAATGCCC TAAATGTGAA AAGAAGTATA A CGCATTCTT | 3145 |
| CTGTGAAGCA GATGCTAGGG GATTAAAGAA AAAGTGCCCA TACTGTGGTA C TGAACTTGT | 3205 |
| CAGTGCAATT TAAGACTCAA ATAGAAGGTA AAAATATTTT TATACTGAAT A ATGAGTTGT | 3265 |
| TTTACGCTGA TACGGATATA GTTATTCGAA ATCAAGATTT TATTAAGAAA C TCACCTTTA | 3325 |
| CACAATATAA TAAGATTGCC TATATTGACA TGGACATAGA AACGACAGAA T TTAAGATAT | 3385 |
| TAAGATTAGT AGTGTGTAAA ACTAGAATAA ATATTTATGT TTGCAACGTA A TTGGTAAAT | 3445 |
| TGAAAGAAAC TAATTTTGAA AA | 3467 |

(2) INFORMATION FOR SEQ ID NO: 4:

(i) SEQUENCE CHARACTERISTICS:
        (A) LENGTH: 680 amino acids
        (B) TYPE: amino acid
        (D) TOPOLOGY: linear (ii) MOLECULE TYPE: protein (xi) SEQUENCE DESCRIPTION: SEQ ID NO: 4:

```
Met Ala Ser Pro Gly Ser Asn His Gly Tyr Asp Val Ile Asp His Ser
 1               5                  10                  15

Arg Ile Asn Asp Glu Leu Gly Gly Lys Glu Tyr Arg Arg Leu Ile
             20                  25                  30

Glu Thr Ala His Thr Ile Gly Leu Gly Ile Ile Gln Asp Ile Val Pro
             35                  40                  45

Asn His Met Ala Val Asn Ser Leu Asn Trp Arg Leu Met Asp Val Leu
         50                  55                  60

Lys Met Gly Lys Lys Ser Lys Tyr Tyr Thr Tyr Phe Asp Phe Phe Pro
 65                  70                  75                  80

Glu Asp Asp Lys Ile Arg Leu Pro Ile Leu Gly Glu Asp Leu Asp Thr
                 85                  90                  95

Val Ile Ser Lys Gly Leu Leu Lys Ile Val Lys Asp Gly Asp Glu Tyr
                100                 105                 110

Phe Leu Glu Tyr Phe Lys Trp Lys Leu Pro Leu Thr Glu Val Gly Asn
             115                 120                 125

Asp Ile Tyr Asp Thr Leu Gln Lys Gln Asn Tyr Thr Leu Met Ser Trp
 130                 135                 140

Lys Asn Pro Pro Ser Tyr Arg Arg Phe Phe Asp Val Asn Thr Leu Ile
145                 150                 155                 160

Gly Val Asn Val Glu Lys Asp His Val Phe Gln Glu Ser His Ser Lys
                165                 170                 175

Ile Leu Asp Leu Asp Val Asp Gly Tyr Arg Ile Asp His Ile Asp Gly
             180                 185                 190

Leu Tyr Asp Pro Glu Lys Tyr Ile Asn Asp Leu Arg Ser Ile Ile Lys
         195                 200                 205

Asn Lys Ile Ile Ile Val Glu Lys Ile Leu Gly Phe Gln Glu Glu Leu
 210                 215                 220

Lys Leu Asn Ser Asp Gly Thr Thr Gly Tyr Asp Phe Leu Asn Tyr Ser
225                 230                 235                 240

Asn Leu Leu Phe Asn Phe Asn Gln Glu Ile Met Asp Ser Ile Tyr Glu
             245                 250                 255

Asn Phe Thr Ala Glu Lys Ile Ser Ile Ser Glu Ser Ile Lys Lys Ile
             260                 265                 270

Lys Ala Gln Ile Ile Asp Glu Leu Phe Ser Tyr Glu Val Lys Arg Leu
275                 280                 285

Ala Ser Gln Leu Gly Ile Ser Tyr Asp Ile Leu Arg Asp Tyr Leu Ser
         290                 295                 300

Cys Ile Asp Val Tyr Arg Thr Tyr Ala Asn Gln Ile Val Lys Glu Cys
305                 310                 315                 320

Asp Lys Thr Asn Glu Ile Glu Glu Ala Thr Lys Arg Asn Pro Glu Ala
             325                 330                 335

Tyr Thr Lys Leu Gln Gln Tyr Met Pro Ala Val Tyr Ala Lys Ala Tyr
             340                 345                 350

Glu Asp Thr Phe Leu Phe Arg Tyr Asn Arg Leu Ile Ser Ile Asn Glu
             355                 360                 365

Val Gly Ser Asp Leu Arg Tyr Tyr Lys Ile Ser Pro Asp Gln Phe His
 370                 375                 380

Val Phe Asn Gln Lys Arg Arg Gly Lys Ile Thr Leu Asn Ala Thr Ser
385                 390                 395                 400

Thr His Asp Thr Lys Phe Ser Glu Asp Val Arg Met Lys Ile Ser Val
             405                 410                 415
```

```
Leu Ser Glu Phe Pro Glu Glu Trp Lys Asn Lys Val Glu Glu Trp His
        420                 425                 430
Ser Ile Ile Asn Pro Lys Val Ser Arg Asn Asp Glu Tyr Arg Tyr Tyr
        435                 440                 445
Gln Val Leu Val Gly Ser Phe Tyr Glu Gly Phe Ser Asn Asp Phe Lys
        450                 455                 460
Glu Arg Ile Lys Gln His Met Ile Lys Ser Val Arg Glu Ala Lys Ile
465                 470                 475                 480
Asn Thr Ser Trp Arg Asn Gln Asn Lys Glu Tyr Glu Asn Arg Val Met
                485                 490                 495
Glu Leu Val Glu Glu Thr Phe Thr Asn Lys Asp Phe Ile Lys Ser Phe
                500                 505                 510
Met Lys Phe Glu Ser Lys Ile Arg Arg Ile Gly Met Ile Lys Ser Leu
                515                 520                 525
Ser Leu Val Ala Leu Lys Ile Met Ser Ala Gly Ile Pro Asp Phe Tyr
                530                 535                 540
Gln Gly Thr Glu Ile Trp Arg Tyr Leu Leu Thr Asp Pro Asp Asn Arg
545                 550                 555                 560
Val Pro Val Asp Phe Lys Lys Leu His Glu Ile Leu Glu Lys Ser Lys
                565                 570                 575
Lys Phe Glu Lys Asn Met Leu Glu Ser Met Asp Asp Gly Arg Ile Lys
                580                 585                 590
Met Tyr Leu Thr Tyr Lys Leu Leu Ser Leu Arg Lys Gln Leu Ala Glu
                595                 600                 605
Asp Phe Leu Lys Gly Glu Tyr Lys Gly Leu Asp Leu Glu Glu Gly Leu
                610                 615                 620
Cys Gly Phe Ile Arg Phe Asn Lys Ile Leu Val Ile Ile Lys Thr Lys
625                 630                 635                 640
Gly Ser Val Asn Tyr Lys Leu Lys Leu Glu Glu Gly Ala Ile Tyr Thr
                645                 650                 655
Asp Val Leu Thr Gly Glu Glu Ile Lys Lys Glu Val Gln Ile Asn Glu
                660                 665                 670
Leu Pro Arg Ile Leu Val Arg Met
                675                 680

(2) INFORMATION FOR SEQ ID NO: 5:

(i) SEQUENCE CHARACTERISTICS:
        (A) LENGTH: 2691 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 639..2315

(ix) FEATURE:
        (A) NAME/KEY: mat_ peptide
        (B) LOCATION: 639..2315

(xi) SEQUENCE DESCRIPTION: SEQ ID NO: 5:

CTGCAGTAAC TAGCGCTATC GAAGACGTTA TAAAGAGAAG GATAAATAGA G TTCCAGTGA    60

GTCTAGAAGA CCTTTTTGAA TAAGGACTTT AATATCATTT AAATTTATTT T TTGGAACAT   120

GCAGAGGTAA ACCCATGAAT GTCATTTTCG ACGTATTAAA CGAGATCCAT G GGTTTTTTG   180

GTGCATTGTG GGCGGGAGCA GCTCTACTTA ACTACTTAGT TAAGCCTCAA G ATAAGAGGC   240

AATTTGAGAG AATAGGGAAA TTCTTCATGA TAAACTCAGT CATTACAGTA A TAACTGGGA   300
```

```
TAATAATTTT CGCCTACATT TACCTAGCCC CTTATCAAGG GAATTTATTT C TAGTAGCGG       360

CAATTCTACG TTCAAGCCTT GACATTAGGT TAAGGGCCTT ACTAAACTTA A TAGGAGGAG      420

CGTTTGGGTT ATTGGCTTTT GGGGCAGGGA TAGTTATAAG CAATAGGATA A GGCTTATGG     480

TACGTGTTAA GGAAGGTGAC GCTACAATCC TAGAGTTGAG GAATAGTATT G CCAATTTAT    540

CTAAAATTAG TTTAATCTTC TTATTACTTT CCTTAGCCAT GATGATACTT G CTGGTTCCA    600

TAGCACAAGT TATAAGTTAG AGTTGAAAGA AAAATTTA ATG ACG TTT  GCT TAT         653
                                            Met Thr Phe Ala Tyr
                                             1               5
```

| | | |
|---|---|---|
| AAA ATA GAT GGA AAT GAG GTA ATC TTT ACC T TA TGG GCA CCT TAT CAA<br>Lys Ile Asp Gly Asn Glu Val Ile Phe Thr L eu Trp Ala Pro Tyr Gln<br>                10                   15                     20 | 701 |

```
AAA ATA GAT GGA AAT GAG GTA ATC TTT ACC T TA TGG GCA CCT TAT CAA       701
Lys Ile Asp Gly Asn Glu Val Ile Phe Thr L eu Trp Ala Pro Tyr Gln
                10                  15                   20

AAG AGC GTT AAA CTA AAG GTT CTA GAG AAG G GA CTT TAC GAA ATG GAA       749
Lys Ser Val Lys Leu Lys Val Leu Glu Lys G ly Leu Tyr Glu Met Glu
                25                  30                   35

AGA GAT GAA AAA GGT TAC TTC ACC ATT ACC T TA AAC AAC GTA AAG GTT       797
Arg Asp Glu Lys Gly Tyr Phe Thr Ile Thr L eu Asn Asn Val Lys Val
        40                  45                  50

AGA GAT AGG TAT AAA TAC GTT TTA GAT GAT G CT AGT GAA ATA CCA GAT       845
Arg Asp Arg Tyr Lys Tyr Val Leu Asp Asp A la Ser Glu Ile Pro Asp
        55                  60                  65

CCA GCA TCC AGA TAC CAA CCA GAA GGT GTA C AT GGG CCT TCA CAA ATT       893
Pro Ala Ser Arg Tyr Gln Pro Glu Gly Val H is Gly Pro Ser Gln Ile
70                  75                  80                  85

ATA CAA GAA AGT AAA GAG TTC AAC AAC GAG A CT TTT CTG AAG AAA GAG       941
Ile Gln Glu Ser Lys Glu Phe Asn Asn Glu T hr Phe Leu Lys Lys Glu
                90                  95                  100

GAC TTG ATA ATT TAT GAA ATA CAC GTG GGG A CT TTC ACT CCA GAG GGA       989
Asp Leu Ile Ile Tyr Glu Ile His Val Gly T hr Phe Thr Pro Glu Gly
                105                 110                  115

ACG TTT GAG GGA GTG ATA AGG AAA CTT GAC T AC TTA AAG GAT TTG GGA      1037
Thr Phe Glu Gly Val Ile Arg Lys Leu Asp T yr Leu Lys Asp Leu Gly
                120                 125                  130

ATT ACG GCA ATA GAG ATA ATG CCA ATA GCT C AA TTT CCT GGG AAA AGG      1085
Ile Thr Ala Ile Glu Ile Met Pro Ile Ala G ln Phe Pro Gly Lys Arg
        135                 140                  145

GAT TGG GGT TAT GAT GGA GTT TAT TTA TAT G CA GTA CAG AAC TCT TAC      1133
Asp Trp Gly Tyr Asp Gly Val Tyr Leu Tyr A la Val Gln Asn Ser Tyr
150                 155                 160                  165

GGA GGG CCA GAA GGT TTT AGA AAG TTA GTT G AT GAA GCG CAC AAG AAA      1181
Gly Gly Pro Glu Gly Phe Arg Lys Leu Val A sp Glu Ala His Lys Lys
                170                 175                  180

GGT TTA GGA GTT ATT TTA GAC GTA GTA TAC A AC CAC GTT GGA CCA GAG      1229
Gly Leu Gly Val Ile Leu Asp Val Val Tyr A sn His Val Gly Pro Glu
                185                 190                  195

GGA AAC TAT ATG GTT AAA TTG GGG CCA TAT T TC TCA CAG AAA TAC AAA      1277
Gly Asn Tyr Met Val Lys Leu Gly Pro Tyr P he Ser Gln Lys Tyr Lys
                200                 205                  210

ACG CCA TGG GGA TTA ACC TTT AAC TTT GAC G AT GCT GAA AGC GAT GAG      1325
Thr Pro Trp Gly Leu Thr Phe Asn Phe Asp A sp Ala Glu Ser Asp Glu
        215                 220                  225

GTT AGG AAG TTC ATC TTA GAA AAC GTT GAG T AC TGG ATT AAG GAA TAT      1373
Val Arg Lys Phe Ile Leu Glu Asn Val Glu T yr Trp Ile Lys Glu Tyr
230                 235                 240                  245

AAC GTT GAT GGG TTT AGA TTA GAT GCG GTT C AT GCA ATT ATT GAC ACT      1421
Asn Val Asp Gly Phe Arg Leu Asp Ala Val H is Ala Ile Ile Asp Thr
                250                 255                  260
```

```
TCT CCT AAG CAC ATC TTG GAG GAA ATA GCT G AC GTT GTG CAT AAG TAT     1469
Ser Pro Lys His Ile Leu Glu Glu Ile Ala A sp Val Val His Lys Tyr
        265                 270                 275

AAT AGG ATT GTC ATA GCC GAA AGT GAT TTA A AC GAT CCT AGA GTC GTT     1517
Asn Arg Ile Val Ile Ala Glu Ser Asp Leu A sn Asp Pro Arg Val Val
            280                 285                 290

AAT CCC AAG GAA AAG TGT GGA TAT AAT ATT G AT GCT CAA TGG GTT GAC     1565
Asn Pro Lys Glu Lys Cys Gly Tyr Asn Ile A sp Ala Gln Trp Val Asp
295                 300                 305

GAT TTC CAT CAT TCT ATT CAC GCT TAC TTA A CT GGT GAG AGG CAA GGC     1613
Asp Phe His His Ser Ile His Ala Tyr Leu T hr Gly Glu Arg Gln Gly
310                 315                 320                 325

TAT TAT ACG GAT TTC GGT AAC CTT GAC GAT A TA GTT AAA TCG TAT AAG     1661
Tyr Tyr Thr Asp Phe Gly Asn Leu Asp Asp I le Val Lys Ser Tyr Lys
                330                 335                 340

GAC GTT TTC GTA TAT GAT GGT AAG TAC TCC A AT TTT AGA AGA AAA ACT     1709
Asp Val Phe Val Tyr Asp Gly Lys Tyr Ser A sn Phe Arg Arg Lys Thr
            345                 350                 355

CAC GGA GAA CCA GTT GGT GAA CTA GAC GGA T GC AAT TTC GTA GTT TAT     1757
His Gly Glu Pro Val Gly Glu Leu Asp Gly C ys Asn Phe Val Val Tyr
            360                 365                 370

ATA CAA AAT CAC GAT CAA GTC GGA AAT AGA G GC AAA GGT GAA AGA ATA     1805
Ile Gln Asn His Asp Gln Val Gly Asn Arg G ly Lys Gly Glu Arg Ile
375                 380                 385

ATT AAA TTA GTC GAT AGG GAA AGC TAC AAG A TC GCT GCA GCC CTT TAC     1853
Ile Lys Leu Val Asp Arg Glu Ser Tyr Lys I le Ala Ala Ala Leu Tyr
390                 395                 400                 405

CTT CTT TCC CCC TAT ATT CCA ATG ATT TTC A TG GGA GAG GAA TAC GGT     1901
Leu Leu Ser Pro Tyr Ile Pro Met Ile Phe M et Gly Glu Glu Tyr Gly
                410                 415                 420

GAG GAA AAT CCC TTT TAT TTC TTT TCT GAT T TT TCA GAT TCA AAA CTG     1949
Glu Glu Asn Pro Phe Tyr Phe Phe Ser Asp P he Ser Asp Ser Lys Leu
            425                 430                 435

ATA CAA GGT GTA AGG GAA GGG AGA AAA AAG G AA AAC GGG CAA GAT ACT     1997
Ile Gln Gly Val Arg Glu Gly Arg Lys Lys G lu Asn Gly Gln Asp Thr
            440                 445                 450

GAC CCT CAA GAT GAA TCA ACT TTT AAC GCT T CC AAA CTG AGT TGG AAG     2045
Asp Pro Gln Asp Glu Ser Thr Phe Asn Ala S er Lys Leu Ser Trp Lys
455                 460                 465

ATT GAC GAG GAA ATC TTT TCA TTT TAC AAG A TT TTA ATA AAA ATG AGA     2093
Ile Asp Glu Glu Ile Phe Ser Phe Tyr Lys I le Leu Ile Lys Met Arg
470                 475                 480                 485

AAG GAG TTG AGC ATA GCG TGT GAT AGG AGA G TA AAC GTC GTG AAT GGC     2141
Lys Glu Leu Ser Ile Ala Cys Asp Arg Arg V al Asn Val Val Asn Gly
                490                 495                 500

GAA AAT TGG TTG ATC ATC AAG GGA AGA GAA T AC TTT TCA CTC TAC GTT     2189
Glu Asn Trp Leu Ile Ile Lys Gly Arg Glu T yr Phe Ser Leu Tyr Val
            505                 510                 515

TTC TCT AAA TCA TCT ATT GAA GTT AAG TAC A GT GGA ACT TTA CTT TTG     2237
Phe Ser Lys Ser Ser Ile Glu Val Lys Tyr S er Gly Thr Leu Leu Leu
            520                 525                 530

TCC TCA AAT AAT TCA TTC CCT CAG CAT ATT G AA GAA GGT AAA TAT GAG     2285
Ser Ser Asn Asn Ser Phe Pro Gln His Ile G lu Glu Gly Lys Tyr Glu
535                 540                 545

TTT GAT AAG GGA TTT GCT TTA TAT AAA CTT T AGGACAGGA GAGTTTAAAA       2335
Phe Asp Lys Gly Phe Ala Leu Tyr Lys Leu
550                 555

ATTTCTATGA ATGATTATAC TTTAGATGAT GAGTAAAAGC AAGATCGATG A GGAAGAGAA   2395

AAGGAGAAGA GAAGAAGTCA AAAAGTTAGT AATGCTCTTA GCAATGTTAA G ATAATGTTT  2455
```

-continued

```
TTTTAAACTC AAATAATAAT AAATACCATC ATGTCAATAT TCTTCAGAAC T AGAGATAGA      2515

CCTTTACGTC CCGGAGATCC GTATCCATTA GGTTCAAATT GGATAGAAGA T GAGGATGGC      2575

GTAAATTTTT CCTTGTTCTC AGAGAATGCA GACAAAGTGG AGTTGATTCT T TATTCACAA      2635

ACAAATCAAA AGTATCCAAA GGAGATAATA GAGGTTAAGA ATAGAACGGG G GATCC         2691
```

(2) INFORMATION FOR SEQ ID NO: 6:

(i) SEQUENCE CHARACTERISTICS:
     (A) LENGTH: 559 amino acids
     (B) TYPE: amino acid
     (D) TOPOLOGY: linear (ii) MOLECULE TYPE: protein (xi) SEQUENCE DESCRIPTION: SEQ ID NO: 6:

```
Met Thr Phe Ala Tyr Lys Ile Asp Gly Asn G lu Val Ile Phe Thr Leu
 1               5                  10                 15

Trp Ala Pro Tyr Gln Lys Ser Val Lys Leu L ys Val Leu Glu Lys Gly
             20                  25                 30

Leu Tyr Glu Met Glu Arg Asp Glu Lys Gly T yr Phe Thr Ile Thr Leu
         35                  40                 45

Asn Asn Val Lys Val Arg Asp Arg Tyr Lys T yr Val Leu Asp Asp Ala
     50                  55                 60

Ser Glu Ile Pro Asp Pro Ala Ser Arg Tyr G ln Pro Glu Gly Val His
 65                  70                 75                 80

Gly Pro Ser Gln Ile Ile Gln Glu Ser Lys G lu Phe Asn Asn Glu Thr
                 85                  90                 95

Phe Leu Lys Lys Glu Asp Leu Ile Ile Tyr G lu Ile His Val Gly Thr
             100                 105                110

Phe Thr Pro Glu Gly Thr Phe Glu Gly Val I le Arg Lys Leu Asp Tyr
         115                 120                125

Leu Lys Asp Leu Gly Ile Thr Ala Ile Glu I le Met Pro Ile Ala Gln
     130                 135                140

Phe Pro Gly Lys Arg Asp Trp Gly Tyr Asp G ly Val Tyr Leu Tyr Ala
145                 150                 155                160

Val Gln Asn Ser Tyr Gly Gly Pro Glu Gly P he Arg Lys Leu Val Asp
                 165                 170                175

Glu Ala His Lys Lys Gly Leu Gly Val Ile L eu Asp Val Val Tyr Asn
             180                 185                190

His Val Gly Pro Glu Gly Asn Tyr Met Val L ys Leu Gly Pro Tyr Phe
         195                 200                205

Ser Gln Lys Tyr Lys Thr Pro Trp Gly Leu T hr Phe Asn Phe Asp Asp
     210                 215                220

Ala Glu Ser Asp Glu Val Arg Lys Phe Ile L eu Glu Asn Val Glu Tyr
225                 230                 235                240

Trp Ile Lys Glu Tyr Asn Val Asp Gly Phe A rg Leu Asp Ala Val His
                 245                 250                255

Ala Ile Ile Asp Thr Ser Pro Lys His Ile L eu Glu Glu Ile Ala Asp
             260                 265                270

Val Val His Lys Tyr Asn Arg Ile Val Ile A la Glu Ser Asp Leu Asn
         275                 280                285

Asp Pro Arg Val Val Asn Pro Lys Glu Lys C ys Gly Tyr Asn Ile Asp
     290                 295                300

Ala Gln Trp Val Asp Asp Phe His His Ser I le His Ala Tyr Leu Thr
```

```
305                 310                 315                 320

Gly Glu Arg Gln Gly Tyr Tyr Thr Asp Phe Gly Asn Leu Asp Asp Ile
                325                 330                 335

Val Lys Ser Tyr Lys Asp Val Phe Val Tyr Asp Gly Lys Tyr Ser Asn
                340                 345                 350

Phe Arg Arg Lys Thr His Gly Glu Pro Val Gly Glu Leu Asp Gly Cys
                355                 360                 365

Asn Phe Val Val Tyr Ile Gln Asn His Asp Gln Val Gly Asn Arg Gly
370                 375                 380

Lys Gly Glu Arg Ile Ile Lys Leu Val Asp Arg Glu Ser Tyr Lys Ile
385                 390                 395                 400

Ala Ala Ala Leu Tyr Leu Leu Ser Pro Tyr Ile Pro Met Ile Phe Met
                405                 410                 415

Gly Glu Glu Tyr Gly Glu Glu Asn Pro Phe Tyr Phe Phe Ser Asp Phe
                420                 425                 430

Ser Asp Ser Lys Leu Ile Gln Gly Val Arg Glu Gly Arg Lys Lys Glu
                435                 440                 445

Asn Gly Gln Asp Thr Asp Pro Gln Asp Glu Ser Thr Phe Asn Ala Ser
                450                 455                 460

Lys Leu Ser Trp Lys Ile Asp Glu Glu Ile Phe Ser Phe Tyr Lys Ile
465                 470                 475                 480

Leu Ile Lys Met Arg Lys Glu Leu Ser Ile Ala Cys Asp Arg Arg Val
                485                 490                 495

Asn Val Val Asn Gly Glu Asn Trp Leu Ile Ile Lys Gly Arg Glu Tyr
                500                 505                 510

Phe Ser Leu Tyr Val Phe Ser Lys Ser Ile Glu Val Lys Tyr Ser
                515                 520                 525

Gly Thr Leu Leu Ser Ser Asn Asn Ser Phe Pro Gln His Ile Glu
                530                 535                 540

Glu Gly Lys Tyr Glu Phe Asp Lys Gly Phe Ala Leu Tyr Lys Leu
545                 550                 555

(2) INFORMATION FOR SEQ ID NO: 7:

(i) SEQUENCE CHARACTERISTICS:
        (A) LENGTH: 3600 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1176..2843

(ix) FEATURE:
        (A) NAME/KEY: mat_ peptide
        (B) LOCATION: 1176..2843

(xi) SEQUENCE DESCRIPTION: SEQ ID NO: 7:

ATTCGTTTTG AGTCACTCGG CGTAGGTCTG TAGTCTTTCT TGGCGAGGGC T AATAAGTTG        60

AGATAATGCT TGCCAAGAAT CGAAGAAGGC GTCCTGCCCT GCATGAAATC G ATTACCTCG       120

GCACTAACTC CGAGCTCCGC GAGTTTAGTA GTCACGAATT TGCGTACATA T TTCGGCGCT       180

ATCCCTTTCT CATGCAATAA ATTCTTCGCG TAGTTGTACG TTATATCAGT C TTAGCTATA       240

GACGAAATGT GAAAGACATA GAACACTTTC TTTGGCCCTC TAGTCCAGTT G AGCGTGTAT       300

ACGTAGAAGC CGTCCTCTTT CACGTTGTTC TTCTCGTCAT ACTCATTGAG A ACCTTTACA       360

GCCTCCCTAA GCCTTATACC GCTCTCAAGG AGGAGCTTGA AGACTAGCTC T ACCTCAATA       420
```

```
CCTCTAACAG CCTCCAACCA CCTCCCTATC TCGTCAGCTC CTGGAACCTT A AGATCAACA        480

CCAGACTTTT TCGTTTTCAG CTTTTTCCAT GCCTCAAGAT CCCCTTTCCA C TTGTAGAAC        540

TTCTTCCAGG CTAGGATAGA GTTCTTAGCA TTACTAGGGG GCTTCTTCAG A TAATTGATA        600

TACTGCCTGC AAGTTTCCTC ACTGGCCATT TTCAAACAAT ATTCATAAAA T TCAATTAAT        660

TCCTTTTCCG TGAGACCATT TTTGCCCTCC CTAGAAGTAA GGGAGTTTAG G GCAAATCCC        720

TTACTCTCTT CATCATTTGA AAGAGGGGTT TTAGGGGATT CCTCCCCTAA C CAGGGCTTT        780

GGCCCCTGGG ACCAGGGTTC GAGTCCCTGC CCGGCTACCT TTGAAAGGTT A GGGGGATAC        840

ACCCTAATAC CCCACTTCTA TCTTACAATT TCAGGTAAGT CTTTACTAGG T CAACTAAAG        900

CACCAACGTA AGTCTCCTTC GTCTTACCAC CTTGACTCTT CTTGATAAAG T AAACATAAT        960

ATCATCCATA GACTTACCTT ATTCTTATAT TACCATATGA TTTTATTATT T TGTATTTCT       1020

ATTAGATAAG TCCCACTCAT AGAACAAATG ATGGTTTTAA CTTATATACT A AATACTCTA       1080

ATAACTCAAC AATAATAAGA ATTTAATCAG TTCTGATAAG TATTTTCACT C GAAAACATT       1140

TAAATATATT AAGACATAAT TTCTATTTAA ACAGC ATG TTT TCG TTC GGT GGA           1193
                                     Met Phe Ser Phe Gly Gly
                                      1               5

AAT ATT GAA AAA AAT AAA GGT ATC TTT AAG T TA TGG GCA CCT TAT GTT         1241
Asn Ile Glu Lys Asn Lys Gly Ile Phe Lys L eu Trp Ala Pro Tyr Val
             10               15                  20

AAT AGT GTT AAG CTG AAG TTA AGC AAA AAA C TT ATT CCA ATG GAA AAA         1289
Asn Ser Val Lys Leu Lys Leu Ser Lys Lys L eu Ile Pro Met Glu Lys
         25                  30                  35

AAC GAT GAG GGA TTT TTC GAA GTA GAA ATA G AC GAT ATC GAG GAA AAT         1337
Asn Asp Glu Gly Phe Phe Glu Val Glu Ile A sp Asp Ile Glu Glu Asn
     40                  45                  50

TTA ACC TAT TCT TAT ATT ATA GAA GAT AAG A GA GAG ATA CCT GAT CCC         1385
Leu Thr Tyr Ser Tyr Ile Ile Glu Asp Lys A rg Glu Ile Pro Asp Pro
 55                  60                  65                  70

GCA TCA CGA TAT CAA CCT TTA GGA GTT CAT G AC AAA TCA CAA CTT ATA         1433
Ala Ser Arg Tyr Gln Pro Leu Gly Val His A sp Lys Ser Gln Leu Ile
                 75                  80                  85

AGA ACA GAT TAT CAG ATT CTT GAC CTT GGA A AA GTA AAA ATA GAA GAT         1481
Arg Thr Asp Tyr Gln Ile Leu Asp Leu Gly L ys Val Lys Ile Glu Asp
             90                  95                 100

CTA ATA ATA TAT GAA CTC CAC GTT GGT ACT T TT TCC CAA GAA GGA AAT         1529
Leu Ile Ile Tyr Glu Leu His Val Gly Thr P he Ser Gln Glu Gly Asn
        105                 110                 115

TTC AAA GGA GTA ATA GAA AAG TTA GAT TAC C TC AAG GAT CTA GGA ATC         1577
Phe Lys Gly Val Ile Glu Lys Leu Asp Tyr L eu Lys Asp Leu Gly Ile
    120                 125                 130

ACA GGA ATT GAA CTG ATG CCT GTG GCA CAA T TT CCA GGG AAT AGA GAT         1625
Thr Gly Ile Glu Leu Met Pro Val Ala Gln P he Pro Gly Asn Arg Asp
135                 140                 145                 150

TGG GGA TAC GAT GGT GTT TTT CTA TAC GCA G TT CAA AAT ACT TAT GGC         1673
Trp Gly Tyr Asp Gly Val Phe Leu Tyr Ala V al Gln Asn Thr Tyr Gly
                155                 160                 165

GGA CCA TGG GAA TTG GCT AAG CTA GTA AAC G AG GCA CAT AAA AGG GGA         1721
Gly Pro Trp Glu Leu Ala Lys Leu Val Asn G lu Ala His Lys Arg Gly
            170                 175                 180

ATA GCC GTA ATT TTG GAT GTT GTA TAT AAT C AT ATA GGT CCT GAG GGA         1769
Ile Ala Val Ile Leu Asp Val Val Tyr Asn H is Ile Gly Pro Glu Gly
        185                 190                 195

AAT TAC CTT TTA GGA TTA GGT CCT TAT TTT T CA GAC AGA TAT AAA ACT         1817
Asn Tyr Leu Leu Gly Leu Gly Pro Tyr Phe S er Asp Arg Tyr Lys Thr
```

```
                200                      205                      210
CCA TGG GGA TTA ACA TTT AAT TTT GAT GAT A GG GGA TGT GAT CAA GTT              1865
Pro Trp Gly Leu Thr Phe Asn Phe Asp Asp A rg Gly Cys Asp Gln Val
215                 220                 225                 230

AGA AAA TTC ATT TTA GAA AAT GTC GAG TAT T GG TTT AAG ACC TTT AAA              1913
Arg Lys Phe Ile Leu Glu Asn Val Glu Tyr T rp Phe Lys Thr Phe Lys
                    235                 240                 245

ATC GAT GGT CTG AGA CTG GAT GCA GTT CAT G CA ATT TTT GAT AAT TCG              1961
Ile Asp Gly Leu Arg Leu Asp Ala Val His A la Ile Phe Asp Asn Ser
                250                 255                 260

CCT AAG CAT ATC CTC CAA GAG ATA GCT GAA A AA GCC CAT CAA TTA GGA              2009
Pro Lys His Ile Leu Gln Glu Ile Ala Glu L ys Ala His Gln Leu Gly
            265                 270                 275

AAA TTT GTT ATT GCT GAA AGT GAT TTA AAT G AT CCA AAA ATA GTA AAA              2057
Lys Phe Val Ile Ala Glu Ser Asp Leu Asn A sp Pro Lys Ile Val Lys
        280                 285                 290

GAT GAT TGT GGA TAT AAA ATA GAT GCT CAA T GG GTT GAC GAT TTC CAC              2105
Asp Asp Cys Gly Tyr Lys Ile Asp Ala Gln T rp Val Asp Asp Phe His
295                 300                 305                 310

CAC GCA GTT CAT GCA TTC ATA ACA AAA GAA A AA GAT TAT TAT TAC CAG              2153
His Ala Val His Ala Phe Ile Thr Lys Glu L ys Asp Tyr Tyr Tyr Gln
                315                 320                 325

GAT TTT GGA AGG ATA GAA GAT ATA GAG AAA A CT TTT AAA GAT GTT TTT              2201
Asp Phe Gly Arg Ile Glu Asp Ile Glu Lys T hr Phe Lys Asp Val Phe
            330                 335                 340

GTT TAT GAT GGA AAG TAT TCT AGA TAC AGA G GA AGA ACT CAT GGT GCT              2249
Val Tyr Asp Gly Lys Tyr Ser Arg Tyr Arg G ly Arg Thr His Gly Ala
        345                 350                 355

CCT GTA GGT GAT CTT CCA CCA CGT AAA TTT G TA GTC TTC ATA CAA AAT              2297
Pro Val Gly Asp Leu Pro Pro Arg Lys Phe V al Val Phe Ile Gln Asn
360                 365                 370

CAC GAT CAA GTA GGA AAT AGA GGA AAT GGG G AA AGA CTT TCC ATA TTA              2345
His Asp Gln Val Gly Asn Arg Gly Asn Gly G lu Arg Leu Ser Ile Leu
375                 380                 385                 390

ACC GAT AAA ACG ACA TAC CTT ATG GCA GCC A CA CTA TAT ATA CTC TCA              2393
Thr Asp Lys Thr Thr Tyr Leu Met Ala Ala T hr Leu Tyr Ile Leu Ser
                395                 400                 405

CCG TAT ATA CCG CTA ATA TTT ATG GGC GAG G AA TAT TAT GAG ACG AAT              2441
Pro Tyr Ile Pro Leu Ile Phe Met Gly Glu G lu Tyr Tyr Glu Thr Asn
            410                 415                 420

CCT TTT TTC TTC TTC TCT GAT TTC TCA GAT C CC GTA TTA ATT AAG GGT              2489
Pro Phe Phe Phe Phe Ser Asp Phe Ser Asp P ro Val Leu Ile Lys Gly
        425                 430                 435

GTT AGA GAA GGT AGA CTA AAG GAA AAT AAT C AA ATG ATA GAT CCA CAA              2537
Val Arg Glu Gly Arg Leu Lys Glu Asn Asn G ln Met Ile Asp Pro Gln
440                 445                 450

TCT GAG GAA GCG TTC TTA AAG AGT AAA CTT T CA TGG AAA ATT GAT GAG              2585
Ser Glu Glu Ala Phe Leu Lys Ser Lys Leu S er Trp Lys Ile Asp Glu
455                 460                 465                 470

GAA GTT TTA GAT TAT TAT AAA CAA CTG ATA A AT ATC AGA AAG AGA TAT              2633
Glu Val Leu Asp Tyr Tyr Lys Gln Leu Ile A sn Ile Arg Lys Arg Tyr
                475                 480                 485

AAT AAT TGT AAA AGG GTA AAG GAA GTT AGG A GA GAA GGG AAC TGT ATT              2681
Asn Asn Cys Lys Arg Val Lys Glu Val Arg A rg Glu Gly Asn Cys Ile
            490                 495                 500

ACT TTG ATC ATG GAA AAA ATA GGA ATA ATT G CA TCG TTT GAT GAT ATT              2729
Thr Leu Ile Met Glu Lys Ile Gly Ile Ile A la Ser Phe Asp Asp Ile
        505                 510                 515

GTA ATT AAT TCT AAA ATT ACA GGT AAT TTA C TT ATA GGC ATA GGA TTT              2777
```

```
Val Ile Asn Ser Lys Ile Thr Gly Asn Leu Leu Ile Gly Ile Gly Phe
            520                 525                 530

CCG AAA AAA TTG AAA AAA GAT GAA TTA ATT A AG GTT AAC AGA GGT GTT        2825
Pro Lys Lys Leu Lys Lys Asp Glu Leu Ile Lys Val Asn Arg Gly Val
535                 540                 545                 550

GGG GTA TAT CAA TTA GAA TGAAAGATCG ACCATTAAAG C CTGGTGAAC                2873
Gly Val Tyr Gln Leu Glu
                555

CTTATCCTTT AGGGCAACT TGGATAGAGG AAGAAGATGG AGTTAATTTT G TACTATTCT        2933

CTGAGAACGC CACAAAAGTA GAACTGTTAA CGTACTCTCA GACTAGACAA G ATGAGCCAA       2993

AGGAAATAAT AGAACTTAGA CAGAGAACCG GAGATCTCTG GCATGTTTTT G TACCTGGTT       3053

TAAGACCAGG TCAGTTGTAT GGGTACAGGG TGTATGGTCC ATATAAACCA G AGGAAGGGT       3113

TAAGGTTTAA TCCTAATAAA GTACTGATAG ATCCTTATGC AAAAGCTATA A ACGGATTAT       3173

TACTATGGGA TGATTCGGTC TTTGGATATA AAATTGGAGA TCAGAACCAG G ATCTCAGTT       3233

TCGATGAGAG AAAAGACGAT AAATTTATAC CTAAAGGGGT CATAATAAAT C CTTATTTTG       3293

ATTGGGAGGA CGAGCATTTC TTCTTTAGAA GAAAGATACC TTTTAAGGAT A GTATAATTT       3353

ATGAGACACA TATAAAAGGA ATAACTAAAT TAAGGCAAGA TTTACCGGAG A ACGTTAGAG       3413

GCACTTTTTT GGGTTTAGCA TCAGATACTA TGATTGATTA CCTAAAAGAT T TAGGAATTA       3473

CAACCGTTGA GATAATGCCT ATTCAGCAAT TTGTAGATGA GAGATTCATT G TCGATAAAG       3533

GGTTAAAGAA CTACTGGGGT TACAATCCGA TAAATTATTT CTCTCCTGAA T GTAGATACT      3593

CAAGCTC                                                                 3600

(2) INFORMATION FOR SEQ ID NO: 8:

(i) SEQUENCE CHARACTERISTICS:
        (A) LENGTH: 556 amino acids
        (B) TYPE: amino acid
        (D) TOPOLOGY: linear (ii) MOLECULE TYPE: protein (xi) SEQUENCE DESCRIPTION: SEQ ID NO: 8:

Met Phe Ser Phe Gly Gly Asn Ile Glu Lys A sn Lys Gly Ile Phe Lys
 1               5                  10                  15

Leu Trp Ala Pro Tyr Val Asn Ser Val Lys L eu Lys Leu Ser Lys Lys
            20                  25                  30

Leu Ile Pro Met Glu Lys Asn Asp Glu Gly P he Phe Glu Val Glu Ile
            35                  40                  45

Asp Asp Ile Glu Glu Asn Leu Thr Tyr Ser T yr Ile Ile Glu Asp Lys
 50                  55                  60

Arg Glu Ile Pro Asp Pro Ala Ser Arg Tyr G ln Pro Leu Gly Val His
 65                  70                  75                  80

Asp Lys Ser Gln Leu Ile Arg Thr Asp Tyr G ln Ile Leu Asp Leu Gly
            85                  90                  95

Lys Val Lys Ile Glu Asp Leu Ile Ile Tyr G lu Leu His Val Gly Thr
            100                 105                 110

Phe Ser Gln Glu Gly Asn Phe Lys Gly Val I le Glu Lys Leu Asp Tyr
            115                 120                 125

Leu Lys Asp Leu Gly Ile Thr Gly Ile Glu L eu Met Pro Val Ala Gln
            130                 135                 140

Phe Pro Gly Asn Arg Asp Trp Gly Tyr Asp G ly Val Phe Leu Tyr Ala
145                 150                 155                 160
```

```
Val Gln Asn Thr Tyr Gly Gly Pro Trp Glu Leu Ala Lys Leu Val Asn
                165                 170                 175

Glu Ala His Lys Arg Gly Ile Ala Val Ile Leu Asp Val Val Tyr Asn
                180                 185                 190

His Ile Gly Pro Glu Gly Asn Tyr Leu Leu Gly Leu Gly Pro Tyr Phe
                195                 200                 205

Ser Asp Arg Tyr Lys Thr Pro Trp Gly Leu Thr Phe Asn Phe Asp Asp
210                 215                 220

Arg Gly Cys Asp Gln Val Arg Lys Phe Ile Leu Glu Asn Val Glu Tyr
225                 230                 235                 240

Trp Phe Lys Thr Phe Lys Ile Asp Gly Leu Arg Leu Asp Ala Val His
                245                 250                 255

Ala Ile Phe Asp Asn Ser Pro Lys His Ile Leu Gln Glu Ile Ala Glu
                260                 265                 270

Lys Ala His Gln Leu Gly Lys Phe Val Ile Ala Glu Ser Asp Leu Asn
                275                 280                 285

Asp Pro Lys Ile Val Lys Asp Cys Gly Tyr Lys Ile Asp Ala Gln
                290                 295                 300

Trp Val Asp Asp Phe His His Ala Val His Ala Phe Ile Thr Lys Glu
305                 310                 315                 320

Lys Asp Tyr Tyr Tyr Gln Asp Phe Gly Arg Ile Glu Asp Ile Glu Lys
                325                 330                 335

Thr Phe Lys Asp Val Phe Val Tyr Asp Gly Lys Tyr Ser Arg Tyr Arg
                340                 345                 350

Gly Arg Thr His Gly Ala Pro Val Gly Asp Leu Pro Pro Arg Lys Phe
                355                 360                 365

Val Val Phe Ile Gln Asn His Asp Gln Val Gly Asn Arg Gly Asn Gly
                370                 375                 380

Glu Arg Leu Ser Ile Leu Thr Asp Lys Thr Thr Tyr Leu Met Ala Ala
385                 390                 395                 400

Thr Leu Tyr Ile Leu Ser Pro Tyr Ile Pro Leu Ile Phe Met Gly Glu
                405                 410                 415

Glu Tyr Tyr Glu Thr Asn Pro Phe Phe Phe Phe Ser Asp Phe Ser Asp
                420                 425                 430

Pro Val Leu Ile Lys Gly Val Arg Glu Gly Arg Leu Lys Glu Asn Asn
                435                 440                 445

Gln Met Ile Asp Pro Gln Ser Glu Glu Ala Phe Leu Lys Ser Lys Leu
450                 455                 460

Ser Trp Lys Ile Asp Glu Glu Val Leu Asp Tyr Tyr Lys Gln Leu Ile
465                 470                 475                 480

Asn Ile Arg Lys Arg Tyr Asn Asn Cys Lys Arg Val Lys Glu Val Arg
                485                 490                 495

Arg Glu Gly Asn Cys Ile Thr Leu Ile Met Glu Lys Ile Gly Ile Ile
                500                 505                 510

Ala Ser Phe Asp Asp Ile Val Ile Asn Ser Lys Ile Thr Gly Asn Leu
                515                 520                 525

Leu Ile Gly Ile Gly Phe Pro Lys Lys Leu Lys Lys Asp Glu Leu Ile
                530                 535                 540

Lys Val Asn Arg Gly Val Gly Val Tyr Gln Leu Glu
545                 550                 555
```

(2) INFORMATION FOR SEQ ID NO: 9:

(i) SEQUENCE CHARACTERISTICS:

```
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 9:

Val Ile Arg Glu Ala Lys
1               5

(2) INFORMATION FOR SEQ ID NO: 10:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 10:

Ile Ser Ile Arg Gln Lys
1               5

(2) INFORMATION FOR SEQ ID NO: 11:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 11:

Ile Ile Tyr Val Glu
1               5

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 12:

Met Leu Tyr Val Lys
1               5

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 13:

Ile Leu Ser Ile Asn Glu Lys
1               5

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 14:

Val Val Ile Leu Thr Glu Lys
1               5
```

(2) INFORMATION FOR SEQ ID NO: 15:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 15:

```
Asn Leu Glu Leu Ser Asp Pro Arg Val Lys
1               5                   10
```

(2) INFORMATION FOR SEQ ID NO: 16:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 16:

```
Met Ile Ile Gly Thr Tyr Arg Leu Gln Leu A sn Lys
1               5                   10
```

(2) INFORMATION FOR SEQ ID NO: 17:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 17:

```
Val Ala Val Leu Phe Ser Pro Ile Val
1               5
```

(2) INFORMATION FOR SEQ ID NO: 18:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 18:

```
Ile Asn Ile Asp Glu Leu Ile Ile Gln Ser L ys
1               5                   10
```

(2) INFORMATION FOR SEQ ID NO: 19:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO: 19:

```
Glu Leu Gly Val Ser His Leu Tyr Leu Ser P ro Ile
1               5                   10
```

(2) INFORMATION FOR SEQ ID NO: 20:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 20:

Asp Glu Val Phe Arg Glu Ser
1               5

(2) INFORMATION FOR SEQ ID NO: 21:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO: 21:

Asp Tyr Phe Lys
1

(2) INFORMATION FOR SEQ ID NO: 22:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 22:

Asp Gly Leu Tyr Asn Pro Lys
1               5

(2) INFORMATION FOR SEQ ID NO: 23:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 23:

Asp Ile Asn Gly Ile Arg Glu Cys
1               5

(2) INFORMATION FOR SEQ ID NO: 24:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 24:

Asp Phe Glu Asn Phe Glu Lys
1               5

(2) INFORMATION FOR SEQ ID NO: 25:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 25:

Asp Leu Leu Arg Pro Asn Ile
1               5

(2) INFORMATION FOR SEQ ID NO: 26:

```
    (i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 26:

Asp Ile Ile Glu Asn
1               5

(2) INFORMATION FOR SEQ ID NO: 27:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 27:

Asp Asn Ile Glu Tyr Arg Gly
1               5

(2) INFORMATION FOR SEQ ID NO: 28:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 28:

YTCWCKRAAW ACYTCATC                                          18

(2) INFORMATION FOR SEQ ID NO: 29:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 29:

GATAAYATWG ARTAYAGRGG                                        20

(2) INFORMATION FOR SEQ ID NO: 30:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 30:

Arg Asn Pro Glu Ala Tyr Thr Lys
1               5

(2) INFORMATION FOR SEQ ID NO: 31:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 31:

Asp His Val Phe Gln Glu Ser His Ser
1               5
```

(2) INFORMATION FOR SEQ ID NO: 32:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 32:

Ile Thr Leu Asn Ala Thr Ser Thr
1               5

(2) INFORMATION FOR SEQ ID NO: 33:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 33:

Ile Ile Ile Val Glu Lys
1               5

(2) INFORMATION FOR SEQ ID NO: 34:

(i) SEQUENCE CHARACTERISTICS:
        (A) LENGTH: 11 amino acids
        (B) TYPE: amino acid
        (C) STRANDEDNESS: single
        (D) TOPOLOGY: linear (xi) SEQUENCE DESCRIPTION: SEQ ID NO: 34:

Leu Gln Gln Tyr Met Pro Ala Val Tyr Ala Lys
1               5                   10

(2) INFORMATION FOR SEQ ID NO: 35:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 35:

Asn Met Leu Glu Ser
1               5

(2) INFORMATION FOR SEQ ID NO: 36:

(i) SEQUENCE CHARACTERISTICS:
        (A) LENGTH: 13 amino acids
        (B) TYPE: amino acid
        (C) STRANDEDNESS: single
        (D) TOPOLOGY: linear (xi) SEQUENCE DESCRIPTION: SEQ ID NO: 36:

Lys Ile Ser Pro Asp Gln Phe His Val Phe Asn Gln Lys
1               5                   10

(2) INFORMATION FOR SEQ ID NO: 37:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO: 37:

Gln Leu Ala Glu Asp Phe Leu Lys
1               5

(2) INFORMATION FOR SEQ ID NO: 38:

(i) SEQUENCE CHARACTERISTICS:
          (A) LENGTH: 10 amino acids
          (B) TYPE: amino acid
          (C) STRANDEDNESS: single
          (D) TOPOLOGY: linear (xi) SEQUENCE DESCRIPTION: SEQ ID NO: 38:

Lys Ile Leu Gly Phe Gln Glu Glu Leu Lys
1               5                   10

(2) INFORMATION FOR SEQ ID NO: 39:

(i) SEQUENCE CHARACTERISTICS:
          (A) LENGTH: 10 amino acids
          (B) TYPE: amino acid
          (C) STRANDEDNESS: single
          (D) TOPOLOGY: linear (xi) SEQUENCE DESCRIPTION: SEQ ID NO: 39:

Ile Ser Val Leu Ser Glu Phe Pro Glu Glu
1               5                   10

(2) INFORMATION FOR SEQ ID NO: 40:

(i) SEQUENCE CHARACTERISTICS:
          (A) LENGTH: 9 amino acids
          (B) TYPE: amino acid
          (C) STRANDEDNESS: single
          (D) TOPOLOGY: linear (xi) SEQUENCE DESCRIPTION: SEQ ID NO: 40:

Leu Lys Leu Glu Glu Gly Ala Ile Tyr
1               5

(2) INFORMATION FOR SEQ ID NO: 41:

(i) SEQUENCE CHARACTERISTICS:
          (A) LENGTH: 8 amino acids
          (B) TYPE: amino acid
          (C) STRANDEDNESS: single
          (D) TOPOLOGY: linear (xi) SEQUENCE DESCRIPTION: SEQ ID NO: 41:

Glu Val Gln Ile Asn Glu Leu Pro
1               5

(2) INFORMATION FOR SEQ ID NO: 42:

(i) SEQUENCE CHARACTERISTICS:
          (A) LENGTH: 5 amino acids
          (B) TYPE: amino acid
          (C) STRANDEDNESS: single
          (D) TOPOLOGY: linear (xi) SEQUENCE DESCRIPTION: SEQ ID NO: 42:

Asp His Ser Arg Ile
1               5

(2) INFORMATION FOR SEQ ID NO: 43:

(i) SEQUENCE CHARACTERISTICS:

```
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO: 43:

Asp Leu Arg Tyr Tyr Lys
1               5

(2) INFORMATION FOR SEQ ID NO: 44:

(i) SEQUENCE CHARACTERISTICS:
        (A) LENGTH: 14 amino acids
        (B) TYPE: amino acid
        (C) STRANDEDNESS: single
        (D) TOPOLOGY: linear (xi) SEQUENCE DESCRIPTION: SEQ ID NO: 44:

Asp Val Tyr Arg Thr Tyr Ala Asn Gln Ile V al Lys Glu Cys
1               5                   10

(2) INFORMATION FOR SEQ ID NO: 45:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 45:

Thr Phe Ala Tyr Lys Ile Asp Gly Asn Glu
1               5                   10

(2) INFORMATION FOR SEQ ID NO: 46:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 46:

Leu Gly Pro Tyr Phe Ser Gln
1               5

(2) INFORMATION FOR SEQ ID NO: 47:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO: 47:

Asp Val Phe Val Tyr Asp Gly
1               5

(2) INFORMATION FOR SEQ ID NO: 48:

(i) SEQUENCE CHARACTERISTICS:
        (A) LENGTH: 19 amino acids
        (B) TYPE: amino acid
        (C) STRANDEDNESS: single
        (D) TOPOLOGY: linear (xi) SEQUENCE DESCRIPTION: SEQ ID NO: 48:

Tyr Asn Arg Ile Val Ile Ala Glu Ser Asp L eu Asn Asp Pro Arg Val
1               5                   10                  15
```

Val Asn Pro (2) INFORMATION FOR SEQ ID NO: 49:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO: 49:

Leu Asp Tyr Leu Lys
1               5

(2) INFORMATION FOR SEQ ID NO: 50:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO: 50:

Lys Arg Glu Ile Pro Asp Pro Ala Ser Arg Tyr Gln Pro Leu Gly Val
1               5                   10                  15
His (2) INFORMATION FOR SEQ ID NO: 51:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 51:

Lys Asp Val Phe Val Tyr Asp Gly Lys
1               5

(2) INFORMATION FOR SEQ ID NO: 52:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO: 52:

His Ile Leu Gln Glu Ile Ala Glu Lys
1               5

(2) INFORMATION FOR SEQ ID NO: 53:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO: 53:

Lys Leu Trp Ala Pro Tyr Val Asn Ser Val
1               5                   10

(2) INFORMATION FOR SEQ ID NO: 54:

(i) SEQUENCE CHARACTERISTICS:

```
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO: 54:

Met Phe Ser Phe Gly Gly Asn
1               5

(2) INFORMATION FOR SEQ ID NO: 55:

(i) SEQUENCE CHARACTERISTICS:
            (A) LENGTH: 14 amino acids
            (B) TYPE: amino acid
            (C) STRANDEDNESS: single
            (D) TOPOLOGY: linear (xi) SEQUENCE DESCRIPTION: SEQ ID NO: 55:

Asp Tyr Tyr Gln Asp Phe Gly Arg Ile G lu Asp Ile Glu
1               5                   10

(2) INFORMATION FOR SEQ ID NO: 56:

(i) SEQUENCE CHARACTERISTICS:
            (A) LENGTH: 7 amino acids
            (B) TYPE: amino acid
            (C) STRANDEDNESS: single
            (D) TOPOLOGY: linear (xi) SEQUENCE DESCRIPTION: SEQ ID NO: 56:

Lys Ile Asp Ala Gln Trp Val
1               5

(2) INFORMATION FOR SEQ ID NO: 57:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (xi) SEQUENCE DESCRIPTION: SEQ ID NO: 57:

AGCWAGKAGM TAYCARCC                                            18

(2) INFORMATION FOR SEQ ID NO: 58:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO: 58:

YTTHCCATCR TAWACRAAWA CATC                                     24
```

TRANSFERASE AND AMYLASE, PROCESS FOR PRODUCING THE ENZYMES, USE THEREOF, AND GENE CODING FOR THE SAME

This application is a Divisional of application Ser. No. 08/750,569, filed Feb. 24, 1997, which is a national stage of PCT/JP95/01189 filed Jun. 14, 1995.

TECHNICAL FIELD

The present invention relates to:

I. a novel transferase, a process for producing the same, a process for producing an oligosaccharide by using the enzyme, a gene coding for the enzyme, and use thereof; and II. a novel amylase, a process for producing the same, a process for producing α,α-trehalose by using the enzyme, a gene coding for the enzyme, and use thereof. More specifically, as follows.

I. The present invention relates to a novel transferase which acts on a substrate saccharide, the substrate saccharide being composed of at least three sugar units wherein at least three glucose residues from the reducing end are α-1,4-linked, so as to transfer the α-1,4 linkages to α1,α-1 linkages; and a process for producing the transferase. More particularly, the present invention relates to the above-mentioned enzyme produced from archaebacteria belonging to the order Sulfolobales, for example, bacteria of the genus Sulfolobus or Acidianus.

Further, the present invention relates to a novel process for producing trehaloseoligosaccharides or the like by using the above-mentioned novel enzyme, and more particularly, relates to an efficient and high-yield process for producing trehaloseoligosaccharides such as glucosyltrehalose and maltooligosyltrehaloses by using a maltooligosaccharide or the like as a raw material.

Moreover, the present invention relates to a DNA fragment coding for the above-mentioned novel transferase and to the use of the DNA fragment in genetic engineering.

II. The present invention relates to a novel amylase which acts on a substrate saccharide, the saccharide being composed of at least three sugar units wherein at least three sugar units from the reducing end are glucose residues, so as to liberate principally monosaccharides and/or disaccharides by hydrolyzing the substrate from the reducing end; and a process for producing the amylase. More particularly, the present invention relates to a novel amylase which has an principal activity of acting on a substrate saccharide, the substrate saccharide being composed of at least three sugar units wherein at least three sugar units from the reducing end side are glucose residues and the linkage between the first and the second glucose residues from the reducing end side is α-1,α-1 while the linkage between the second and the third glucose residues from the reducing end side is α-1,4, so as to liberate α,α-trehalose by hydrolyzing the α-1,4 linkage between the second and the third glucose residues; and a process for producing the amylase. The novel amylase also has another activity of endotype-hydrolyzing one or more α-1,4 linkages within the molecular chain of the substrate, and can be produced by bacteria belonging to the genus Sulfolobus. This enzyme is available for the starch sugar industry, textile industry, food industry, and the like.

Further, the present invention relates to a process for producing α,α-trehalose, characterized by using the above novel amylase in combination with the above novel transferase. In detail, the present invention relates to a process for producing α,α-trehalose in a high yield by using, as a raw material, any one of starch, starch hydrolysate and maltooligosaccharides, or a mixture of maltooligosaccharides, and as enzymes, the novel transferase and amylase of the present invention.

Moreover, the present invention relates to a DNA fragment coding for the above novel amylase, and use of the DNA fragment in genetic engineering.

BACKGROUND ART

I. Background Art of Transferase

Hitherto, in relation to glycosyltransferase acting on starch and starch hydrolysates such as maltooligosaccharides, various glucosyltransferases, cyclodextringlucanotransferases (CGTase), and others have been found [c.f. "Seibutsu-kagaku Jikken-hou" 25 ("Experimental Methods in Biochemistry", Vol. 25), 'Denpun.Kanren Toushitsu Kouso Jikken-hou' ('Experimental Methods in Enzymes for Starch and Relating Saccharides'), published by Gakkai-shuppan-sentah, Bioindustry, Vol. 9, No. 1 (1992), p. 39–44, and others]. These enzymes transfer a glucosyl group to the α-1,2, α-1,3, α-1,4, or α-1,6 linkage. However, an enzyme which transfers a glucosyl group to the α-1,α-1 linkage has not been found yet. Though trehalase has been found as an enzyme which acts on the α-1,α-1 linkage, trehalose is absolutely the only substrate for the enzyme, and the equilibrium or the reaction rate lies to the degrading reaction.

Recently, oligosaccharides were found to have physicochemical properties such as moisture-retaining ability, shape-retaining ability, viscous ability and browning-preventive ability, and bioactivities such as a low-calorigenetic property, an anticariogenic property and a bifidus-proliferation activity. In relation to that, various oligosaccharides such as maltooligosaccharides, branched-chain oligosaccharides, fructooligosaccharide, galactooligosaccharide, and xylooligosaccharide have been developed [c.f. "Kammiryo" ("Sweetener") (1989), Medikaru-risahchi-sha (Medical Research Co.) (1989), Gekkan Fuhdokemikaru (*Monthly Foodchemical*) (1993), February p. 21–29, and others].

Among oligosaccharides, the oligosaccharides which have no reducing end may include fructooligosaccharide having a structure composed of sucrose which is not reductive, and being produced by fructosyltransferase. Meanwhile, among starch hydrolysates such as maltooligosaccharides, the oligosaccharides which have no reducing end may include cyclodextrins produced by the above-mentioned CGTase, α,β-trehalose (neotrehalose), and reduced oligosaccharides chemically synthesized by hydrogenating the reducing end (oligosaccharide alcohol). These oligosaccharides having no reducing end have various physicochemical properties and bioactivities which are not possessed by conventional starch syrups and maltooligosaccharides. Accordingly, among maltooligosaccharides, the oligosaccharides the reducing ends of which are modified with an α-1,α-1 linkage may be also expected to have the similar physicochemical properties and bioactivities to those possessed by the above-mentioned oligosaccharide having no reducing end, since such oligosaccharides also have no reducing end.

Here, the oligosaccharides the reducing ends of which are modified with an α-1,α-1 linkage as described above may be recognized as a trehaloseoligosaccharide in which α,α-trehalose is linked with glucose or a maltooligoshaccharide. Accordingly, such a trehaloseoligosaccharide may be expected to have the physicochemical properties and bioactivities which are possessed by the oligosaccharide having no reducing end, and in addition, may be expected to have the specific activities as exhibited by α,α-trehalose (c.f. Japanese Patent Laid-open Publication No. 63-500562).

Though it was reported that a trace amount of trehaloseoligosaccharides could be detected in yeast [*Biosci. Biotech. Biochem.*, 57(7), p. 1220–1221 (1993)], this is the only report referring to its existence in nature. On the other hand, as to its synthesis by using an enzyme, though there has been a report of such synthesis [Abstracts of "1994 Nihon Nougei-kagaku Taikai" ("Annual Meeting of the Japan Society for Bioscience, Biotechnology and Agrochemistry in 1994"), p. 247], the method described in the report uses trehalose, which is expensive, as the raw material. Therefore, production at low cost has not yet been established.

Recently, Lama, et al. found that a cell extract from the *Sulfolobus solfataricus* strain MT-4 (DSM 5833), a species of archaebacteria, has a thermostable starch-hydrolyzing activity [*Biotech. Forum. Eur.* 8, 4, 2–1 (1991)]. They further reported that the activity is also of producing trehalose and glucose from starch. The above-mentioned report, however, does not at all refer to the existence of trehaloseoligosaccharides such as glucosyltrehalose and maltooligosyltrehalose. Moreover, no investigation in archaebacteria other than the above-mentioned strain has been attempted.

Meanwhile, an efficient process for obtaining the novel transferase should be established to efficiently produce trehaloseoligosaccharides.

Accordingly, mass-production of trehaloseoligosaccharides requires obtaining this novel transferase in a large amount. For achievement of this, it is preferable to obtain a gene coding for such transferase, and to produce the transferase in a genetic engineering manner. When such a gene can be obtained, it can be also expected, by using technologies of protein engineering, to obtain an enzyme having an improved thermostability, an improved pH stability, and an enhanced reaction rate. No report has, however, been made about gene cloning of such a gene yet.

An object of the present invention is to provide a novel transferase principally catalyzing the production of trehaloseoligosaccharides such as glucosyltrehalose and maltooligosyltrehaloses, and a process for producing the enzyme, and further, to provide a novel, efficient and high-yield process for producing principally trehaloseoligosaccharides such as glucosyltrehalose and maltooligosyltrehaloses by using such an enzyme from a raw material such as maltooligosaccharides.

Inventors earnestly investigated the trehalose-producing activity of archaebacteria and found that glucosyltrehalose can be produced from maltotriose as a substrate by cell extracts from various archaebacteria such as those belonging to the order Sulfolobales, and more specifically, the genera Sulfolobus, Acidianus, and others. Here, though production of trehalose and glucose was confirmed using an activity-measuring method described by Lama, et al. in which the substrate is starch, Inventors found that detection of trehaloseoligosaccha-rides such as glucosyltrehalose is extremely difficult. Also, Inventors found that the trehalose-producing activity as found by Lama, et al. disappears during the step for purification of cell extracts from archaebacteria. Consequently, the inventors recognized that the purification and characterization of the enzymes themselves which have such activities were substantially impossible.

Under such circumstances, Inventors made further investigations and conceived a novel activity-measuring method in which the substrate is a maltooligosaccharide such as maltotriose, and the index is activity of producing a trehaloseoligosaccharide such as glucosyl-trehalose. Then, it was found by a practice of the measuring method that a trehaloseoligosaccharide such as glucosyltrehalose can be easily detected. Further, the Inventor attempted to purify the enzyme having such activity from various bacterial strains, and found, surprisingly, that the enzyme thus obtained is quite a novel transferase which acts on maltotriose or a larger saccharide wherein at least three glucose residues from the reducing end are α-1,4-linked, and which transfers the linkage between the glucose residues at the reducing end into an α-1,α-1linkage to produce trehaloseoligosaccharides such as glucosyltrehalose. Incidentally, the existence of trehaloseoligosaccharides which are produced from maltooligosaccharides or the like by transferring the linkage between glucose residues at the reducing end into an α-1,α-1linkage was confirmed by $^1$H-NMR and $^{13}$C-NMR (c.f. Examples I-1, 7 and 8).

Inventors further found that such a novel enzyme is available for producing a large amount of trehaloseoligosaccharides, for example, glucosyltrehalose and maltooligosyltrehalose from saccharides such as maltooligosaccharides, and have accomplished the present invention.

Moreover, Inventors isolated the genes coding for such a novel enzyme, and have now established a process for producing the novel transferase by using such genes in a genetic engineering manner.

II. Background Art of Amylase

"Amylase" is a generic term for the enzymes which hydrolyze starch. Among them, α-amylase is an enzyme which endotype-hydrolyzes an α-1,4 glucoside linkage. Alpha-amylase widely exists in the living world. In mammals, α-amylase can be found in saliva and pancreatic fluid. In plants, malt has the enzyme in large amounts. Further, α-amylase widely exists in microorganisms. Among them, α-amylase or the like which is produced by some fungi belonging to the genus Aspergillus or some bacteria belonging to the genus Bacillus is utilized in the industrial fields ["Amirahze" ("Amylase"), edited by Michinori Nakamura, published by Gakkai-shuppan-sentah, 1986].

Such α-amylase is industrially and widely used for various purposes, for example, for starch-liquefying processes in starch sugar industries, and for desizing processes in textile industries, and therefore, the enzyme is very important from an industrial view. The following are listed as important conditions for the starch-liquefying process in "Kouso-Ouyou no Chishiki" (written by Toshiaki Komaki, published by Sachi-Shobou, 1986): 1) the starch molecules should be liquefied as completely as possible, 2) the products produced by the liquefaction are favorable for the purpose of the subsequent saccharifying process, 3) the condition does not cause retrogradation of the products by the liquefaction, and 4) the process should be carried out in a high concentration as much as possible (30–35%) in view of reducing cost. A starch-liquefying process may be performed, for example, by a continuous liquefaction method at a constant temperature, or by the Jet-Cooker method. Ordinarily, a thick starch-emulsion containing α-amylase is instantaneously heated to a high temperature (85–110° C.), and then the α-amylase is put into action to perform liquefaction at the same time as starch begins to be gelatinized and swollen. In other words, the starch-liquefying process requires a temperature sufficient to cause the starch to swell before the enzyme can act. Enzymes capable of being used in such fields are, for example, the above-mentioned thermostable α-amylases produced by fungi of the *Aspergillus oryzae* group belonging to the genus Aspergillus or bacteria belonging to the genus Bacillus. In some cases, the addition of calcium is required for further improving thermostability of these enzymes. In the starch-liquefying process, once the temperature declines while the α-amylase has not yet acted on the starch-micelles which are swelled and going to be cleaved, starch will be agglutinated again to form new micelles (insoluble starch) which are rarely liquefied by α-amylase. As a result, the liquid sugar thus produced will be turbid and hard to filtrate, as is a known problem. Some methods which increase the liquefaction degree, i.e. dextrose equivalent (DE), are used in order to prevent such an event. However, in some cases, such as an enzymatic production of maltose, DE should be maintained as low as possible, namely, the polymerization degree of the sugar chain should be maintained to a high degree in order to keep a high yield. Accordingly, when an enzyme is further used for a process subsequent to a starch-liquefying process, use of an enzyme thermostable enough for use in a series of high temperatures will allow the progress of the reaction without producing slightly soluble starch even by using a high concentration of starch, and at the same time, such use will be advantageous in view of process control and sanitary control because the risk of contamination with microorganisms can be decreased. Meanwhile, when the enzyme is immobilized in a bioreactor to use the enzyme recyclically, it is believed to be important that the enzyme has high stability, and especially high thermostability, since the enzyme may be exposed to a relatively high temperature during immobilization. If the enzyme has a low thermostability, it will possibly be inactivated during the immobilization procedure. As is obvious from the above, an enzyme having a high thermostability can be used very advantageously in several industrial fields, for example, a starch-liquefying process, and such an enzyme is desired.

In addition, screening of thermophilic and hyperthermophilic bacteria has been widely carried out in recent years in order to obtain thermostable enzymes including amylase. Archaebacteria belonging to the order Thermococcales and the genus Pyrococcus are also the objects of screening, and were reported to produce α-amylase [*Applied and Environmental Microbiology*, pp.1985–1991, (1990); Japanese Patent Laid-open Publication No. 6-62869; and others]. Additionally, archaebacteria belonging to the genus Sulfolobus are the objects of screening, and isolation of thermostable enzymes was reported. Here, archaebacteria belonging to the genus Sulfolobus are taxonomically defined by the following characteristics:

being highly thermophilic: being possible to grow in a temperature range of 55° C.–88° C.;

being acidophilic: being possible to grow in a pH range of 1–6;

being aerobic; and being sulfur bacteria: being cocci having irregular form, and a diameter of 0.6–2 μm. Accordingly, if an archaebacterium belonging to the genus Sulfolobus produces an amylase, the amylase is expected to be also thermo-stable. Lama, et al.found that a thermostable starch-hydrolyzing activity exists in a cell extract from the *Sulfolobus solfataricus* strain MT-4 (DSM 5833) [Biotech. Forum. Eur. 8, 4, 2–1 (1991)]. This article reported that α,α-trehalose and glucose can be produced from starch by this activity. However, purification of the active substance was performed only partially, and the true substance exhibiting the activity has not yet been identified. In addition, the enzymatic characteristics of the activity has not been clarified at all. The Inventors' investigations, the details of which will be described below, revealed that the active substance derived from the above-mentioned bacterial strain and allowed to act on starch by Lama, et al. was a mixture containing a plurality of enzymes, and that α,α-trehalose and glucose are the final products obtained by using the mixture.

As another characteristic, α-amylase has an activity of, at an initial stage, decreasing the quantity of iodo-starch reaction, namely, an activity of endotype-hydrolyzing α-1, 4-glucan (liquefying activity). There are several modes in the reaction mechanism of such liquefying-type amylase. In other words, it is known that each amylase has common characteristics in view of endotype-hydrolyzing activity but has individual characteristics in view of patterns for hydrolyzing maltooligosaccharides. For example, some recognize a specific site for hydrolysis of the substrate from the non-reducing end, and others recognize a specific site for hydrolysis of the substrate from the reducing end. Further, some hydrolyze the substrate to principally produce glucose, others to principally produce maltose or maltooligosaccharides. More specifically, the α-amylase derived from pancreas hydrolyzes the α-1,4 linkage second or third from the reducing end ["Denpun.Kanren Toushitsu Kouso Jikkenhou" ("Experimental methods in enzymes for starch and relating saccharides"), written by Michinori Nakamura and Keiji Kainuma, published by Gakkai-Shuppan-Sentah, 1989]. The α-amylase derived from *Bacillus subtilis* hydrolyzes the α-1,4 linkage sixth from the non-reducing end or third from the reducing end ["Kouso-Ouyou no Chishiki" ("Knowledge in Application of Enzymes"), written by Toshiaki Komaki, published by Sachi-Shobou, 1986]. It is believed that such a difference between the reaction modes of α-amylases can be attributed to the structure of each enzyme, and the "Subsite theory" is proposed for explanation of these events. Additionally, the existence of an α-amylase having transferring activities or condensation activities has been confirmed. Further, a particular α-amylase which produces a cyclodextrin has been found.

On the other hand, α,α-trehalose consists of two glucose molecules which are α-1,α-1-linked together at the reducing group of each molecule. It is known that α,α-trehalose exists in many living things, plants and microorganisms of the natural world, and has many function such as preventing the biomembrane from freezing or drying, and being an energy source in insects. Recently, α,α-trehalose was evaluated in the fields of medicine, cosmetics and food as a protein stabilizer against freezing and drying (Japanese Examined Patent Publication No. 5-81232, Japanese Patent Laid-open Publication No. 63-500562, and others). However, α,α-trehalose is not often used practically. This may be because no mass-productive process has been established yet.

Examples of the conventional process for producing α,α-trehalose are as follows:

a process comprising extraction from an yeast (Japanese Patent Laid-open Publications Nos. 5-91890 and 4-360692, and others);

a process comprising intracellular production by an yeast (Japanese Patent Laid-open Publication No. 5-292986, European Patent No. 0451896, and others); and a process comprising production by a microorganism belonging to the genus Sclerotium or the genus Rhizoctonia (Japanese Patent Laid-open Publication No. 3-130084). However, these processes, as comprising intracellular production, require a purification process comprising multiple steps for spallation of bacterial bodies and removal of debris. Meanwhile, several investigations were made into extracellular production by a fermentation using a microorganism, for example, a microorganism belonging to the genus Arthrobacter (Suzuki T, et al., *Agric. Biol. Chem.*, 33, No. 2, 190, 1969) or the genus Nocardia (Japanese Patent Laid-open Publication No. 50-154485), and glutamate-producing bacteria (French Patent No. 2671099, Japanese Patent Laid-open Publication No. 5-211882, and others). Further, production by a gene encoding an enzyme for α,α-trehalose metabolism was attempted (PCT Patent No. 93-17093). Any of the above processes use glucose or the like as the sugar source, and utilize a metabolic system which requires ATP and/or UTP as the energy source. These processes, therefore, require a complicated purification process to obtain α,α-trehalose from the culture medium. Moreover, some investigations were attempted into production by an enzymatic process using, for example, trehalose phosphorylase (Japanese Examined Patent Publication No. 63-60998), or trehalase (Japanese Patent Laid-open Publication No. 7-51063). These processes, however, have some problems in mass-production of the enzymes, stability of the enzymes, and others. All of the processes of the prior art as described above have problems such as a low yield, complexity in the purification process, low production, and complexity in preparation of the enzyme. Therefore, a process having industrial applicability has not been established yet. Under the circumstances, a process for more efficiently producing α,α-trehalose is strongly desired to be established.

As described above, α,α-trehalose was found widely in nature, and the existence of it in archaebacteria was also confirmed (*System. Appl. Microbiol.* 10, 215, 1988). Specifically, as mentioned above, Lama, et al. found that a thermostable starch-hydrolyzing activity exists in a cell extract from an archaebacterium species, the *Sulfolobus solfataricus* strain MT-4 (DSM 5833), and confirmed the existence of α,α-trehalose in the hydrolyzed product [*Biotech. Forum. Eur.* 8, 4, 2–1 (1991), cited before]. This article reported that the activity was of producing α,α-trehalose and glucose from starch. The article, however, actually reported only an example in which the substrate was 0.33% soluble starch, the amount of α,α-trehalose produced thereby was extremely small, and besides, the ratio of produced α,α-trehalose to produced glucose was 1:2. Accordingly, an isolation process is necessary to remove glucose which is produced in a large amount as a by-product, and the purpose of establishing a process for mass-producing α,α-trehalose cannot be achieved at all.

Inventors, as described above, found that an archaebacteria belonging to the order Sulfolobales produce a transferase which acts on a substrate saccharide, the substrate saccharide being composed of at least three sugar units wherein at least three glucose residues from the reducing end are α-1,4-linked, so as to transfer the first α-1,4 linkage from the reducing end into an α-1,α-1linkage. Further, Inventors invented a process for producing trehaloseoligosaccharides such as glucosyltrehalose and maltooligosyltrehaloses from maltooligosaccharides by using this enzyme. Here, the trehaloseoligosaccharide is a maltooligosaccharide the reducing end side of which is modified with an α-1,α-1 linkage.

In the meantime, no report has been made, as far as Inventors know, as to an formerly-known enzyme capable of acting on a trehaloseoligosaccharide which is derived from a maltooligosaccharide by transforming the first linkage from the reducing end into an α-1,α-1 linkage, and capable of hydrolyzing specifically the α-1,4 linkage next to the α-1,α-1 linkage to liberate α,α-trehalose in a high yield. In other words, conventional amylase cannot hydrolyze trehaloseoligosaccharide specifically at the α-1,4 linkage between the second and third glucose residues from the reducing end side to liberate α,α-trehalose. It will, therefore, markedly benefit the mass-production of α,α-trehalose if an amylase can be developed, such amylase being capable of catalyzing the reaction for producing α,α-trehalose as well as hydrolyzing the α-1,4 linkage in the molecular chain of starch or starch hydrolysate.

In addition, mass-production of α,α-trehalose requires obtaining the novel amylase in a large amount. For this purpose, it is preferable to obtain a gene coding for the amylase and to produce the enzyme in a genetic engineering manner. Further, if such a gene can be obtained, it can also be expected to obtain, by using a technology of protein engineering, an enzyme which has improved thermostability, improved pH stability, and an enhanced reaction rate.

An object of the present invention is to provide a novel amylase which has an activity of endotype-hydrolyzing the α-1,4 linkage in the molecular chain of starch or starch hydrolysate, and which can catalyze the reaction of liberating α,α-trehalose, wherein the enzyme acts on a trehaloseoligosaccharide which is derived from a maltooligosaccharide by transforming the first linkage from the reducing end into an α-1,α-1linkage, and hydrolyzes specifically the α-1,4 linkage between the second and third glucose residues from the reducing end side, and is to provide a process for producing such an enzyme. Another object of the present invention is to provide a novel process for efficiently producing α,α-trehalose in a high yield from a low-cost raw material such as starch, starch hydrolysate, and maltooligosaccharides by using the enzyme.

Inventors energetically investigated starch-hydrolyzing activity derived from archaebacteria. As a result, Inventors found that a thermostable starch-hydrolyzing activity exists in cell extracts from various archaebacteria belonging to the order Sulfolobales, and more specifically, the genus Sulfolobus. The saccharides produced by hydrolysis of starch were found to be glucose and α,α-trehalose, similar to the description in the article by Lama, et al. Inventors then examined extracts from various bacterial strains for characteristics of the starch-hydrolyzing activity. As a result, Inventors found that the enzymes produced by those strains are mixtures of enzymes comprising various endotype or exotype amylases such as liquefying amylase and glucoamylase, and transferase, in view of enzymatic activity such as starch-hydrolyzing activity and α,α-trehalose-producing activity. In addition, such enzymatic activities were found to be attributed to synergism by activities of these mixed enzymes. Further, when the activity-measuring method proposed by Lama, et al. is employed in purification of each enzyme, in which the index is decrement of blue color derived from iodo-starch reaction, the purification of each enzyme having such an activity resulted in a low yield on the whole, and such purification procedure was found to be very difficult. These events may be attributed to low sensitivity and low quantifying ability of the activity-measuring method. Moreover, the Inventors' strict examination revealed that purification and isolation could not be accomplished at all, in terms of protein, by the partial-purification method described in the article by Lama, et al.

Under such circumstances, Inventors have made further investigation, and conceived a new activity-measuring method in which the substrate is a trehaloseoligosaccharide such as maltotriosyltrehalose, and the index is activity of liberating α,α-trehalose. By a practice of this measuring method, it was revealed that amylase activity can be easily detected using such a method. Inventors then tried to achieve purification of the enzyme having such an activity in various bacterial strains, and finally, succeeded in purification and isolation of such an amylase. Further, Inventors examined enzymatic characteristics of the isolated and purified amylase, and found, surprisingly, that the enzyme thus obtained has a novel action mechanism, namely, has the following characteristics together:

The enzyme exhibits an activity of endotype-hydrolyzing starch or starch hydrolysate;

the enzyme exhibits an activity of hydrolyzing starch hydrolysate, a maltooligosaccharide or the like from the reducing end to produce monosaccharides and/or disaccharides;

the enzyme exhibits a higher reactivity to a saccharide which is composed of at least three sugar units wherein the linkage between the first and second glucose residues from the reducing end side is $\alpha$-1,$\alpha$-1, and the linkage between the second and third glucose residues from the same end side is $\alpha$-1,4 (for example, trehaloseoligosaccharides), as compared with the reactivity to each of the corresponding maltooligosaccharides; and the enzyme has an activity of acting on such substrate saccharides composed of at least three sugar units so as to liberate $\alpha,\alpha$-trehalose by hydrolyzing the $\alpha$-1,4 linkage between the second and third glucose residues from the reducing end side.

Moreover, Inventors isolated a gene coding for such novel enzyme, and now, have established a process for producing, in a genetic engineering manner, a recombinant novel amylase by utilizing such a gene.

DISCLOSURE OF INVENTION

I. Novel Transferase

The present invention provides a novel transferase (hereinafter referred to as "novel transferase of the present invention", or simply referred to as "the enzyme of the present invention" or "the present enzyme") which acts on a substrate saccharide, the substrate saccharide being composed of at least three sugar units wherein at least three glucose residues from the reducing end are $\alpha$-1,4-linked, so as to transfer the first $\alpha$-1,4 linkage from the reducing end into an $\alpha$-1,$\alpha$-1 linkage.

In another aspect, the present invention provides a novel transferase which acts on a substrate maltooligosaccharide, all of the constituting glucose residues of the maltooligosaccharide being $\alpha$-1,4-linked, so as to transfer the first $\alpha$-1,4 linkage from the reducing end into an $\alpha$-1,$\alpha$-1linkage.

Further, the present invention provides a process for producing the novel transferase of the present invention, wherein a bacterium capable of producing a transferase having such activities is cultivated in a culture medium, and the transferase is isolated and purified from the culture on the basis of an activity-measuring method in which the substrate is a maltooligosaccharide, and the index is the activity of producing trehaloseoligosaccharides.

Moreover, the present invention provides a process for producing a saccharide having an end composed of a couple of $\alpha$-1,$\alpha$-1-linked sugar units, characterized in that the enzyme of the present invention is used and allowed to act on a substrate saccharide, the substrate saccharide being composed of at least three sugar units wherein at least three glucose residues from the reducing end are $\alpha$-1,4-linked, so as to produce the objective saccharide in which at least three sugar units from the reducing end side are glucose residues and the linkage between the first and second glucose residues from the reducing end side is $\alpha$-1,$\alpha$-1 while the linkage between the second and third glucose residues from the reducing end side is $\alpha$-1,4.

Furthermore, the present invention provides a process for producing a trehaloseoligosaccharide, wherein the enzyme of the present invention is used, and the substrate is each of maltooligosaccharides or a mixture thereof.

Additionally, an object of the present invention is to provide a gene coding for the transferase.

Further, another object of the present invention is to provide a recombinant novel transferase and a process for producing the same by using the above-mentioned gene.

Moreover, an object of the present invention is to provide an efficient process for producing trehaloseoligosaccharides such as glucosyltrehalose and maltoglucosyltrehalose by using a recombinant novel transferase.

Accordingly, the DNA fragment based on the present invention comprises a gene coding for a novel transferase which acts on a substrate saccharide, the substrate saccharide being composed of at least three sugar units wherein at least three glucose residues from the reducing end are $\alpha$-1,4-linked, so as to transfer the first $\alpha$-1,4 linkage from the reducing end into an $\alpha$-1,$\alpha$-1 linkage.

Further, the recombinant novel transferase according to the present invention is the product achieved by expression of the above-mentioned DNA fragment.

Moreover, the process for producing a recombinant novel transferase according to the present invention comprises:

culturing a host cell transformed with the above-mentioned gene;

producing said recombinant novel transferase in the culture; and collecting the products.

II. Novel Amylase

The present invention provides a novel amylase which acts on a substrate saccharide, the substrate saccharide being composed of at least three sugar units wherein at least three sugar units from the reducing end are glucose residues, so as to liberate principally monosaccharides and/or disaccharides by hydrolyzing the substrate from the reducing end side.

In another aspect, the present invention provides a novel amylase which has a principal activity of acting on a substrate saccharide, the substrate saccharide being composed of at least three sugar units wherein at least three sugar units from the reducing end side are glucose residues and the linkage between the first and the second glucose residues from the reducing end side is $\alpha$-1,$\alpha$-1 while the linkage between the second and the third glucose residues from the reducing end side is $\alpha$-1,4, so as to liberate $\alpha,\alpha$-trehalose by hydrolyzing the $\alpha$-1,4 linkage between the second and the third glucose residues.

Further, in another aspect, the present invention provides a novel amylase which also has an activity of endotype-hydrolyzing one or more $\alpha$-1,4 linkages in the molecular chain of the substrate as well as the above-described activity.

Moreover, the present invention provides a process for producing aforementioned amylase, wherein a bacterium capable of producing the above amylase of the present invention is cultivated in a culture medium, and then the amylase is isolated and purified from the culture on the basis of an activity-measuring method in which the substrate is a trehaloseoligosaccharide, and the index is the activity of producing $\alpha,\alpha$-trehalose.

Inventors allowed the above amylase of the present invention in combination with the aforementioned transferase of the present invention to act on a glucide raw material such as starch, starch hydrolysate, and maltooligosaccharides, and found that $\alpha,\alpha$-trehalose can be efficiently produced thereby with a high yield.

Accordingly, the present invention also provides a process for producing $\alpha,\alpha$-trehalose, wherein the above amylase and transferase of the present invention are used in combination.

Additionally, an object of the present invention is to provide a novel amylase and a gene coding for the same.

Further, another object of the present invention is to provide a recombinant novel amylase and a process for producing the same by using the aforementioned gene.

Moreover, another object of the present invention is to provide a process for producing α,α-trehalose by using a recombinant novel amylase.

Therefore, the gene coding for the amylase according to the present invention comprises a DNA sequence coding for a novel amylase which has the following activities:

(1) An activity of endotype-hydrolyzing an α-1,4 glucoside linkage in a sugar chain;
(2) an activity of acting on a substrate saccharide, the substrate saccharide being composed of at least three sugar units wherein at least three sugar units from the reducing end are α-1,4-linked glucose residues, so as to liberate principally monosaccharides and/or disaccharides by hydrolyzing the substrate from the reducing end side; and
(3) a principal activity of acting on a substrate saccharide, the substrate saccharide being composed of at least three sugar units wherein at least three sugar units from the reducing end side are glucose residues and the linkage between the first and second glucose residues from the reducing end side is α-1,α-1 while the linkage between the second and third glucose residues from the reducing end side is α-1,4, so as to liberate α,α-trehalose by hydrolyzing the α-1,4 linkage between the second and third glucose residues.

Further, the recombinant novel amylase according to the present invention is a product achieved by expression of the above-described gene.

Furthermore, the process for producing α,α-trehalose according to the present invention comprises a step to put the above-described recombinant novel amylase and a novel transferase into contact with a saccharide of which at least three glucose residues from the reducing end are α-1,4-linked, wherein the transferase can act on a substrate saccharide, the substrate saccharide being composed of at least three sugar units wherein at least three glucose residues from the reducing end are α-1,4-linked, so as to transfer the first α-1,4-linkage from the reducing end into an α-1,α-1 linkage.

BRIEF DESCRIPTION OF DRAWINGS

FIGS. 1, 1A & 1B is a graph showing the results of an analysis by TSK-gel Amide-80 HPLC, performed on the product which is obtained in Example I-1 by using the cell extract derived from the *Sulfolobus solfataricus* strain KM1.

FIG. 31 is an illustration showing the homology between the amino acid sequence of the novel transferase derived from the *Sulfolobus solfataricus* strain KM1 and that derived from the *Sulfolobus acidocaldarius* strain ATCC 33909.

FIGS. 32, 32A, 32B is an illustration showing the homology between the base sequence of the gene coding for the novel transferase derived from the *Sulfolobus solfataricus* strain KM1 and that derived from the *Sulfolobus acidocaldarius* strain ATCC 33909.

FIGS. 33A, 33B is a graph showing the results of an analysis by AMINEX HPX-42A HPLC, performed on the product derived from a maltooligosaccharide mixture by using the recombinant novel transferase.

FIG. 40 is an illustration showing the homology between the amino acid sequence of the novel amylase derived from the *Sulfolobus acidocaldarius* strain ATCC 33909 and that derived from the *Sulfolobus solfataricus* strain KM1.

FIGS. 41A, 41B is an illustration showing the homology between the base sequence of the gene coding for the novel amylase derived from the *Sulfolobus acidocaldarius* strain ATCC 33909 and that derived from the *Sulfolobus solfataricus* strain KM1.

BEST MODE FOR CARRYING OUT THE INVENTION

Deposit of Microorganisms

Figure 1:
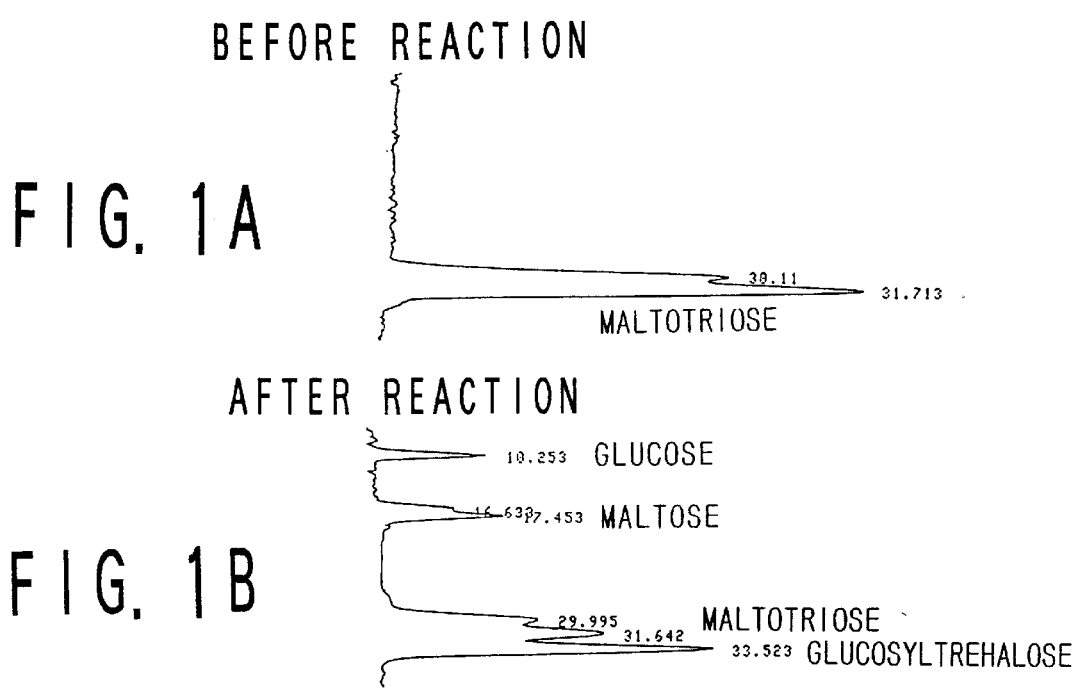

The below-mentioned novel bacterial strain KM1, which was substantially purely isolated from nature by the Inventor, was deposited in the National Research Institutes, the Life Science Laboratory for Industry on Apr. 1, 1994 as acceptance No. FERM BP-4626.

The *Escherichia coli* strain JM109/pKT22 transformed with the plasmid pKT22 according to the present invention (c.f. below-described Example I-14), and the *Escherichia coli* strain JM109/p09T1 transformed with the plasmid p09T1 (c.f. below-described Example I-16), which contain the gene coding for the novel transferase according to the present invention, were deposited in the National Research Institutes, the Life Science Laboratory for Industry on Oct. 21, 1994 as acceptance No. FERM BP-4843 and on May 9, 1995 as the acceptance No. FERM BP-5093, respectively.

Further, the *Escherichia coli* strain JM109/pKA2 transformed with the plasmid pKA2 according to the present invention (c.f. below-described Example II-19), and the *Escherichia coli* strain JM109/p09A1 transformed with the plasmid p09A1 (c.f. below-described Example II-22), which contain the gene coding for the novel amylase according to the present invention, were deposited in the National Research Institutes, the Life Science Laboratory for Industry on Oct. 31, 1994 as acceptance No. FERM BP-4857 and on May 9, 1995 as acceptance No. FERM BP-5092, respectively.

I. Novel Transferase

Microorganisms Producing the Novel Transferase of the Present Invention

The archaebacteria which can be used in the present invention may include the *Sulfolobus solfataricus* strain ATCC 35091 (DSM 1616), the *Sulfolobus solfataricus* strain DSM 5833, the *Sulfolobus solfataricus* strain KM1 (the below-described novel bacterial strain which was substantially purely isolated from nature by Inventors), the *Sulfolobus acidocaldarius* strain ATCC 33909 (DSM 639), and the *Acidianus brierleyi* strain DSM 1651.

As described above, a fairly wide variety of archaebacteria taxonomically classified under the order Sulfolobales, to which the genera Sulfolobus and Acidianus belong, may be considered as the microorganisms which can produce the novel transferase of the present invention. Here, the archaebacterium belonging to the order Sulfolobales are taxonomically defined as being highly acidophilic and thermophilic, being aerobic, and being sulfur bacteria (coccal bacteria). The aforementioned *Acidianus brierleyi* strain DSM 1651, which belongs to the genus Acidianus, had been formerly classified as *Sulfolobus brierleyi* strain DSM 1651, and the aforementioned *Sulfolobus solfataricus* strain DSM 5833 had been named as *Caldariella acidophila*. From these facts, microorganisms which are closely related to the above-described archaebacteria genetically or taxonomically and which are capable of producing the enzyme of the same kind can be used in the present invention.

*Sulfolobus solfataricus* Strain KM1

Among the above-illustrated microorganisms, the *Sulfolobus solfataricus* strain KM1 is the bacterial strain which Inventors isolated from a hot spring in Gunma Prefecture, and which exhibits the following characteristics.

(1) Morphological Characteristics

The shape and size of the bacterium: Coccoid (no regular form), and a diameter of 0.62–2$\mu$m.

(2) Optimum Growth Conditions pH: Capable of growing in pH of 3–5.5, and optimally, in pH of 3.5–4.5.

Temperature: Capable of growing in a temperature range of 55° C.–85° C., and optimally in a temperature range of 75° C.–80° C.

Capable of metabolize sulfur.

(3) Classification in view of aerobic or anaerobic: aerobic

According to the above characteristics, identification of the bacterial strain was carried out on the basis of Bergey's Manual of Systematic Bacteriology Volume 3 (1989). As a result, the strain was found to be one of *Sulfolobus solfataricus*, and thus named as *Sulfolobus solfataricus* strain KM1.

In culturing the above bacterial strain, the culture medium to be used may be either liquid or solid, and ordinarily, a concussion culturing or a culturing with aeration and stirring is performed using a liquid culture medium. In other words, the culture medium to be used is not limited as long as it is suitable for the bacterial growth, and the suitable examples of such culture media may include the *Sulfolobus solfataricus* Medium which is described in Catalogue of Bacteria and Pharges 18th edition (1992) published by American Type Culture Collection (ATCC), and in Catalogue of Strains 5th edition (1993) published by Deutsche Sammlung von Mikroorganismen und Zellkulturen GmbH (DSM). Starch, maltooligosaccharide and/or the like may be further added as a sugar source. Moreover, the culturing conditions are also not limited as long as they are based on the above-described growable temperature and pH.

Cultivation of the Microorganisms which Produce the Novel Transferase of the Present Invention The culturing conditions for producing the novel transferase of the present invention may suitably be selected within ranges in which the objective transferase can be produced. When a concussion culturing or a culturing with aeration and stirring using a liquid medium is employed, the culturing for 2–7 days should suitably be performed at a pH and a temperature which allow the growth of each microorganism. The culture medium to be suitably used is, for example, the *Sulfolobus solfataricus* Medium which is described in Catalogue of Bacteria and Pharges 18th edition (1992) published by American Type Culture Collection (ATCC), and in Catalogue of Strains 5th edition (1993) published by Deutsche Sammlung von Mikroorganismen und Zellkulturen GmbH (DSM). Starch, maltooligosaccharide and/or the like may be further added as a sugar source.

Purification of the Novel Transferase of the Present Invention

The novel transferase of the present invention which is produced by the above-described microorganisms can be extracted as follows: At first, the bacterial bodies are collected from the culture obtained in a culturing process as described above by a publicly-known procedure, for example, by centrifugation; the resultant is suspended in a proper buffer solution; the bacterial bodies are then crushed by freeze thawing, a ultrasonic treatment, grinding and/or the like; and the resultant is centrifuged or filtrated to obtain a cell extract containing the objective transferase.

To purify the novel transferase of the present invention which is contained in the cell extract, publicly-known processes for isolation and purification can be employed in proper combination. Examples of such processes may include a process utilizing solubility, such as salt precipitation and solvent precipitation; a process utilizing difference in molecular weight, such as dialysis, ultrafiltration, gel filtration and SDS-Polyacryl-amide gel electrophoresis; a process utilizing a difference in electric charge, such as ion exchange chromatography; a process utilizing specific affinity, such as affinity chromatography; a process utilizing a difference in hydrophobicity, such as hydrophobic chromatography and reversed phase chromatography; and further, a process utilizing a difference in isoelectric point, such as isoelectric focusing. Practical examples of these processes are shown in Examples I-2–I-5 below. Finally, Native Polyacrylamide gel electrophoresis, SDS-Polyacrylamide gel electrophoresis or isoelectric focusing is performed to obtain a purified enzyme which appears therein as a single band.

As to measurement of activity in the enzyme or enzyme-containing substance isolated by the above various purification processes, starch is used as the substrate in the activity-measuring method offered by Lama, et al. By this method, though the production of trehalose and glucose can be confirmed, the production of trehaloseoligosaccharides cannot be detected at all, and as a serious problem, even the trehalose-producing activity becomes undetectable due to its disappearance during purification. Therefore, the purification and characterization of the true substance of the enzyme activity had been substantially impossible. Under such circumstances, Inventors employed a new activity-measuring method in which the substrate is a maltooligosaccharide such as maltotriose, and the index is activity of producing a trehaloseoligosaccharide such as glucosyltrehalose. As a result, isolation and purification of the objective enzyme could be achieved for the first time by this method, and finally, the true substance of the novel transferase activity of the present invention could be practically purified and specified.

Characteristics of the Novel Transferase According to the Present Invention

As examples of the enzyme of the present invention, the transferases produced by the *Sulfolobus solfataricus* strain KM1, the *Sulfolobus solfataricus* strain DSM 5833, the *Sulfolobus acidocaldarius* strain ATCC 33909, and the *Acidianus brierleyi* strain DSM 1651, respectively, are taken up, and the enzymatic characteristics of these transferases are shown in Table 1 below in summary. Here, data in the table is based on the practical examples shown in Examples I-6 and I-7.

TABLE 1

| Physicochemical properties | Sulfolobus solfataricus KM1 | Sulfolobus solfataricus DSM5833 | Sulfolobus acidocaldarius ATCC33909 | Acidianus brierieyi DSM1651 |
|---|---|---|---|---|
| (1) Enzyme action and Substrate specificity | Acts on glucose polymers composed of more than maltotriose wherein glucoses are α-1, 4-linked, so as to combine two sugar moieties from the reducing end into an α-1, α-1 linkage by transfer. Not acts on maltose or glucose. | | | |
| (2) Optimum pH | 5.0–6.0 | 4.5–5.5 | 4.5–5.5 | 4.5–5.5 |
| (3) pH Stability | 4.0–10.0 | 4.5–12.0 | 4.0–10.0 | 4.0–12.0 |
| (4) Optimum temperature | 60–80° C. | 70–80° C. | 70–80° C. | 70–80° C. |
| (5) Thermal stability | 85° C., 6 hr 91% remained | 85° C., 6 hr 90% remained | 85° C., 6 hr 90% remained | 85° C., 6 hr 98% remained |
| (6) Molecular weight | | | | |
| SDS-PAGE | 76000 | 75000 | 74000 | 74000 |
| Gel-permeation | 54000 | 56000 | 56000 | 135000 |
| (7) Isoelectric point | 6.1 | 5.3 | 5.6 | 6.3 |
| (8) Inhibitor | 5 mM CuSO$_4$ 100% inhibited | 5 mM CuSO$_4$ 100% inhibited | 5 mM CuSO$_4$ 100% inhibited | 5 mM CuSO$_4$ 100% inhibited |

Note 1: Time-course Change

When maltotriose was used as the substrate, glucosyltrehalose as a product in the principal reaction, and besides, equal moles of maltose and glucose were produced as products in a side reaction.

When a saccharide having a polymerization degree, n, which is equal to or higher than that of maltotetraose, was used, a saccharide of which the glucose residue at the reducing end is α-1,α-1-linked was produced in the principal reaction, and besides, equal moles of glucose and a saccharide having a polymerization degree of n-1 were produced in a side reaction.

Note 2: Enzymatic Action/Mode of Enzymatic Reaction

It is considered that the enzyme has an activity of acting on maltotriose or a larger saccharide, three glucose residues from the reducing end of the saccharide being α-1,4-linked, so as to transfer the first linkage from the reducing end into an α-1,α-1-linkage. As a side reaction, the enzyme also has an activity of liberating glucose from a glucose polymer, when, for example, the concentration of the substrate is low, or the reaction time is long. The details are as shown in the practical example of Example I-7.

The characteristics of the present enzyme have been described above. As described in the above item titled "Enzymatic Action/Mode of Enzymatic Reaction", the present enzyme has an activity of acting on maltotriose or a larger saccharide, three glucose residues from the reducing end of the saccharide being α-1,4-linked, so as to transfer the first linkage from the reducing end into an α-1,α-1-linkage, and such an activity is quite a novel enzymatic activity. However, as obvious in the examples below, the characteristics of the present enzyme other than such enzymatic activities slightly vary according to the difference in genus or species between the bacterial strains.

Production of Trehaloseoligosaccharides such as Glucosyltrehalose and Maltooligosyltrehalose The present invention provides a process for producing a saccharide having an end composed of a couple of α-1,α-1-linked sugar units, characterized in that the enzyme of the present invention is used and allowed to act on a substrate saccharide, the substrate saccharide being composed of at least three sugar units wherein at least three glucose residues from the reducing end are α-1,4-linked, so as to produce the objective saccharide in which at least three sugar units from the reducing end side are glucose residues and the linkage between the first and second glucose residues from the reducing end side is α-1,α-1 while the linkage between the second and third glucose residues from the reducing end side is α-1,4. The process according to the present invention will be illustrated below with the most typical example, namely, with a process for producing trehaloseoligosaccharides such as glucosyltrehalose and maltooligosyltrehaloses.

In the process for producing trehaloseoligosaccharides such as glucosyltrehalose and maltooligosyltrehaloses according to the present invention, trehaloseoligosaccharides such as glucosyltrehalose and maltooligosyltrehaloses are produced from a saccharide such as maltooligosaccharides, typically, from each or a mixture of maltooligosaccharides by the present enzyme derived from archaebacteria. Accordingly, the mode of contact between the present transferase and a saccharide such as maltooligosaccharides is not specifically limited as long as the present enzyme produced by archaebacteria can act of the saccharide such as maltooligosaccharides in such mode. In practice, the following procedure may ordinarily be performed: A crude enzyme is obtained from the bacterial bodies or crushed bacterial bodies of an archaebacterium; and the purified enzyme obtained in each of the various purification steps, or the enzyme isolated and purified through various purification means, is made to act directly on a saccharide such as maltooligosaccharides. Alternatively, the above-described enzyme may be put into contact with a saccharide such as maltooligosaccharides in a form of a immobilized enzyme which is immobilized to a carrier in the usual way. Additionally, two or more of the present enzymes derived from two or more species of archaebacteria may coexist and be put into contact with a saccharide such as maltooligosaccharides.

The mixture of maltooligosaccharides, which is a typical raw material of the substrate in the above-described producing process of the present invention, may be prepared, for example, by properly hydrolyzing or acidolyzing starch using an endotype amylase, a debranching enzyme or the like so that at least three glucose residues from the reducing end of the product are α-1,4-linked. The endotype amylases to be used herein may include enzymes derived from bacteria belonging to the genus Bacillus, fungi belonging to the genus Aspergillus, and plants such as malt, and others. On the other hand, the debranching enzymes to be used herein may include pullulanase derived from bacteria belonging to the genus Bacillus, Klebsiella or the like, or isoamylase derived from bacteria belonging to the genus Pseudomonas. Further, these enzymes may be used in combination.

The concentration of a saccharide such as maltooligosaccharides should be suitably selected within the range in which the saccharide to be used is dissolved, considering the specific activity of the present enzyme, the reaction temperature and others. A range of 0.5–70% is ordinary, and a range of 5–40% is preferable. The reaction temperature and pH condition in the reaction of the saccharide with the enzyme should be optimum for the present transferase. Accordingly, the reaction is performed ordinarily at 50–85° C. and pH 3.5–6.5, approximately, and more preferably, at 60–80° C. and pH 4.5–6.0.

The produced reaction mixture which contains trehaloseoligosaccharides such as glucosyltrehalose or maltooligosyltrehalose can be purified according to a publicly-known process. For example, the obtained reaction mixture is desalted with an ion-exchange resin; the objective saccharide fraction is then isolated and crystallized by chromatography using activated charcoal, an ion-exchange resin (HS03 type), cation-exchange resin (Ca type) or the like as a separating material, and by a subsequent condensation to, be optionally performed; and finally, trehaloseoligosaccharides are yielded within a high purity.

A Gene Coding for the Novel Transferase

According to the present invention, a gene coding for the above novel transferase is further provided. For example, the DNA fragments illustrated by restriction maps shown in FIGS. 26 and 29 can be listed as DNA fragments comprising a gene coding for the novel transferase according to the present invention.

These DNA fragment can be obtain from an archaebacterium belonging to the order Sulfolobales, and preferably, belonging to the genus Sulfolobus. More preferably, the fragment can be isolated from the below-described *Sulfolobus solfataricus* strain KM1 or *Sulfolobus acidocaldarius* strain ATCC 33909. The suitable process for the isolation from the *Sulfolobus solfataricus* strain KM1 or the *Sulfolobus acidocaldarius* strain ATCC 33909 is illustrated in detail in the below-described Examples.

The practical examples of the origin from which the DNA fragments can be derived may further include the *Sulfolobus solfataricus* strains DSM 5354, DSM 5833, ATCC 35091 and ATCC 35092; the *Sulfolobus acidocaldarius* strain ATCC 49426; the *Sulfolobus shibatae* strain DSM 5389; the *Acidianus brierleyi* strain DSM 1651; and others. It is obvious from the following facts that these archaebacteria can be the origins of the DNA fragments according to the present invention: The novel transferase gene derived from the *Sulfolobus solfataricus* strain KM1 forms a hybrid with the chromosome DNA derived from each of those archaebacteria in the below-described hybridization test performed in Example I-17; and further, the characteristics of the enzymes themselves very closely resemble each other as described above. Moreover, the results in the aforementioned Example suggestively indicate that the novel transferase gene according to the present invention is highly conserved, specifically in archaebacteria belonging to the order Sulfolobales.

The preferable mode for carrying out the present invention provides a DNA fragment comprising a DNA sequence coding for the amino acid sequence shown in Sequence No. 2 or 4 as a suitable example of the gene coding for the novel transferase of the present invention. Further, the sequence from 335th base to 2518th base among the base sequence shown in Sequence No. 1 can be listed as a suitable example of the DNA sequence coding for the amino acid sequence shown in Sequence No. 2. The sequence from 816th base to 2855th base among the base sequence shown in Sequence No. 3 can be listed as a suitable example of the DNA sequence coding for the amino acid sequence shown in Sequence No. 4.

In general, when given the amino acid sequence of a protein, the base sequence coding therefor can- be easily determined by referring to what is called the Codon Table. Therefore, several base sequences which code for the amino acid sequence shown in Sequence No. 2 or 4 can be suitably selected. Accordingly, in the present invention, "the DNA sequence coding for the amino acid shown in Sequence No. 2" implies the DNA sequence comprising the sequence from 335th base to 2518th base of the base sequence shown in Sequence No. 1; and also, the DNA sequences which comprise the same base sequence as above except that one or more codons are replaced with the codons having a relationship of degeneracy therewith, and which still code for the amino acid shown in Sequence No. 2. Similarly, "the DNA sequence coding for the amino acid shown in Sequence No. 4" implies the DNA sequence comprising the sequence from 816th base to 2855th base of the base sequence shown in Sequence No. 3; and also, the DNA sequences which comprise the same base sequence as above except that one or more codons are replaced with the codons having a relationship of degeneracy therewith, and which still code for the amino acid shown in Sequence No. 4.

Further, as described below, the scope of the novel transferase according to the present invention also includes the sequences equivalent to the amino acid sequence shown in Sequence No. 2 or 4. The scope of the DNA fragment according to the present invention, therefore, further includes the base sequences which code for such equivalent sequences.

Incidentally, Inventors surveyed the existence of a base sequence homologous to the base sequence shown in Sequence No. 1 or 3 through a data bank on base sequences (EMBL) by using sequence-analyzing software, GENETYX (by Software Development Co.). As a result, Inventors have confirmed that such a base sequence does not exist.

Since the base sequence of the DNA fragment comprising the sequence from 335th base to 2518th base of the base sequence shown in Sequence No. 1, and the base sequence of the DNA fragment comprising the sequence from 816th base to 2518th base of the base sequence shown in Sequence No. 3 have been determined, a means for obtaining these DNA fragments is producing them based on a process for polynucleotide synthesis.

Further, these sequences can be obtained by using a process of gene engineering from the above-described archaebacteria belonging to the order Sulfolobales, and preferably, from the *Sulfolobus solfataricus* strain KM1 or the *Sulfolobus acidocaldarius* strain ATCC 33909. For example, they can be suitably obtained by a process described in Molecular Cloning: A Laboratory Manual [Sambrook, Mainiatis, et al., published by Cold Spring Harbour Laboratory Press (1989)], and others. The practical method is illustrated in detail in the below-described examples.

Recombinant Novel Transferase

Since the gene coding for the novel transferase is provided as described above, the expressed product from this gene, a recombinant novel transferase, can be obtained according to the present invention.

Figure 26:
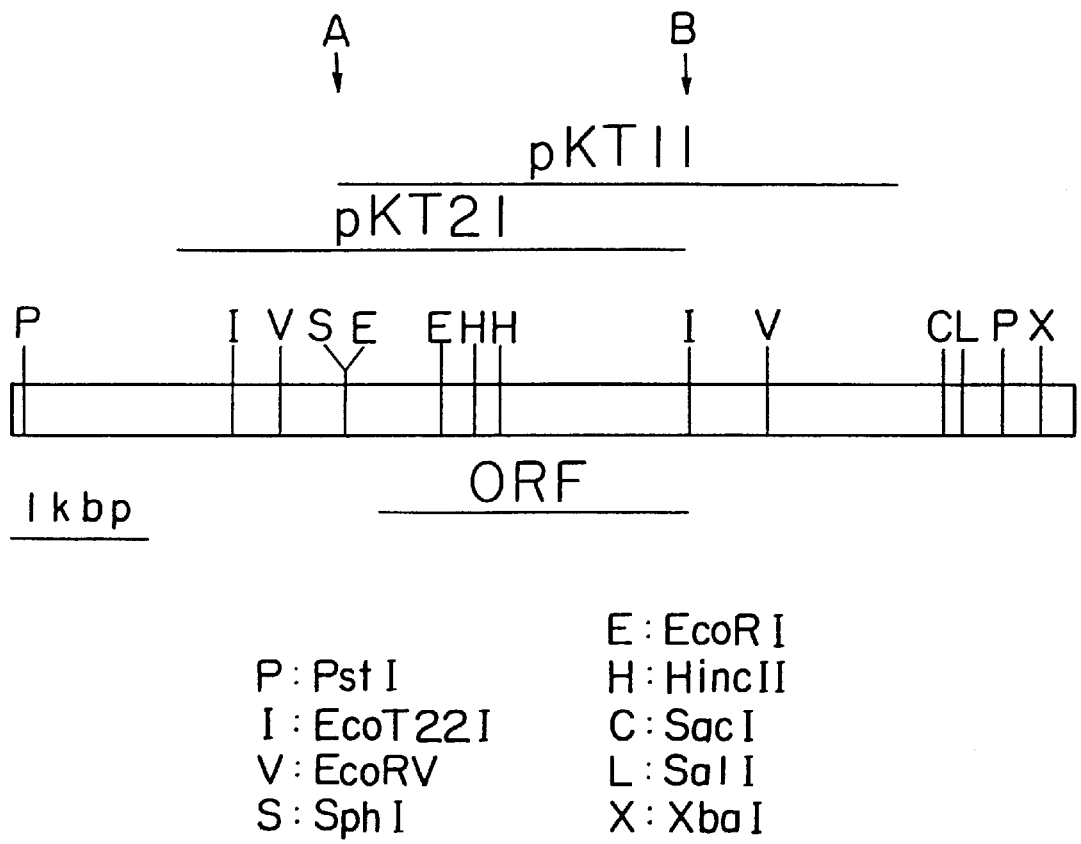
FIG. 26 is an illustration showing the restriction map of each insertional fragment pKT1,pKT11 or pKT21, containing a gene which codes for the novel transferase, and is obtained in Example I-12 from the *Sulfolobus solfataricus* strain KM1.
Figure 29:
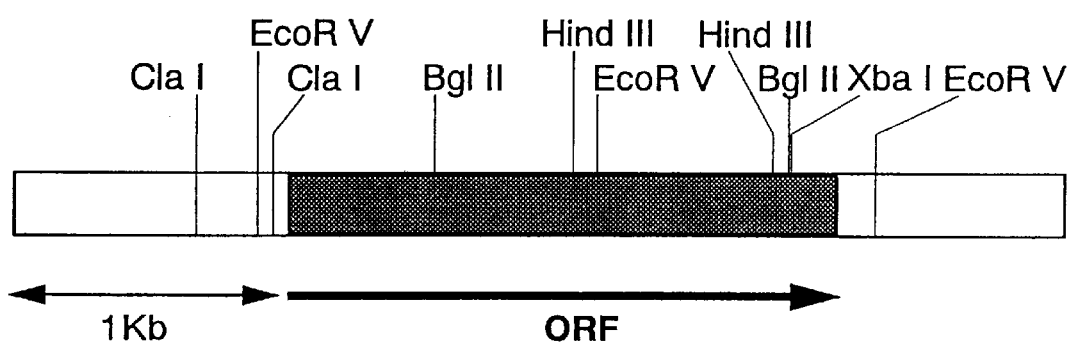
FIG. 29 is an illustration showing the restriction map of the insertional fragment p09T1 containing a gene which codes for the novel transferase, and is obtained in Example I-16 from the *Sulfolobus acidocaldarius* strain ATCC-33909.

Suitable examples of the recombinant novel transferase according to the present invention may include an expressed product from the DNA fragment illustrated with the restriction map shown in FIG. 26 or 29.

Also, the suitable examples may include a polypeptide comprising the amino acid sequence shown in Sequence No.

2 or 4 of the Sequence Table, or the equivalent sequence thereof. Here, the term "equivalent sequence" stands for the amino acid sequence which basically has the amino acid sequence shown in Sequence No. 2 or 4; but has undergone insertion, replacement or deletion of some amino acids, or addition of some amino acids to each terminus; and still keeps the activity of the novel transferase. The state in which the equivalent sequence keeps the activity of the novel transferase means that it keeps an activity sufficient for similar use in similar conditions as compared to the polypeptide having the complete sequence shown in Sequence No. 2 or 4, when the activity is applied in a practical mode for use. Obviously, persons skilled in the art can select and produce such an "equivalent sequence" by referring to the sequences shown in Sequence Nos. 2 and 4 without any special difficulty, since it is revealed in Example I-18 that the same activity is kept in the enzymes derived from the *Sulfolobus solfataricus* strain KM1 and the *Sulfolobus acidocaldarius* strain ATCC 33909 though the homology between the amino acid sequences of the novel transferases from these 2 strains is 49% when calculated considering gaps.

As clarified in Example I-17 below, each of the DNA fragments having the sequences shown in Sequence Nos. 1 and 3, respectively, can hybridize with each of DNA fragments derived from some bacterial strains other than the *Sulfolobus solfataricus* strain KM1 and the *Sulfolobus acidocaldarius* strain ATCC 33909 which are the origins of said DNA fragments, respectively. Meanwhile, as described above, Inventors have now confirmed the existence of a novel transferase having very close characteristics in those bacterial strains. Further, as revealed in Example I-18 below, the homology between the amino acid sequences of the novel transferases derived from the *Sulfolobus solfataricus* strain KM1 and the *Sulfolobus acidocaldarius* strain ATCC 33909 is 49% when calculated considering gaps. It is, therefore, obvious to persons skilled in the art that the activity of the novel transferase can be kept in a sequence which is homologous, to some extent, with the amino acid sequence shown in Sequence No. 2 or 4.

Incidentally, Inventors surveyed the existence of a sequence homologous to the amino acid sequence shown in Sequence No. 2 or 4 through a data bank on amino acid sequences (Swiss prot and NBRF-PFB) by using sequence-analyzing software, GENETYX (by Software Development Co.). As a result, Inventors have confirmed that such a sequence does not exist.

Expression of a Gene Coding for the Novel Transferase

The recombinant novel transferase according to the present invention can be produced in a host cell by transforming the host cell with a DNA molecule, and especially with an expression vector, which can replicate in the host cell, and contains the DNA fragment coding for the novel transferase according to the present invention so as to express the transferase gene.

The present invention, therefore, further provides a DNA molecule, and particularly, an expression vector, which contains a gene coding for the novel transferase according to the present invention. Such a DNA molecule can be obtained by integrating the DNA fragment coding for the novel transferase of the present invention into a vector molecule. According to the preferable mode for carrying out the present invention, the vector is a plasmid.

The DNA molecule according to the present invention can be prepared on the basis of the process described in the aforementioned Molecular Cloning: A Laboratory Manual.

The vector to be used in the present invention can suitably be selected from viruses, plasmids, cosmid vectors, and others considering the type of the host cell to be used. For example, a bacteriophage of λ phage type, a plasmid of pBR or pUC type can be used when the host cell is *Escherichia coli;* a plasmid of pUB type can be used when the host cell is *Bacillus subtilis;* and a vector of YEp or YCp type can be used when the host cell is yeast.

The plasmid should preferably contain a selective marker for detection of the transformant, and a drug-resistance marker and an auxotrophy marker can be used as such a selective marker.

Further, the DNA molecule as an expression vector according to the present invention should preferably contain DNA sequences necessary for expression of the novel transferase gene, for example, a transcription-controlling signal, a translation-controlling signal and/or the like such as a promoter, a transcription-initiating signal, a ribosome-binding site, a translation-stopping signal, and a transcription-finishing signal.

Examples of the promoter to be suitably used may include, as well as a promoter functional in the host which contains the insertional fragment, a promoter such as a lactose operon (lac) and a tryptophan operon (trp) for *Escherichia coli,* a promoter such as an alcohol dehydrogenase gene (ADH), an acid phosphatase gene (PHO), a galactose gene (GAL), and a glyceraldehyde 3-phosphate dehydrogenase gene (GPD) for yeast.

Here, the base sequence comprising the sequence from 1st base to 2578th base of the base sequence shown in Sequence No. 1, and the base sequence comprising the sequence from 1st base to 3467th base of the base sequence shown in Sequence No. 3 are recognized as containing the aforementioned sequences necessary for expression. It is, therefore, also suitable to use these sequences as they are.

Moreover, when the host cell is *Bacillus subtilis* or yeast, it will be advantageous to use a,secretory vector so as to excrete the recombinant novel transferase outside of the host's body.

In addition to *Escherichia coli, Bacillus subtilis,* yeast, and advanced eukaryotes, can be used as a host cell. Microorganisms belonging to the genus Bacillus such as *Bacillus subtilis* are suitably used. Some strains belonging to this genus are known to excrete a protein outside of the bacterial body in a large amount. Therefore, a large amount of the recombinant novel amylase can be excreted in the culture medium by using a secretory vector. This is preferable because the purification from the supernant of the culture will be easy. Further, some strains belonging to the genus Bacillus are known to excrete a very little amount of protease outside of the bacterial body. It is preferable to use such strains because the recombinant novel amylase can be efficiently produced thereby. Moreover, it will be very advantageous to select a microorganism which does not produce glucoamylase and to use it as a host cell, because the recombinant novel transferase of the present invention which is obtained as a cell extract or a simply-purified crude enzyme can be directly used for the below-described production of trehaloseoligosaccharides.

The recombinant novel transferase produced by the aforementioned transformant can be obtained as follows: At first, the above-described host cell is cultivated under proper conditions; the bacterial bodies are collected from the resultant culture by a publicly-known method, for example, by centrifugation, and suspended in a proper buffer solution; the bacterial bodies are then crushed by freeze thawing, a ultrasonic treatment, grinding and/or the like; and the resultant is centrifuged or filtrated to obtain a cell extract containing the recombinant novel transferase.

Purification of the recombinant novel transferase existing in the cell extract can be performed by a proper combination of publicly-known processes for isolation and purification. Examples of the processes may include a process utilizing a difference in thermostability, such as a heat treatment; a process utilizing a difference in solubility, such as salt precipitation and solvent precipitation, a process utilizing a difference in molecular weight, such as dialysis, ultrafiltration, gel filtration and SDS-Polyacryl-amide gel electrophoresis; a process utilizing a difference in electric charge, such as ion exchange chromatography; a process utilizing specific affinity, such as affinity chromatography; a process utilizing a difference in hydrophobicity, such as hydrophobic chromatography and reversed phase chromatography; and further, a process utilizing a difference in isoelectric point, such as isoelectric focusing. Since the recombinant novel transferase is thermostable, the purification can be very easily performed using heat treatment, by which proteins in the host can be denatured and made into precipitation suitable for removal.

Production of Trehaloseoligosaccharides Using the Recombinant Novel Transferase

The present invention further provides a process for producing so called trehaloseoligosaccharide such as glucosyltrehalose and maltooligosyltrehalose, wherein the above-described recombinant novel transferase is used.

Specifically, the process according to the present invention is a process for producing a trehaloseoligosaccharide in which at least three sugar units from the reducing end side are glucose residues and the linkage between the first and second glucose residues from the reducing end side is α-1,α-1while the linkage between the second and third glucose residues from the reducing end side is α-1,4. And the process comprises putting the above-described recombinant novel transferase into contact with a saccharide, the saccharide being composed of at least three sugar units wherein at least three glucose residues from the reducing end are α-1,4-linked.

Though the saccharide composed of at least three sugar units in which at least three glucose residues from the reducing end are α-1,4-linked is not specifically limited, starch, starch hydrolysate, maltooligosaccharides, and others can be listed as an example of such a saccharide. Examples of starch hydrolysate may include a product produced by properly hydrolyzing or acidolyzing starch using an endotype amylase, a debranching enzyme or the like so that at least three glucose residues from the reducing end of the product are α-1,4-linked. Examples of endotype amylase to be used herein may include enzymes derived from bacteria belonging to the genus Bacillus, fungi belonging to the genus Aspergillus, and plants such as malt, and others. On the other hand, Examples of the debranching enzymes may include pullulanase derived from bacteria belonging to the genus Bacillus, Klebsiella or the like, or isoamylase derived from bacteria belonging to the genus Pseudomonas. Further, these enzymes may be used in combination.

The mode and conditions for contact between the recombinant novel transferase of the present invention and the saccharide composed of at least three sugar units in which at least three glucose residues from the reducing end are α-1,4-linked is not specifically limited as long as the recombinant novel transferase can act on the saccharide therein. An example of a suitable mode for performing the contact in a solution is as follows. The concentration of a saccharide such as maltooligosaccha-rides should be suitably selected within the range in which the saccharide to be used is dissolved, considering the specific activity of the recombinant novel transferase, the reaction temperature and others. A range of 0.5–70t is ordinary, and a range of 5–40% is preferable. The reaction temperature and pH condition in the reaction of the saccharide with the enzyme should be optimum for the recombinant novel transferase. Accordingly, the reaction is performed ordinarily at 50–85° C. and pH 3.5–6.5, approximately, and more preferably, at 60–80° C. and pH 4.5– 6.0.

Additionally, the purification degree of the recombinant novel transferase can be properly selected. For example, a crude enzyme derived from the crushed bodies of a transformant can be used as it is, and the purified enzyme obtained in each of the various purification steps can be also used, and further, the enzyme isolated and purified through various purification means can be used.

Alternatively, the above-described enzyme may be put into contact with a saccharide such as maltooligosaccharides in a form of a immobilized enzyme which is immobilized to a carrier in the usual way.

The produced trehaloseoligosaccharides such as glucosyltrehalose and maltooligosyltrehalose can be recovered by purifying the reaction mixture using according to a publicly-known process. For example, the obtained reaction mixture is desalted with an ion-exchange resin; the objective saccharide fraction is then isolated and crystallized by chromatography using activated charcoal, an ion-exchange resin (HS03 type), cation-exchange resin (Ca type) or the like as a separating material, and by a subsequent condensation to be optionally performed; and finally, trehaloseoligosaccharides are yielded within a high purity.

II. Novel Amylase

Microorganisms Producing Novel Amylase of the Present Invention

Examples of the archaebacteria to be used in the present invention may include the *Sulfolobus solfataricus* strain KM1 (the above-described novel bacterial strain which was substantially purely isolated from nature by Inventors), the *Sulfolobus solfataricus* strain DSM 5833, and the *Sulfolobus acidocaldarius* strain ATCC 33909 (DSM 639).

As described above, a fairly wide variety of archaebacteria taxonomically classified under the order Sulfolobales may be considered as the microorganisms which can produce the novel amylase of the present invention. Here, the archaebacterium belonging to the order Sulfolobales are taxonomically defined as being highly acidophilic (capable of growing in a temperature range of 55–88° C.), being thermophilic (capable of growing in a pH range of 1–6), being aerobic, and being sulfur bacteria (being coccal bacteria having no regular form and a diameter of 0.6–2 μm). The aforementioned *Sulfolobus solfataricus* strain DSM 5833 had formerly been named as *Caldariella acidophila*. From the fact like this, microorganisms which are closely related to the above-described archaebacteria genetically or taxonomically and which are capable of producing the enzyme of the same kind, and mutants derived from these strains by treatment with various mutagens can be used in the present invention.

Among the above-illustrated microorganisms, the *Sulfolobus solfataricus* strain KM1 is the bacterial strain which Inventors isolated from a hot spring in Gunma Prefecture, and the characteristics and deposition of this strain are as described above in detail.

Cultivation of the Microorganisms which Produce the Novel Amylase of the Present Invention The culture conditions for producing the novel amylase of the present invention may suitably be selected within ranges in which the objective amylase can be produced. When a concussion culturing or a culturing with aeration and stirring using a liquid medium is employed, the culturing for 2–7 days should suitably be performed at a pH and a temperature which allow the growth of each microorganism. The culture medium to be suitably used is, for example, any of the culture media which are described in Catalogue of Bacteria and Pharges 18th edition (1992) published by American Type Culture Collection (ATCC), and in Catalogue of Strains 5th edition (1993) published by Deutsche Sammlung von Mikroorganismen und Zellkulturen GmbH (DSM). Starch, maltooligosaccharide and/or the like may be further added as a sugar source.

Purification of the Novel Amylase of the Present Invention

The novel amylase of the present invention which is produced by the above-described microorganisms can be extracted as follows: At first, the bacterial bodies are collected from the culture obtained in a culture process as described above by a publicly-known procedure, for example, by centrifugation; the resultant is suspended in a proper buffer solution; the bacterial bodies are then crushed by freeze thawing, an ultrasonic treatment, grinding and/or the like; and the resultant is centrifuged or filtrated to obtain a cell extract containing the objective amylase.

To purify the novel amylase of the present invention which is contained in the cell extract, publicly-known processes for isolation and purification can be employed in a proper combination. Examples of such processes may include a process utilizing solubility, such as salt precipitation and solvent precipitation; a process utilizing a difference in molecular weight, such as dialysis, ultrafiltration, gel filtration and SDS-Polyacryl-amide gel electrophoresis; a process utilizing a difference in electric charge, such as ion exchange chromatography; a process-utilizing specific affinity, such as affinity chromatography; a process utilizing a difference in hydrophobicity, such as hydrophobic chromatography and reversed phase chromatography; and further, a process utilizing a difference in isoelectric point, such as isoelectric focusing. The practical examples of these processes are shown in Examples II-2–II-4 below. Finally, Native Polyacrylamide gel electrophoresis, SDS-Polyacrylamide gel electrophoresis or isoelectric focusing is performed to obtain a purified enzyme which appears therein as a single band.

As to measurement of activity in the enzyme or enzyme-containing substance isolated by the above various purification processes, starch is used as the substrate in the activity-measuring method offered by Lama, et al. By this method, when various amylases coexist in the reaction system, the production of starch hydrolysate can be detected. In contrast, when each of the individually isolated products of these amylases is used, both of the detecting sensitivity and quantifying ability become low, and as a serious problem, the starch-hydrolyzing activity becomes undetectable due to its disappearance during purification. Therefore, the purification and characterization of the true substance of the enzyme activity had been substantially impossible. Under such circumstances, Inventors employed a new activity-measuring method in which the substrate is a trehaloseoligosaccharide such as maltotriosyltrehalose, and the index is activity of hydrolyzing it into α,α-trehalose and maltooligosaccharides such as maltotriose. As a result, this method was found to have an extremely high specificity, detecting sensitivity and quantifying ability, and isolation and purification of the objective enzyme could be achieved for the first time, and finally, the true substance of the novel amylase activity of the present invention could be practically purified and specified.

Characteristics of the Novel Amylase According to the Present Invention

As examples of the enzyme of the present invention, the amylases produced by the *Sulfolobus solfataricus* strain KM1, the *Sulfolobus solfataricus* strain DSM 5833, and the *Sulfolobus acidocaldarius* strain ATCC 33909 (DSM 639), respectively, are taken up, and the enzymatic characteristics of these amylases are shown in Table 2 below in summary. Here, the data in the table are based on the practical examples shown in Example II-5.

TABLE 2

| Physicochemical properties | *Sulfolobus solfataricus* KM1 | *Sulfolobus solfataricus* DSM5833 | *Sulfolobus acidocaldarius* ATCC33909 |
|---|---|---|---|
| (1) Enzyme action and Substrate specificity | Acts of glucose polymers composed of more than maltotriose, so as to hydrolyze by endo-type and liberates principally monosaccharide or disaccharide from the reducing end. Especially liberates α,α-trehalose from trehaloseoligosaccharide wherein the linkage between two glucoses from the reducing end side is α-1,α-1 while the other linkages are α-1,4. | | |
| (2) Optimum pH | 4.5–5.5 | 4.5–5.5 | 5.0–5.5 |
| (3) pH Stability | 3.5–10.0 | 3.0–12.0 | 4.0–13.0 |
| (4) Optimum temperature | 70–85° C. | 70–85° C. | 60–80° C. |
| (5) Thermal stability | 85° C., 6 hr 100% remained | 85° C., 6 hr 100% remained | 80° C., 6 hr 100% remained |
| (6) Molecular weight | | | |
| SDS-PAGE | 61000 | 62000 | 64000 |
| (7) Isoelectric point | 4.8 | 4.3 | 5.4 |
| (8) Inhibitor | 5 mM $CuSO_4$ 100% inhibited | 5 mM $CuSO_4$ 100% inhibited | 5 mM $CuSO_4$ 100% inhibited |

Note 1: Time-course Change

When soluble starch was used as the substrate, the iodine-starch complex quickly disappeared in the early stage of the enzymatic reaction, and subsequently, the hydrolyzing reaction progressed so as to produce maltose and glucose as principal products, and maltotriose and maltotetraose in slight amounts.

Note 2: Enzymatic Action/Mode of Enzymatic Reaction

The present enzyme principally produces glucose and maltose, and produces small amounts of maltotriose and maltotetraose, when starch, starch hydrolysate and/or maltooligosaccharide are used as the substrate. As to the action mechanisms, the present enzyme has an amylase activity of endotype-hydrolyzing these substrates, and an activity of producing principally monosaccharide and/or disaccharide from the reducing end side.

In particular, the enzyme has a high reactivity to a saccharide composed of at least three sugar units wherein the linkage between the first and the second glucose residues from the reducing end side is α-1,α-1 while the linkage between the second and third glucose residues from the reducing end side is α-1,4 (for example, trehaloseoligosaccharide). When these saccharides are used as the substrate, the enzyme has an activity of hydrolyzing the α-1,4 linkage between the second and third glucose residues from the reducing end side, and specifically liberates α,α-trehalose in the early stage of the reaction.

Consequently, the present enzyme can be recognized as a novel amylase. The details are as practically described in Example II-5.

The characteristics of the present enzyme have been described above. However, as is obvious from Table 2 and the examples below, the characteristics of the present enzyme other than such enzymatic activities are found to slightly vary according to the difference in genus or species between the bacterial strains.

Transferase to be Used in Production of α,α-Trehalose

The transferase of the present invention which is described in detail in the above-described item "I. Novel Transferase" can be used for production of α,α-trehalose according to the present invention. Specifically, examples of such a transferase may include transferases derived from the *Sulfolobus solfataricus* strain ATCC 35091 (DSM 1616), the *Sulfolobus solfataricus* strain DSM 5833, the *Sulfolobus solfataricus* strain KM1, the *Sulfolobus acidocaldarius* strain ATCC 33909 (DSM 639), and the *Acidianus brierleyi* strain DSM 1651.

These transferases can be produced according to, for example, the processes described in Examples I-1–I-5 below. The transferases thus obtained have various characteristics shown in Example I-6 below.

Production of α,α-Trehalose

The present invention provides a process for producing α,α-trehalose by using the novel amylase and transferase of the present invention. The process according to the present invention will be illustrated below with the most typical example, namely, with a process for producing α,α-trehalose from a glucide raw material such as starch, starch hydrolysate and/or maltooligosaccharide. Incidentally, the probable reaction-mechanisms of the above two enzymes are considered as follows: At first, the novel amylase of the present invention acts on starch, starch hydrolysate or maltooligosaccharide by its endotype-hydrolyzing activity to produce amylose or maltooligosaccharide; subsequently, the first α-1,4 linkage from the reducing end of the resultant amylose or maltooligosaccharide is transferred into an α-1, α-1 linkage by the activity of the transferase; further, the novel amylase acts again to produce α,α-trehalose, and amylose or maltooligosaccharide which is deprived of the polymerization degree by two; and the amylase or maltooligosaccharide thus derived undergoes the above reactions repeatedly, so that α,α-trehalose would be produced in a high yield.

Such reaction mechanisms may be attributed to the specific reaction-mode as follows, which is possessed by the novel amylase of the present invention: The enzyme has a higher reactivity to a saccharide composed of at least three sugar units wherein the linkage between the first and the second glucose residues from the reducing end side is α-1,α-1 while the linkage between the second and third glucose residues from the reducing end side is an α-1,4 (for example, trehaloseoligosac-charide), as compared with the reactivity to each of the corresponding maltooligosaccharide; and the enzyme specifically hydrolyzes the α-1,4 linkage between the second and third glucose residues from the reducing end side of the above saccharide, and liberates α,α-trehalose.

As far as Inventors know, there is no formerly-known amylase which can act on maltooligosyltrehalose derived from maltooligosaccharide by modifying the reducing end with an α-1,α-1 linkage, and which has an activity of specifically hydrolyzing the α-1,4 linkage next to the α-1, α-1 linkage to liberate α,α-trehalose in a high yield. Accordingly, it has been almost impossible to produce α,α-trehalose in a high yield.

In the process for producing α,α-trehalose according to the present invention, the mode of contact between the present amylase and transferase, and starch, starch hydrolysate and/or maltooligosaccharides is not specifically limited as long as the amylase of the present invention (the present enzyme) produced by archaebacteria can act on the starch, starch hydrolysate and/or maltooligosaccharides in such mode. In practice, the following procedure may ordinarily be performed: A crude enzyme is obtained from the bacterial bodies or crushed bacterial bodies of an archaebacterium; and the purified enzyme obtained in each of the various purification steps, or the enzyme isolated and purified through various purification means, is made to act directly on glucide such as starch, starch hydrolysate and maltooligosaccharide. Alternatively, the enzyme thus obtained may be put into contact with glucide such as starch, starch hydrolysate and maltooligosaccharide in a form of a immobilized enzyme which is immobilized to a carrier. Additionally, two or more of the present enzymes derived from two or more species of archaebacteria may coexist and be put into contact with glucide such as starch, starch hydrolysate and maltooligosaccharide.

In the process for producing α,α-trehalose according to the present invention, the above-described amylase and transferase should be used in amounts within the optimum ranges. An excess amount of amylase will act on the starch, starch hydrolysate or maltooligosaccharide on which the transferase have not acted to modify its reducing end, while an excess amount of transferase will, in the side reaction, hydrolyze the trehaloseoligo-saccharide such as maltooligosyltrehalose which has been produced by the transferase itself, and produce glucose.

The practical concentrations of the amylase and transferase relative to the amount of substrate are 1.5 U/ml or higher, and 0.1 U/ml or higher, respectively. Preferably, the concentrations should be 1.5 U/ml or higher, and 1.0 U/ml or higher, respectively, and more preferably, 15 U/ml or higher, and 1.0 U/ml or higher, respectively. Meanwhile, the ratio of amylase concentration to transferase concentration should be 100–0.075, and preferably, 40–3.

The concentration of glucide such as starch, starch hydrolysate and maltooligosaccharide should be suitably selected within the range in which the glucide to be used is dissolved, considering the specific activity of each enzyme to be used, the reaction temperature, and others. A range of 0.5–70% is ordinary, and a range of 5–40% is preferable. The reaction temperature and pH condition in the reaction of the glucide with the enzymes should be optimum for the amylase and the transferase. Accordingly, the reaction is performed ordinarily at 50–85° C. and pH 3.5–8, approximately, and more preferably, at 60–75° C. and pH 4.5–6.0.

Additionally, when the glucide raw material to be used is starch, starch hydrolysate or the like having a high polymerization degree, the production of α,α-trehalose can be further promoted by using another endotype liquefying amylase together as a supplement. Such a debranching enzyme as pullulanase and isoamylase can also be used herein. The endotype amylase, pullulanase, isoamylase or the like may not be such an enzyme as derived from archaebacteria, and therefore, it is not specifically limited. For example, amylase derived from bacteria belonging to the genus Bacillus, fungi belonging to the genus Aspergillus and plants such as malt, and others can be used. The debranching enzyme may be pullulanase (including thermostable pullulanase) derived from bacteria belonging to the genus Bacillus, Klebsiella or the like, or isoamylase derived from bacteria belonging to the genus Pseudomonas. Further, these enzymes may be used in combination.

However, the addition of an excess amount of amylase will possibly cause production of glucose and maltose which the transferase will not act on. Similarly, the addition of an excess amount of a debranching enzyme will cause a decrease in solubility of the substrate due to cleavage of the 1,6-linkage, and lead to production of a highly-viscous and insoluble substance (amylose). For that reason, the amounts of amylase and the debranching enzyme should carefully be controlled so as not to produce excessive glucose, maltose, or an insoluble substance. As to debranching enzymes, the concentration should be properly selected within a range in which an insoluble substance is not produced, considering the specific activity of the present amylase, the reaction temperature, and the like. Specifically, when the treatment is performed at 40° C. for one hour, the ordinary concentration relative to the substrate is within a range of 0.01–100 U/ml, and preferably, within a range of 0.1–25 U/ml. (As to definition of the activity of debranching enzymes, please refer to Examples II-6, II-13 and II-14.) The procedure for treatment with a debranching enzyme may be either of the following: The substrate is pre-treated with the debranching enzyme before the α,α-trehalose-producing reaction; or the debranching enzyme is allowed to coexist with the amylase and transferase at any one of the stages during the α,α-trehalose-producing reaction. Preferably, debranching enzymes should be used one or more times at any of the stages, and particularly, should be used one or more times at any of earlier stages. Incidentally, when a thermostable debranching enzyme is used, similar effects can be exhibited by only one time of addition at any one of the stages or earlier stages during the α,α-trehalose-producing reaction.

The produced reaction mixture which contains α,α-trehalose can be purified according to a publicly-known process. For example, the obtained reaction mixture is desalted with an ion-exchange resin; the objective saccharide fraction is then isolated and crystallized by chromatography using activated charcoal, an ion-exchange resin (HS03 type), cation-exchange resin (Ca type) or the like as a separating material, and by a subsequent condensation to be optionally performed; and finally, α,α-trehalose is yielded within a high purity.

A Gene Coding for the Novel Amylase

The present invention further provides a gene coding for the above novel amylase.

Figure 34:
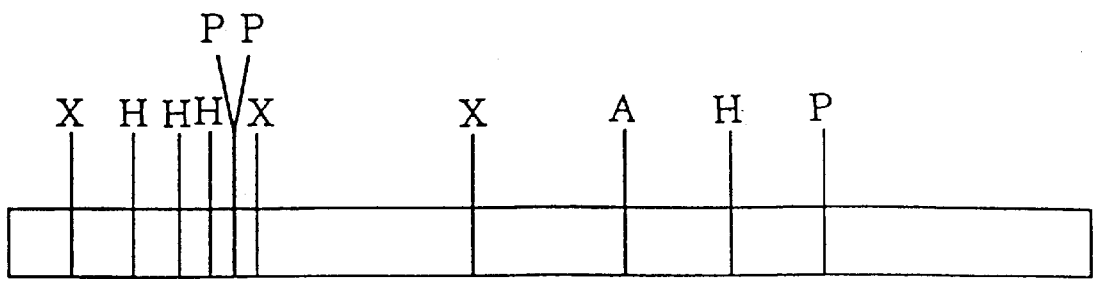
FIG. 34 is an illustration showing the restriction map of the insertional fragment pKA1 containing a gene which codes for the novel amylase, and is derived from the *Sulfolobus solfataricus* strain KM1.
Figure 38:
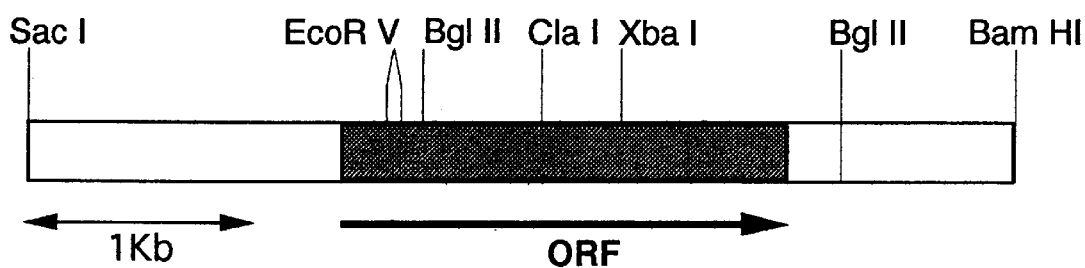
FIG. 38 is an illustration showing the restriction map of the insertional fragment p09A1 containing a gene which codes for the novel amylase, and is derived from the *Sulfolobus acidocaldarius* strain ATCC 33909.

The practical examples of the gene coding for the novel amylase according to the present invention may include the DNA fragments illustrated with restriction maps shown in FIGS. 34 and 38.

These DNA fragments can be derived from archaebacteria belonging to the order Sulfolobales, and preferably, can be isolated from the *Sulfolobus solfataricus* strain KM1 or the *Sulfolobus acidocaldarius* strain ATCC 33909 described below. The suitable process for isolation from the *Sulfolobus solfataricus* strain KM1 or the *Sulfolobus acidocaldarius* strain ATCC 33909 is illustrated in detail in the examples below.

Examples of the origin from which such a DNA fragments can be obtained may also include the *Sulfolobus solfataricus* strains DSM 5354, DSM 5833, ATCC 35091 and ATCC 35092; the *Sulfolobus acidocaldarius* strain ATCC 49426; the *Sulfolobus shibatae* strain DSM 5389; and the *Acidianus brierleyi* strain DSM 1651. It is obvious from the following facts that these archaebacteria can be the origins of the DNA fragments according to the present invention: The novel amylase gene derived from the *Sulfolobus solfataricus* strain KM1 or the *Sulfolobus acidocaldarius* strain ATCC 33909 forms a hybrid with the chromosome DNA derived from each of those archaebacteria in the below-described hybridization test performed in Example II-24; and further, the characteristics of the enzymes themselves very closely resemble each other as described above. Moreover, the results in the same example suggestively indicate that the novel amylase gene according to the present invention is highly conserved, specifically in archaebacteria belonging to the order Sulfolobales.

The preferable mode for carrying out the present invention provides a DNA fragment comprising a DNA sequence coding for the amino acid sequence shown in Sequence No. 6 or 8 as a suitable example of the gene coding for the novel amylase of the present invention. Further, the base sequence from 642nd base to 2315th base among the base sequence shown in Sequence No. 5 can be listed as a suitable example of the DNA sequence coding for the amino acid sequence shown in Sequence No. 6. The sequence from 1176th base to 2843rd base among the base sequence shown in Sequence No. 7 can be listed as a suitable example of the DNA sequence coding for the amino acid sequence shown in Sequence No. 8.

In general, when given the amino acid sequence of a protein, the base sequence coding therefor can be easily determined by referring to what is called the Codon Table. Therefore, several base sequences which code for the amino acid sequence shown in Sequence No. 6 or 8 can be suitably selected. Accordingly, in the present invention, "the DNA sequence coding for the amino acid shown in Sequence No. 6" implies the DNA sequence comprising the sequence from 642nd base to 2315th base of the base sequence shown in Sequence No. 5; and also, the DNA sequences which comprise the same base sequence as above except that one or more codons are replaced with the codons having a relationship of degeneracy therewith, and which still code for the amino acid shown in Sequence No. 6. Similarly, "the DNA sequence coding for the amino acid shown in Sequence No. 8" implies the DNA sequence comprising the sequence from 1176th base to 2843rd base of the base sequence shown in Sequence No. 7; and also, the DNA sequences which comprise the same base sequence as above except that one or more codons are replaced with the codons having a relationship of a degeneracy therewith, and which still code for the amino acid shown in Sequence No. 8.

Further, as described below, the scope of the novel amylase according to the present invention also includes the sequences equivalent to the amino acid sequence shown in Sequence No. 6 or 8. The scope of the DNA fragment according to the present invention, therefore, further includes the base sequences which code for such equivalent sequences.

Moreover, the scope of the novel amylase according to the present invention includes a sequence comprising the amino acid sequence shown in Sequence No. 6 and a Met residue added to the N terminus of this amino acid sequence. Accordingly, the scope of the DNA fragment containing the gene coding for the novel amylase of the present invention also includes the sequence from 639th base to 2315th base of the base sequence shown in Sequence No. 5.

Incidentally, Inventors surveyed the existence of a base sequence homologous to the base sequence shown in Sequence No. 5 or 7 through a data bank on base sequences (EMBL) by using sequence-analyzing software, GENETYX (by Software Development Co.). As a result, Inventors have confirmed that such a base sequence does not exist.

Since the base sequence of the DNA fragment comprising the sequence from 639th or 642nd base to 2315th base of the base sequence shown in Sequence No. 5, and the base sequence of the DNA fragment comprising the sequence from 1176th base to 2843rd base of the base sequence shown in Sequence No. 7 have been determined, a means for obtaining these DNA fragments is producing them based on a process for polynucleotide synthesis.

Further, these sequences can be obtained by, using a process of gene engineering from the above-described archaebacteria belonging to the order Sulfolobales, and preferably, from the *Sulfolobus solfataricus* strain KM1 or the *Sulfolobus acidocaldarius* strain ATCC 33909. For example, they can be suitably obtained by a process described in Molecular Cloning: A Laboratory Manual [Sambrook, Mainiatis, et al., published by Cold Spring Harbour Laboratory Press (1989)], and others. The practical method is illustrated in detail in the below-described examples.

Recombinant Novel Amylase

Since the gene coding for the novel amylase is provided as described above, the expressed product from this gene, a recombinant novel amylase, can be obtained according to the present invention.

Suitable examples of the recombinant novel amylase according to the present invention may include an expressed product from the DNA fragment illustrated with the restriction map shown in FIG. 34 or 38.

Also, the suitable examples may include a polypeptide comprising the amino acid sequence shown in Sequence No. 6 or 8 of the Sequence Table, or the equivalent sequence thereof. Here, the term "equivalent sequence" stands for the amino acid sequence which basically has the amino acid sequence shown in Sequence No. 6 or 8; but has undergone insertion, replacement or deletion of some amino acids, or addition of some amino acids to each terminus; and still keeps the activity of the above novel amylase. The state in which the equivalent sequence keeps the activity of the novel amylase means that it keeps an activity sufficient for similar use in similar conditions as compared to the polypeptide having the complete sequence shown in Sequence No. 6 or 8, when the activity is applied in a practical mode for use. Obviously, persons skilled in the art can select and produce such an "equivalent sequence" by referring to the sequences shown in Sequence Nos. 6 and 8 without any special difficulty, since it is revealed in Example II-23 that the same activity is kept in the enzymes derived from the *Sulfolobus solfataricus* strain KM1 and the *Sulfolobus acidocaldarius* strain ATCC 33909 though the homology between the amino acid sequences of the novel amylases from these 2 strains is 59% when calculated considering gaps.

Further, the amino acid sequence which comprises the amino acid sequence shown in Sequence No. 6 and a Met residue added to the N terminus of this amino acid sequence is provided according to another mode for carrying out the present invention. The novel amylase of the natural type according to the present invention has the sequence shown in Sequence No. 6. However, as described below, when the novel amylase is obtained from the genetic information of the isolated gene by a recombinant technology using said sequence, the obtained sequence will be found to further have a Met residue in addition to the amino acid sequence shown in Sequence No. 6. Additionally, it is obvious that the obtained sequence has an activity of the novel amylase. Accordingly, the amino acid sequence to which a Met residue is added is also included within the scope of the present invention.

As clarified in Example II-24 below, the DNA fragment having the sequence from 1393th base to 2116th base of the sequence shown in Sequence No. 7 can hybridize with each of the DNA fragments derived from some bacterial strains other than the *Sulfolobus acidocaldarius* strain ATCC 33909 and the *Sulfolobus solfataricus* strain KM1 which are the origins of said DNA fragment. Meanwhile, as described above, Inventors have now confirmed the existence of a novel amylase having very close characteristics in those bacterial strains. Further, as revealed in Example II-23 below, the homology between the amino acid sequences of the novel amylases derived from the *Sulfolobus solfataricus* strain KM1 and the *Sulfolobus acidocaldarius* strain ATCC 33909 is 59% when calculated considering gaps. It is, therefore, obvious to persons skilled in the art that the activity of the novel amylase can be kept in a sequence which is homologous, to some extent, with the amino acid sequence shown in Sequence No. 6 or 8.

Incidentally, Inventors surveyed the existence of a sequence homologous to the amino acid sequence shown in Sequence No. 6 or 8 through a data bank on amino acid sequences (Swiss prot and NBRF-PFB) by using sequence-analyzing software, GENETYX (by Software Development Co.). As a result, Inventors have confirmed that such a sequence does not exist.

Expression of a Gene Coding for the Novel Amylase

The recombinant novel amylase according to the present invention can be produced in a host cell by transforming the host cell with a DNA molecule, and especially with an expression vector, which can replicate in the host cell, and contains the DNA fragment coding for the novel amylase according to the present invention so as to express the amylase gene.

The present invention, therefore, further provides a DNA molecule, and particularly, an expression vector, which contains a gene coding for the novel amylase according to the present invention. Such a DNA molecule can be obtained by integrating the DNA fragment coding for the novel amylase of the present invention into a vector molecule. According to the preferable mode for carrying out the present invention, the vector is a plasmid.

The DNA molecule according to the present invention can be prepared on the basis of the process described in the aforementioned Molecular Cloning: A Laboratory Manual.

The vector to be used in the present invention can suitably be selected from viruses, plasmids, cosmid vectors, and others considering the type of the host cell to be used. For example, a bacteriophage of λ phage type, a plasmid of pBR or pUC type can be used when the host cell is *Escherichia coli;* a plasmid of pUB type can be used when the host cell is *Bacillus subtilis;* and a vector of YEp or YCp type can be used when the host cell is yeast.

The plasmid should preferably contain a selective marker for detection of the transformant, and a drug-resistance marker and an auxotrophy marker can be used as such a selective marker.

Further, the DNA molecule as an expression vector according to the present invention should preferably contain DNA sequences necessary for expression of the novel amylase gene, for example, a transcription-controlling signal, a translation-controlling signal and/or the like such as a promoter, a transcription-initiating signal, a ribosome-binding site, a translation-stopping signal, and a transcription-finishing signal.

Examples of the promoter to be suitably used may include, as well as a promoter functional in the host which contains the insertional fragment, a promoter such as a lactose operon (lac) and a tryptophan operon (trp) for *Escherichia coli,* a promoter such as an alcohol dehydrogenase gene (ADH), an acid phosphatase gene (PHO), a galactose gene (GAL), and a glyceraldehyde 3-phosphate dehydrogenase gene (GPD) for yeast.

Here, the base sequence comprising the sequence from 1st base to 2691th base of the base sequence shown in Sequence No. 5, and the base sequence comprising the sequence from 1st base to 3600th base of the base sequence shown in Sequence No. 7 are expressed in *Escherichia coli* to efficiently produce the novel amylase. Accordingly, the DNA sequences shown in Sequence Nos. 5 and 7 are recognized as containing at least sequences necessary for expression in *Escherichia coli*. It is, therefore, also suitable to use these sequences as they are.

Moreover, when the host cell is *Bacillus subtilis* or yeast, it will be advantageous to use a secretory vector so as to excrete the recombinant novel amylase outside of the host's body.

In addition to *Escherichia coli, Bacillus subtilis,* yeast, and advanced eukaryotes, can be used as a host cell. Microorganisms belonging to the genus Bacillus such as *Bacillus subtilis* are suitably used. Some strains belonging to this genus are known to excrete a protein outside of the bacterial body in a large amount. Therefore, a large amount of the recombinant novel amylase can be excreted in the culture medium by using a secretory vector. This is preferable because the purification from the supernatant of the culture will be easy. Further, some strains belonging to the genus Bacillus are known to excrete a very little amount of protease outside of the bacterial body. It is preferable to use such strains because the recombinant novel amylase can be efficiently produced thereby. Moreover, it will be very advantageous to select a microorganism which does not produce glucoamylase and to use it as a host cell, because the recombinant novel amylase of the present invention which is obtained as a cell extract or a simply-purified crude enzyme can be directly used for the below-described production of α,α-trehalose.

The recombinant novel amylase produced by the aforementioned transformant can be obtained as follows: At first, the above-described host cell is cultivated under proper conditions; the bacterial bodies are collected from the resultant culture by a publicly-known method, for example, by centrifugation, and suspended in a proper buffer solution; the bacterial bodies are then crushed by freeze thawing, an ultrasonic treatment, grinding and/or the like; and the resultant is centrifuged or filtrated to obtain a cell extract containing the recombinant novel amylase.

Purification of the recombinant novel amylase existing in the cell extract can be performed by a proper combination of publicly-known processes for isolation and purification. Examples of the processes may include a process utilizing a difference in thermostability, such as a heat treatment; a process utilizing a difference in solubility, such as salt precipitation and solvent precipitation, a process utilizing a difference in molecular weight, such as dialysis, ultrafiltration, gel filtration and SDS-Polyacrylamide gel electrophoresis; a process utilizing a difference in electric charge, such as ion exchange chromatography; a process utilizing specific affinity, such as affinity chromatography; a process utilizing a difference in hydrophobicity, such as hydrophobic chromatography and reversed phase chromatography; and further, a process utilizing a difference in isoelectric point, such as isoelectric focusing. Since the recombinant novel amylase is thermostable, the purification can be very easily performed using heat treatment, by which proteins in the host can be denatured and made into precipitation suitable for removal.

Production of α,α-Trehalose Using the Recombinants

The present invention further provides a process for producing α,α-trehalose by using the above recombinant novel amylase and the aforementioned recombinant novel transferase.

According to the preferable mode for producing α,α-trehalose, the recombinant novel amylase and the recombinant transferase of the present invention may be mixed and put into contact at the same time with glucide such as starch, starch hydrolysate and maltooligosaccharide. Also, it is preferable to substitute either of the recombinant transferase and the recombinant novel amylase with a corresponding enzyme derived from nature.

The concentration of glucide such as starch, starch hydrolysate and maltooligosaccharide should be suitably selected within the range in which the glucide to be used is dissolved, considering the specific activities of the present enzymes, the reaction temperature and others. A range of 0.5–70% is ordinary, and a range of 5–40% is preferable. The reaction temperature and pH condition in the reaction of the glucide with the enzymes should be optimum for the recombinant novel amylase and the recombinant novel transferase. Accordingly, the reaction is performed ordinarily at 50–850° C. and pH 3.5–8, approximately, and more preferably, at 60–75° C. and pH 4.5–6.0.

Additionally, when the glucide to be used is starch, starch hydrolysate, or the like having a high polymerization degree, the production of α,α-trehalose can be further promoted by using another endotype liquefying amylase together as a supplement. For example, enzymes derived from bacteria belonging to the genus Bacillus, fungi belonging to the genus Aspergillus, and plants such as malt, and others can be used as such an endotype liquefying amylase. The debranching enzyme to be used may be pullulanase derived from bacteria belonging to the genus Bacillus, Klebsiella or the like, isoamylase derived from bacteria belonging to the genus Pseudomonas, or the like. Further, these enzymes may be used in combination.

However, the addition of an excess amount of an endotype liquefying amylase will cause production of glucose and maltose which the novel transferase will not act on. Similarly, the addition of an excess amount of pullulanase will cause a decrease in solubility of the substrate due to cleavage of the 1,6-linkage, and lead to production of a highly-viscous and insoluble substance which can not be utilized. For that reason, the amounts of endotype liquefying amylase and pullulanase should be controlled so as not to produce excessive glucose, maltose, or an insoluble substance.

Any of the procedures may be employed when pullulanase is used, for example, pre-treating the substrate with pullulanase, or putting pullulanase into coexistence together with the recombinant novel amylase and the recombinant novel transferase at any one of the stages during the α,α-trehalose-producing reaction.

The produced reaction mixture which contains α,α-trehalose can be purified according to a publicly-known process. For example, the obtained reaction mixture is desalted with an ion-exchange resin; the objective saccharide fraction is then isolated and crystallized by chromatography using activated charcoal, an ion-exchange resin ($HSO_3$ type), cation-exchange resin (Ca type) or the like as a separating material, and by a subsequent condensation to be optionally performed; and finally, α,α-trehalose is yielded within a high purity.

The present invention will be further illustrated in detail with practical examples below, though, needless to say, the scope of the present invention is not limited to within those examples.

EXAMPLE I-1

Glucosyltrehalose-Producing Activities of Archaebacteria

The bacterial strains listed in Table 3 below were examined for glucosyltrehalose-producing activity. The examination was performed as follows: The cultivated bacterial bodies of each strain was crushed by an ultrasonic treatment and centrifuged; the substrate, maltotriose, was added to the supernatant so that the final concentration would be 10%; the mixture was then put into a reaction at 60° C. for 24 hours; after that, the reaction was stopped by a heat-treatment at 100° C. for 5 min.; and the glucosyltrehalose thus produced was subjected to a measurement according to the HPLC analysis under the below-described conditions.

Column: TOSOH TSK-gel Amide-80 (4.6×250 mm)
Solvent: 75% acetonitrile
Flow rate: 1.0 ml/min.
Temperature: Room temperature
Detector: Refractive Index Detector The enzyme activities were expressed with such a unit as 1 Unit equals the activity of converting maltotriose into 1 $\mu$mol of glucosyltrehalose per hour. Incidentally, in Table 3, the activity was expressed in terms of units per one gram of bacterial cell (Units/g-cell).

FIG. 1(B) is the HPLC chart obtained herein. As is recognized from the figure, the principal reaction product appeared slightly behind the non-reacted substrate in the HPLC chart as one peak without any anomer. The aliquot of this principal reaction product through TSK-gel Amide-80 HPLC column was subjected to $^1$H-NMR analysis and $^{13}$C-NMR analysis, and was confirmed to be glucosyltrehalose. The chemical formula is as follows.

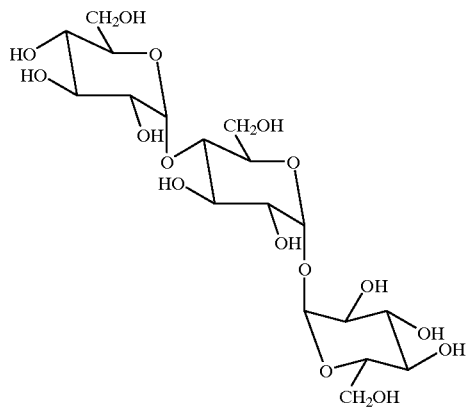

Consequently, each of the cell extracts from the bacterial strains belonging to the order Sulfolobales has a glucosyltrehalose-producing activity, namely, the transferase activity as the enzyme of the present invention.

TABLE 3

| Strain | | Enzyme activity (Uints/g-cell) |
|---|---|---|
| *Sulfolobus solfataricus* | ATCC 35091 | 6.8 |
| | ATCC 35092 | 6.0 |
| | DSM 5354 | 13.0 |
| | DSM 5833 | 5.6 |
| | KM1 | 13.5 |
| *Sulfolobus acidocaldarius* | ATCC 33909 | 13.0 |
| | ATCC 49426 | 2.4 |
| *Sulfolobus shibatae* | DSM 5389 | 12.0 |
| *Acidianus brierleyi* | DSM 1651 | 6.7 |

EXAMPLE I-2
Purification of the Present Transferase Derived from the *Sulfolobus solfataricus* Strain KM1

The *Sulfolobus solfataricus* strain KM1 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80° C. The yield of the bacterial cell was 3.3 g/liter.

Two hundred grams of the bacterial cells obtained above were suspended in 400 ml of a 50 mM sodium acetate buffer solution (pH 5.5) containing 5 mM of EDTA, and subjected to an ultrasonic treatment for bacteriolysis at 0° C. for 15 min. The resultant was then centrifuged to obtain a supernatant, and ammonium sulfate was added to the supernatant so as to be 60% saturation.

The precipitate obtained by centrifugation was dissolved in a 50 mM sodium acetate buffer solution (pH 5.5) containing 1 M of ammonium sulfate and 5 mM of EDTA, and applied to a hydrophobic chromatography using the TOSOH TSK-gel Phenyl-TOYOPEARL 650S column (volume: 800 ml) equilibrated with the same buffer solution as above. The column was then washed with the same buffer solution, and the objective transferase was eluted with 600 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM sodium acetate buffer solution (pH 5.5).

Next, the resultant was subjected to ion-exchange chromatography using the TOSOH TSK-gel DEAE-TOYOPEARL 650S column (volume: 300 ml) equilibrated with the same buffer solution. The column was then washed with the same buffer solution, and the objective transferase was eluted with 900 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM of EDTA.

Subsequent to that, the desalted and concentrated solution thus obtained was subjected to gel filtration chromatography using the Pharmacia HiLoad 16/60 Superdex 200 pg column, and the objective transferase was eluted with the same buffer solution. The fractions exhibiting the activity were concentrated using an ultrafiltration membrane (critical molecular weight: 13,000), and subsequently, washed and desalted with a 50 mM sodium acetate buffer solution (pH 5.5).

Next, ammonium sulfate was dissolved in the desalted and concentrated solution thus obtained so that the concentration of ammonium sulfate would be 1 M. The resultant was then subjected to hydrophobic chromatography using TOSOH TSK-gel Phenyl-5PW HPLC column equilibrated with the same buffer solution. The column was then washed with the same buffer solution, and the objective transferase was eluted with 30 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM sodium acetate buffer solution (pH 5.0).

Further, the resultant was subjected to ion-exchange chromatography using the TOSOH TSK-gel DEAE 5PW HPLC column equilibrated with the same buffer solution. The column was then washed with the same buffer solution, and the objective transferase was eluted with 30 ml of sodium chloride solution at a linear concentration gradient from 0 M to 0.3 M. The fractions exhibiting the activity were concentrated using an ultrafiltration membrane (critical molecular weight: 13,000).

Finally, Native Polyacrylamide gel electrophoresis, SDS-Polyacrylamide gel electrophoresis and isoelectric focusing were performed to obtain the purified enzyme which appeared as single band.

Incidentally, the activity was measured in the same manner as in Example I-1.

Total enzyme activity, total protein and specific activity at each of the purification steps are shown in Table 4 below.

TABLE 4

| Purified fraction | Total enzyme activity (units) | Total protein (mg) | Specific activity (units/mg) | Yield (%) | Purity (fold) |
| --- | --- | --- | --- | --- | --- |
| Crude extract | 653 | 17000 | 0.038 | 100 | 1 |
| 60% saturated $(NH_4)_2SO_4$ precipitation | 625 | 15000 | 0.04 | 95.7 | 1.1 |
| Phenyl | 83 | 533 | 0.16 | 12.7 | 4.2 |
| DEAE | 150 | 31 | 4.90 | 23.0 | 129 |
| Gel-permeation | 111 | 2 | 55.7 | 17.0 | 1466 |
| Phenyl rechromatography | 48 | 0.17 | 277 | 7.4 | 7289 |
| DEAE rechromatography | 30 | 0.05 | 598 | 4.6 | 15737 |

EXAMPLE I-3

Purification of the Present Transferase Derived from *Sulfolobus solfataricus* Strain DSM 5833

The *Sulfolobus solfataricus* strain DSM 5833 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80° C. The yield of the bacterial cell was 1.7 g/liter.

Fifty six grams of the bacterial cells obtained above were suspended in 100 ml of a 50 mM sodium acetate buffer solution (pH 5.5) containing 5 mM of EDTA, and subjected to an ultrasonic treatment for bacteriolysis at 0° C. for 15 min. The resultant was then centrifuged to obtain a supernatant.

Next, ammonium sulfate was dissolved in the supernatant so that the concentration of ammonium sulfate would be 1 M. The resultant was then subjected to hydrophobic chromatography using TOSOH TSK-gel Phenyl-TOYOPEARL 650S column (volume: 200 ml) equilibrated with a 50 mM sodium acetate buffer solution (pH 5.5) containing 1 M of sodium sulfate and 5 mM of EDTA. The column was then washed with the same buffer solution, and the objective transferase was eluted with 600 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM Tris-HCl buffer solution (pH 7.5).

Subsequent to that, the resultant was subjected to ion-exchange chromatography using the TOSOH TSK-gel DEAE-TOYOPEARL 650S column (volume: 300 ml) equilibrated with the same buffer solution. The column was then washed with the same buffer solution, and the objective transferase was eluted with 900 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Next, ammonium sulfate was dissolved in the desalted and concentrated solution thus obtained so that the concentration of ammonium sulfate would be 1 M. The resultant was then subjected to hydrophobic chromatography using TOSOH TSK-gel Phenyl-TOYOPEARL 650S column (volume: 200 ml) equilibrated with the same buffer solution. The column was then washed with the same buffer solution, and the objective transferase was eluted with 600 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM of EDTA.

Further, the desalted and concentrated solution thus obtained was subjected to gel filtration chromatography using the Pharmacia HiLoad 16/60 Superdex 200 pg column, and the objective transferase was eluted with the same buffer solution. The fractions exhibiting the activity were concentrated using an ultrafiltration membrane (critical molecular weight: 13,000), and subsequently, dialyzed with a 25 mM Bis-Tris-HCl buffer solution (pH 6.7).

Next, the resultant was subjected to a chromatofocusing using the Pharmacia Mono P HR/5/20 column equilibrated with the same buffer solution. Immediately after the sample was injected, the objective transferase was eluted with 10% polybuffer 74-HCl (pH 5.0; manufactured by Pharmacia Co.). The fractions exhibiting the activity were concentrated using an ultrafiltration membrane (critical molecular weight: 13,000), and subsequently, dialyzed with a 25 mM Bis-Tris-HCl buffer solution (pH 6.7).

Further, another chromatofocusing was performed under the same conditions, and the objective transferase was eluted. The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Finally, Native polyacrylamide gel electrophoresis, SDS-polyacrylamide gel electrophoresis and isoelectric focusing were performed to obtain the purified enzyme which appeared as single band.

Incidentally, the activity was measured in the same manner as in Example I-1.

Total enzyme activity, total protein and specific activity at each of the purification steps are shown in Table 5 below.

TABLE 5

| Purified fraction | Total enzyme activity (units) | Total protein (mg) | Specific activity (units/mg) | Yield (%) | Purity (fold) |
|---|---|---|---|---|---|
| Crude extract | 541 | 10000 | 0.06 | 100 | 1 |
| Phenyl | 1039 | 988 | 1.05 | 192 | 19 |
| DEAE | 383 | 147 | 2.60 | 70.7 | 47 |
| Pheny rechromatography | 248 | 49.5 | 5.00 | 45.8 | 91 |
| Gel-permeation | 196 | 3.69 | 53.0 | 36.1 | 964 |
| Mono P | 92 | 0.32 | 287 | 17.0 | 5218 |
| Mono P rechromatography | 64 | 0.13 | 494 | 11.9 | 8982 |

EXAMPLE I-4

Purification of the Present Transferase Derived from the *Sulfolobus acidocaldarius* Strain ATCC 33909

The *Sulfolobus acidocaldarius* strain ATCC 33909 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80° C. The yield of the bacterial cell was 2.9 g/liter.

Ninety two and a half grams of the bacterial cells obtained above were suspended in 200 ml of a 50 mM sodium acetate buffer solution (pH 5.5) containing 5 mM of EDTA, and subjected to an ultrasonic treatment for bacteriolysis at 0° C. for 15 min. The resultant was then centrifuged to obtain a supernatant.

Next, ammonium sulfate was dissolved in the supernatant so that the concentration of ammonium sulfate would be 1 M. The resultant was then subjected to hydrophobic chromatography using TOSOH TSK-gel Phenyl-TOYOPEARL 650S column (volume: 400 ml) equilibrated with a 50 mM sodium acetate buffer solution (pH 5.5) containing 1 M of sodium sulfate and 5 mM EDTA. The column was then washed with the same buffer solution, and the objective transferase was eluted with 600 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM Tris-HCl buffer solution (pH 7.5).

Subsequent to that, the resultant was subjected to ion-exchange chromatography using the TOSOH TSK-gel DEAE-TOYOPEARL 650S column (volume: 300 ml) equilibrated with the same buffer solution. The column was then washed with the same buffer solution, and the objective transferase was eluted with 900 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Next, ammonium sulfate was dissolved in the desalted and concentrated solution thus obtained so that the concentration of ammonium sulfate would be 1 M. The resultant was then subjected to hydrophobic chromatography using TOSOH TSK-gel Phenyl-TOYOPEARL 650S column (volume: 200 ml) equilibrated with the same buffer solution. The column was then washed with the same buffer solution, and the objective transferase was eluted with 600 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM EDTA.

Further, the desalted and concentrated solution thus obtained was subjected to gel filtration chromatography using the Pharmacia HiLoad 16/60 Superdex 200 pg column, and the objective transferase was eluted with the same buffer solution. The fractions exhibiting the activity were concentrated using an ultrafiltration membrane (critical molecular weight: 13,000), and subsequently, dialyzed with a 25 mM Bis-Tris-HCl buffer solution (pH 6.7).

Next, the resultant was subjected to a chromatofocusing using the Pharmacia Mono P HR/5/20 column equilibrated with the same buffer solution. Immediately after the sample was injected, the objective transferase was eluted with 10% polybuffer 74-HCl (pH 5.0; manufactured by Pharmacia Co.). The fractions exhibiting the activity were concentrated using an ultrafiltration membrane (critical molecular weight: 13,000), and subsequently, dialyzed with a 25 mM Bis-Tris-HCl buffer solution (pH 6.7).

Further, another chromatofocusing was performed under the same conditions, and the objective transferase was eluted. The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Finally, Native polyacrylamide gel electrophoresis, SDS-polyacrylamide gel electrophoresis and isoelectric focusing were performed to obtain the purified enzyme which appeared as single band.

Incidentally, the activity was measured in the same manner as in Example I-1.

Total enzyme activity, total protein and specific activity at each of the purification steps are shown in Table 6 below.

TABLE 6

| Purified fraction | Total enzyme activity (units) | Total protein (mg) | Specific activity (units/mg) | Yield (%) | Purity (fold) |
|---|---|---|---|---|---|
| Crude extract | 912 | 38000 | 0.24 | 100 | 1 |
| Phenyl | 559 | 660 | 0.85 | 61.3 | 3.5 |

TABLE 6-continued

| Purified fraction | Total enzyme activity (units) | Total protein (mg) | Specific activity (units/mg) | Yield (%) | Purity (fold) |
|---|---|---|---|---|---|
| DEAE | 806 | 150 | 5.40 | 88.4 | 23 |
| Phenyl rechromatography | 636 | 35.1 | 18.1 | 69.7 | 75 |
| Gel-permeation | 280 | 2.68 | 104 | 30.7 | 433 |
| Mono P | 129 | 0.35 | 411 | 13.8 | 1713 |
| Mono P rechromatography | 86.9 | 0.24 | 362 | 9.5 | 1508 |

EXAMPLE I-5
Purification of the Present Transferase Derived from the *Acidianus brierleyi* strain DSM 1651

The *Acidianus brierleyi* strain DSM 1651 was cultivated at 70° C. for 3 days in the culture medium which is identified as No. 150 in Catalogue of Strains 5th edition (1993) published by Deutsche Sammlung von Mikroorganismen und Zellkulturen GmbH (DSM). The cultivated bacteria was collected by centrifugation and stored at −80° C. The yield of the bacterial cell was 0.6 g/liter.

Twelve grams of the bacterial cells obtained above were suspended in 120 ml of a 50 mM sodium acetate buffer solution (pH 5.5) containing 5 mM of EDTA, and subjected to an ultrasonic treatment for bacteriolysis at 0° C. for 15 min. The resultant was then centrifuged to obtain a supernatant.

Next, ammonium sulfate was dissolved in the supernatant so that the concentration of ammonium sulfate would be 1 M. The resultant was then subjected to hydrophobic chromatography using TOSOH TSK-gel Phenyl-TOYOPEARL 650S column (volume: 200 ml) equilibrated with a 50 mM sodium acetate buffer solution (pH 5.5) containing 1 M of sodium sulfate and 5 mM of EDTA. The column was then washed with the same buffer solution, and the objective transferase was eluted with 600 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM Tris-HCl buffer solution (pH 7.5).

Subsequent to that, the resultant was subjected to ion-exchange chromatography using the TOSOH TSK-gel DEAE-TOYOPEARL 650S column (volume: 300 ml) equilibrated with the same buffer solution. The column was then washed with the same buffer solution, and the objective transferase was eluted with 900 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Further, the desalted and concentrated solution thus obtained was subjected to gel filtration chromatography using the Pharmacia HiLoad 16/60 Superdex 200 pg column, and the objective transferase was eluted with the same buffer solution. The fractions exhibiting the activity were concentrated using an ultrafiltration membrane (critical molecular weight: 13,000), and subsequently, dialyzed with a 25 mM Bis-Tris-HCl buffer solution (pH 6.7).

Next, the resultant was subjected to a chromatofocusing using the Pharmacia Mono P HR/5/20 column equilibrated with the same buffer solution. Immediately after the sample was injected, the objective transferase was eluted with 10% polybuffer 74-HCl (pH 5.0; manufactured by Pharmacia Co.). The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Finally, Native Polyacrylamide gel electrophoresis, SDS-Polyacrylamide gel electrophoresis and isoelectric focusing were performed to obtain the purified enzyme which appeared as single band.

Incidentally, the activity was measured in the same manner as in Example I-1.

Total enzyme activity, total protein and specific activity at each of the purification steps are shown in Table 7 below.

TABLE 7

| Purified fraction | Total enzyme activity (units) | Total protein (mg) | Specific activity (units/mg) | Yield (%) | Purity (fold) |
|---|---|---|---|---|---|
| Crude extract | 310 | 264 | 1.17 | 100 | 1 |
| Phenyl | 176 | 19.2 | 9.20 | 56.9 | 7.9 |
| DEAE | 70 | 5.02 | 13.8 | 22.5 | 12 |
| Gel-permeation | 54 | 0.18 | 298 | 17.3 | 255 |
| Mono P | 27 | 0.07 | 378 | 8.6 | 323 |

EXAMPLE I-6
Examination of the Present Transferase for Various Characteristics

The purified enzyme obtained in Example I-2 was examined for enzymatic characteristics.

(1) Molecular Weight

The molecular weight of the purified enzyme in its native state was measured by gel filtration chromatography using the Pharmacia HiLoad 16/60 Superdex 200 pg column. Marker proteins having molecular weights of 200,000, 97,400, 68,000, 43,000, 29,000, 18,400 and 14,300, respectively, were used.

As a result, the molecular weight of the transferase was estimated at 54,000.

Meanwhile, the molecular weight was also measured by SDS-polyacrylamide gel electrophoresis (gel concentration; 6%). Marker proteins having molecular weights of 200,000, 116,300, 97,400, 66,300, 55,400, 36,500, 31,000, 21,500 and 14,400, respectively, were used.

As a result, the molecular weight of the transferase was estimated at 76,000.

The difference between molecular weight values measured by gel filtration chromatography and SDS-Polyacrylamide gel electrophoresis may be attributed to a certain interaction which may be generated between the packed material of the gel filtration column and proteins. Accordingly, the molecular weight value estimated by gel filtration does not necessarily represent the molecular weight of the present enzyme in its native state.

(2) Isoelectric Point

The isoelectric point was found to be pH 6.1 by agarose gel isoelectric focusing.

(3) Stability

Figure 2:
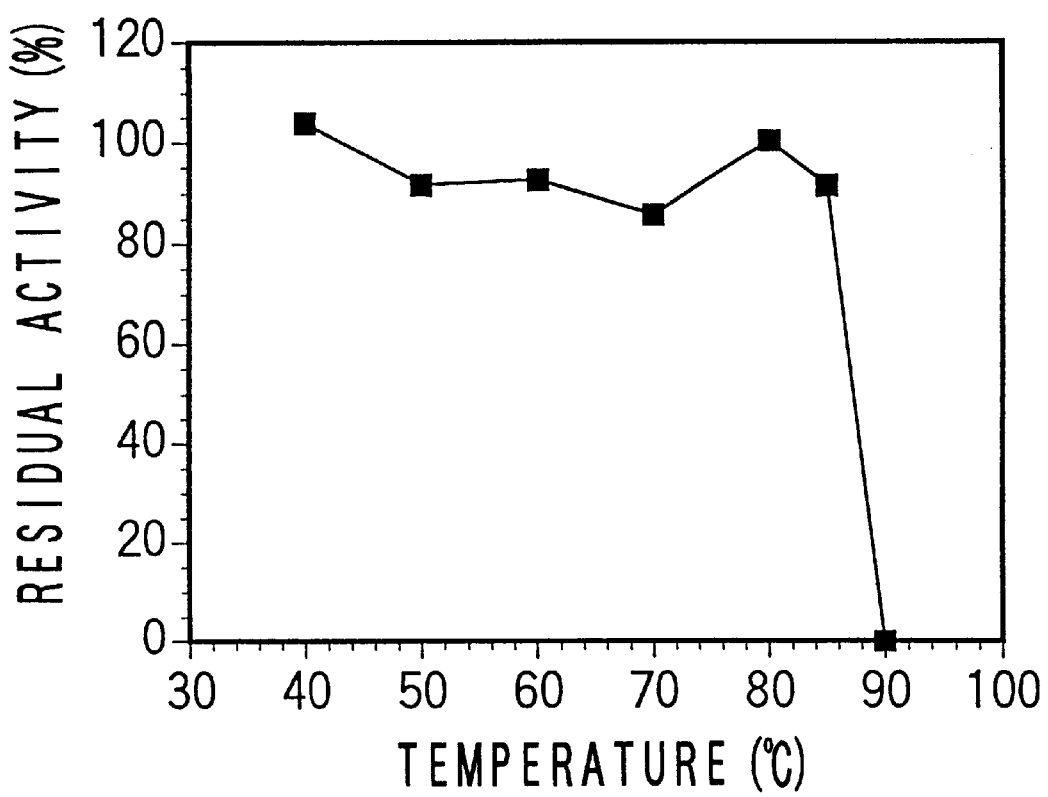
FIG. 2 is a graph showing thermostability of the present transferase which is obtained in Example I-2 from the *Sulfolobus solfataricus* strain KM1.
Figure 3:
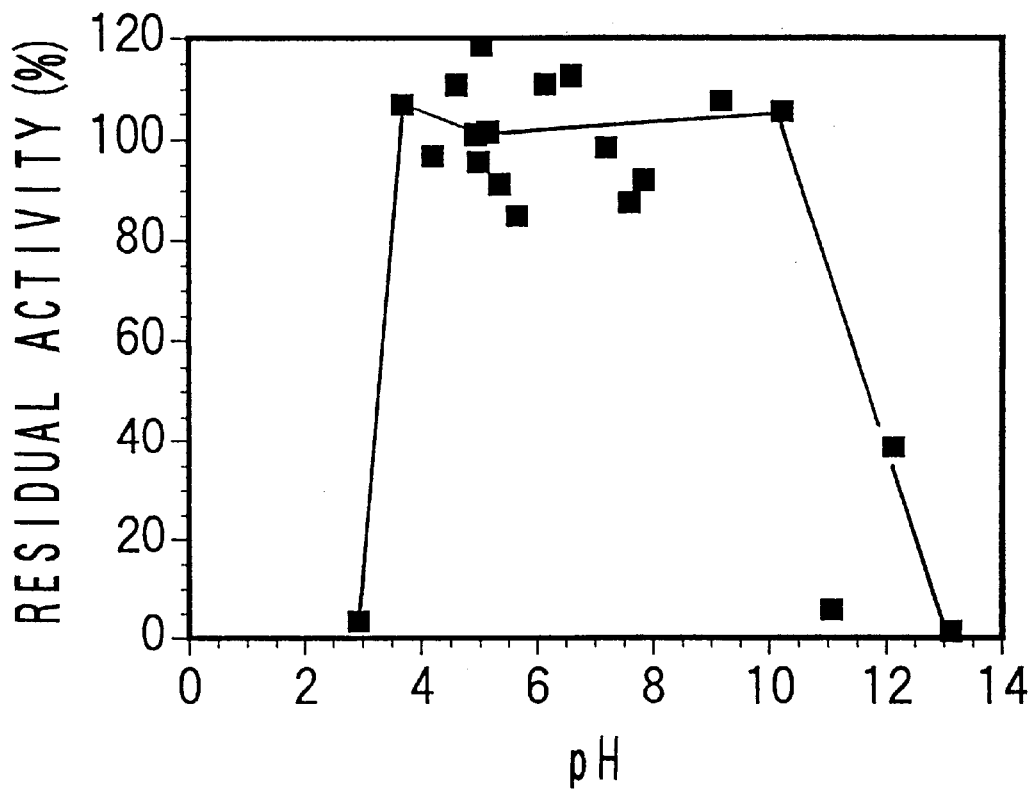
FIG. 3 is a graph showing pH stability of the present transferase which is obtained in Example I-2 from the *Sulfolobus solfataricus* strain KM1.

The stability changes of the obtained enzyme according to temperature and pH value are shown in FIGS. 2 and 3, respectively. In measurement, a glycine-HCl buffer solution was used in a pH range of 3–5, and similarly, a sodium acetate buffer solution in a pH range of 4–6, a sodium phosphate buffer solution in a pH range of 5–8, a Tris-HCl buffer solution in a pH range of 8–9, a sodium bicarbonate buffer solution in a pH range of 9–10, and a KCl-NaOH buffer solution in a pH range of 11–13, respectively, were also used.

The present enzyme was stable throughout the treatment at 85° C. for 6 hours, and also, was stable throughout the treatment at pH 4.0–10.0 and room temperature for 6 hours.

(4) Reactivity

Figure 4:
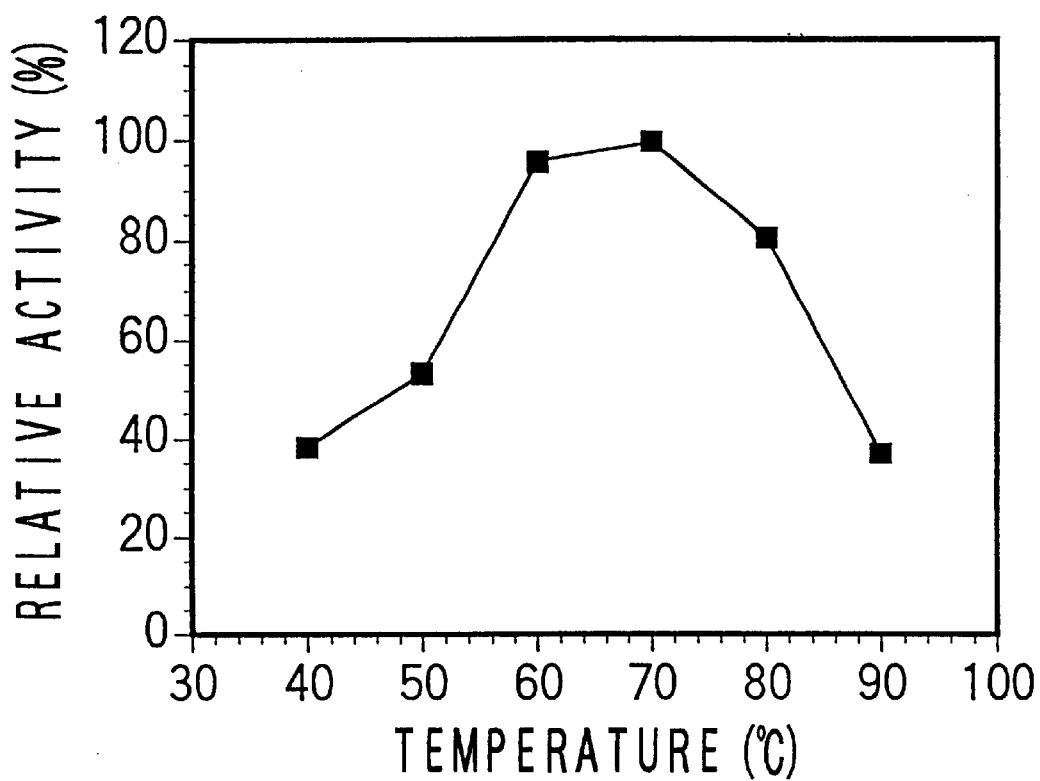
FIG. 4 is a graph showing reactivity of the present transferase which is obtained in Example I-2 from the *Sulfolobus solfataricus* strain KM1, when examined at each temperature.
Figure 5:
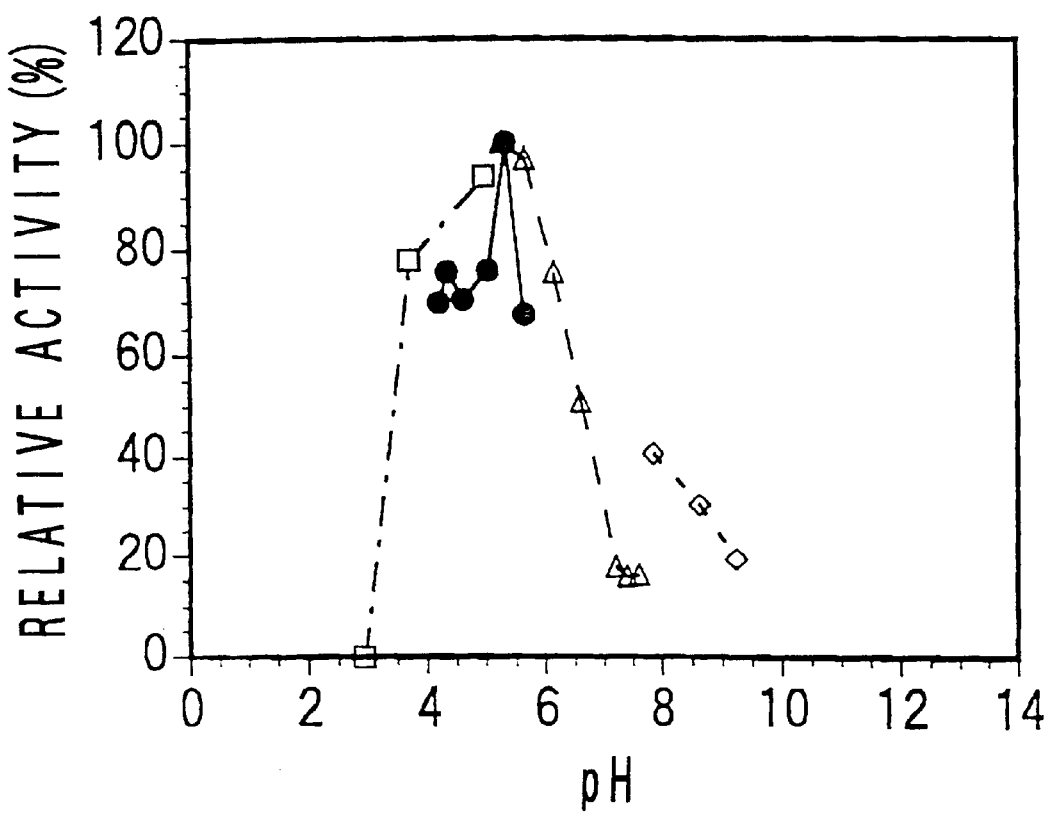
FIG. 5 is a graph showing optimum pH for reaction of the present transferase which is obtained in Example I-2 from the *Sulfolobus solfataricus* strain KM1.

As to the obtained enzyme, reactivity of at various temperatures and reactivity at various pH are shown in FIGS. 4 and 5, respectively. In measurement, a glycine-HCl buffer solution was used in a pH range of 3–5 (□), similarly, a sodium acetate buffer solution in a pH range of 4–5.5 (●), a sodium phosphate buffer solution in a pH range of 5–7.5 (Δ), and a Tris-HCl buffer solution in a pH range of 8–9 (◇), respectively, were also used.

The optimum reaction temperature of the present enzyme is within 60–80° C., approximately, and the optimum reaction pH of the present enzyme is within 5.0–6.0, approximately.

(5) Influence of Various Activators and Inhibitors

The influence of each substance listed in Table 8, such as an activating effect or inhibitory effect, was evaluated using similar activity-measuring method to that in Example I-1. Specifically, the listed substances were individually added together with the substrate to the same reaction system as that in the method for measuring glucosyltrehalose-producing activity employed in Example I-1. As a result, copper ion and SDS were found to have inhibitory effects. Though many glucide-relating enzymes have been found to be activated with calcium ion, the present enzyme would not be activated with calcium ion.

TABLE 8

| Activator/Inhibitor | Concentration (mM) | Residual activity (%) |
| --- | --- | --- |
| Control (not added) | | 100.0 |
| CaCl$_2$ | 5 | 93.6 |
| MgCl$_2$ | 5 | 111.3 |
| MnCl$_2$ | 5 | 74.2 |
| CuSO$_4$ | 5 | 0.0 |
| CoCl$_2$ | 5 | 88.5 |
| FeSO$_4$ | 5 | 108.3 |
| FeCl$_3$ | 5 | 90.0 |
| AgNO$_3$ | 5 | 121.0 |
| EDTA | 5 | 96.8 |
| 2-Mercaptoethanol | 5 | 100.3 |
| Dithiothreitol | 5 | 84.5 |
| SDS | 5 | 0.0 |
| Glucose | 0.5 | 107.3 |
| Trehalose | 0.5 | 107.8 |
| Maltotetraose | 0.5 | 97.4 |
| Malatopentaose | 0.5 | 101.9 |
| Maltohexaose | 0.5 | 91.0 |
| Maltoheptaose | 0.5 | 93.5 |

(6) Substrate Specificity

It was investigated whether or not the present enzyme acts on each of the substrates listed in Table 9 below to produce its α-1,α-1-transferred isomer. Here, the activity measurement was performed in the same manner as in Example I-1.

TABLE 9

| Substrate | Reactivity |
| --- | --- |
| Glucose | − |
| Maltose | − |
| Maltotriose (G3) | + |
| Maltotetraose (G4) | ++ |
| Malotopentaose (G5) | ++ |
| Maltohexaose (G6) | ++ |
| Maltoheptaose (G7) | ++ |
| Isomaltotriose | − |
| Isomaltotetraose | − |
| Isomaltopentaose | − |
| Panose | − |

As a result, the present enzyme was found to produce trehaloseoligosaccharides from the substrates of maltotriose (G3)–maltoheptaose (G7). Meanwhile, the present enzyme did not act on any of isomaltotriose, isomaltotetraose, isomaltopentaose or panose, which have α-1,6 linkages at 1st to 4th linkages from the reducing end or have the α-1,6 linkage at 2nd linkage from the reducing end.

Incidentally, each of the purified enzymes which were obtained in Examples I-3–I-5 and derived from the *Sulfolobus solfataricus* strain DSM 5833, the *Sulfolobus acidocaldarius* strain ATCC 33909, and the *Acidianus brierleyi* strain DSM 1651, respectively, was examined for enzymatic characteristics by using similar manner. The results are shown in Table 1 above.

EXAMPLE I-7

Production of Glucosyltrehalose and Maltooligosyltrehalose from Maltooligosaccharides As the substrates, maltotriose (G3)–maltoheptaose (G7) were used in a concentration of 100 mM. The purified enzyme obtained in Example I-2 was then allowed to act on each of the above substrates in an amount of 13.5 Units/ml (in terms of the enzyme activity when the substrate is maltotriose) to produce a corresponding α-1,α-1-transferred isomer. Each product was analyzed by the method in Example I-1, and investigated its yield and enzyme activity. The results was shown in Table 10 below. Incidentally, in Table 10, each enzymatic activity value was expressed with such a unit as 1 Unit equals the activity of converting the maltooligosaccharide into 1 umol of corresponding α-1,α-1-transferred isomer per hour.

TABLE 10

| Substrate | Enzyme activity (units/ml) | Yield (%) |
| --- | --- | --- |
| Maltotriose (G3) | 13.5 | 44.6 |
| Maltotetraose (G4) | 76.3 | 73.1 |
| Maltopentaose (G5) | 111.3 | 68.5 |
| Maltohexaose (G6) | 100.9 | 63.5 |
| Maltoheptaose (G7) | 70.5 | 68.7 |

As is shown in Table 10, the enzyme activity was highest when the substrate was G5, which exhibited approximately 8 times as much activity as G3. Further, the yield was 44.6% in G3, while 63.5–73.1% in G4 or larger.

Figure 6:
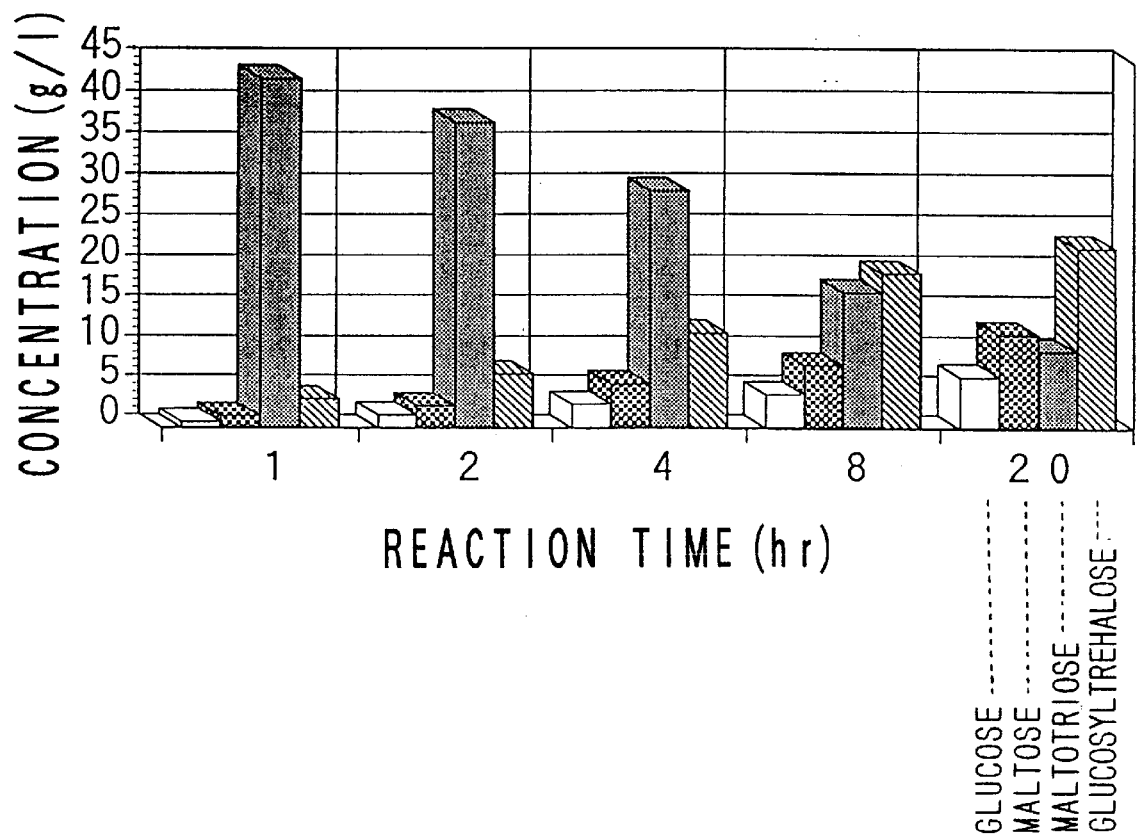
FIG. 6 is a graph showing patterns of reaction products derived from maltotriose by using the present transferase which is obtained in Example I-2 from the *Sulfolobus solfataricus* strain KM1.
Figure 7:
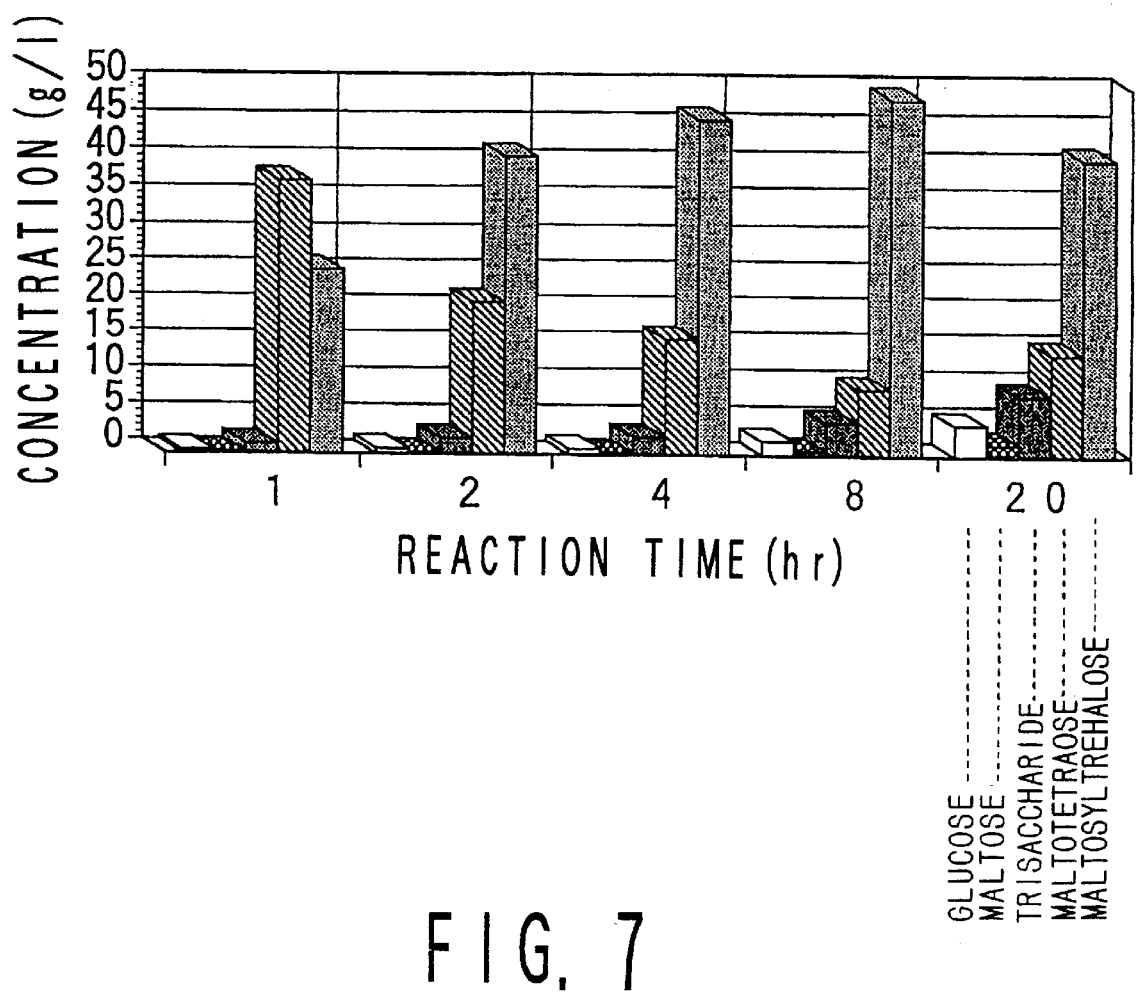
FIG. 7 is a graph showing patterns of reaction products derived from maltotetraose by using the present transferase which is obtained in Example I-2 from the Sulfolobus solfataricus strain KM1.
Figure 8:
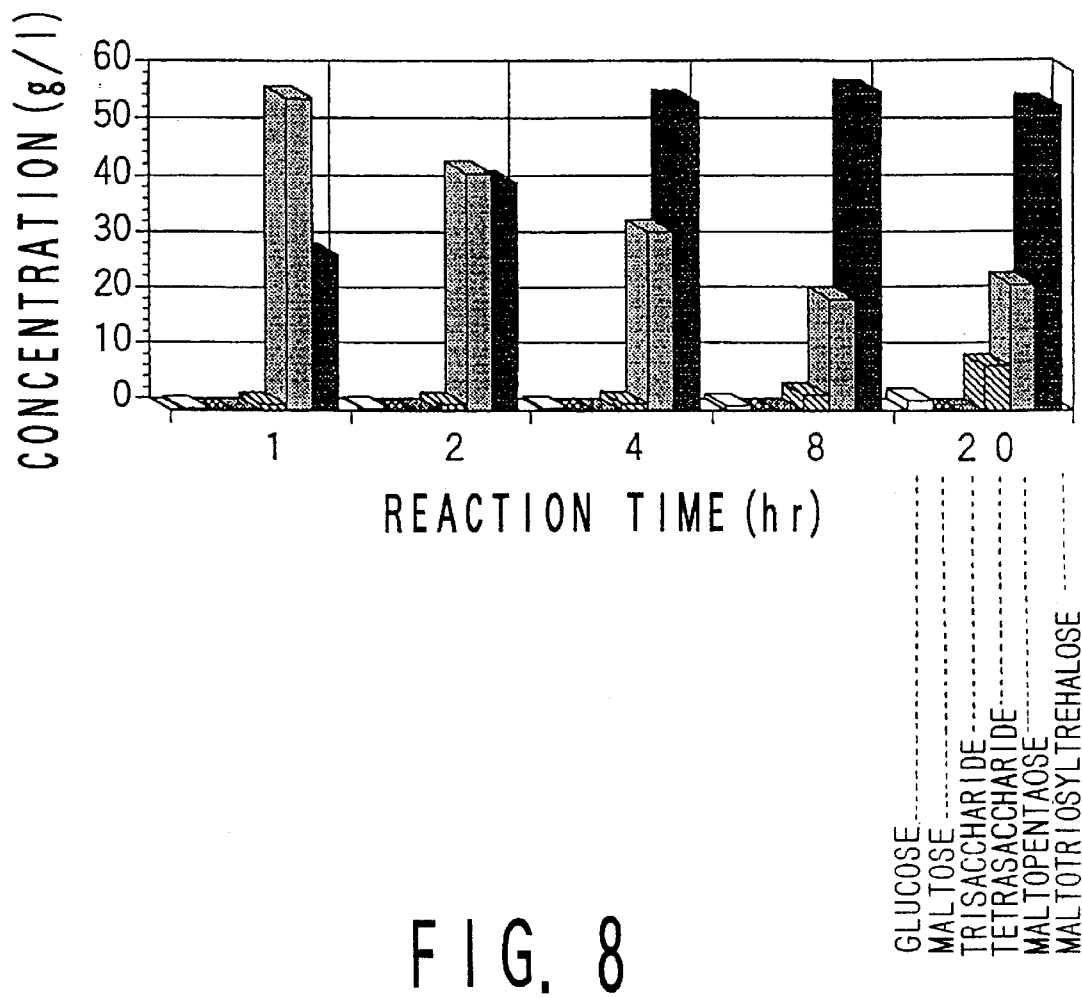
FIG. 8 is a graph showing patterns of reaction products derived from maltopentaose by using the present transferase which is obtained in Example I-2 from the *Sulfolobus solfataricus* strain KM1.

Additionally, the composition of each product which was obtained from G3, G4 or G5 assigned for a substrate was investigated. The results are shown in FIGS. 6–8, respectively.

Specifically, when maltotriose was used as a substrate, glucosyltrehalose was produced as a product in the principal reaction, and in addition, equal moles of maltose and glucose were produced as products in the side reaction.

When the substrate was a saccharide having a polymerization degree, n, which is equal to or higher than that of maltotetraose, the product in the principal reaction was a saccharide, of which the polymerization degree is n, and the glucose residue at the reducing end is α-1,α-1-linked. And in addition, equal moles of glucose and a saccharide having a polymerization degree of n-1 were produced in the side reaction. Additionally, when the reaction further progressed in these saccharides, the saccharide having a polymerization degree of n-1 secondarily underwent the reactions similar to the above. (Incidentally, in FIGS. 7 and 8, saccharides indicated as trisaccharide and tetrasaccharide include non-reacted maltotriose and maltotetraose, respectively, and also include the saccharides, of which the linkage at an end is α-1,α-1, were produced when the reactions similar to the above progressed secondarily.) Meanwhile, the production of such a saccharide as having a polymerization degree of n+1 or higher, namely, an intermolecularly-transferred isomer, was not detected. Incidentally, hydrolysis as the side reaction occurred less frequently when the chain length was the same as or longer than that of G4.

The trisaccharide, the tetrasaccharide and the pentasaccharide which are the principal products from the substrates, G3, G4 and G5, respectively, were sampled by the TSK-gel Amide-80 HPLC column as examples of principal products in the above, and analyzed by $^1$H-NMR and $^{13}$C-NMR. As a result, it was found that the glucose residue at the reducing end of each saccharide was α-1,α-1-linked, and those saccharides were recognized as glucosyltrehalose (α-D-maltosyl α-D-glucopyranoside), maltosyltrehalose (α-D-maltotriosyl α-D-glucopyranoside), and maltotriosyltrehalose (α-D-maltotetraosyl α-D-glucopyranoside), respectively. The chemical formulae of these saccharides are as follows.

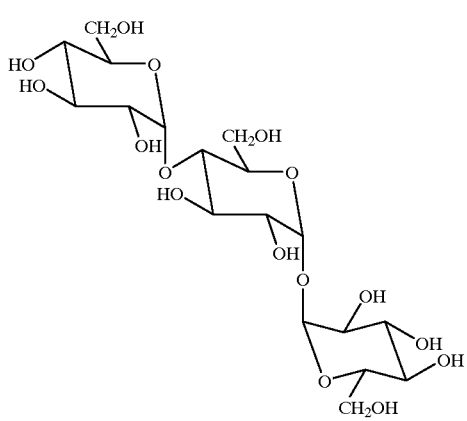

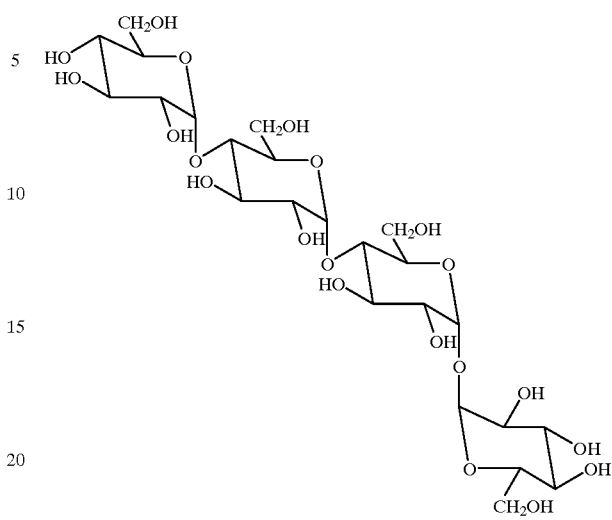

-continued

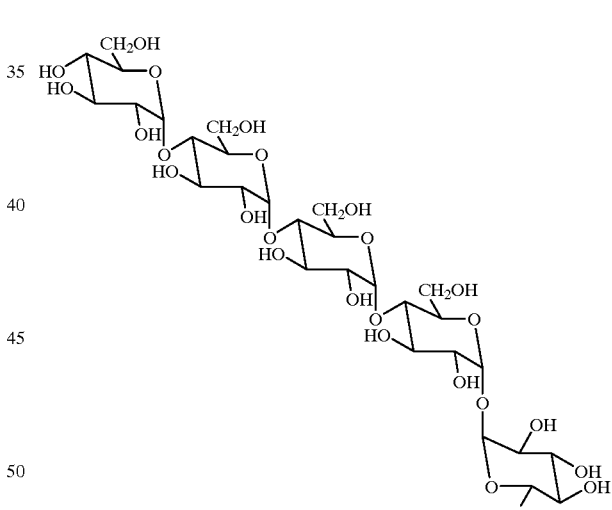

From the above results, it can be concluded that the enzyme of the present invention acts on maltotriose or a larger glucose polymers in which the glucose residues are α-1,4-linked, and transfers the first linkage from the reducing end into an α-1,α-1-linkage. Further, the enzyme of the present invention was found to hydrolyze the first linkage from the reducing end utilizing a $H_2O$ molecule as the receptor to liberate a molecule of glucose, as is often observed in glycosyltransferases.

Example I-8

Production of Glucosyltrehalose and Maltooligosyltrehalose from a Mixture of Maltooligosaccharides Production of glucosyltrehalose and various maltooligosyltrehaloses was attempted by using 10 Units/ml of the purified enzyme obtained in Example I-2, and by using hydrolysate of a soluble starch product (manufactured by Nacalai tesque Co., special grade) with α-amylase as the substrate, wherein the soluble starch product had been hydrolyzed into oligosaccharides which did not exhibit the color of the iodo-starch reaction, by the α-amylase which was the A-0273 derived from *Aspergillus oryzae* manufactured by Sigma Co. The resultant reaction mixture was analyzed by an HPLC analysis method under the conditions below.

Figure 9:
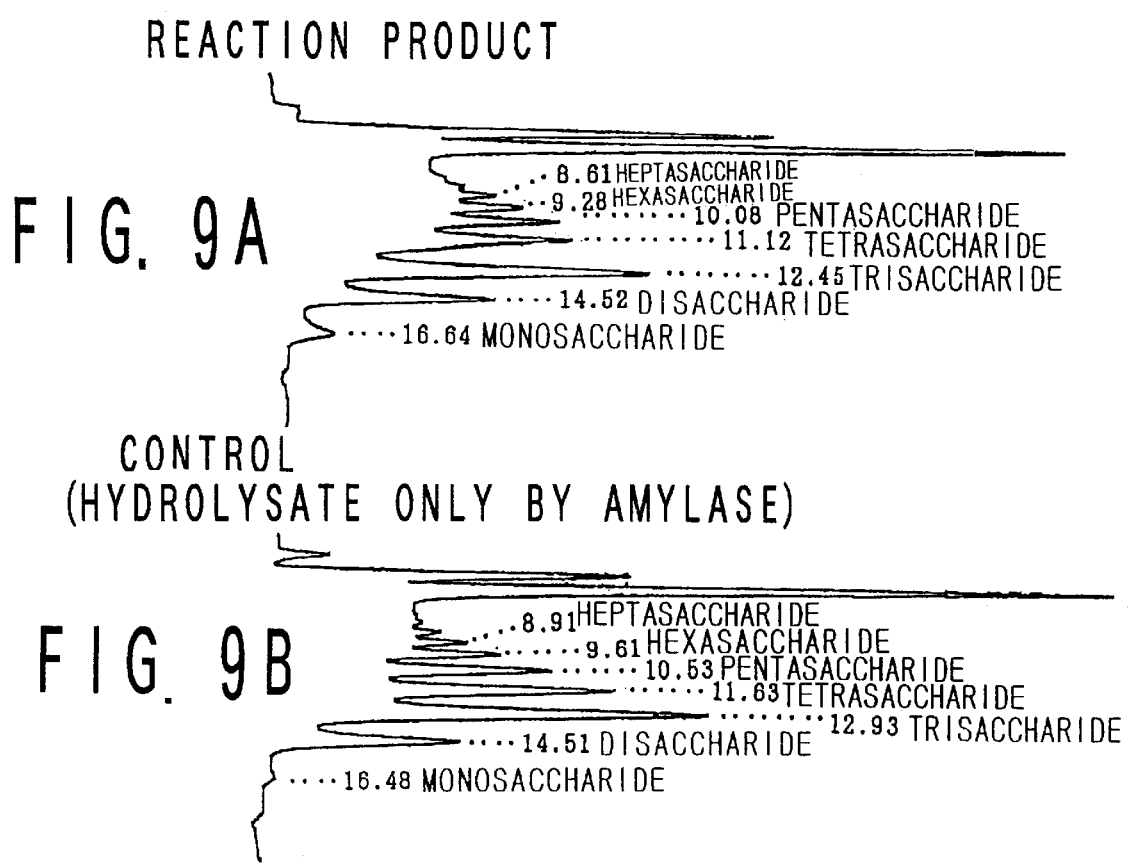
FIGS. 9A, 9B is a graph showing the results of an analysis by AMINEX HPX-42A HPLC, performed on the reaction product derived from a mixture of maltooligosaccharides by using the present transferase which is obtained in Example I-2 from the *Sulfolobus solfataricus* -strain KM1.

Column: BIORAD AMINEX HPX-42A (7.8×300 mm)
Solvent: Water
Flow rate: 0.6 ml/min.
Temperature: 85° C.
Detector: Refractive Index Detector FIG. 9(A) is an HPLC analysis chart obtained herein. As a control, the HPLC chart of the case performed without the addition of the present transferase is shown in FIG. 9(B).

As a result, each of the oligosaccharides as the reaction products was found to have a retention time shorter than that of the control product which was produced using amylase only, wherein the shorter retention time is attributed to the α-1,α-1-transference of the reducing end of the oligosaccharides. Similar to Example I-7, the trisaccharide, the tetrasaccharide and the pentasaccharide were sampled and analyzed by $^1$H-NMR and $^{13}$C-NMR. As a result, it was found that the glucose residue at the reducing end of each saccharide was α-1,α-1-linked, and those saccharides were recognized as glucosyltrehalose (α-D-maltosyl α-D-glucopyranoside), maltosyltrehalose (α-D-maltotriosyl α-D-glucopyranoside), and maltotriosyltrehalose (α-D-maltotetraosyl α-D-glucopyranoside), respectively. The chemical formulae of these saccharides are as follows.

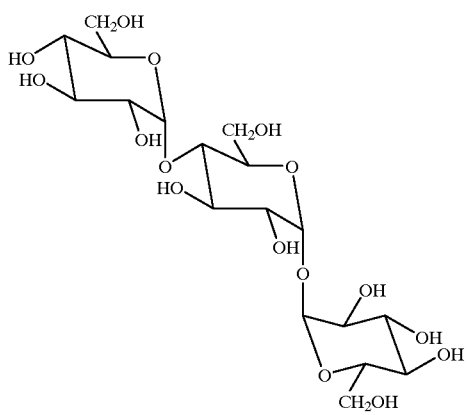

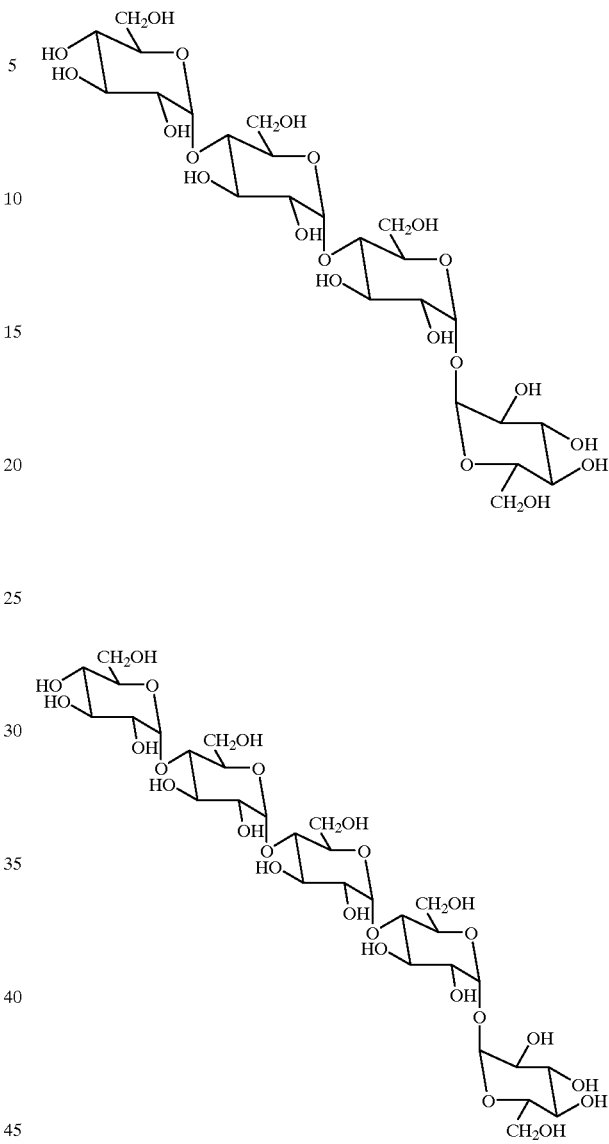

The reagents and materials described below, which were used in Examples II-1–II-14 (including Comparative Examples II-1 and II-2, and Referential Examples II-1–II-4), were obtained from the manufacturers described below, respectively.

α,α-trehalose: manufactured by Sigma Co.

Soluble starch: manufactured by Nacalai tesque Co., special grade

Pullulanase derived from *Klebsiella pneumoniae*: manufactured by Wako pure chemical Co., #165-15651

Pine-dex #1 and Pine-dex #3: manufactured by Matsutani Kagaku Co.

Maltose (G2): manufactured by Wako pure chemical Co.

Maltotriose (G3), Maltotetraose (G4), Maltopentaose (G5), Maltohexaose (G6), Maltoheptaose (G7), and Amylose DP-17: manufactured by Hayashibara Biochemical Co.

Amylopectin: manufactured by Nacalai tesque Co., special grade

Isomaltose: manufactured by Wako pure chemical Co.

Isomaltotriose: manufactured by Wako pure chemical Co.

Isomaltotetraose: manufactured by Seikagaku Kougyou Co.

Isomaltopentaose: manufactured by Seikagaku Kougyou Co.

Panose: manufactured by Tokyo Kasei Kougyou Co.

EXAMPLE II-1

Measurement of Trehaloseoligosaccharide-hydrolyzing Activity and Starch-liquefying Activity Possessed by Archaebacteria The bacterial strains listed in Table 11 below were examined for enzymatic activity. The measurement was performed as follows: The cultivated cells of each bacterial strain were crushed by ultrasonic treatment and centrifuged; maltotriosyltrehalose as a substrate was added to the resultant supernatant, namely, a crude enzyme solution, so that the final concentration of maltotriosyltrehalose would be 10 mM; the mixture thus obtained was subjected to a reaction at 60° C. and pH 5.5 (50 mM sodium acetate buffer solution); the reaction was then stopped by heat-treatment at 100° C. for 5 min.; and the α,α-trehalose thus produced was analyzed by an HPLC method under the conditions below.

Column: TOSOH TSK-gel Amide-80 (4.6×250 mm)

Solvent: 72.5% acetonitrile

Flow rate: 1.0 ml/min.

Temperature: Room temperature

Detector: Refractive index detector

The trehaloseoligosaccharide-hydrolyzing activity is expressed with such a unit as 1 Unit equals the activity of liberating 1 μmol of α,α-trehalose per hour from maltotriosyltrehalose. Incidentally, in Table 11, the activity is expressed in terms of units per one gram of bacterial cell. Here, maltotriosyltrehalose was prepared as follows: The purified transferase derived from the *Sulfolobus solfataricus* strain KM1 was added to a 10% maltopentaose solution containing 50 mM of acetic acid (pH 5.5) so that the concentration of the transferase would be 10 Units/ml; the mixture thus obtained was subjected to a reaction at 60° C. for 24 hours; and the resultant was subjected to the above TSK-gel Amide-80 HPLC column to obtain maltotriosyltrehalose. As to the activity of the purified transferase derived from the *Sulfolobus solfataricus* strain KM1, 1 Unit is defined as equalling the activity of producing 1 μmol of glucosyltrehalose per hour at 60° C. and pH 5.5 when maltotriose is used as the substrate.

Figure 10:
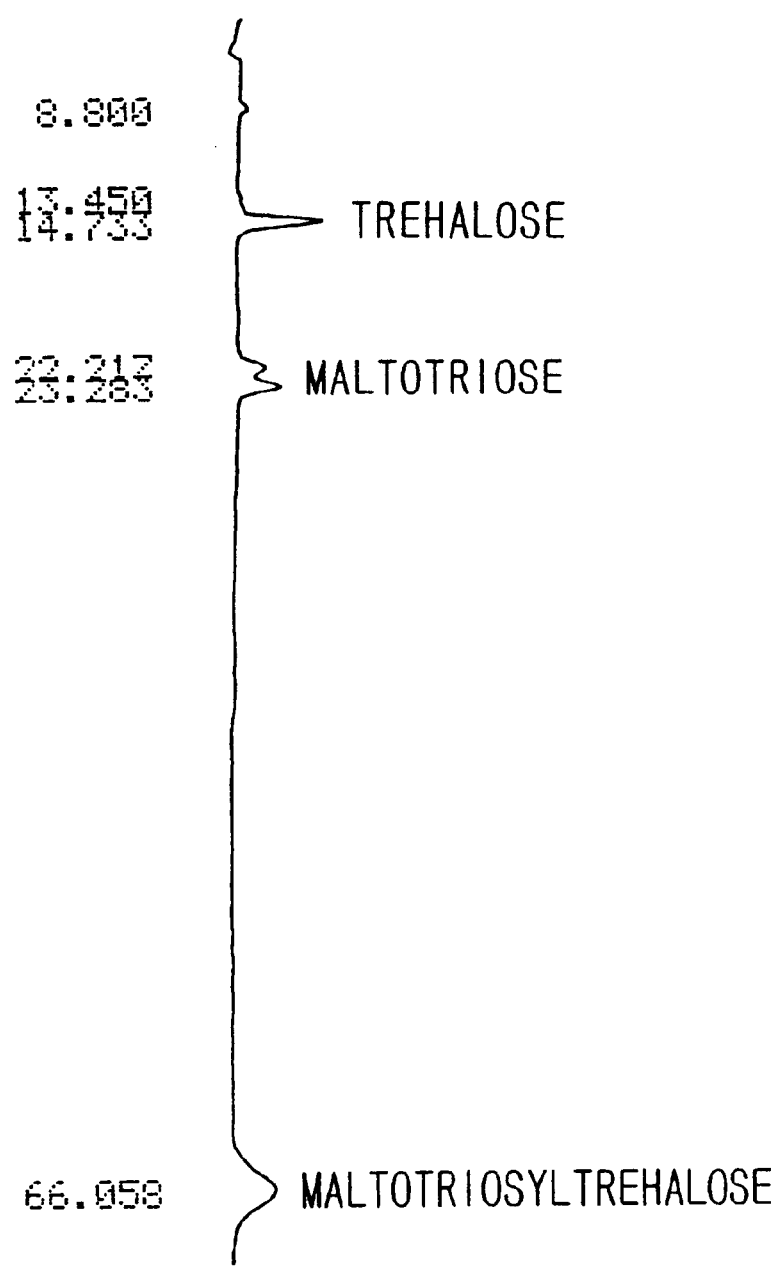
FIG. 10 is a graph showing the results of an analysis by TSK-gel Amide-80 HPLC, performed on the reaction product derived from maltotriosyltrehalose subjected to reaction with the crude enzyme solution which is obtained in Example II-1 from the *Sulfolobus solfataricus* strain KM1.

FIG. 10 is the HPLC chart obtained herein. As is recognized from the figure, a peak exhibiting the same retention time as that of α,α-trehalose without any anomer, and a peak exhibiting the same retention time as that of maltotriose appeared in the chart. Additionally, the product of the former peak was sampled by the TSK-gel Amide-80 HPLC column, and analyzed by $^1$H-NMR and $^{13}$C-NMR. As a result, the product was confirmed to be α,α-trehalose.

Further, 2% soluble starch contained in a 100 mM sodium acetate buffer solution (pH 5.5) was subjected to a reaction with the above crude enzyme solution (the supernatant) at 60° C. by adding 0.5 ml of the supernatant to 0.5 ml of the starch solution. Time-course sampling was performed, and to each sample, twice volume of 1 N HCl was added for stopping the reaction. Subsequently, two-thirds volume of a 0.1% potassium iodide solution containing 0.01% of iodine was added, and further, 1.8-fold volume of water was added. Finally, absorptivity at 620 nm was measured,. and the activity was estimated from the time-course change of the absorptivity.

The saccharides produced in the reaction were analyzed by an HPLC analysis method under the conditions shown below after the reaction was stopped by treatment at 100° C. for 5 min.

Column: BIORAD AMINEX HPX-42A (7.8×300 mm)

Solvent: Water

Flow rate: 0.6 ml/min.

Temperature: 85° C.

Detector: Refractive index detector

As to starch-hydrolyzing activity, 1 Unit is defined as equalling the amount of the enzyme with which the absorptivity at 620 nm corresponding to the violet color of the starch-iodine complex decreases at a rate of 10% per 10 min. Incidentally, in Table 11, the activity was expressed in terms of units per one gram of bacterial cell.

TABLE 11

| Strain | | Enzyme activity (units/g-cell) | |
| --- | --- | --- | --- |
| | | Hydrolyzing activity of starch | Hydrolyzing activity of trehalose oligosaccharide |
| *Sulfolobus solfataricus* | ATCC 35091 | 13.3 | 118.0 |
| | DSM 5354 | 13.3 | 116.8 |
| | DSM 5833 | 8.4 | 94.9 |
| | KM1 | 13.4 | 293.2 |
| *Sulfolobus acidocaldarius* | ATCC 33909 | 12.5 | 161.8 |
| *Sulfolobus shibatae* | DSM 5389 | 11.2 | 281.2 |

Figure 11:
FIG. 11 is a graph showing the results of an analysis by AMINEX HPX-42A HPLC, performed on the reaction product derived from soluble starch subjected to reaction with the crude enzyme solution which is obtained in Example II-1 from the *Sulfolobus solfataricus* strain KM1.

FIG. 11 shows the results of an analysis by AMINEX HPX-42A HPLC performed on the products by the reaction with the crude enzyme solution derived from the *Sulfolobus solfataricus* strain KM1.

From the above results, the cell extract of a bacterial strain belonging to the genus Sulfolobus was found to have an activity of hydrolyzing trehaloseoligosaccharides to liberate α,α-trehalose, and an activity of hydrolyzing starch to liberate principally monosaccharides or disaccharides.

EXAMPLE II-2

Purification of the Present Amylase Derived from the *Sulfolobus solfataricus* Strain KM1

The *Sulfolobus solfataricus* strain KM1 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80° C. The yield of the bacterial cell was 3.3 g/liter.

Two hundred grams of the bacterial cells obtained above were suspended in 400 ml of a 50 mM sodium acetate buffer solution (pH 5.5) containing 5 mM of EDTA, and subjected to ultrasonic treatment for bacteriolysis at 0° C. for 15 min. The resultant was then centrifuged to obtain a supernatant, and ammonium sulfate was added to the supernatant so as to be 60% saturation.

The precipitate obtained by centrifugation was dissolved in a 50 mM sodium acetate buffer solution (pH 5.5) containing 1 M of ammonium sulfate and 5 mM of EDTA, and subjected to hydrophobic chromatography using the TOSOH TSK-gel Phenyl-TOYOPEARL 650S column (volume: 800 ml) equilibrated with the same buffer solution as above. The column was then washed with the same buffer solution, and the objective amylase was eluted with 600 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM Tris-HCl buffer solution (pH 7.5).

Next, the resultant was subjected to ion-exchange chromatography using the TOSOH TSK-gel DEAE-TOYOPEARL 650S column (volume: 300 ml).equilibrated with the same buffer solution. The column was then washed with the same buffer solution, and the objective amylase was eluted with 900 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM of EDTA.

Subsequent to that, the desalted and concentrated solution thus obtained was subjected to gel filtration chromatography using the Pharmacia HiLoad 16/60 Superdex 200 pg column, and the objective amylase was eluted with the same buffer solution. The fractions exhibiting the activity were concentrated using an ultrafiltration membrane (critical molecular weight: 13,000), and subsequently, washed and desalted with a 25 mM Bis-Tris-HCl buffer solution (pH 6.3).

Next, the desalted and concentrated solution thus obtained was subjected to a chromatofocusing using the Pharmacia Mono P HR/5/20 column equilibrated with the same buffer solution. The objective amylase was then eluted with 10% polybuffer 74 (manufactured by Pharmacia Co., and adjusted at pH 4.0 with HCl ). The fractions exhibiting the activity were concentrated using an ultrafiltration membrane (critical molecular weight: 13,000), and subsequently, washed and desalted with a 10 mM sodium acetate buffer solution (pH 6.8).

Further, to this desalted and concentrated solution, a quarter volume of a sample buffer [62.5 mM Tris-HCl buffer solution (pH 6.8), 10% glycerol, 2% SDS, and 0.0125% Bromophenolblue] was added, and subjected to 10% SDS-Polyacrylamide gel electrophoresis (SDS-PAGE) (apparatus: BIO-RAD Prep Cell Model 491) to elute the objective amylase. The fractions exhibiting the activity were separated and concentrated using an ultrafiltration membrane (critical molecular weight: 13,000), and subsequently, washed and desalted with a 10 mM sodium acetate buffer solution (pH 5.5).

Finally, Native polyacrylamide gel electrophoresis, SDS-polyacrylamide gel electrophoresis and isoelectric focusing were performed to obtain the purified enzyme which appeared as single band.

Incidentally, for the activity measurement, in this purification procedure, maltotriosyltrehalose was used as the substrate, and the same manner as in the TSK-gel Amide-80 HPLC analysis method shown in Example II-1 was employed.

Total enzyme activity, total protein and specific activity at each of the purification steps are shown in Table 12 below.

TABLE 12

| Purified fraction | Total enzyme activity (units) | Total protein (mg) | Specific activity (units/mg) | Yield (%) | Purity (fold) |
| --- | --- | --- | --- | --- | --- |
| 60% saturated (NH$_4$)$_2$SO$_4$ precipitation | 58640 | 17000 | 3.45 | 100 | 1 |
| Phenyl | 52251 | 1311 | 39.9 | 89 | 12 |
| DEAE | 49284 | 195 | 253 | 84 | 73 |
| Gel-permeation | 2197 | 26.7 | 82.2 | 3.7 | 24 |
| Mono P | 1048 | 0.40 | 2640 | 1.8 | 765 |
| SDS-PAGE | 401 | 0.08 | 5053 | 0.7 | 1465 |

EXAMPLE II-3

Purification of the Present Amylase Derived from the *Sulfolobus solfataricus* Strain DSM 5833

The *Sulfolobus solfataricus* strain DSM 5833 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80° C. The yield of the bacterial cell was 1.2 g/liter.

Twenty five grams of the bacterial cells obtained above were suspended in 50 ml of a 50 mM sodium acetate buffer solution (pH 5.5) containing 5 mM of EDTA, and subjected to ultrasonic treatment for bacteriolysis at 0° C. for 15 min. The resultant was then centrifuged to obtain a supernatant.

To this supernatant, ammonium sulfate was added so as to be 1 M. The resultant was then subjected to hydrophobic chromatography using TOSOH TSK-gel Phenyl-TOYOPEARL 650S column (volume: 100 ml) equilibrated with a 50 mM sodium acetate buffer solution (pH 5.5) containing 1 M of sodium sulfate and 5 mM of EDTA. The column was then washed with the same buffer solution, and the objective amylase was eluted with 300 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM Tris-HCl buffer solution (pH 7.5).

Next, the resultant was subjected to ion-exchange chromatography using the TOSOH TSK-gel DEAE-TOYOPEARL 650S column (volume: 100 ml) equilibrated with the same buffer solution. The column was then washed with the same buffer solution, and the objective amylase was eluted with 300 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM of EDTA.

Subsequent to that, the desalted and concentrated solution thus obtained was subjected to gel filtration chromatography using the Pharmacia HiLoad 16/60 Superdex 200 pg column, and the objective amylase was eluted with the same buffer solution. The fractions exhibiting the activity were concentrated using an ultrafiltration membrane (critical molecular weight: 13,000), and subsequently, washed and desalted with a 25 mM Bis-Tris-iminodiacetic acid buffer solution (pH 7.1).

Next, the desalted and concentrated solution thus obtained was subjected to a chromatofocusing using the Pharmacia Mono P HR5/20 column equilibrated with the same buffer solution. The objective amylase was then eluted with 10% Polybuffer 74 (manufactured by Pharmacia, and adjusted at pH 4.0 with iminodiacetic acid). The fractions exhibiting the activity were concentrated using an ultrafiltration membrane (critical molecular weight: 13,000), and subsequently, washed and desalted with a 25 mM bis-Tris-iminodiacetic acid buffer solution (pH 7.1).

Further, the desalted and concentrated solution thus obtained was subjected to a chromatofocusing using the Pharmacia Mono P HR5/20 column equilibrated with the same buffer solution. The objective amylase was then eluted with 10% Polybuffer 74 (manufactured by Pharmacia, and adjusted at pH 4.0 with iminodiacetic acid). The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM of EDTA.

Moreover, the desalted and concentrated solution thus obtained was subjected to gel filtration chromatography using the TSK-gel G3000SW HPLC column, and the objective amylase was then eluted with the same buffer solution. The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Finally, Native Polyacrylamide gel electrophoresis, SDS-Polyacrylamide gel electrophoresis and isoelectric focusing were performed to obtain the purified enzyme which appeared as single band.

Incidentally, for the activity measurement, in this purification procedure, maltotriosyltrehalose was used as the substrate, and the same manner as in the TSK-gel Amide-80 HPLC analysis method shown in Example II-1 was employed.

Total enzyme activity, total protein and specific activity at each of the purification steps are shown in Table 13 below.

TABLE 13

| Purified fraction | Total enzyme activity (units) | Total protein (mg) | Specific activity (units/mg) | Yield (%) | Purity (fold) |
| --- | --- | --- | --- | --- | --- |
| Crude extract | 3345 | 1394 | 2.40 | 100 | 1 |
| Phenyl | 2112 | 266 | 7.9 | 63 | 3.3 |
| DEAE | 1365 | 129 | 10.6 | 41 | 4.4 |
| Gel-permeation | 651 | 7.8 | 83.5 | 19 | 35 |
| Mono P | 467 | 0.76 | 612 | 14 | 255 |
| Mono P rechromatography | 156 | 0.12 | 1301 | 4.7 | 542 |
| Gel-permeation rechromatography | 98 | 0.01 | 13652 | 2.9 | 5687 |

EXAMPLE II-4

Purification of the Present Amylase Derived from the *Sulfolobus acidocaldarius* Strain ATCC 33909

The *Sulfolobus acidocaldarius* strain ATCC 33909 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80C. The yield of the bacterial cell was 2.7 g/liter.

Twenty five grams of the bacterial cells obtained above were suspended in 50 ml of a 50 mM sodium acetate buffer solution (pH 5.5) containing 5 mM of EDTA, and subjected to ultrasonic treatment for bacteriolysis at 0° C. for 15 min. The resultant was then centrifuged to obtain a supernatant.

To this supernatant, ammonium sulfate was added so as to be 1 M. The resultant was then subjected to hydrophobic chromatography using TOSOH TSK-gel Phenyl-TOYOPEARL 650S column (volume: 100 ml) equilibrated with a 50 mM sodium acetate buffer solution (pH 5.5) containing 1 M of sodium sulfate and 5 mM of EDTA. The column was then washed with the same buffer solution, and the objective amylase was eluted with 300 ml of ammonium sulfate solution at a linear concentration gradient from 1 M to 0 M. The fractions exhibiting the activity were concentrated using an ultrafiltration membrane (critical molecular weight: 13,000), and subsequently, washed and desalted with a 10 mM Tris-HCl buffer solution (pH 7.5). p Next, the resultant was subjected to ion-exchange chromatography using the TOSOH TSK-gel DEAE-TOYOPEARL 650S column (volume: 100 ml) equilibrated with the same buffer solution. The column was then washed with the same buffer solution, and the objective amylase was eluted with 300 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM of EDTA.

Subsequent to that, the desalted and concentrated solution thus obtained was subjected to gel filtration chromatography using the Pharmacia HiLoad 16/60 Superdex 200 pg column, and the objective amylase was eluted with the same buffer solution. The fractions exhibiting the activity were concentrated using an ultrafiltration membrane (critical molecular weight: 13,000), and subsequently, washed and desalted with a 50 mM sodium acetate buffer solution (pH 5.5).

Next, ammonium sulfate was dissolved in the desalted and concentrated solution so that the concentration of ammonium sulfate would be 1M. The resultant was then subjected to hydrophobic chromatography using TOSOH TSK-gel Phenyl-5PW HPLC column equilibrated with the same buffer solution. The column was then washed with the same buffer solution, and the objective amylase was eluted with 30 ml of ammonium sulfate solution at a linear concentration gradient from 1 M to 0 M. The fractions exhibiting the activity were concentrated using an ultiafiltration membrane (critical molecular weight: 13,000), and subsequently, washed and desalted with a 25 mM bis-Tris-iminodiacetic acid buffer solution (pH 7.1).

Further, the desalted and concentrated solution thus obtained was subjected to a chromatofocusing using the Pharmacia Mono P HR5/20 column equilibrated with the same buffer solution. The objective amylase was then eluted with 10% Polybuffer 74 (manufactured by Pharmacia, and adjusted at pH 4.0 with iminodiacetic acid). The fractions exhibiting the activity were concentrated using an ultrafiltration membrane (critical molecular weight: 13,000), and subsequently, washed and desalted with a 50 mM sodium acetate buffer solution (pH 5.5) containing 5 mM of EDTA.

Finally, Native Polyacrylamide gel electrophoresis, SDS-Polyacrylamide Polyacrylamide gel electrophoresis and isoelectric focusing were performed to obtain the purified enzyme which appeared as single band.

Incidentally, for the activity measurement, in this purification procedure, maltotriosyltrehalose was used as the substrate, and the same manner as in the TSK-gel Amide-80 HPLC analysis method shown in Example II-1 was employed.

Total enzyme activity, total protein and specific activity at each of the purification steps are shown in Table 14 below.

TABLE 14

| Purified fraction | Total enzyme activity (units) | Total protein (mg) | Specific activity (units/mg) | Yield (%) | Purity (fold) |
| --- | --- | --- | --- | --- | --- |
| Crude extract | 4534 | 760 | 5.97 | 100 | 1 |
| Phenyl | 2428 | 88.0 | 27.6 | 54 | 4.6 |
| DEAE | 927 | 9.20 | 101 | 20 | 17 |
| Gel-permeation | 600 | 1.10 | 546 | 13 | 92 |
| Phenyl rechromatography | 392 | 0.16 | 2449 | 9.1 | 411 |
| Mono P | 120 | 0.04 | 3195 | 2.6 | 558 |

EXAMPLE II-5

Examination of the Present Amylase for Various Characteristics

The purified enzyme obtained in Example II-2 was examined for enzymatic characteristics.

(1) Molecular Weight

The molecular weight was measured by SDS-polyacrylamide gel electrophoresis (gel concentration; 6%). Marker proteins having molecular weights of 200,000, 116, 300, 97,400, 66,300, 55,400, 36,500, 31,000, 21,500 and 14,400, respectively, were used.

As a result, the molecular weight of the amylase was estimated at 61,000.

(2) Isoelectric Point

The isoelectric point was found to be pH 4.8 by agarose gel isoelectric focusing.

(3) Stability

Figure 12:
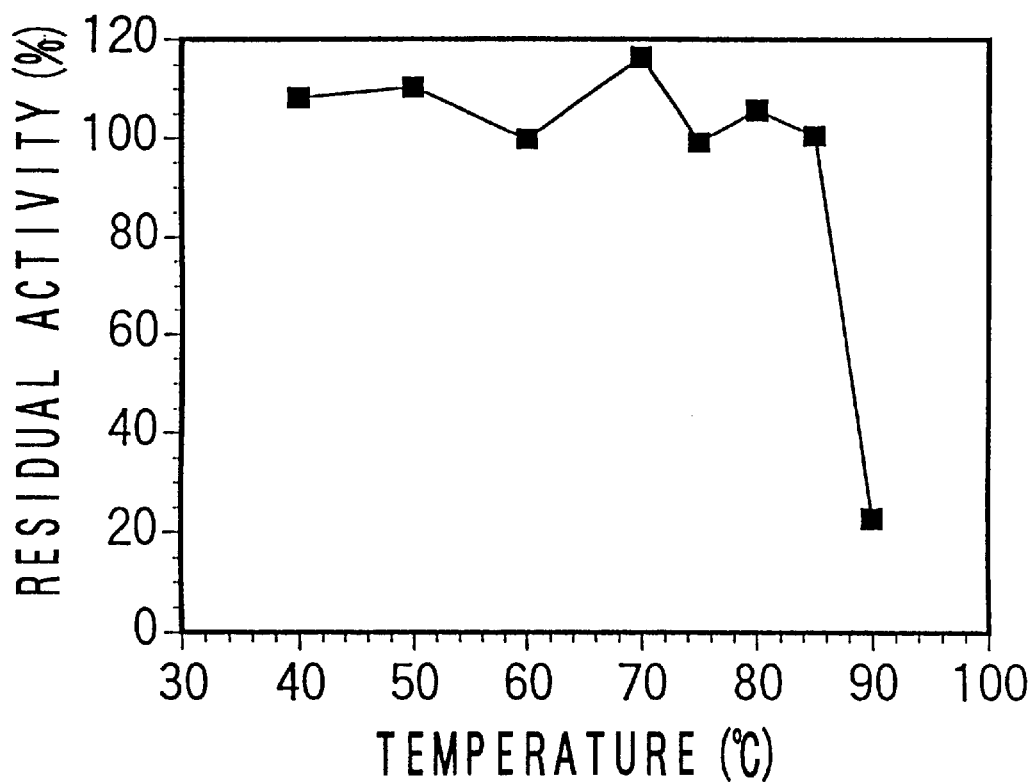
FIG. 12 is a graph showing thermostability of the present amylase which is obtained in Example II-2 from the *Sulfolobus solfataricus* strain KM1.
Figure 13:
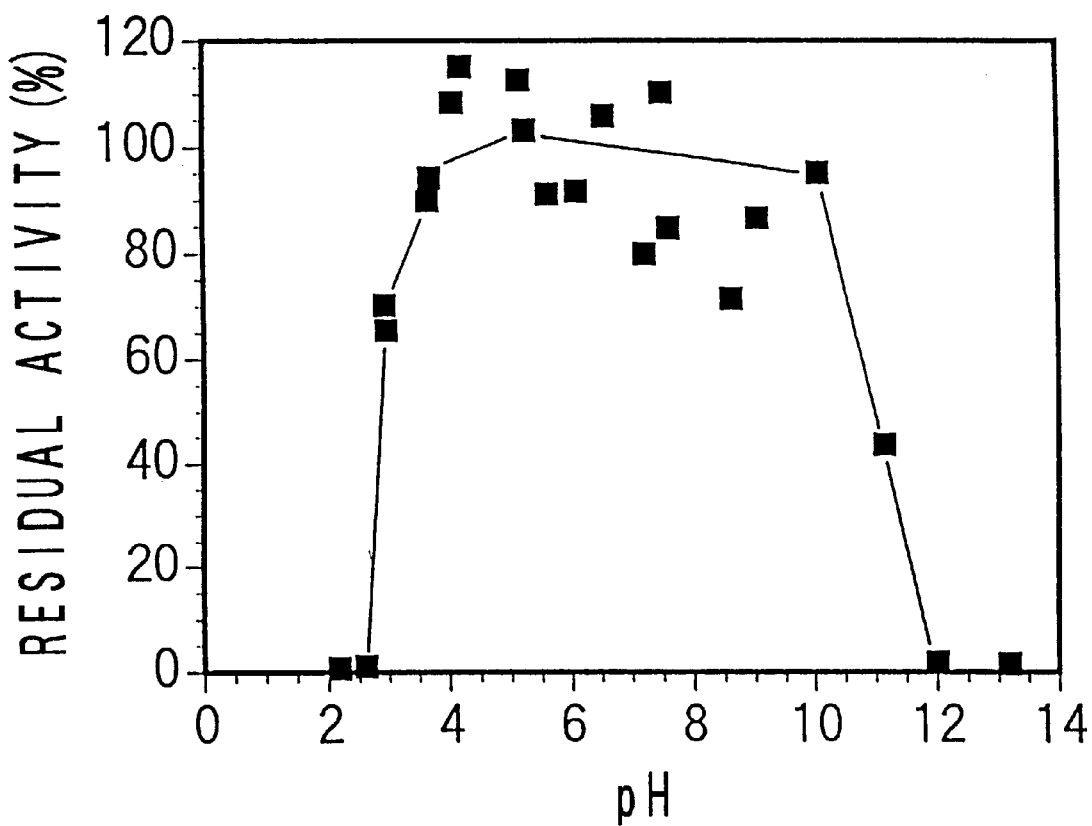
FIG. 13 is a graph showing pH stability of the present amylase which is obtained in Example II-2 from the *Sulfolobus solfataricus* strain KM1.

The stability changes of the obtained enzyme according to temperature and pH value are shown in FIGS. 12 and 13, respectively. The measurement of enzymatic activity was carried out according to the measurement method in Example II-1 using maltotriosyltrehalose, and a glycine-HCl buffer solution was used in a pH range of 3–5, and similarly, a sodium acetate buffer solution in a pH range of 4–6, a sodium phosphate buffer solution in a pH range of 5–8, a Tris-HCl buffer solution in a pH range of 8–9, a sodium bicarbonate buffer solution in a pH range of 9–10, and a KCl-NaOH buffer solution in a pH range of 11–13.5, respectively, were also used.

The present enzyme was stable throughout the treatment at 85° C. for 6 hours, and also, was stable throughout the treatment at pH 3.5–10.0 and room temperature for 6 hours.

(4) Reactivity

Figure 14:
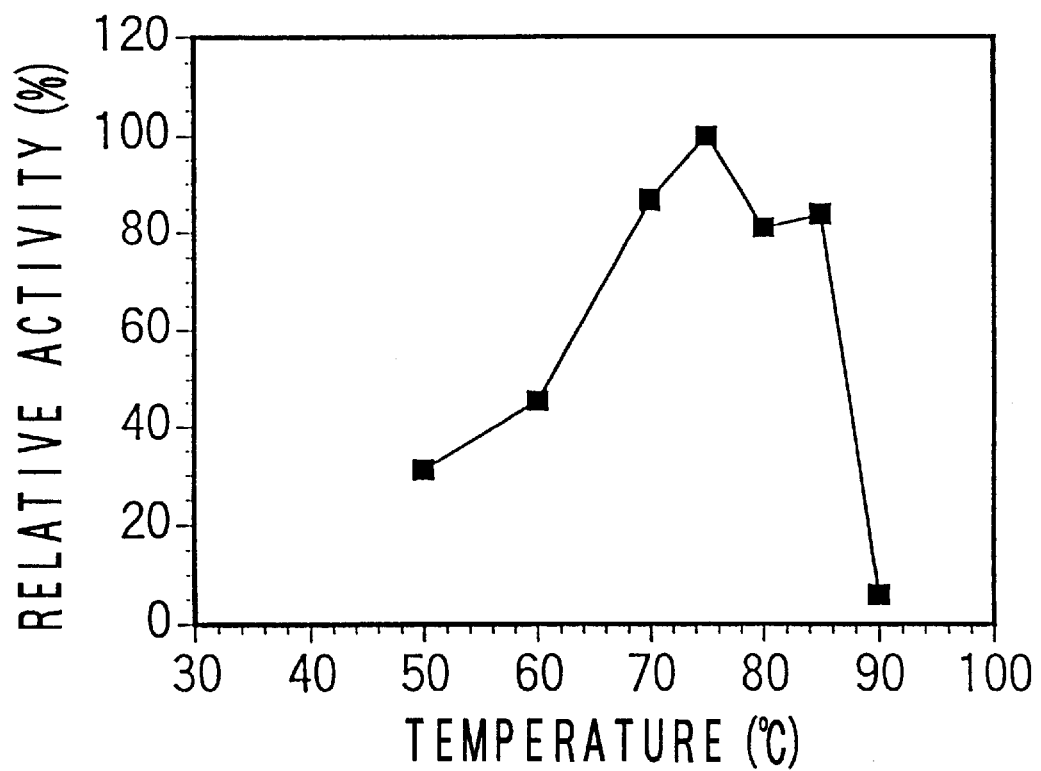
FIG. 14 is a graph showing reactivity of the present amylase which is obtained in Example II-2 from the *Sulfolobus solfataricus* strain KM1, examined at each reaction temperature.
Figure 15:
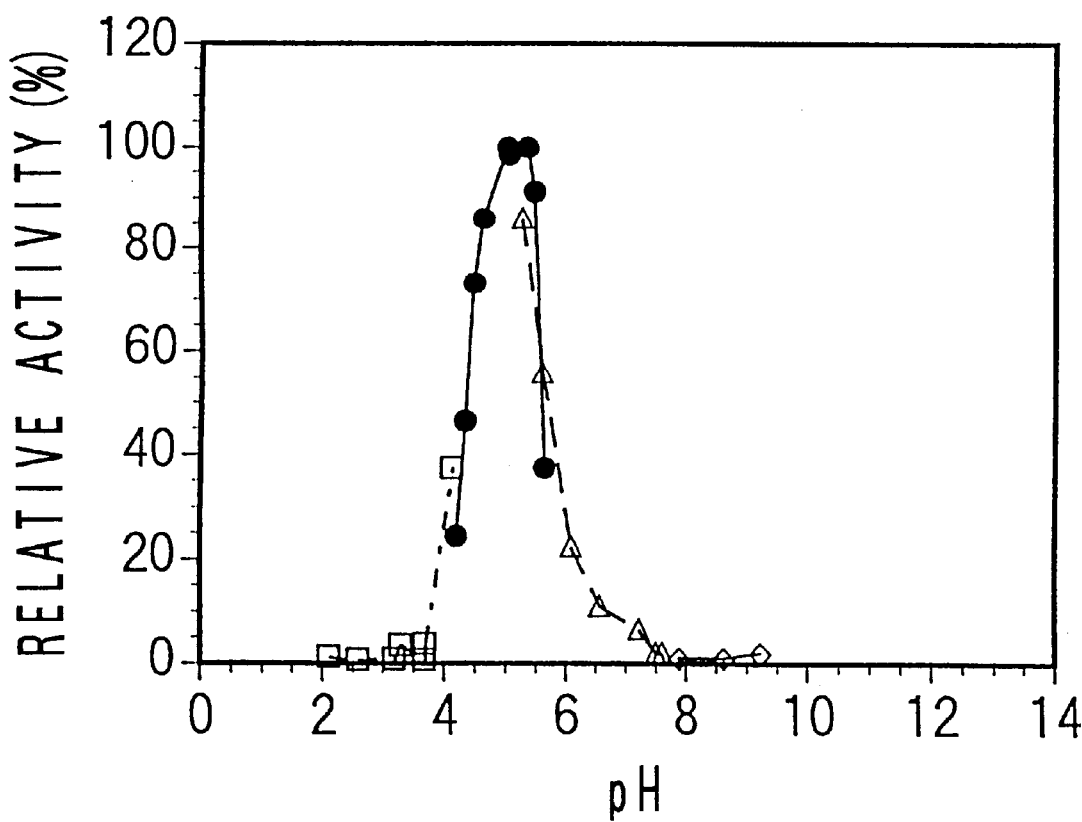
FIG. 15 is a graph showing optimum pH for reaction of the present amylase which is obtained in Example II-2 from the *Sulfolobus solfataricus* strain KM1.
Figure 16:
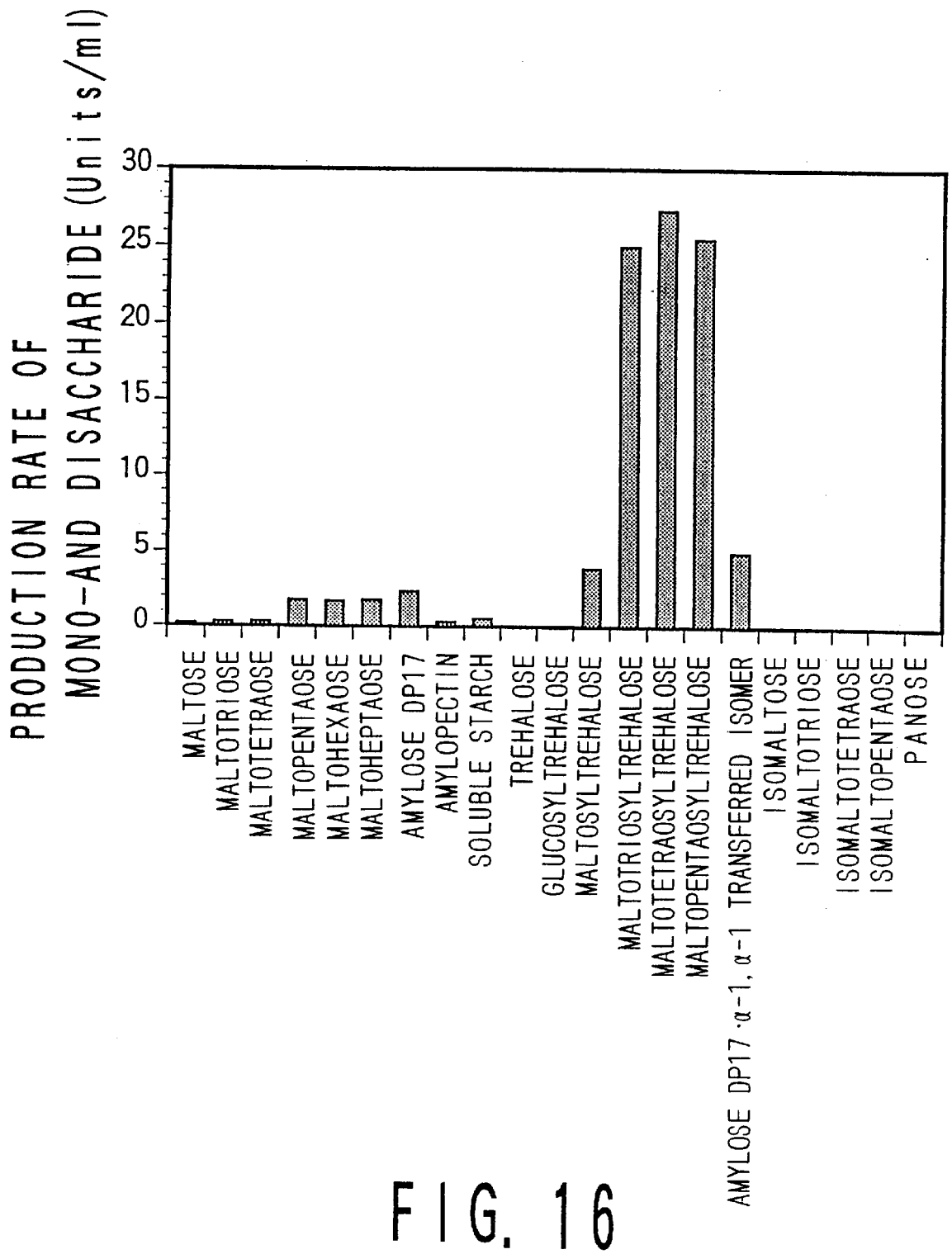
FIG. 16 is a graph showing reactivity of the present amylase to various substrates, the amylase being obtained in Example II-2 from the *Sulfolobus solfataricus* strain KM1 .

As to the obtained enzyme, reactivity at various temperatures and reactivity at various pH are shown in FIGS. 14 and 15, respectively. The measurement of enzymatic activity was carried out according to the measurement method in Example II-1 using maltotriosyltrehalose, and a sodium citrate buffer solution was used in a pH range of 2–4 (□), and similarly, a sodium acetate buffer solution in a pH range of 4–5.5 (●), a sodium phosphate buffer solution in a pH range of 5–7.5 (Δ), and a Tris-HCl buffer solution in a pH range of 8–9 (◇), respectively, were also used.

The optimum reaction temperature of the present enzyme is within 70–85° C., approximately, and the optimum reaction pH of the present enzyme is within 4.5–5.5, approximately.

(5) Influence of various Activators and Inhibitors

The influence of each substance listed in Table 15, such as an activating effect or inhibitory effect, was evaluated using similar activity-measuring method to that in Example II-1. Specifically, the listed substances were individually added together with the substrate to the same reaction system as that in the method for measuring maltotriosyltrehalose-hydrolyzing activity employed in Example II-1. As a result, copper ion and sodium dodecyl sulfate (SDS) were found to have inhibitory effects. As to the inhibitory effect by SDS, however, the enzymatic activity revived after SDS was removed by dialysis, ultrafiltration or the like. Though many glucide-relating enzymes have been found to be activated with calcium ion, the present enzyme would not be activated with calcium ion.

TABLE 15

| Activator/Inhibitor | Concentration (mM) | Residual activity (%) |
| --- | --- | --- |
| Control (not added) | | 100.0 |
| CaCl$_2$ | 5 | 97.1 |
| MgCl$_2$ | 5 | 93.5 |
| MnCl$_2$ | 5 | 101.8 |
| CuSO$_4$ | 5 | 0 |
| CoCl$_2$ | 5 | 97.1 |
| FeSO$_4$ | 5 | 73.5 |
| FeCl$_3$ | 5 | 38.0 |
| AgNO$_3$ | 5 | 105.7 |
| EDTA | 5 | 106.3 |
| 2-Mercaptoethanol | 5 | 141.7 |
| Dithiothreitol | 5 | 116.2 |
| SDS | 5 | 0 |
| Glucose | 0.5 | 109.4 |
| α,α-Trehalose | 0.5 | 98.2 |
| Maltotetraose | 0.5 | 108.5 |
| Malatopentaose | 0.5 | 105.8 |
| Maltohexaose | 0.5 | 123.8 |
| Maltoheptaose | 0.5 | 129.2 |

(6) Substrate Specificity

The hydrolyzing properties were analyzed by allowing 25.0 Units/ml (in terms of the enzymatic activity when maltotriosyltrehalose is used as the substrate) of the present purified enzyme to act on the various 10 mM substrates (except amylopectin and soluble starch were used as 2.8% solutions) listed in Table 16 below, and the hydrolyzed products were also analyzed. The analysis was performed by TSK-gel Amide-80 HPLC described in Example II-1, wherein the index was the activity of producing both monosaccharide and disaccharide when the substrate was each of the various maltooligosaccharides, Amylose DP-17, amylopectin, soluble starch, various isomaltooligosaccharides, and panose; the activity of producing α,α-trehalose when the substrate was each of the various trehaloseoligosaccharides, and α-1,α-1-transferred isomer of Amylose DP-17 (the oligosaccharide derived from Amylose DP-17 by transferring the linkage between the first and second glucose residues from the reducing end into an α-1,α-1 linkage); and the activity of producing glucose when the substrate was maltose or α,α-trehalose.

Incidentally, each enzymatic activity in Table 16 is expressed with such a unit as 1 Unit equals the activity of liberating 1 μmol of each of the monosaccharide and disaccharide per hour.

The results are as shown in Table 16 below and in FIGS. 16–19.

TABLE 16

| Substrate | Liberated oligosaccharide | Production rate of mono- and disaccharides (units/ml) |
| --- | --- | --- |
| Maltose (G2) | Glucose | 0.19 |
| Maltotriose (G3) | Glucose + G2 | 0.30 |
| Maltotetraose (G4) | Glucose + G2 + G3 | 0.31 |
| Maltopentaose (G5) | Glucose + G2 + G3 + G4 | 1.79 |
| Maltohexaose (G6) | Glucose + G2 + G4 + G5 | 1.74 |
| Maltoheptaose (G7) | Glucose + G2 + G5 + G6 | 1.80 |
| Amylose DP-17 | Glucose + G2 | 2.35 |
| Amylopectin | Glucose + G2 | 0.33 |
| Soluble starch | Glucose + G2 | 0.55 |
| α,α-Trehalose | not decomposed | 0 |
| Glucosyltrehalose | Glucose + Trehalose | 0.04 |
| Maltosyltrehalose | G2 + Trehalose | 3.93 |
| Maltotriosyltrehalose | G3 + Trehalose | 25.0 |
| Maltotetraosyltrehalose | G4 + Trehalose | 27.3 |
| Maltopentaosyltrehalose | G5 + Trehalose | 25.5 |
| Amylose DP-17, α-1, α-1-transferred isomer | Trehalose | 4.98 |
| Isomaltose | not decomposed | 0 |
| Isomaltotriose | not decomposed | 0 |
| Isomaltotetraose | not decomposed | 0 |
| Isomaltopentaose | not decomposed | 0 |
| Panose | not decomposed | 0 |

Notes: Each of glucosyltrehalose, maltosyltrehalose, maltotetraosyltrehalose, maltopentaosyltrehalose, and α-1, α-1-transferred isomer of Amylose DP-17 was prepared according to the method for preparing maltotriosyltrehalose in Example II-1.

Figure 17A:
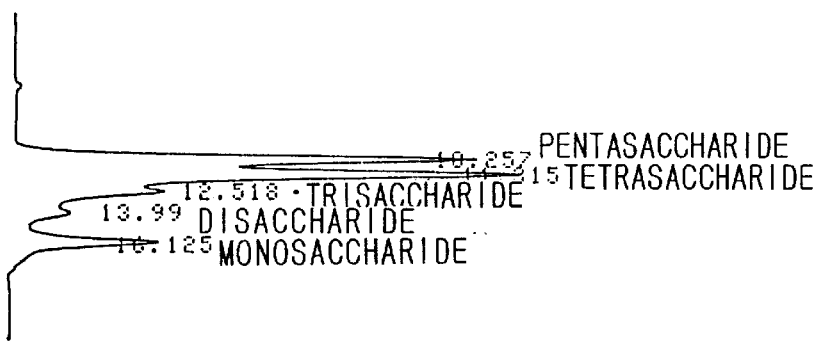
FIGS. 17A, 17B, 17C contains graphs showing the results of analyses by AMINEX HPX-42A HPLC, performed on the reaction products derived from maltopentaose, Amylose DP-17, and soluble starch, respectively, subjected to reaction with the present amylase which is obtained in Example II-2 from the *Sulfolobus solfataricus* strain KM1.
Figure 17B:
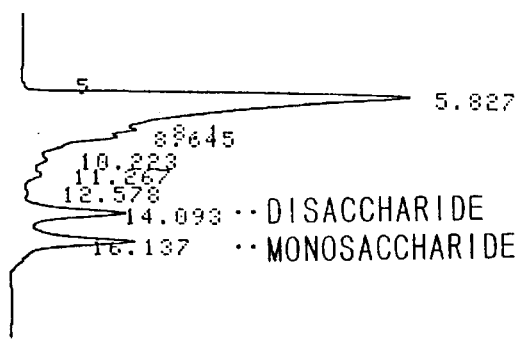
Figure 17C:
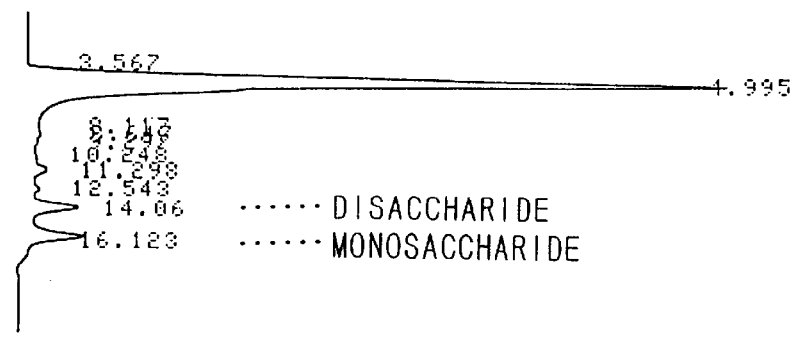
Figure 18:
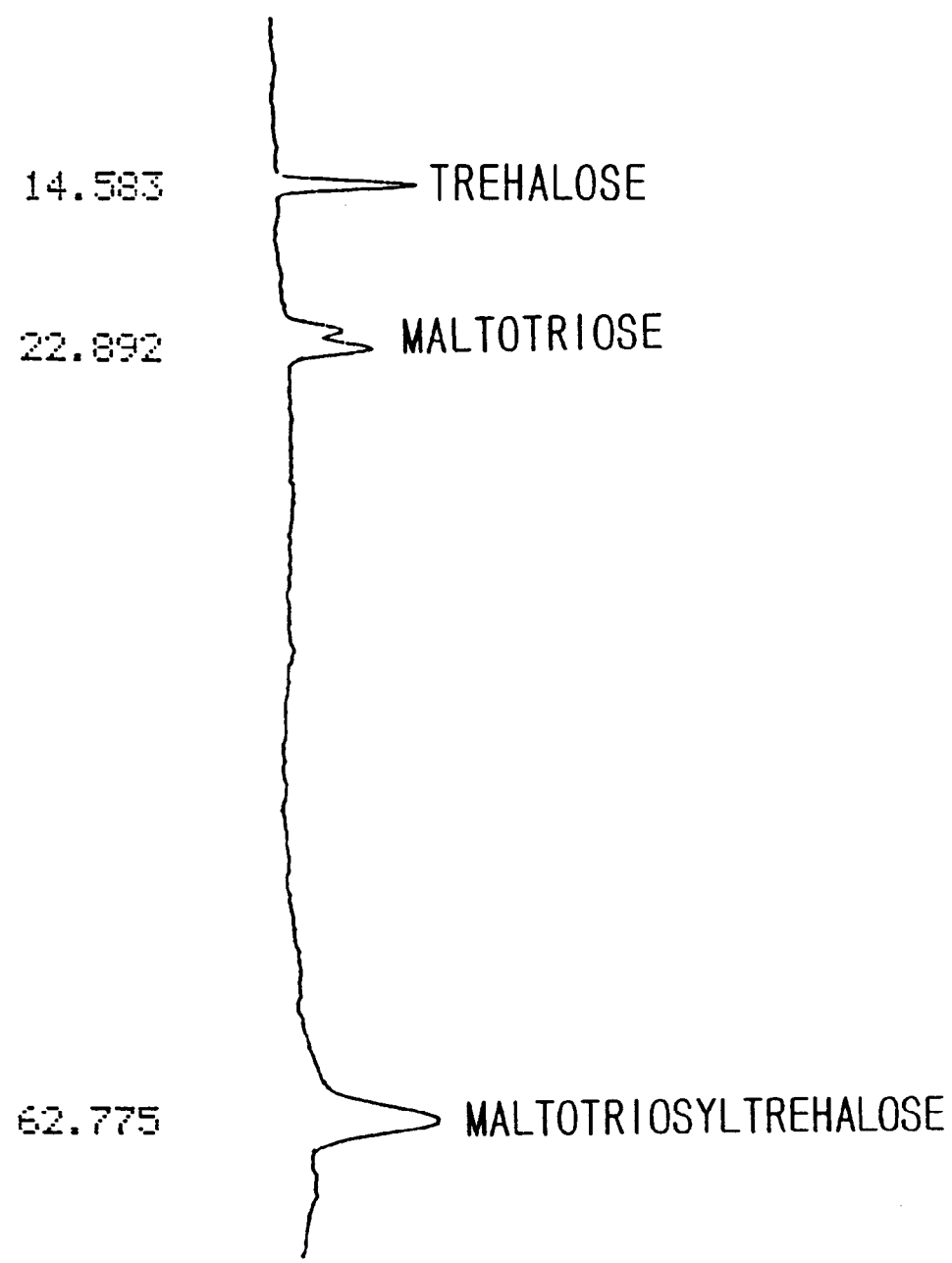
FIG. 18 is a graph showing the results of an analysis by TSK-gel Amide-80 HPLC, performed on the reaction product derived from maltotriosyltrehalose subjected to reaction with the present amylase which is obtained in Example II-2 from the *Sulfolobus solfataricus* strain KM1.
Figure 19:
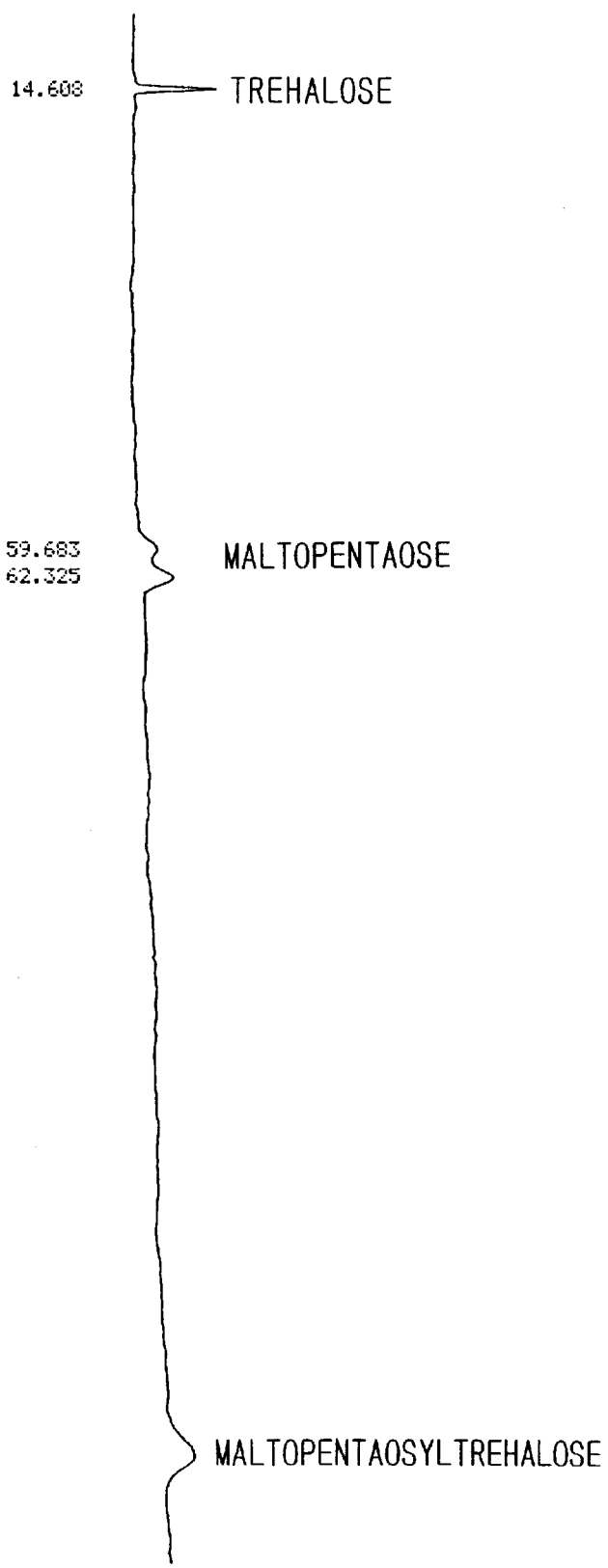
FIG. 19 is a graph showing the results of an analysis by TSK-gel Amide-80 HPLC, performed on the reaction product derived from maltopentaosyltrehalose subjected to reaction with the present amylase which is obtained in Example II-2 from the *Sulfolobus solfataricus* strain KM1.

The results of the analyses by AMINEX HPX-42A HPLC performed on reaction products from maltopentaose, Amylose DP-17 and soluble starch are shown in A, B and C of FIG. 17, respectively. Further, the results of the analyses by TSK-gel Amide-80 HPLC performed on reaction products from maltotriosyltrehalose and maltopentaosyltrehalose are shown in FIGS. 18 and 19, respectively.

From the results, the present purified enzyme was confirmed to markedly effectively act on a trehaloseoligosaccharide, of which the glucose residue at the reducing end side is α-1,α-1-linked, such as maltotoriosyltrehalose, to liberate α,α-trehalose and a corresponding maltooligosac-charide which has a polymerization degree reduced by two. Further, the present purified enzyme was confirmed to liberate principally glucose or maltose from maltose (G2)–maltoheptaose (G7), amylose, and soluble starch. The present purified enzyme, however, did not act on α,α-trehalose, which has an α-1,α-1 linkage; isomaltose, isomaltotriose, isomaltotetraose and isomaltopentaose, of which all the sugar units are α-1,6-linked; and panose, of which the second linkage from the reducing end is α-1,6.

(7) Endotype Amylase Activity

Two hundred Units/ml (in terms of the enzymatic activity when maltotriosyltrehalose is used as the substrate) of the present purified enzyme was allowed to act on soluble starch, and the time-lapse changes in the coloring degree by the iodo-starch reaction, and the starch-hydrolyzing rate estimated from the produced amounts of monosaccharide and disaccharide were analyzed using the method for measuring starch-hydrolyzing activity described in Example II-1, and the AMINEX HPX-42A HPLC analyzing method.

Figure 20:
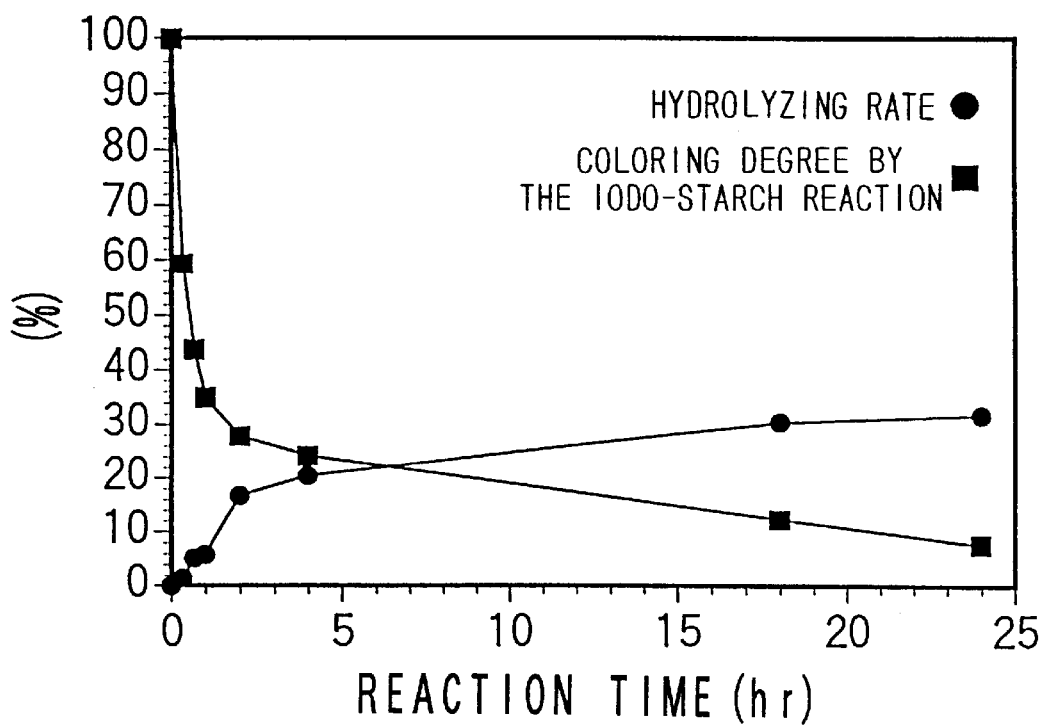
FIG. 20 is a graph showing time-course changes in disappearance of color generated by iodo, and starch-hydrolyzing percentage when the present amylase which is obtained in Example II-2 from the *Sulfolobus solfataricus* strain KM1 is made to act on soluble starch.

As shown in FIG. 20, the hydrolyzing rate of the present purified enzyme at the point where the coloring degree by the iodo-starch reaction decreased to 50% was as low as 3.7%. Accordingly, the present purified enzyme was confirmed to have a property of an endotype amylase.

(8) Investigation of the Action Mechanism

Uridinediphosphoglucose [glucose-6-$^3$H] and maltotetraose were put into a reaction with glycogen synthase (derived from rabbit skeletal muscle, G-2259 manufactured by Sigma Co.) to synthesize maltopentaose, of which the glucose residue of the non-reducing end was radiolabeled with $^3$H, and the maltopentaose was isolated and purified. To 10 mM of this maltopentaose radiolabeled with $^3$H as a substrate, 10 Units/ml (in terms of the enzymatic activity when maltotriose is used as the substrate) of the purified transferase derived from the Sulfolobus solfataricus strain KM1 was added and put into a reaction at 60° C. for 3 hours. Maltotriosyltrehalose, of which the glucose residue of the non-reducing end was radiolabeled with $^3$H, was synthesized thereby, and the product was isolated and purified. [Incidentally, it was confirmed by the following procedure that the glucose residue of the non-reducing end had been radiolabeled: The above product was completely decomposed into glucose and α,α-trehalose by glucoamylase (derived from Rhizopus, manufactured by Seikagaku Kougyou Co.); the resultants were sampled by thin-layer chromatography, and their radioactivities were measured by a liquid scintillation counter; as a result, radioactivity was not observed in the α,α-trehalose fraction but in the glucose fraction.]

The above-prepared maltopentaose and maltotriosyltrehalose, of which the glucose residues of the non-reducing ends were radiolabeled with $^3$H, were used as substrates, and were put into reactions with 50 Units/ml and 5 Units/ml of purified enzyme obtained in Example II-2, respectively. Sampling was performed before the reaction; and 0.5, 1 and 3 hours after the start of the reaction performed at 60° C. The reaction products were subjected to development by thin-layer chromatography (Kieselgel 60 manufactured by Merck Co.; solvent: butanol/ethanol/water=5/5/3). Each spot thus obtained and corresponding to each saccharide was collected, and its radiation was measured with a liquid scintillation counter. The results are shown in FIGS. 21 and 22, respectively.

Figure 21:
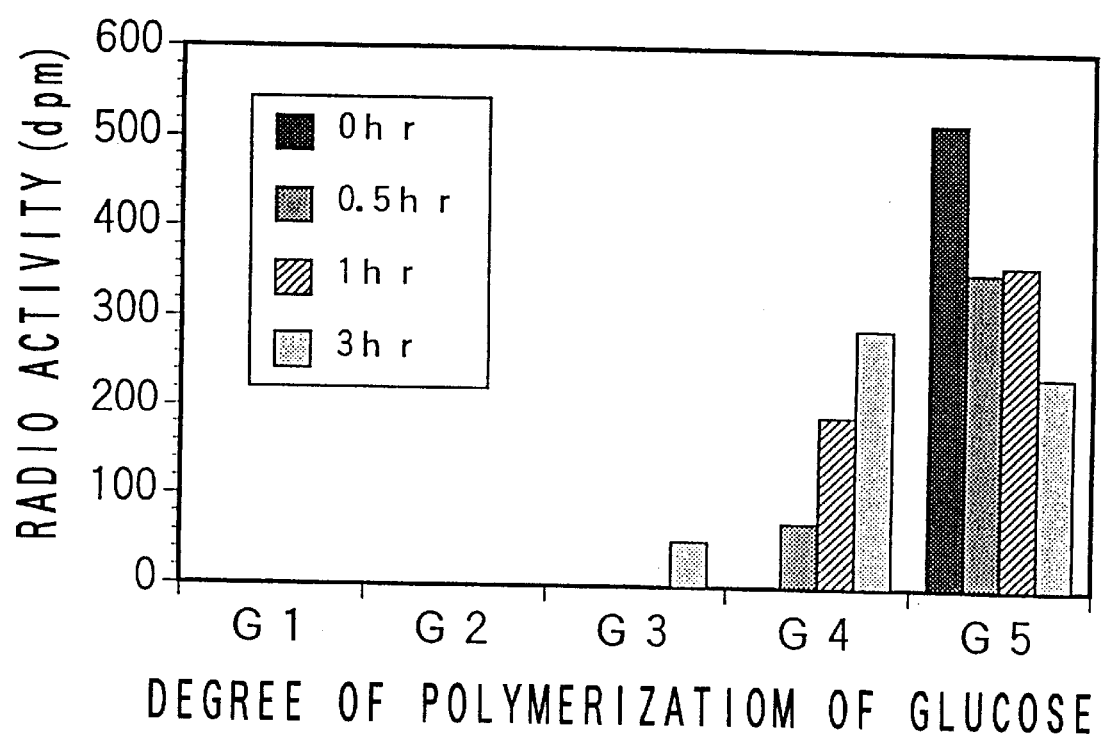
FIG. 21 is a graph showing time-course change in radioactivity of the reaction product derived from radiolabeled maltopentaose subjected to reaction with the present amylase which is obtained in Example II-2 from the *Sulfolobus solfataricus* strain KM1.
Figure 22:
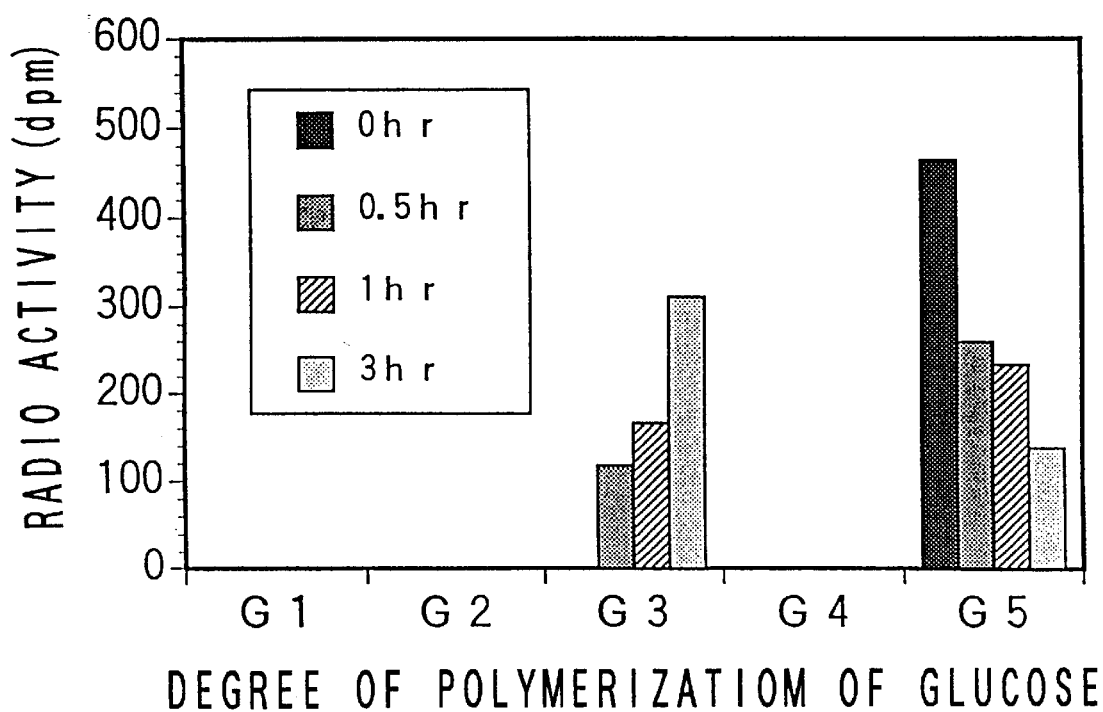
FIG. 22 is a graph showing time-course change in radio-activity of the reaction product derived from radiolabeled maltotriosyltrehalose subjected to reaction with the present amylase which is obtained in Example II-2 from the *Sulfolobus solfataricus* strain KM1.

As is obvious from FIGS. 21 and 22, when maltopentaose was used as a substrate, radioactivity was not detected in the fractions of the hydrolysates, i.e. glucose and maltose, but in the fractions of maltotetraose and maltotriose. On the other hand, when maltotriosyltrehalose was used as a substrate, radioactivity was not detected in the fraction of the hydrolysate, i.e. α,α-trehalose, but in the fraction of maltotriose.

Consequently, as to the action mechanism, the present purified enzyme was found to have an amylase activity of the endotype function, and in addition, an activity of principally producing monosaccharide and disaccharide from the reducing end side.

Additionally, each of the purified enzymes obtained in Examples II-3 and II-4, i.e. derived from the *Sulfolobus solfataricus* strain DSM 5833 and the *Sulfolobus acidocaldarius* strain ATCC 33909, respectively, was also examined for the enzymatic characteristics in a similar manner. The results are shown in Table 2 above.

Comparative Example II-1
Properties of Pancreatic α-Amylase in Hydrolyzing Various Oligosaccharides, and Analysis of the Hydrolysates Swine pancreatic α-amylase is known to hydrolyze maltooligosaccharide from the reducing end by two or three sugar units ["Denpun.Kanren Toushitsu Kouso Jikken-hou" ("Experimental methods in enzymes for starch and relating saccharides"), p 135, written by Michinori Nakamura and Keiji Kainuma, published by Gakkai-Shuppan-Sentah]. Upon this, a swine pancreatic α-amylase (manufactured by Sigma Co., A-6255) was analyzed the hydrolyzing properties and the hydrolysates as a comparative example for the novel amylase of the present invention. Specifically, 1 Unit/ml of the swine pancreatic α-amylase was allowed to act on 10 mM of each substrate listed in below-described Table 17 at pH 6.9 and 20° C., wherein 1 Unit is defined as equalling the amount of the enzyme with which 1 mg per 3 min. of a reducing saccharide corresponding to maltose is produced at pH 6.9 and 20° C. from starch assigned for the substrate. The activity of producing disaccharide and trisaccharide was employed as the index of the enzymatic activity, and the analysis was performed by the TSK-gel Amide-80 HPLC analyzing method described in Example II-1.

Incidentally, the enzymatic activity values in Table 17 were expressed with such a unit as 1 Unit equals the activity of liberating 1 umol of each oligosaccharide per hour.

Figure 23:
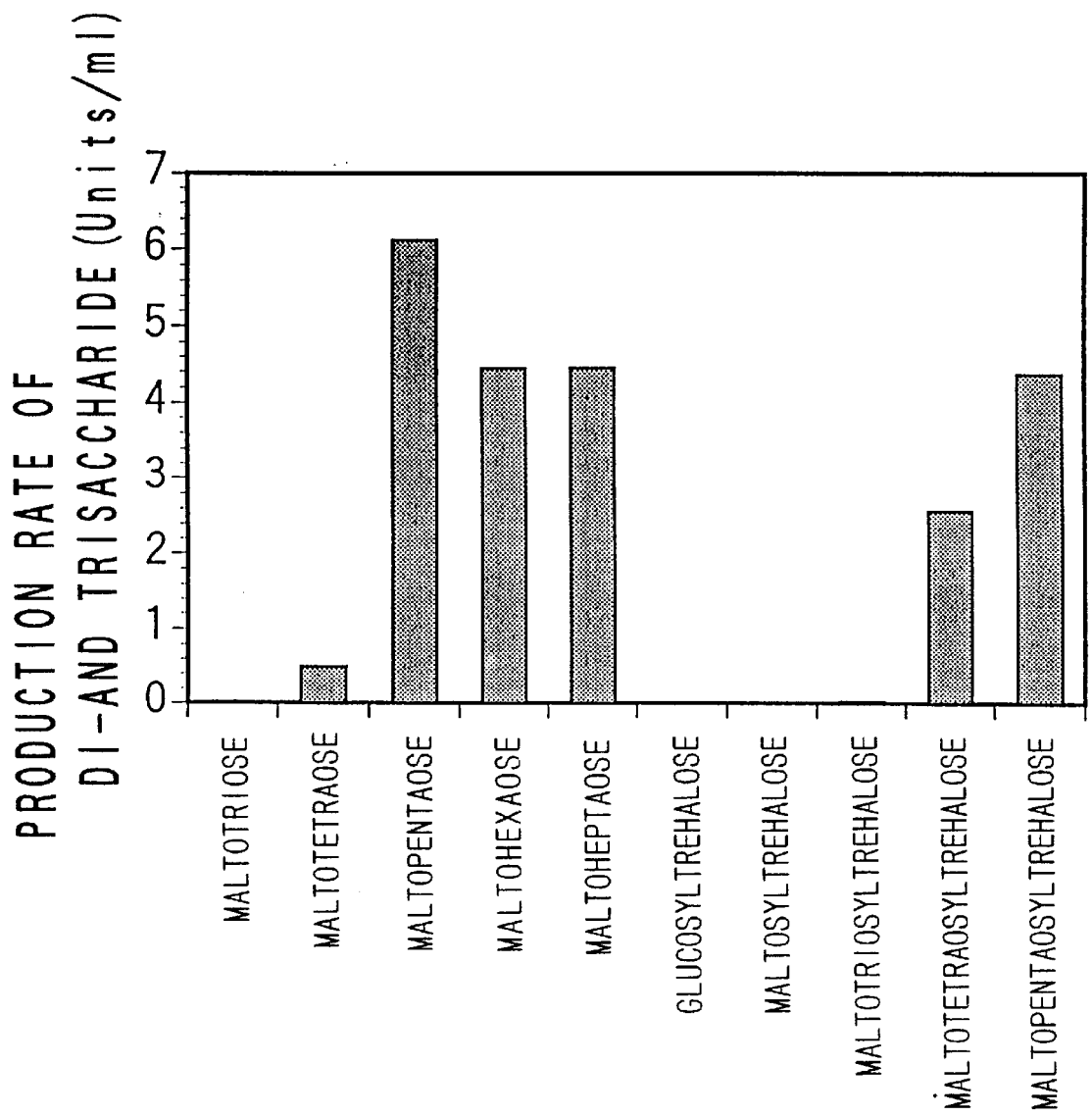
FIG. 23 is a graph showing reactivity of α-amylase derived from porcine pancreas to various substrates.

The results are shown in Table 17 below and in FIGS. 23 and 24.

TABLE 17

| Substrate | Liberated oligosaccharide | Production rate of di- and trisaccharides (units/ml) |
|---|---|---|
| Maltotriose (G3) | not decomposed | 0 |
| Maltotetraose (G4) | Glucose + G2 + G3 | 0.49 |
| Maltopentaose (G5) | G2 + G3 | 6.12 |
| Maltohexaose (G6) | G2 + G3 + G4 | 4.44 |
| Maltoheptaose (G7) | G2 + G3 + G4 + G5 | 4.45 |
| Glucosyltrehalose | not decomposed | 0 |
| Maltosyltrehalose | not decomposed | 0 |
| Maltotriosyltrehalose | G2 + Glucosyltrehalose | 0.03 |
| Maltotetraosyltrehalose | G3 + Glucosyltrehalose | 2.57 |
| Maltopentaosyltrehalose | G3 + Maltosyltrehalose | 4.36 |

Notes: Each of glucosyltrehalose, maltosyltrehalose, maltotetraosyltrehalose, and maltopentaosyltrehalose was prepared according to the method for preparing maltotriosyltrehalose in Example II-1.

Figure 24:
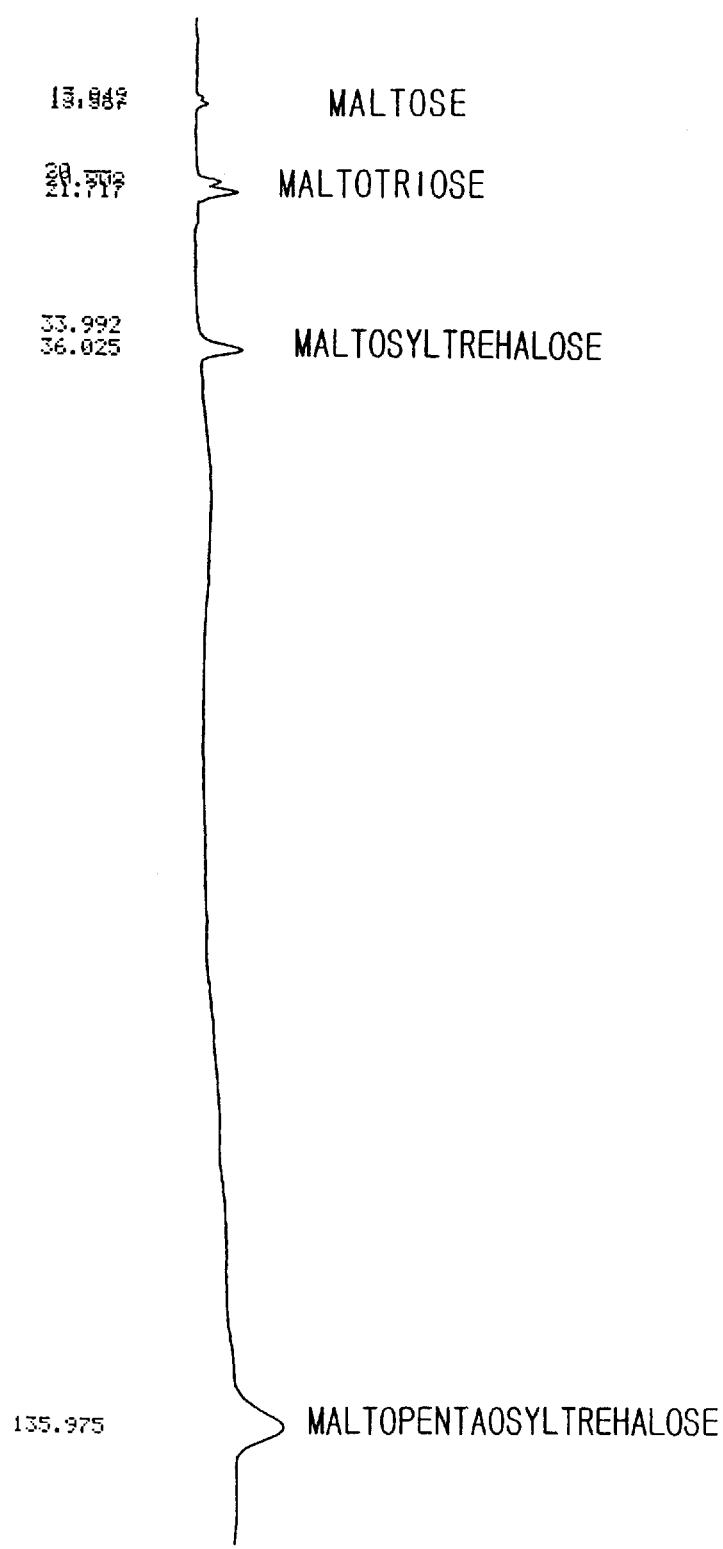
FIG. 24 is a graph showing the results of an analysis by TSK-gel Amide-80 HPLC, performed on the reaction product derived from maltopentaosyltrehalose subjected to reaction with α-amylase which is derived from porcine pancreas

The results of analyses by TSK-gel Amide-80 HPLC performed on reaction products from maltopentaosyltrehalose are shown in FIG. 24.

From the results, the pancreatic amylase was confirmed to produce, from each of maltotetraose (G4)–maltoheptaose (G7), maltose or maltotriose, and a corresponding maltooligosaccharide which had a polymerization degree reduced by two or three; but not to liberate α,α-trehalose from trehaloseoligosaccharides such as glucosyltrehalose and maltooligosyltrehalose, of which the glucose residue at the reducing end side is α-1,α-1-linked; and in addition, to have small reactivity to such trehaloseoligosaccharides.

EXAMPLE II-6
Production of α,α-Trehalose from Soluble Starch and Various Starch Hydrolysates Production of α,α-trehalose utilizing the synergism between enzymes was attempted as follows:

The enzymes used were 150 Units/ml of the present purified enzyme obtained in Example II-2, and 10 Units/ml of the purified transferase derived from the *Sulfolobus solfataricus* strain KM1;

substrates were a soluble starch (manufactured by Nacalai tesque Co., special grade), as a starch hydrolysate, a soluble starch which had been subjected to hydrolysis of the α-1,6 linkages beforehand under the conditions of 40° C. for 1 hour with 25 Units/ml of pullulanase (manufactured by Wako pure chemical Co.) derived from *Klebsiella pneumoniae*, as another starch hydrolysate, a soluble starch which had been subjected to partial hydrolysis beforehand under the conditions of 30° C. for 2.5 hours with 12.5 Units/ml of α-amylase (manufactured by Boehringer Mannheim Co.) derived from *Bacillus amylolichefaciens*, Pinedex #1 and Pine-dex #3 (both manufactured by Matsutani Kagaku Co.), each maltooligosaccharide of G3–G7 (manufactured by Hayashibara Biochemical Co.), and Amylose DP-17 (manufactured by Hayashibara Biochemical Co.);

the final concentration of each substrate was 10%; and each reaction was performed under the conditions of 60° C. at pH 5.5 for 100 hours, approximately.

Each reaction mixture was analyzed by the AMINEX HPX-42A HPLC method described in Example II-1, according to the case in which soluble starch was used as the substrate.

After the non-reacted substrate was hydrolyzed with glucoamylase, the yield of α,α-trehalose was analyzed by the TSK-gel Amide-80 HPLC analyzing method described in Example II-1.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

As to activity of pullulanase, 1 Unit is defined as the enzymatic activity of-producing 1 μmol of maltotriose per minute at pH 6.0 and 30° C. from pullulan assigned for the substrate.

The results are shown in Table 18 below.

TABLE 18

| Substrate | Yield of α,α-trehalose (%) |
|---|---|
| Soluble starch | 37.0 |
| Pullulanase-treated starch | 62.1 |
| Amylase-treated starch | 42.2 |

TABLE 18-continued

| Substrate | Yield of α,α-trehalose (%) |
|---|---|
| Pinedex #1 | 49.9 |
| Pinedex #3 | 40.4 |
| Maltotriose (G3) | 36.4 |
| Maltotetraose (G4) | 47.8 |
| Maltopentaose (G5) | 60.0 |
| Maltohexaose (G6) | 61.8 |
| Maltoheptaose (G7) | 67.1 |
| Amylose DP-17 | 83.5 |

Figure 25:
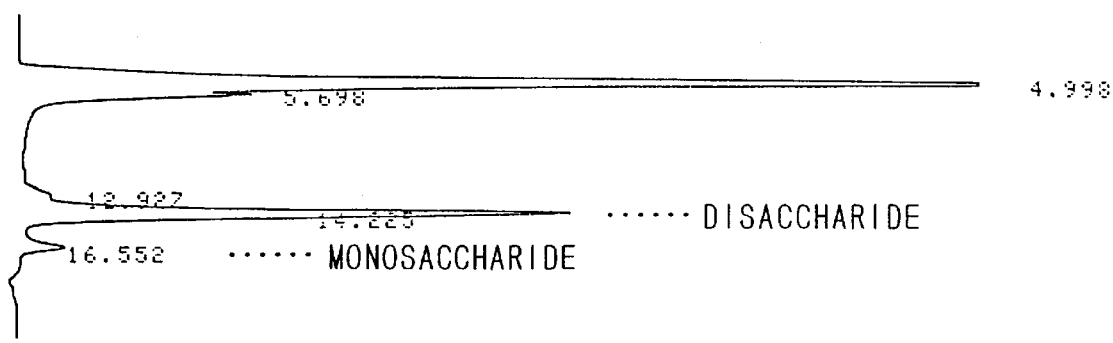
FIG. 25 is a graph showing the results of an analysis by AMINEX HPX-42A HPLC, performed on the reaction product derived from soluble starch subjected to reaction with transferase and the present amylase which is obtained in Example II-2 from the *Sulfolobus solfataricus* strain KM1.

The results of the analysis by AMINEX HPX-42A HPLC performed on the reaction product from the soluble starch are shown in FIG. 25.

Specifically, when soluble starch was used as the 5 substrate, α,α-trehalose was produced in a yield of 37.0%. As to the various starch hydrolysates, the yield was 62.1% when soluble starch which had been subjected to hydrolysis of the α-1,4 linkages was used as the substrate. Further, in the various maltooligosaccharides and Amylose DP-17, in which all of the linkages are α-1,4 linkages, the yields were 36.4–67.1%, and 83.5%, respectively. These results suggest that the yield of the final product, i.e. α,α-trehalose, becomes higher when such a substrate as having a longer α-1,4-linked straight-chain is used.

EXAMPLE II-7

Production of α,α-Trehalose from Soluble Starch in Various Enzyme-Concentrations Production of α,α-trehalose utilizing the synergism between enzymes was attempted by adding the enzymes having concentrations listed in Table 19, respectively, to a substrate (final concentration: 10%). Specifically, the enzymes were the present purified enzyme obtained in Example II-2, and the purified transferase derived from the *Sulfolobus solfataricus* strain KM1; the substrate was a soluble starch which had been pre-treated under the conditions of 40° C. for 1 hour with 25 Units/ml of pullulanase (manufactured by Wako pure chemical Co.) derived from *Klebsiella pneumoniae*; and the reaction was performed under the conditions of 60° C. at pH 5.5 for 100 hours, approximately. After the non-reacted substrate was hydrolyzed with glucoamylase, the reaction mixture was analyzed by the TSK-gel Amide-80 HPLC analyzing method described in Example II-1 to examine the yield of the produced α,α-trehalose.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

As to activity of pullulanase, 1 Unit is defined as the enzymatic activity of producing 1 μmol of maltotriose per minute at pH 6.0 and 30° C. from pullulan assigned for the substrate.

The results are shown in Table 19 below.

TABLE 19

| Concentration of amylase | Yield of α,α-trehalose (%) |||||
|---|---|---|---|---|---|
|  | Concentration of transferase (units/ml) |||||
| (units/ml) | 0.1 | 1 | 5 | 10 | 20 |
| 1.5 | 7.8 | 28.0 | 9.6 | 8.8 | 9.7 |
| 15 | 10.0 | 45.3 | 34.3 | 33.6 | 35.2 |
| 150 | 8.6 | 51.8 | 59.3 | 62.1 | 65.1 |
| 450 | 1.6 | 45.1 | 58.9 | 61.7 | 64.2 |
| 700 | 1.3 | 19.0 | 39.3 | 44.5 | 46.8 |
| 2000 | 1.7 | 12.9 | 31.5 | 40.3 | 42.7 |

As is obvious from the results shown in the table, the yield of α,α-trehalose reached its maximum, i.e. 65.1%, in such a case with 20 Units/ml of the transferase and 150 Units/ml of the amylase.

Comparative Example II-2

Production of α,α-Trehalose Using Amylases Derived from the Other Organisms

Production of α,α-trehalose utilizing the synergism between enzymes was attempted as follows:

Amylases derived from *Bacillus subtilis, Bacillus licheniformis* and *Aspergillus oryzae* (100200 manufactured by Seikagaku Kougyou Co, A-3403 and A-0273 manufactured by Sigma Co., respectively; all of them are active at 60° C.) were used as comparative substitutions for the novel amylase of the present invention;

the purified transferase used together was derived from the *Sulfolobus solfataricus* strain KM1;

the substrate was a soluble starch (final concentration: 10%) which had been pre-treated under the conditions of 40° C. and 1 hour with 25 Units/ml of pullulanase (manufactured by Wako pure chemical Co.) derived from *Klebsiella pneumoniae*;

the enzymes having concentrations listed in Table 20, respectively, was added to the substrate; and the reaction was performed under the conditions of 60° C. at pH 5.5 for 100 hours, approximately. After the non-reacted substrate was hydrolyzed with glucoamylase, the reaction mixture was analyzed by the TSK-gel Amide-80 HPLC analyzing method described in Example II-1 to examine the yield of the produced α,α-trehalose.

As to enzymatic activity of each amylase, 1 Unit is defined as equalling the amount of the enzyme with which the absorptivity at 620 nm corresponding to the violet color of the starch-iodine complex decreases at a rate of 10% per 10 min. under the same reaction conditions as in Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

As to activity of pullulanase, 1 Unit is defined as the enzymatic activity of producing 1 μmol of maltotriose per minute at pH 6.0 and 30° C. from pullulan assigned for the substrate.

The results are shown in Table 20 below.

TABLE 20

Yield of α,α-trehalose (%)

| Concentration of transferase (units/ml) | Origin of α-amylase | Concentration of α-amylase (units/ml) | Yield of α,α-trehalose (%) |
|---|---|---|---|
| 10 | Bacillus subtilis | 1.0 | 28.9 |
| 10 |  | 10.0 | 27.7 |
| 5 | Bacillus licheniformis | 10.0 | 26.4 |
| 10 |  | 10.0 | 26.8 |
| 5 | Aspergillus oryzae | 1.0 | 23.2 |
| 10 |  | 1.0 | 23.1 |

As is obvious from the results shown in the table, though α,α-trehalose can be produced by using amylases derived from the other organisms, the yield in each case is lower than that in the case using the novel enzyme of the present invention.

EXAMPLE II-8
Production of α,α-Trehalose from Amylose DP-17 in Various Enzyme-Concentrations Production of α,α-trehalose utilizing the synergism between enzymes was attempted by adding the enzymes having concentrations listed in Table 21, respectively, to a substrate (final concentration: 10%). Specifically, the enzymes were the present purified enzyme obtained in Example II-2, and the purified transferase derived from the *Sulfolobus solfataricus* strain KM1; the substrate was Amylose DP-17 (manufactured by Hayashibara Biochemical Co.); and the reaction was performed under the conditions of 60° C. at pH 5.5 for 100 hours, approximately. After the non-reacted substrate was hydrolyzed with glucoamylase, the reaction mixture was analyzed by the TSK-gel Amide-80 HPLC analyzing method described in Example II-1 to examine the yield of the produced α,α-trehalose.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

The results are shown in Table 21 below.

TABLE 21

Yield of α,α-trehalose (%)

| Concentration of amylase (units/ml) | Concentration of transferase (units/ml) | | | | |
|---|---|---|---|---|---|
|  | 0.1 | 1 | 5 | 10 | 20 |
| 1.5 | 11.9 | 46.8 | 52.1 | 48.4 | 40.4 |
| 15 | 25.6 | 77.9 | 79.7 | 81.8 | 77.4 |
| 150 | 10.7 | 62.1 | 76.9 | 83.4 | 81.9 |
| 200 | 2.8 | 47.9 | 73.2 | 76.1 | 79.2 |
| 700 | 1.2 | 17.0 | 49.1 | 61.8 | 68.4 |
| 2000 | 0.6 | 9.2 | 27.5 | 36.7 | 48.7 |

As is obvious from the results shown in the table, when Amylose DP-17, which consists of a straight-chain constructed with α-1,4-linkages, was used as the substrate, the yield of α,α-trehalose reached its maximum, i.e. 83.4%, in such a case with 10 Units/ml of the transferase and 150 Units/ml of the amylase.

EXAMPLE II-9
Production of α,α-Trehalose in Various Concentrations of Soluble Starch Production of α,α-trehalose utilizing the synergism between enzymes was attempted by adding the enzymes having concentrations listed in Table 22, respectively, to a substrate, the final concentration of which would be adjusted at 5%, 10%, 20% or 30%. Specifically, the enzymes were the present purified enzyme obtained in Example II-2, and the purified transferase derived from the *Sulfolobus solfataricus* strain KM1; the substrate was soluble starch; and the reaction was performed under the conditions of 60° C. at pH 5.5 for 100 hours, approximately. During the reaction, from 0 hours to 96 hours after the start, a treatment at 40° C. for 1 hour with the addition of pullulanase (a product derived from *Klebsiella pneumoniae*, manufactured by Wako pure chemical Co.) so as to be 5 Units/ml was performed every 12 hours, namely, totaling 9 times inclusive of the treatment at 0 hours.

After the non-reacted substrate was hydrolyzed with glucoamylase, the reaction mixture was analyzed by the TSK-gel Amide-80 HPLC analyzing method described in Example II-1 to examine the yield of the produced α,α-trehalose.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

As to activity of pullulanase, 1 Unit is defined as the enzymatic activity of producing 1 μmol of maltotriose per minute at pH 6.0 and 30° C. from pullulan assigned for the substrate.

The results are shown in Table 22 below.

TABLE 22

| Concentration of soluble starch (%) | Concentration of transferase (units/ml) | Concentration of amylase (units/ml) | Yield of α,α-trehalose (%) |
|---|---|---|---|
| 5 | 2 | 50 | 76.6 |
|  | 5 | 150 | 74.4 |
| 10 | 10 | 150 | 77.4 |
|  | 20 | 150 | 78.2 |
| 20 | 10 | 150 | 75.7 |
|  | 20 | 150 | 75.0 |
| 30 | 10 | 150 | 71.4 |
|  | 20 | 150 | 71.9 |

As is obvious from the results shown in the table, the yield of a α,α-trehalose can be 70% or more even when the concentration of soluble starch as a substrate was varied in a range of 5–30%, provided that the concentrations of the amylase and transferase are adjusted to the optimum conditions.

EXAMPLE II-10
Production of α,α-Trehalose from Soluble Starch with Various Pullulanase Treatments Production of α,α-trehalose utilizing the synergism attempted as follows:

The enzymes were the present purified enzyme obtained in Example II-2, and purified transferase derived from the *Sulfolobus solfataricus* strain KM1;

the substrate was soluble starch (final concentration: 10%);

the enzymes having concentrations listed in Table 23, respectively, was added to the substrate; and the reaction was performed under the conditions of 60° C. at pH 5.5 for 120 hours, approximately. During the reaction, one or more of pullulanase treatments were performed under either of the following schedules: 1 time at 24 hours after the start (a) (hereinafter, "after the start" will be omitted); 1 time at 48 hours (b); 1 time at 72 hours (c); 1 time at 96 hours (d); every 24 hours from 24 hours to 96 hours, totaling 4 times (e); every 12 hours from 0 hours to 96 hours, totaling 9 times inclusive of the treatment at 0 hours (f); and every 3 hours in the early stage of the reaction, i.e. from 0 hours to 12 hours, totaling 5 times inclusive of the treatment at 0 hours, and in addition, every 12 hours from 24 hours to 96 hours, totaling 7 times (g). Any of the pullulanase treatments were performed under the conditions of 40° C. for 1 hour after the addition of pullulanase (a product derived from *Klebsiella pneumoniae*) so as to be the concentrations shown in Table 23, respectively.

After the non-reacted substrate was hydrolyzed with glucoamylase, the reaction mixture was analyzed by the TSK-gel Amide-80 HPLC analyzing method described in Example II-1 to examine the yield of the produced α,α-trehalose.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, Unit is defined as the enzymatic activity of producing 1 μmol of glucosyltrehalose per hour at pH 5.5 and 60° C. from maltotriose assigned for the substrate.

As to activity of pullulanase, 1 Unit is defined as the enzymatic activity of producing 1 μmol of maltotriose per minute at pH 6.0 and 30° C. from pullulan assigned for the substrate.

The results are shown in Table 23 below.

pullulanase treatments are carried out, or a method in which a plurality of pullulanase treatments are carried out in the early stage of the reaction. The yield of α,α-trehalose reached its-maximum, i.e. 80.9%, under the conditions with 10 Units/ml of the transferase, 150 Units/ml of the amylase, the pullulanase treatment schedule (g), and 5 Units/ml of the pullulanase.

EXAMPLE II-11

Production of α,α-Trehalose in Various Concentrations of Amylose DP-17 and Various Reaction Temperatures Production of α,α-trehalose utilizing the synergism between enzymes was attempted as follows:

The present purified enzyme obtained in Example II-2, and the purified transferase derived from the *Sulfolobus solfataricus* strain KM1 were added so as to be 320 Units/g-substrate and 20 Units/g-substrate, respectively;

the substrate was Amylose DP-17; and the reaction was performed for 100 hours, approximately, with the substrate concentration and reaction temperature shown in Table 24 or 25.

After the non-reacted substrate was hydrolyzed with glucoamylase, the reaction mixture was analyzed by the TSK-gel Amide-80 HPLC analyzing method described in Example II-1 to examine the yield of the produced α,α-trehalose and the reaction rate.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, Unit is defined as the enzymatic activity of producing 1 μmol of glucosyltrehalose per hour at pH 5.5 and 60° C. from maltotriose assigned for the substrate.

TABLE 23

| | | | Yield of α,α-trehalose (%) | | | | | |
|---|---|---|---|---|---|---|---|---|
| Method of Pullulanase treatment | Concentration of amylase (units/ml) | Concentration of transferase (units/ml) | Concentration of pullulanase (units/ml) | | | | | |
| | | | 0.1 | 1 | 2 | 5 | 10 | 25 |
| (a) | 150 | 10 | 48.0 | 59.7 | 62.9 | 67.6 | | 71.7 |
| (b) | 150 | 10 | 49.4 | 60.0 | 62.2 | 66.0 | | 71.0 |
| (c) | 150 | 10 | 49.6 | 59.7 | 63.2 | 66.4 | | 70.0 |
| (d) | 150 | 10 | 49.2 | 59.3 | 62.9 | 67.0 | | 70.0 |
| (e) | 150 | 10 | 57.8 | 69.9 | 72.6 | 74.1 | | |
| (f) | 150 | 10 | | 74.0 | 76.6 | 77.4 | | 67.6 |
| | 150 | 20 | | 74.4 | 74.0 | 78.2 | | 67.0 |
| (g) | 150 | 10 | | 75.7 | 76.5 | 80.9 | 61.9 | |
| | 150 | 20 | | 75.9 | 77.9 | 77.0 | 71.5 | |

As is obvious from the results shown in the table, the yield can be improved by introducing a pullulanase treatment during the reaction. Particularly, the yield of α,α-trehalose can be further improved by a method in which a plurality of The results are shown in Tables 24 and 25 below.

Incidentally, as to the reaction rate shown in Table 24, 1 Unit is defined as the rate of liberating 1 μmol of α,α-trehalose per hour.

TABLE 24

| Reaction temperature (° C.) | Reaction rate (units/ml) Substrate concentration (%) | | | |
|---|---|---|---|---|
| | 10 | 20 | 30 | 40 |
| 40 | 1.1 | 1.8 | 4.8 | 6.2 |
| 50 | 3.2 | 8.1 | 7.7 | 12.3 |
| 60 | 6.8 | 16.2 | 23.8 | 23.1 |
| 70 | 12.0 | 29.3 | 32.3 | 55.6 |
| 80 | 13.3 | 30.8 | 66.9 | 88.0 |

TABLE 25

| Reaction temperature (° C.) | Reaction yield (%) Substrate concentration (%) | | | |
|---|---|---|---|---|
| | 10 | 20 | 30 | 40 |
| 40 | 42.7 | 50.3 | 42.6 | 28.8 |
| 50 | 71.0 | 70.2 | 64.6 | 35.2 |
| 60 | 74.6 | 72.5 | 66.2 | 65.8 |
| 70 | 75.1 | 75.0 | 65.4 | 70.7 |
| 80 | 69.3 | 68.2 | 68.4 | 70.9 |

As is obvious from the results shown in the tables, when the reaction temperature is raised to a range of 40–80° C., the reaction rate increases depending on the temperature. Further, with a high substrate concentration (30–40%), the substrate becomes insoluble and the yield markedly decreases when the temperature is low (40–50° C.), while the substrate becomes soluble and the yield can remain high when the temperature is high. The yield reached to 75.1%.

From the results of this example, it can be understood that a preparation at a high temperature in a high concentration will be possible by using the highly thermostable amylase of the present invention, and therefore, a process for producing α,α-trehalose advantageous in view of cost and easy handling can be provided.

EXAMPLE II-12

Production of α,α-Trehalose Using Thermostable Pullulanase in Various Concentrations of Soluble Starch and Various Reaction Temperatures Production of α,α-trehalose utilizing the synergism between enzymes was attempted as follows:

The present purified enzyme obtained in Example II-2, the purified transferase derived from the *Sulfolobus solfataricus* strain KM1, and a commercially available thermostable pullulanase were added so as to be 1280 Units/g-substrate, 80 Units/g-substrate and 32 Units/g-substrate, respectively, wherein the pullulanase (Debranching Enzyme Amano, a product derived from Bacillus sp. manufactured by Amano Pharmaceutical Co.) had been subjected to TOSHO TSK-gel Phenyl-TOYOPEARL 650S hydrophobic chromatography to remove coexisting glucoamylase activity and α-amylase activity;

the substrate was soluble starch; and the reaction was performed for 100 hours, approximately, with the substrate concentration and reaction temperature shown in Table 26 or 27.

After the non-reacted substrate was hydrolyzed with glucoamylase, the reaction mixture was analyzed by the TSK-gel Amide-80 HPLC analyzing method described in Example II-1 to examine the yield of the produced α,α-trehalose and the reaction rate.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

As to activity of pullulanase, 1 Unit is defined as the enzymatic activity of producing 1 μmol of maltotriose per minute at pH 5.5 and 60° C. from pullulan assigned for the substrate.

The results are shown in Tables 26 and 27 below.

Incidentally, as to the reaction rate shown in Table 26, 1 Unit is defined as the rate of liberating 1 μmol of α,α-trehalose per hour.

TABLE 26

| Reaction temperature (° C.) | Reaction rate (units/ml) Substrate concentration (%) | | |
|---|---|---|---|
| | 10 | 20 | 30 |
| 40 | 15.8 | 22.8 | 22.2 |
| 50 | 26.0 | 50.8 | 57.5 |
| 60 | 36.5 | 58.4 | 96.4 |

TABLE 27

| Reaction temperature (° C.) | Reaction yield (%) Substrate concentration (%) | | |
|---|---|---|---|
| | 10 | 20 | 30 |
| 40 | 53.1 | 8.9 | 6.2 |
| 50 | 70.9 | 56.1 | 58.6 |
| 60 | 74.1 | 72.6 | 71.7 |

Incidentally, when the reaction was performed with a substrate concentration of 10% and a reaction temperature of 60° C. under the same conditions as above except that the thermostable pullulanase was not added, the yield was 35.0%.

From the result shown in the tables, it was found that only one addition of the thermostable pullulanase during the reaction brings about a yield-improving effect, and that the reaction rate increases depending on the temperature when the reaction temperature is raised to a range of 40–60° C. Further, with a high substrate concentration (20–30%), the substrate becomes insoluble and the yield markedly decreases when the temperature is low (40–50° C.), while the substrate becomes soluble and the yield can remain high when the temperature is high (60° C.). The yield reached to 74.1%.

EXAMPLE II-13

Production of α,α-Trehalose from Soluble Starch with Isoamylase Treatments

Production of α,α-trehalose utilizing the synergism between enzymes was attempted as follows:

The present purified enzyme obtained in Example II-2, and the purified transferase derived from the *Sulfolobus solfataricus* strain KM1 were added so as to be 1,280 Units/g-substrate and 80 Units/g-substrate, respectively; the substrate was soluble starch (final concentration: 10%); and the reaction was performed at 60° C. and pH 5.0 for 100 hours, approximately. During the reaction, an isoamylase treatment was performed every 3 hours in the early stage of the reaction, i.e. from 0 hours to 12 hours after the start (hereinafter, "after the start" is omitted), totaling 5 times inclusive of the treatment at 0 hours, and in addition, every 24 hours from 24 hours to 96 hours, totaling 3 times. Each isoamylase treatment was performed under the conditions of 40° C. for 1 hour after the addition of isoamylase (a product derived from *Pseudomonas amyloderamosa,* manufactured by Seikagaku Kougyou Co.) so as to be the concentration shown in Table 28.

After the non-reacted substrate was hydrolyzed with glucoamylase, the reaction mixture was analyzed by the TSK-gel Amide-80 HPLC analyzing,method described in Example II-1 to examine the yield of the produced α,α-trehalose.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

The activity of isoamylase was measured as follows: A half milliliter of 1% soluble starch derived from glutinous rice was mixed with 0.1 ml of a 0.5 M acetic acid buffer solution (pH 3.5) and 0.1 ml of an enzyme solution, and subjected to reaction at 40° C.; the absorptivity at 610 nm corresponding to the violet color of the amylose-iodine complex is measured with a cuvette having a width of 1 cm ["Denpun.Kanren Toushitsu Kouso Jikken-hou" ("Experimental methods in enzymes for starch and relating saccharides"), written by Michinori Nakamura and Keiji Kainuma, published by Gakkai-Shuppan-Sentah, 1989]; and 1 Unit is defined as the amount of the enzyme with which the absorptivity increases by 0.1 per hour.

The results are shown in Table 28 below.

TABLE 28

| Concentration of isoamylase (units/ml) | Reaction yield (%) |
|---|---|
| 0 | 35.0 |
| 500 | 75.7 |
| 1000 | 73.7 |
| 2000 | 71.0 |

As is obvious from the results shown in the tables, the yield can be improved by introducing isoamylase treatments during the reaction, similar to pullulanase (a product derived from *Klebsiella pneumoniae*). The yield of α,α-trehalose reached to 75.7%.

EXAMPLE II-14

Production of α,α-Trehalose from Soluble Starch with a Treatment Using a Debranching Enzyme Derived from the *Sulfolobus solfataricus* Strain KM1

Production of α,α-trehalose utilizing the synergism between enzymes was attempted as follows:

The present purified enzyme obtained in Example II-2, the purified transferase derived from the *Sulfolobus solfataricus* strain KM1, and a debranching enzyme derived from the *Sulfolobus solfataricus* strain KM1 (the enzyme isolated and purified from the cell extract according to the method in Referential Example II-3) were added so as to be 1,280 Units/g-substrate, 80 Units/g-substrate, and the concentration shown in the below-described table, respectively;

the substrate was soluble starch (final concentration: 10%); and the reaction was performed at 60° C. and pH 5.0 for 100 hours, approximately.

After the non-reacted substrate was hydrolyzed with glucoamylase, the reaction mixture was analyzed by the TSK-gel Amide-80 HPLC analyzing method described in Example II-1 to examine the yield of the produced α,α-trehalose.

As to activity of the novel amylase of the present invention, 1 Unit is defined as the enzymatic activity of liberating 1 μmol of α,α-trehalose per hour from maltotriosyltrehalose, similar to Example II-1.

As to activity of the purified transferase derived from the *Sulfolobus solfataricus* strain KM1, 1 Unit is defined as the enzymatic activity of producing 1 μmol of glucosyltrehalose per hour at pH 5.5 and 60° C. from maltotriose assigned for the substrate.

The activity of the debranching enzyme derived from the *Sulfolobus solfataricus* strain KM1 was measured as follows: A half milliliter of 1% soluble starch derived from glutinous rice was mixed with 0.1 ml of a 0.5 M acetic acid buffer solution (pH 5.0) and 0.1 ml of an enzyme solution, and subjected to reaction at 60° C.; the absorptivity at 610 nm corresponding to the violet color of the amylose-iodine complex is measured with a cuvette having a width of 1 cm; and 1 Unit is defined as the amount of the enzyme with which the absorptivity increases by 0.1 per hour.

The results are shown in Table 29 below.

TABLE 29

| Concentration of debranching enzyme (units/ml) | Reaction yield (%) |
|---|---|
| 0 | 35.0 |
| 3 | 69.8 |
| 6 | 69.5 |
| 12 | 68.0 |
| 24 | 67.8 |

As is obvious from the results shown in the tables, the yield can be improved by only one addition of the debranching enzyme derived from the *Sulfolobus solfataricus* strain KM1 during the reaction, similar to pullulanase (Debranching Enzyme Amano, a product derived from *Bacillus* sp.). The yield of α,α-trehalose reached to 69.8%.

Referential Example II-1

Production of Transferred Oligosaccharide by Transferase in Various Concentrations of Amylose DP-17 and Various Reaction Temperatures Using Amylose DP-17 as a substrate, the corresponding trehaloseoligosaccharide, of which the glucose residue at the reducing end side is α-1,α-1-linked, was produced by adding the purified transferase derived from the *Sulfolobus solfataricus* strain KM1 so as to be 20 Units/g-substrate, and by performing the reaction in the substrate concentration and reaction temperature shown in Table 30 or 31 for 100 hours, approximately.

As to the corresponding trehaloseoligosaccharide, of which the glucose residue at the reducing end is α-1,α-1-linked, the yield and the reaction rate were estimated from the decrement in the amount of reducing ends which was measured by the dinitrosalicylate method ["Denpun.Kanren Toushitsu Kouso Jikken-hou" ("Experimental methods in enzymes for starch and relating saccharides"), written by Michinori Nakamura and Keiji Kainuma, published by Gakkai-Shuppan-Sentah, 1989].

As to activity of the purified transferase derived from the *Sulfolobus solfataricus* strain KM1, 1 Unit is defined as the enzymatic activity of producing 1 µmol of glucosyltrehalose per hour at pH 5.5 and 60° C. from maltotriose assigned for the substrate.

The results are shown in Tables 30 and 31 below.

Incidentally, as to the reaction rate shown in Table 30, 1 Unit is defined as the rate of liberating 1 µmol of α,α-trehalose per hour.

TABLE 30

| Reaction temperature (° C.) | Reaction rate (units/ml) Substrate concentration (%) | | | |
|---|---|---|---|---|
| | 10 | 20 | 30 | 40 |
| 40 | 0.8 | 2.9 | 3.5 | 4.3 |
| 50 | 3.0 | 5.5 | 8.6 | 8.1 |
| 60 | 1.7 | 6.5 | 10.3 | 16.7 |
| 70 | 4.0 | 7.0 | 12.0 | 19.8 |
| 80 | 3.6 | 9.4 | 15.8 | 20.4 |

TABLE 31

| Reaction temperature (° C.) | Reaction yield (%) Substrate concentration (%) | | | |
|---|---|---|---|---|
| | 10 | 20 | 30 | 40 |
| 40 | 70.7 | 74.5 | 63.4 | 37.6 |
| 50 | 76.0 | 72.8 | 70.5 | 46.7 |
| 60 | 71.6 | 75.1 | 75.3 | 55.1 |
| 70 | 71.6 | 70.4 | 76.6 | 72.6 |
| 80 | 65.6 | 64.8 | 72.7 | 72.5 |

From the result shown in the tables, it was found that the reaction rate increases depending on the temperature when the reaction temperature is raised to a range of 40–80° C. Further, with a high substrate concentration especially 40%), the substrate becomes insoluble and the yield markedly decreases when the temperature is low (40–50° C.), while the substrate becomes soluble and the yield can remain high when the temperature is high. The yield reached to 76%.

Referential Example II-2

Measuring Solubility of Amylose DP-17 in Water

Solubility of Amylose DP-17 was measured as follows: By heat dissolution, 5, 10, 20, 30 and 40% Amylose DP-17 solutions were prepared, and kept in thermostat baths adjusted at 40, 50, 70 and 80° C., respectively; time-lapse sampling was performed and the insoluble matters generated in the samples were filtered; each of the supernatants thus obtained was examined for the concentration of Amylose DP-17; and the solubility at each point was determined according to the saturation point where the concentration had been reached to equilibrium.

The results are shown in Table 32 below.

TABLE 32

| Temperature (° C.) | Solubility (% (w/vol)) |
|---|---|
| 35 | 11.3 |
| 40 | 13.0 |
| 50 | 18.9 |
| 60 | 27.6 |

TABLE 32-continued

| Temperature (° C.) | Solubility (% (w/vol)) |
|---|---|
| 70 | 32.3 |
| 80 | 35.3 |

Referential Example II-3

Purification of the Debranching Enzyme Derived from the *Sulfolobus solfataricus* strain KM1

The *Sulfolobus solfataricus strain KM*1 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80° C. The yield of the bacterial cell was 3.3 g/liter.

Eighty two grams of the bacterial cells obtained above were suspended in 400 ml of a 50 mM sodium acetate buffer solution (pH 5.5) containing 5 mM of EDTA, and subjected to ultrasonic treatment for bacteriolysis at 0° C. for 15 min. The resultant was then centrifuged to obtain a supernatant.

To this supernatant, ammonium sulfate was added so as to be 1 M. The resultant was then subjected to hydrophobic chromatography using TOSOH TSK-gel Phenyl-TOYOPEARL 650S column (volume: 800 ml) equilibrated with a 50 mM sodium acetate buffer solution (pH 5.5) containing 1 M of sodium sulfate and 5 mM of EDTA. The column was then washed with the same buffer solution, and the debranching enzyme was recovered in the fraction passing through the column. Since amylase, transferase and glucoamylase contained in the supernatant were retained and adsorbed in the packed material of the column, Phenyl-TOYOPEARL 650S, the objective debranching enzyme could be separated therefrom.

The fraction exhibiting the activity was concentrated using an ultrafiltration membrane (critical molecular weight: 13,000), and subsequently, washed and desalted with a 10 mM Tris-HCl buffer solution (pH 7.5).

Next, the resultant was subjected to ion-exchange chromatography using the TOSOH TSK-gel DEAE-TOYOPEARL 650S column (volume: 300 ml) equilibrated with the same buffer solution. The column was then washed with the same buffer solution, and the objective debranching enzyme was then eluted with 900 ml of sodium chloride solution at a linear concentration gradient from 0 M to 0.3 M. The fractions exhibiting the activity were concentrated using an ultrafiltration membrane (critical molecular weight: 13,000), and subsequently, washed and desalted with a 50 mM sodium acetate buffer solution (pH 5.5) containing 0.15 M of sodium chloride and 5 mM of EDTA.

Subsequent to that, the desalted and concentrated solution thus obtained was subjected to gel filtration chromatography using the Pharmacia HiLoad 16/60 Superdex 200 pg column, and the objective debranching enzyme was eluted with the same buffer solution. The fractions exhibiting the activity were concentrated using an ultrafiltration membrane. (critical molecular weight: 13,000), and subsequently, washed and desalted with a 25 mM bis-Tris-iminodiacetic acid buffer solution (pH 7.1).

Next, the desalted and concentrated solution thus obtained was subjected to a chromatofocusing using the Pharmacia Mono P HR5/20 column equilibrated with the same buffer solution. The objective debranching enzyme was then eluted with 10% Polybuffer 74 (manufactured by Pharmacia, and adjusted at pH 4.0 with iminodiacetic acid). The fractions exhibiting the activity were concentrated using an ultrafiltration membrane (critical molecular weight: 13,000), and subsequently, washed and desalted with a 10 mM Tris-HCl buffer solution (pH.7.5).

Further, the desalted and concentrated solution thus obtained was subjected to ion-exchange chromatography using the TOSOH TSK-gel DATE 5PW HPLC column equilibrated with the same buffer solution. The column was then washed with the same buffer solution, and the objective debranching enzyme was then eluted with 30 ml of sodium chloride solution at a linear concentration gradient from 0 M to 0.3 M. The fractions exhibiting the activity were concentrated using an ultrafiltration membrane (critical molecular weight: 13,000) to obtain the-partially purified product (liquid product) of the objective debranching enzyme.

Incidentally, in this purification procedure, detection of the objective debranching enzyme was performed by mixing the sample solution with 2 Units/ml of the purified amylase and 32 Units/ml of the purified transferase derived from the *Sulfolobus solfataricus* strain KM1, and by putting the mixture into a reaction at 60° C. and pH 5.5, wherein the index was the activity of achieving a higher yield of α,α-trehalose in comparison with the reaction without the sample solution.

The activity of the partially purified debranching enzyme, obtained by the above-described purification process and derived from the *Sulfolobus solfataricus* strain KM1, was measured as follows: A half milliliter of 1% soluble starch derived from glutinous rice was mixed with 0.1 ml of a 0.5 M acetic acid buffer solution (pH 5.0) and 0.1 ml of an enzyme solution, and subjected to reaction at 60° C.; the absorptivity at 610 nm corresponding to the violet color of the amylose-iodine complex is measured with a cuvette having a width of 1 cm; and 1 Unit is defined as the amount of the enzyme with which the absorptivity increases by 0.1 per hour.

The specific activity of the partially purified debranching enzyme obtained by the above purification procedure was found to be 495 Units/mg.

Referential Example II-4
Examination of the Debranching Enzyme Derived from the *Sulfolobus solfataricus* Strain KM1 for Various Characteristics The partially purified debranching enzyme obtained in Referential Example II-3 was examined for enzymatic characteristics.

(1) Action and Substrate Specificity

The reactivity and action on each substrate were examined using each the substrate and activity-measuring methods shown in Table 33 below.

The dinitrosalicylate method ["Denpun.Kanren Toushitsu Kouso Jikken-hou" ("Experimental methods in enzymes for starch and relating saccharides"), written by Michinori Nakamura and Keiji Kainuma, published by Gakkai-Shuppan-Sentah, 1989] is a method for quantifying the increased amount of reducing ends generated by hydrolysis of α-1,6 linkages.

The iodine-coloring method is carried out in the same way as described in Referential Example II-3.

Specifically, this is the method for quantifying the increased amount of straight-chain amylose generated by hydrolysis of α-1,6 linkages on the basis of increased absorptivity at 610 nm corresponding to the violet color of the amylose-iodine complex.

Analysis of the hydrolyzed products by liquid chromatography (HPLC method) was performed for examination of the produced oligosaccharides by employing the Bio-Rad AMINEX HPX-42A HPLC analyzing method described in Example II-1.

TABLE 33

| | Method of enzyme assay | | |
|---|---|---|---|
| Substrate | Dinitrosalicylate method | Iodine-coloring method | HPLC method |
| Pullulan | +++ | − | Maltotriose |
| Soluble starch | + | + | − |
| Amylopectin | + | + | − |
| Glutinous rice starch | + | + | − |

As is obvious from the above results, the present debranching enzyme can 1) generate reducing ends in pullulan and various kinds of starch; 2) increase the coloring degree in the iodo-starch reaction; 3) produce maltotriose from pullulan; and further, 4) as shown in Example II-14, markedly increase the yield of α,α-trehalose from soluble starch used as a substrate when the present debranching enzyme is put into the reaction with the purified amylase and transferase derived from the *Sulfolobus solfataricus* strain KM1, as compared with the reaction without the addition of the present debranching enzyme. As a consequence of these facts, the present enzyme is recognized as hydrolyzing α-1,6 linkages in starch or pullulan.

(2) Stability

The stability of the obtained partially purified enzyme when treated at various temperatures for 3 hours is shown in Table 34.

TABLE 34

| Temperature (° C.) | Residual activity (%) |
|---|---|
| 50 | 109.1 |
| 60 | 73.3 |
| 65 | 6.1 |
| 70 | 0 |

The present enzyme treated at 60° C. for 3 hours still retains 73.3% of the initial activity.

(3)

As to the obtained partially purified enzyme, reactivity at various temperatures and reactivity at various pH values are shown in Tables 35 and 36, respectively. In the measurement of enzymatic activity, a glycine-HCl buffer solution was used in a pH range of 3–5, and similarly, a sodium acetate buffer solution in a pH range of 4–5.5, and a sodium phosphate buffer solution in a pH range of 5–7.5, respectively, were also used.

TABLE 35

| Reaction pH | Relative enzyme activity (%) |
|---|---|
| 2.7 | 1.8 |
| 3.1 | 21.7 |
| 3.7 | 33.1 |
| 4.1 | 74.0 |
| 5.1 | 100.0 |
| 5.5 | 53.7 |
| 5.6 | 37.5 |
| 6.0 | 22.2 |
| 6.9 | 16.1 |

TABLE 35-continued

| Reaction pH | Relative enzyme activity (%) |
|---|---|
| 7.4 | 11.5 |
| 7.7 | 10.2 |

TABLE 36

| Reaction temperature (° C.) | Relative enzyme activity (%) |
|---|---|
| 40 | 53.8 |
| 50 | 87.0 |
| 60 | 97.6 |
| 65 | 100.0 |
| 70 | 51.4 |

The optimum reaction temperature of the present enzyme is within 60–65° C., approximately, and the optimum reaction pH of the present enzyme is within 4.0–5.5, approximately.

(4) Isoelectric Point

The isoelectric point was found to be pH 4.4 from the result of pH measurement performed on the debranching enzyme fraction isolated by chromatofocusing.

(5) Influence of Various Activators and Inhibitors

The influence of each substance listed in Table 37, such as an activating effect or an inhibitory effect, was evaluated by adding the substance together with the substrate, and by measuring the activity in the same manner as that in Referential Example II-3. As a result, copper ion was found to have inhibitory effects. Though many glucide-relating enzymes have been found to be activated with calcium ion, the present enzyme would not be activated with calcium ion.

TABLE 37

| Activator/Inhibitor | Concentration (mM) | Residual activity (%) |
|---|---|---|
| Control (not added) | 5 | 100.0 |
| $CaCl_2$ | 5 | 105.7 |
| $MgCl_2$ | 5 | 82.9 |
| $MnCl_2$ | 5 | 91.2 |
| $CuSO_4$ | 5 | 0.0 |
| $CoCl_2$ | 5 | 87.2 |
| $FeSO_4$ | 5 | 74.1 |
| $FeCl_3$ | 5 | 39.0 |
| 2-Mercaptoethanol | 5 | 104.1 |
| Dithiothreitol | 5 | 106.0 |

EXAMPLE I-9

Determination of the Partial Amino Acid Sequences of the Novel Transferase Derived from the *Sulfolobus solfataricus* Strain KM1

The partial amino acid sequences of the purified enzyme obtained in Example I-2 were determined by the method disclosed in Iwamatsu, et al. [Seikagaku (Biochemistry) 63, 139 (1991)]. Specifically, the purified novel transferase was suspended in a buffer solution for electrophoresis [10% glycerol, 2.5% SDS, 2% 2-mercaptoethanol, 62 mM Tris-HCl buffer solution (pH 6.8)], and subjected to SDS-polyacrylamide gel electrophoresis. After the electrophoresis, the enzyme was transferred from the gel to a polyvinylidene diflorido (PVDF) membrane (ProBlot, manufactured by Applied Biosystems Co.) by electroblotting (SartoBlot type IIs, manufactured by Sartorius Co.) with 160 mA for 1 hour.

After the transfer, the portion to which the enzyme had been transferred was cut out from the membrane, and soaked in about 300 μl of a buffer solution for reduction [6 M guanidine-HCl, 0.5 M Tris-HCl buffer solution (pH 3.5) containing 0.3% of EDTA and 2% of acetonitrile]. One milligram of dithiothreitol was added to this, and reduction was carried out under an argon atmosphere at 60° C. for 1 hour, approximately. To the resultant, 2.4 mg of monoiodoacetic acid dissolved in 10 μl of 0.5 N sodium hydroxide was added and stirred for 20 min. in the dark. The PVDF membrane was then taken out and washed sufficiently with a 2% acetonitrile solution, and subsequently, stirred in a 0.1% SDS solution for 5 min. After being briefly washed with water, the PVDF membrane was then soaked in 0.5% Polyvinylpyrrolidone-40 dissolved in 100 mM acetic acid, and was left standing for 30 min. Next, the PVDF membrane was briefly washed with water and cut into pieces of 1 square mm, approximately. These pieces were then soaked in a buffer solution for digestion [8% acetonitrile, 90 mM Tris-HCl buffer solution (pH 9.0)], and after the addition of 1 pmol of the Achromobacter Protease I (manufactured by Wako pure chemical Co.), digested at room temperature for 15 hours. The digested products were separated by reversed phase chromatography using a C8 column (μ-Bondashere 5C8, 300A, 2.1×150 mm, manufactured by Millipore Ltd. Japan) to obtain a dozen or more kinds of peptide fragments. Using A solvent (0.05% trifluoroacetic acid) and B solvent (2propanol:acetonitrile=7:3, containing 0.02% of trifluoroacetic acid) as elution solvents, the peptides were eluted with a linear concentration gradient from 2 to 50% relative to B solution and at a flow rate of 0.25 ml/min. for 40 min. As to the peptide fragments thus obtained, the amino acid sequences were determined by the automatic Edman degradation method using a gas-phase peptide sequencer (Model 470 type, manufactured by Applied Biosystems Co.).

Further, the peptide fragments digested with the Achromobacter Protease I were subjected to second digestion with Asp-N, and the resultant peptide fragments were isolated under the same conditions as above to determine their amino acid sequences.

From the results, the partial amino acid sequences were found to be as follows.

Peptide Fragments Digested with Achromobacter Protease

AP-1: Val Ile Arg Glu Ala Lys (Sequence No. 9)
AP-2: Ile Ser Ile Arg Gln Lys (Sequence No. 10)
AP-3: Ile Ile Tyr Val Glu (Sequence No. 11)
AP-4: Met Leu Tyr Val Lys (Sequence No. 12)
AP-5: Ile Leu Ser Ile Asn Glu Lys (Sequence No. 13)
AP-6: Val Val Ile Leu Thr Glu Lys (Sequence No. 14)
AP-7: Asn Leu Glu Leu Ser Asp Pro Arg Val Lys (Sequence No. 15)
AP-8: Met Ile Ile Gly Thr Tyr Arg Leu Gln Leu Asn Lys (Sequence No. 16)
AP-9: Val Ala Val Leu Phe Ser Pro Ile Val (Sequence No. 17)
AP-10: Ile Asn Ile Asp Glu Leu Ile Ile Gln Ser Lys (Sequence No. 18)
AP-11: Glu Leu Gly Val Ser His Leu Tyr Leu Ser Pro Ile (Sequence No. 19)

Peptide Fragments Digested with Asp-N

DN-1: Asp Glu Val Phe Arg Glu Ser (Sequence No. 20)
DN-2: Asp Tyr Phe Lys (Sequence No. 21)
DN-3: Asp Gly Leu Tyr Asn Pro Lys (Sequence No. 22)
DN-4: Asp Ile Asn Gly Ile Arg Glu Cys (Sequence No. 23)
DN-5: Asp Phe Glu Asn Phe Glu Lys (Sequence No. 24)
DN-6: Asp Leu Leu Arg Pro Asn Ile (Sequence No. 25)
DN-7: Asp Ile Ile Glu Asn (Sequence No. 26)
DN-8: Asp Asn Ile Glu Tyr Arg Gly (Sequence No. 27)

EXAMPLE I-10

Preparation of Chromosome DNA of the *Sulfolobus solfataricus* Strain KM1

Bacterial cells of the *Sulfolobus solfataricus* strain KM1 were obtained according to the process described in Example I-2.

To 1 g of the bacterial cells, 10 ml of a 50 mM Tris-HCl buffer solution (pH 8.0) containing 25% of sucrose, 1 mg/ml of lysozyme, 1 mM of EDTA, and 150 mM of NaCl was added for making a suspension, and the suspension was left standing for 30 min. To this suspension, 0.5 ml of 10% SDS and 0.2 ml of 10 mg/ml Proteinase K (manufactured by Wako pure chemical Co.) were added, and the mixture was left standing at 50° C. for 2 hours. Next, the mixture was subjected to extraction with a phenol/chloroform solution. The resultant aqueous phase was then separated and precipitated with ethanol. The precipitated DNA was twisted around a sterilized glass stick and vacuum-dried after being washed with a 70% ethanol solution. As the final product, 1.5 mg of the chromosome DNA was obtained.

EXAMPLE I-1

Preparation of DNA Probes Based on the Partial Amino Acid Sequences and Evaluation of the Probes by PCR Method According to information about the partial amino acid sequences of the novel transferase derived from the *Sulfolobus solfataricus* strain KM1, which is determined in Example I-9, oligonucleotide DNA primers are prepared by using a DNA synthesizer (Model 381 manufactured by Applied Biosystems Co.). Their sequence were as follows.

DN-1

Amino Acid Sequence

N terminus AspGluPheArgGluSer C terminus DNA Primer 5' TTCACGAAAAACCTCATC 3' (Sequence No. 28) Base Sequence C T TG T T

DN-8

Amino Acid Sequence

N terminus AspAsnIleGluTyrArgGly C terminus DNA Primer 5' GATAACATAGAATACAGAGG 3' (Sequence No. 29) Base Sequence T T G T G PCR was performed using 100 pmol of each primer and 100 ng of the chromosome DNA prepared in Example I-10 and derived from the *Sulfolobus solfataricus* strain KM1. The PCR apparatus used herein was the GeneAmp PCR system Model 9600, manufactured by Perkin Elmer Co. In the reaction, 30 cycles of steps were carried out with 100 µl of the total reaction mixture, wherein the 1 cycle was composed of steps at 94° C. for 30 sec., at 50° C. for 1 min., and at 72° C. for 2 min.

Ten microliters of the resultant reaction mixture was analyzed by 1% agarose electrophoresis. As a result, it was found that a DNA fragment having a length of about 1.2 kb was specifically amplified.

The product obtained by the above PCR were blunt-ended, and subcloned into pUC118 at the Hinc II site. The DNA sequence of the insertional fragment in this plasmid was determined using a DNA sequencer, GENESCAN Model 373A manufactured by Applied Biosystems Co. As a result, the DNA sequence was found to correspond to the amino acid sequence obtained in Example I-9.

EXAMPLE I-12

Cloning of a Gene Coding for the Novel Transferase Derived from the *Sulfolobus solfataricus* Strain KM1

One hundred micrograms of the chromosome DNA of the *Sulfolobus solfataricus* strain KM1, prepared in Example I-10, was partially digested with a restriction enzyme, Sau 3AI. The reaction mixture was ultracentrifuged with a density gradient of sucrose to isolate and purify DNA fragments of 5–10 kb. Then, using T4 DNA ligase, the above chromosome DNA fragments having lengths of 5–10 kb and derived from the *Sulfolobus solfataricus* strain KM1 were ligated with a modified vector which had been prepared from a plasmid vector, pUC118, by digestion with Bam HI and by dephosphorylation of the ends with alkaline phosphatase. Next, cells of the *E. coli* strain JM109 were transformed with a mixture containing the modified pUC118 plasmid vectors in which any of the fragments had been inserted. These cells were cultivated on LB agar plates containing 50 µg/ml of ampicillin to grow their colonies and make a DNA library.

As to this DNA library, screening of the recombinant plasmids containing a gene coding for the novel transferase was performed employing a PCR method as follows.

At first, the colonies were scraped and suspended in a TE buffer solution. The suspension was then treated at 100° C. for 5 min. to crush the bacterial bodies and subjected to PCR in the same manner as described in Example I-11.

Next, 10 µl of the reaction mixture obtained in PCR was analyzed by 1% agarose electrophoresis, and the clones from which a DNA fragment having a length of about 1.2 kb can be amplified were assumed to be positive.

As a result, one positive clone was obtained from 600 of the transformants. According to analysis of the plasmid extracted from the clone, it had an insertional fragment of about 8 kb. This plasmid was named as pKT1.

Further, the insertional fragment was shortened by subjecting it to partial digestion with Sau 3AI and PCR in the same manner as above. As a result, such transformants as containing plasmids which have insertional fragments of about 3.8 kb and about 4.5 kb were obtained. These plasmids were named as pKT21 and pKT11, respectively.

The restriction maps of insertional fragments of these plasmids are shown in FIG. 26.

Incidentally, all the restriction enzymes used in the above examples were commercially available (purchased from Takara Shuzou Co.).

EXAMPLE I-13

Determination of the Gene Coding for the Novel Transferase Derived from the *Sulfolobus solfataricus* Strain KM1

The base sequence of the partial DNA which is common both in the insertional fragments, the plasmids pKT11 and pKT21 obtained in Example I-12, was determined.

At first, deletion plasmids were prepared from these plasmid DNAs by using a deletion kit for kilo-sequencing which was manufactured by Takara Shuzou Co. After that, the DNA sequences of the insertional fragments in these plasmids were determined by using a sequenase dye primer sequencing kit, PRISM, a terminator cycle sequencing kit, Taq Dye Deoxy™, both manufactured by Perkin Elmer Japan Co., and a DNA sequencer, GENESCAN Model 373A, manufactured by Applied Biosystems Co.

Among the common sequence, the base sequence from the Sph I site to an end of pKT21 (from A to B in FIG. 26), and the amino sequence anticipated therefrom are shown in Sequences No. 1 and No. 2, respectively.

Sequences corresponding to any of the partial amino acid sequences obtained in Example I-9, respectively, were recognized in the above amino acid sequence. This amino acid sequence was assumed to have 728 amino acid residues and code for a protein, the molecular weight of which estimated as 82 kDa. This molecular weight value almost equals the value obtained by SDS-PAGE analysis of the purified novel transferase derived from the *Sulfolobus solfataricus* strain KM1.

EXAMPLE I-14
Production of the Novel Transferase in a Transformant

Figure 27:
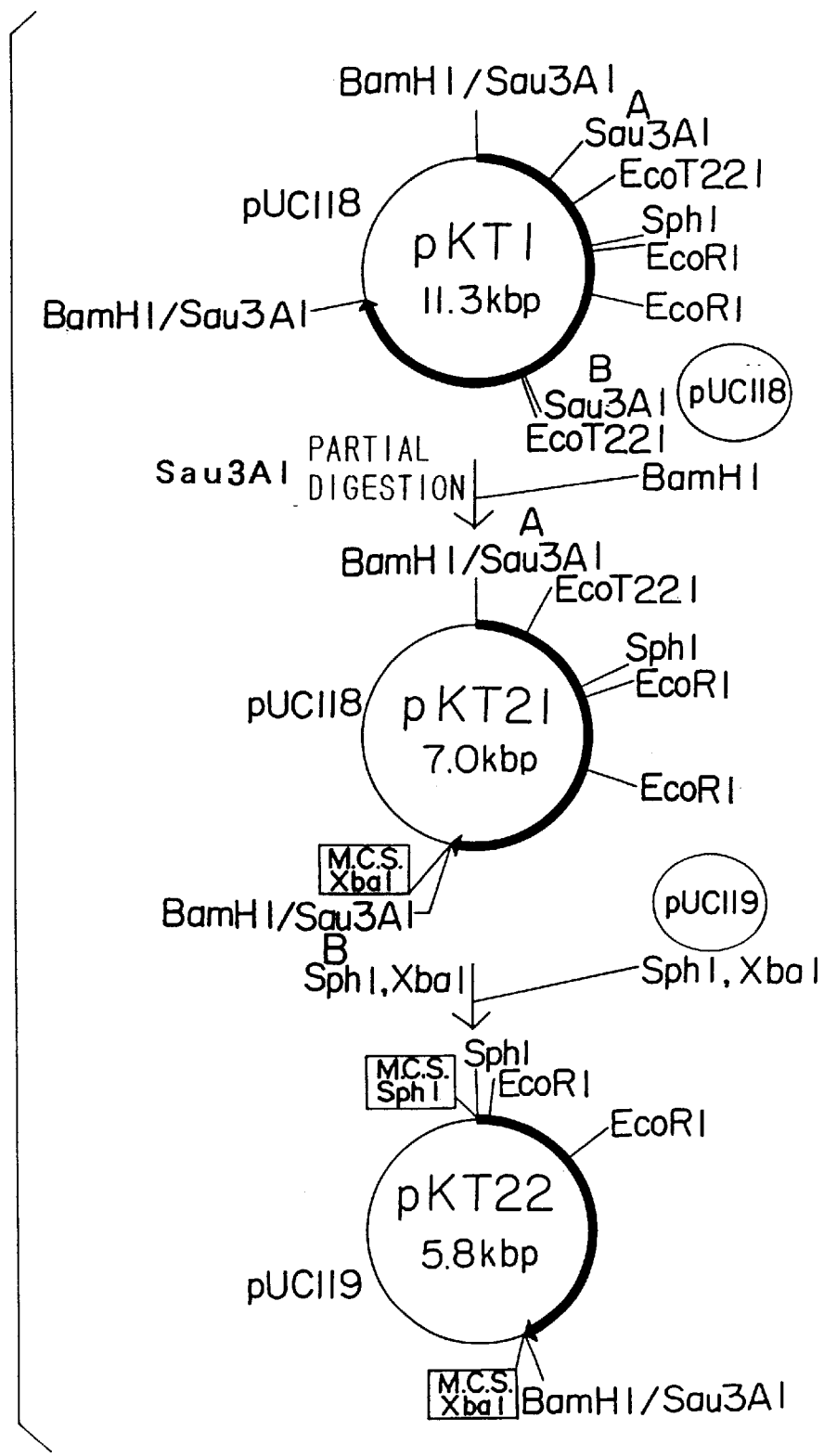
FIG. 27 is an illustration showing a process for constructing the plasmid pKT22.

A plasmid named as pKT22 was obtained by restricting pKT21, which was obtained in Example 1–12, with Sph I and Xba I, and by ligating the resultant with pUC119 (manufactured by Takara Shuzou Co.) which had been restricted with the same restriction enzymes(the methods are shown in FIG. 27). Except for the multi-cloning site, the base sequence of the fragment which was inserted into pKT22 and contains the novel transferase gene equaled the sequence from the 1st base to the 2578th base of Sequence No. 1.

The activity of the novel transferase in the transformant containing this plasmid was examined as follows. At first, the transformant was cultivated overnight in a LB broth containing 100 μg/ml of ampicillin at 37° C. The cells were collected by centrifugation and stored at −80° C. The yield of bacterial cells was 10 g/liter.

Ten grams of the bacterial cells obtained above were then suspended in 40 ml of a 50 mM sodium acetate buffer solution (pH 5.5) containing 5 mM of EDTA, subjected to bacteriolysis with an ultrasonic crushing-treatment at 0° C. for 3 min., and further, centrifuged to obtain a supernatant. This supernatant was heat-treated at 75° C. for 30 min., further centrifuged, and then concentrated with an ultrafiltration membrane (critical molecular weight: 13,000) to produce a crude enzyme solution (6 Units/ml). Maltotriose, as a substrate, was added so that the final concentration would be 10%. The reaction was carried out at pH 5.5 (50 mM sodium acetate) and at 600° C. for 24 hours, and stopped by heat-treatment at 100° C. for 5 min. The produced glucosyltrehalose was analyzed by the same HPLC analyzing method used in Example I-1.

Figure 28A:
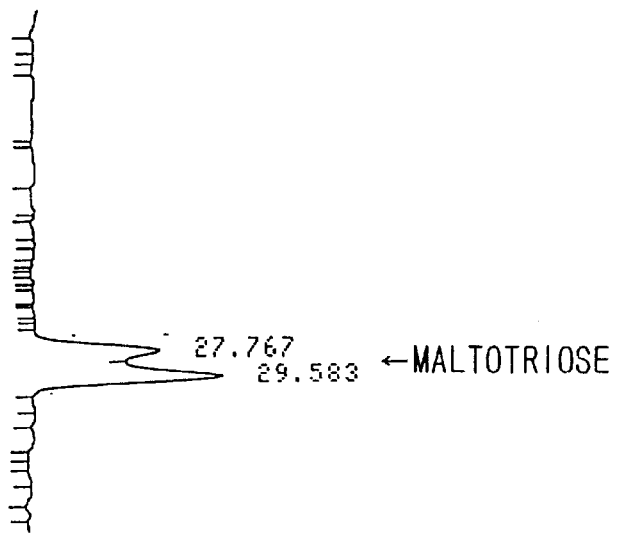
FIGS. 28A, 28B is a graph showing the results of an analysis by TSK-gel Amide-80 HPLC, performed on the product derived from maltotriose by using the recombinant novel transferase.
Figure 28B:
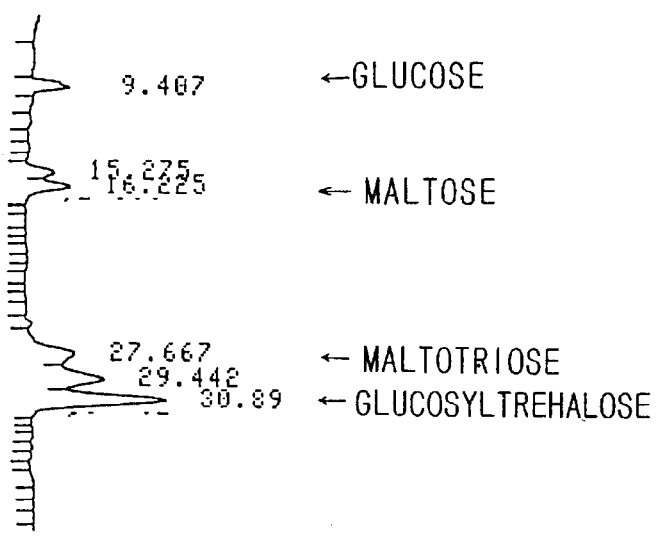

The results of the HPLC analysis are shown in FIG. 28. The principal reaction-product appeared in the HPLC chart as a peak without any anomers, exhibiting such a retention time as slightly behind the non-reacted substrate. Further, the principal product was isolated using a TSK-gel Amide-80 HPLC column, and analyzed by $^1$H-NMR and $^{13}$C-NMR to be confirmed as glucosyltrehalose.

Consequently, the transformant was found to have the activity of the novel transferase derived from the *Sulfolobus solfataricus* strain KM1. Incidentally, no activity of the novel transferase was detected in the transformant prepared by transforming the JM109 with pUC119 alone.

EXAMPLE I-15
Determination of Partial Amino Acid Sequences of the Novel Transferase Derived from the *Sulfolobus solfataricus* Strain KM1

Partial amino acid sequences of the novel transferase obtained in Example I-4 were determined according to the process described in Example I-9. The following are the determined partial amino acid sequences.

Peptide Fragments Digested with Achromobacter Protease

AP-6: Arg Asn Pro Glu Ala Tyr Thr Lys (Sequence No. 30)
AP-8: Asp His Val Phe Gln Glu Ser His Ser (Sequence No. 31)
AP-10: Ile Thr Leu Asn Ala Thr Ser Thr (Sequence No. 32)
AP-12: Ile Ile Ile Val Glu Lys (Sequence No. 33)
AP-13: Leu Gln Gln Tyr Met Pro Ala Val Tyr Ala Lys (Sequence No. 34)
AP-14: Asn Met Leu Glu Ser (Sequence No. 35)
AP-16: Lys Ile Ser Pro Asp Gln Phe His Val Phe Asn Gln Lys (Sequence No. 36)
AP-18: Gln Leu Ala Glu Asp Phe Leu Lys (Sequence No. 37)
AP-19: Lys Ile.Leu Gly Phe Gln Glu Glu Leu Lys (Sequence No. 38)
AP-20: Ile Ser Val Leu Ser Glu Phe Pro Glu Glu (Sequence No. 39)
AP-23: Leu Lys Leu Glu Glu Gly Ala Ile Tyr (Sequence No. 40)
AP-28: Glu Val Gln Ile Asn Glu Leu Pro (Sequence No. 41)

Peptide Fragments Digested with Asp-N
DN-1: Asp His Ser Arg Ile (Sequence No. 42)
DN-5: Asp Leu Arg Tyr Tyr Lys (Sequence No. 43)
DN-6: Asp Val Tyr Arg Thr Tyr Ala Asn Gln Ile Val Lys Glu Cys (Sequence No. 44)

EXAMPLE I-16
Cloning of a Gene Coding for the Novel Transferase Derived from the *Sulfolobus acidocaldarius* Strain ATCC 33909

The chromosome DNA of the *Sulfolobus acidocaldarius* strain ATCC 33909 was obtained according to the process described in Example I-10 from bacterial cells obtained according to the process described in Example I-4. The above chromosome DNA was partially digested with Sau 3AI and subsequently, ligated to a Bam HI-restricted arm of EMBL3 (manufactured by STRATAGENE Co.) by using T4 DNA ligase. Packaging was carried out using Gigapack II Gold, manufactured by STRATAGENE Co. With the library obtained above, the *E. coli* strain LE392 was infected at 37° C. for 15 min., inoculated on NZY agar plates, and incubated at 37° C. for 8–12 hours, approximately, to form plaques. After being stored at 4° C. for about 2 hours, DNA was adsorbed on a nylon membrane (Hybond N+, manufactured by Amersham Co. Baking was performed at 80° C. for 2 hours after brief washing with 2×SSPE. Using the Eco RI-Xba I fragment (corresponding to the sequence from the 824th base to the 2578th base of Sequence No. 1) of pKT22 obtained in Example I-14, the probe was labeled with $^{32}$P employing Megaprime DNA labeling system manufactured by Amersham Co.

Hybridization was performed overnight under the conditions of 60° C. with 6×SSPE containing 0.5% of SDS. Washing was performed by treating twice with 2×SSPE containing 0.5% of SDS at room temperature for 10 min.

Figure 30:
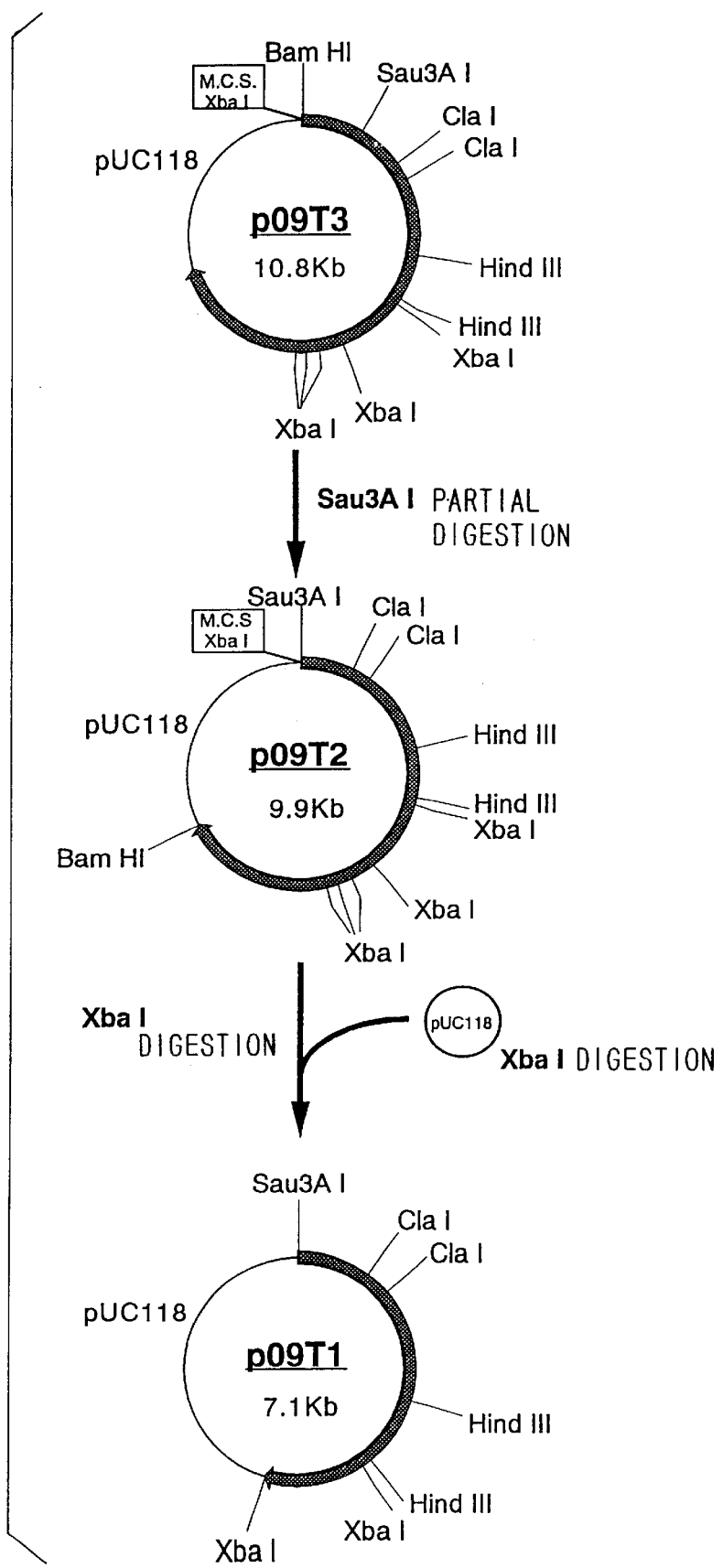
FIG. 30 is an illustration showing a process for constructing the plasmid p09T1.

Screening was started with 5,000 clones, approximately, and 8 positive clones were obtained. From these clones, a Bam HI fragment of about 7.6 kbp was obtained and the fragment was inserted into pUC118 at the corresponding restriction site. The plasmid thus obtained was named as p09T3. Further, the insertional fragments of the above clones were partially digested with Sau 3AI and the obtained fragment of about 6.7 kbp was inserted into pUC118 at the Bam HI site. The plasmid thus obtained was named as p09T2. The Xba I fragment which was derived from this plasmid and had about 3.8 kbp was inserted into pUC118 at the corresponding restriction site. The plasmid thus obtained was named as p09T1. The restriction map of this plasmid is shown in FIG. 29, and the preparation procedure thereof is shown in FIG. 30. As to the above plasmid p09T1, the base sequence, principally of the region coding for the novel transferase, was determined according to the process described in Example I-13. The base sequence thus determined and the amino acid sequence anticipated therefrom are shown in Sequences No. 3 and No. 4, respectively. Sequences corresponding to any of the partial amino acid sequences obtained in Example I-15, respectively, were recognized in this amino acid sequence. This amino acid sequence was assumed to have 680 amino acid residues and code for a protein, the molecular weight of which was estimated as 80.1 kDa. This molecular weight value almost equals the value obtained by SDS-PAGE analysis of the purified novel transferase derived from the *Sulfolobus solfataricus* strain ATCC 33909. Additionally, the existence of the activity of the novel transferase in a transformant containing the plasmid p09T1 was confirmed according to the procedure described in Example I-14.

EXAMPLE I-17
Hybridization Tests Between the Gene Coding for the Novel Transferase Derived from the *Sulfolobus solfataricus* Strain KM1 and Chromosome DNAs Derived from the Other Organisms Chromosome DNAs were obtained from the *Sulfolobus solfataricus* strain DSM 5833, the *Sulfolobus shibatae* strain DSM 5389, and the *E. Coli* strain JM109, and digested with restriction enzymes Pst I and Eco RI.

These digested products were separated by 1% agarose gel electrophoresis and transferred using the Southern blot technique to a Hybond-N membrane manufactured by Amersham Japan Co. The Sph I-Xba I fragment of about 2.6 kbp (corresponding to the sequence shown in Sequence No. 1, or corresponding to the region of A–B in FIG. 26), which derived from pKT21 obtained in Example I-12, was labeled using a DIG system kit manufactured by Boehringer Mannheim Co., and the resultant was subjected to a hybridization test with the above-prepared membrane.

The hybridization was performed under the conditions of 40° C. for 2 hours with 5×SSC, and washing was performed by treating twice with 2×SSC containing 0.1% of SDS at 40° C. for 5 min. and twice with 0.1×SSC containing 0.1% of SDS at 400° C. for 5 min.

As a result, the Sph I-Xba I fragment could hybridize with a fragment of about 5.9 kbp derived from the *Sulfolobus solfataricus* strain DSM 5833, and with fragments of about 5.0 kbp and about 0.8 kbp, respectively, derived from the *Sulfolobus shibatae* strain DSM 5389. On the other hand, no hybrid formation was observed in fragments derived from the *E. coli* strain JM109 which was used as a negative control.

Further, chromosome DNAs were obtained according to the procedure described in Example I-10 from the *Sulfolobus solfataricus* strains KM1, DSM 5354, DSM 5833, ATCC 35091, and ATCC 35092; the *Sulfolobus acidocaldarius* strains ATCC 33909, and ATCC 49426; the *Sulfolobus shibatae* strain DSM 5389; the *Acidianus brierleyi* strain DSM 1651; and the *E. coli* strain JM109, and digested with restriction enzymes, Hind II, Xba I, and Eco RV.

These digested products were separated by 1% agarose gel electrophoresis and transferred using the Southern blot technique to a Hybond-N+ membrane manufactured by Amersham Japan Co. The region (378 bp) from the 1880th base to the 2257th base of Sequence No. 1 was amplified by PCR and labeled with 32p according to the procedure described in Example I-16, and the resultant was subjected to a hybridization test with the above prepared membrane.

The hybridization was performed overnight under the conditions of 60° C. with 6×SSPE containing 0.5% of SDS, and washing was performed by treating twice with 2×SSPE containing 0.1% of SDS at room temperature for 10 min.

As a result, the following fragments were found to form hybrids: the fragments of about 4.4 kbp, about 3.7 kbp, about 3.7 kbp, about 0.8 kbp, and about 3.9 kbp derived from the *Sulfolobus solfataricus* strains KM1, DSM 5354, DSM 5833, ATCC 35091, and ATCC 35092, respectively; the fragments of about 0.8 kbp, and about 0.8 kbp derived from the*Sulfolobus acidocaldarius* strains ATCC 33909, and ATCC 49426, respectively; the fragment of about 4.4 kbp derived from the *Sulfolobus shibatae* strain DSM 5389; and the fragment of about 2.1 kbp derived from the *Acidianus brierleyi* strain DSM 1651. On the other hand, no hybrid formation was observed as to the genome DNA of the strain JM109.

Moreover, it was confirmed, through data banks of amino acid sequences (Swiss prot and NBRF-PDB) and a data bank of base sequences (EMBL), and by using sequence-analyzing software, GENETYX (produced by Software Development Co.), that there is no sequence homologous to any of the amino acid sequences and base sequences within the scopes of Sequences No. 1, No. 2, No. 3, and No. 4. Consequently, the genes coding for the novel transferases were found to be highly conserved specifically in archaebacteria belonging to the order Sulfolobales.

EXAMPLE I-18
Comparisons Between the Base Sequences and Between the Amino Acid Sequences of the Novel Transferases Derived from the *Sulfolobus solfataricus* Strain KM1 and the *Sulfolubus acidocaldarius* Strain ATCC 33909

Considering gapps and using sequence-analyzing software, GENETYX (produced by Software Development Co.), comparative analyses were carried out on the amino acid sequence of the novel transferase derived from the strain KM1, i.e. Sequence No. 2, and that derived from the strain ATCC 33909, i.e. Sequence No. 4; and on the base sequence coding for the novel transferase derived from the strain KM1, i.e. Sequence No. 1, and that derived from the strain ATCC 33909, i.e. Sequence No. 3. The results as to the amino acid sequences are shown in FIG. 31, and the results as to the base sequences are shown in FIG. 32. In each figure, the upper line indicates the sequence derived from the strain 33909, the lower line indicates the sequence derived from the strain KM1, and the symbol "*" in the middle line indicates the portions equal in both strains. Each of the couples indicated with symbol "." in FIG. 31 are a couple of amino acid residues which mutually have similar characteristics. The homology values are 49% and 57% on the levels of the amino acid sequences and the base sequences, respectively.

EXAMPLE I-19
Production of Trehaloseoligosaccharides from a Maltooligosaccharide Mixture Using the Recombinant Novel Transferase Derived from a Transformant Alpha-amylase-hydrolysate obtained by hydrolyzing soluble starch (manufactured by Nacalai tesque Co., special grade) into oligosaccharides which do not cause the iodo-starch reaction was used as a substrate, wherein the α-amylase was A-0273 manufactured by Sigma Co. and derived from *Aspergillus oryzae*. Production of glucosyltrehalose and various maltooligosyltrehaloses was attempted by using the crude enzyme solution obtained in Example I-14 and the above substrate, and according to the reaction conditions described in Example I-14. The obtained reaction mixture was analyzed by a HPLC method under the following conditions.

Column: BIORAD AMINEX HPX-42A (7.8×300 mm)

Solvent: Water

Flow rate: 0.6 ml/min.

Temperature: 85° C.

Detector: Refractive Index Detector

The results by HPLC analysis are shown in FIG. 33(A), and the results by HPLC analysis in a case performed without the recombinant novel transferase are shown in FIG. 33(B). As is obvious from the results, each of the oligosaccharides as the reaction products exhibits a retention time shorter than those of the reaction products produced in the control group, namely, produced only with amylase. Next, the principal products, i.e. trisaccharide, tetrasaccharide, and pentasaccharides derived from the substrates, i.e. maltotriose (G3), maltotetraose (G4), and maltopentaose (G5) (all manufactured by Hayashibara Biochemical Co.), respectively, were isolated using the TSK-gel Amide-80 HPLC column, and were analyzed by $^1$H-NMR and $^{13}$C-NMR. As a result, all of such products were found to have a structure in which the glucose residue at the reducing end is α-1,α-1-linked, and the products were confirmed as glucosyltrehalose (α-D-maltosyl α-D-glucopyranoside), maltosyltrehalose (α-D-maltotriosyl α-D-glucopyranoside), and maltotriosyltrehalose (α-D-maltotetraosyl α-D-glucopyranoside), respectively.

EXAMPLE I-20
Production of Glucosyltrehalose and Maltooligosyltrehalose by Using the Novel Transferase Derived from a Transformant Maltotriose (G3)–Maltoheptaose (G7) (all manufactured by Hayashibara Baiokemikaru Co.) were used as substrates. The crude enzyme solution obtained in Example I-14 was lyophilized, and then suspended in a 50 mM sodium acetate solution (pH 5.5) to make a concentrated enzyme solution. Each of the substrates was subjected to reaction with 12.7 Units/ml (in terms of the enzymatic activity when maltotriose is used as the substrate) of the concentrated enzyme solution to produce a corresponding α-1,α-1-transferred isomer. Each reaction product was analyzed by the method described in Example I-1 to examine the yield and the enzymatic activity. The results are shown in Table 38. Incidentally, as to the enzymatic activity shown in Table 38, 1 Unit is defined as an enzymatic activity of transferring maltooligosaccharide to produce 1 μmol per hour of a corresponding α-1,α-1-transferred isomer.

TABLE 38

| Substrate | Enzyme activity (unit/ml) | Yield (%) |
| --- | --- | --- |
| Maltotriose (G3) | 12.7 | 40.8 |
| Maltotetraose (G4) | 72.5 | 69.8 |
| Maltopentaose (G5) | 103.5 | 65.3 |
| Maltohexaose (G6) | 87.3 | 66.5 |
| Maltoheptaose (G7) | 60.2 | 67.9 |

EXAMPLE II-15
Determination of the Partial Amino Acid Sequences of the Novel Amylase Derived from the *Sulfolobus solfataricus* Strain KM1

The partial amino acid sequences of the purified enzyme obtained in Example II-2 were determined by the method disclosed in Iwamatsu, et al. [Seikagaku (Biochemistry) 63, 139 (1991)], and the amino acid sequence of the N terminus side was determined by the method disclosed in Matsudaira, T. [*J. Biol. Chem.* 262, 10035–10038 (1987)].

At first, the purified novel amylase was suspended in a buffer solution for electrophoresis [10% glycerol, 2.5% SDS, 2% 2-mercaptoethanol, 62 mM Tris-Hcl buffer solution (pH 6.8)], and subjected to SDS-Polyacrylamide gel electrophoresis. After the electrophoresis, the enzyme was transferred from the gel to a polyvinylidene diflorido (PVDF) membrane (ProBlot, manufactured by Applied Biosystems Co.) by electroblotting (SartoBlot type IIs, manufactured by Sartorius Co.) with 160 mA for 1 hour.

After the transfer, the portion to which the enzyme had been transferred was cut out from the membrane, and soaked in about 300 μl of a buffer solution for reduction [6 M guanidine-HCl, 0.5 M Tris-HCl buffer solution (pH 3.5) containing 0.3% of EDTA and 2% of acetonitrile]. One milligram of dithiothreitol was added to this, and reduction was carried out under an argon atmosphere at 60° C. for 1 hour, approximately. To the resultant, 2.4 mg of monoiodoacetic acid dissolved in 10 μl of 0.5 N sodium hydroxide was added and stirred for 20 min. in the dark. The PVDF membrane was then taken out and washed sufficiently with a 2% acetonitrile solution, and subsequently, stirred in a 0.1% SDS solution for 5 min. After being briefly washed with water, the PVDF membrane was then soaked in a 100 mM acetic acid solution containing 0.5% of Polyvinylpyrrolidone-40, and was left standing for 30 min. Next, the PVDF membrane was briefly washed with water, and cut into pieces of 1 square mm, approximately. For determination of the amino acid sequence of the N terminus side, these pieces from the membrane were directly analyzed with a gas-phase sequencer. For determination of the partial amino acid sequences, these pieces were further soaked in a buffer solution for digestion [8% acetonitrile, 90 mM Tris-HCl buffer solution (pH 9.0)], and after the addition of 1 μmol of the Achromobacter Protease I (manufactured by Wako pure chemical Co.), digested at room temperature spending 15 hours. The digested products were separated by reversed phase chromatography using a C8 column (μ-Bondashere 5C8, 300A, 2.1×150 mm, manufactured by Millipore Ltd. Japan) to obtain a dozen or more kinds of peptide fragments. Using A solvent (0.05% trifluoroacetic acid) and B solvent (2-propanol:acetonitrile=7:3, containing 0.02% of trifluoroacetic acid) as elution solvents, the peptides were eluted with a linear concentration gradient from 2 to 50% relative to B solution and at a flow rate of 0.25 ml/min. for 40 min. As to the peptide fragments thus obtained, the amino acid sequences were determined by the automatic Edman degradation method using a gas-phase peptide sequencer (model 470, manufactured by Applied Biosystems Co.).

The amino acid sequence of the N terminus and the partial amino acid sequences thus determined are as follows.

Amino Acid Sequence of the N Terminus Side
Thr Phe Ala Tyr Lys Ile Asp Gly Asn Glu (Sequence No. 45)
Partial Amino Acid Sequences
P-6: Leu Gly Pro Tyr Phe Ser Gln (Sequence No. 46)
P-7: Asp Val Phe Val Tyr Asp Gly (Sequence No. 47)
P-10: Tyr Asn Arg Ile Val Ile Ala Glu Ser Asp Leu Asn Asp Pro Arg Val Val Asn Pro (Sequence No. 48)

EXAMPLE II-16
Preparation of Chromosome DNA of the *Sulfolobus solfataricus* Strain KM1

The *Sulfolobus solfataricus* strain KM1 was cultivated at 75° C. for 3 days in the culture medium which is identified as No. 1304 in Catalogue of Bacteria and Phages 18th edition (1992) published by American Type Culture Collection (ATCC), and which contained 2 g/liter of soluble starch and 2 g/liter of yeast extract. The cultivated bacteria was collected by centrifugation and stored at −80° C. The yield of the bacterial cell was 3.3 g/liter.

To 1 g of the bacterial bodies, 10 ml of a 50 mM Tris-HCl buffer solution (pH 8.0) containing 25% of sucrose, 1 mg/ml of lysozyme, 1 mM of EDTA, and 150 mM of NaCl was added for making a suspension, and the suspension was left standing for 30 min. To this suspension, 0.5 ml of 10% SDS and 0.2 ml of 10 mg/ml Proteinase K (manufactured by Wako pure chemical Co.) were added, and the mixture was left standing at 37° C. for 2 hours. Next, the mixture was subjected to extraction with a phenol/chloroform solution, and then subjected to ethanol precipitation. The precipitated DNA was twisted around a sterilized glass stick and vacuum-dried after being washed with a 70% ethanol solution. As the final product, 1.5 mg of the chromosome DNA was obtained.

EXAMPLE II-17

Expression Cloning of a Gene Coding for the Novel Amylase Derived from the *Sulfolobus solfataricus* Strain KM1 by an Activity Staining Method One hundred micrograms of the chromosome DNA of the *Sulfolobus solfataricus* strain KM1, prepared in Example II-16, was partially digested with a restriction enzyme, Sau 3AI. The reaction mixture was ultracentrifuged with a density gradient of sucrose to isolate and purify DNA fragments of 5–10 kb. Then, using T4 DNA ligase, the above chromosome DNA fragments having lengths of 5–10 kb were ligated with a modified vector which had been prepared from a plasmid vector, pUC118 (manufactured by Takara Shuzou Co.), by digestion with Bam HI and by dephosphorylation of the ends with alkaline phosphatase. Next, cells of the *E. coli* strain JM109 (manufactured by Takara Shuzou Co.) were transformed with a mixture containing the modified pUC118 plasmid vectors in which any of the fragments had been inserted. These cells were cultivated on LB agar plates containing 50 µg/ml of ampicillin to grow their colonies and make a DNA library.

Screening of the transformants which have a recombinant plasmid containing a gene coding for the novel amylase derived from the *Sulfolobus solfataricus* strain KM1 was performed by an activity staining method.

At first, the obtained transformants were replicated on filter paper and cultivated on an LB agar plate for colonization. The filter paper was dipped in a 50 mM Tris-HCl buffer solution (pH 7.5) containing 1 mg/ml of lysozyme (manufactured by Seikagaku Kougyou Co.) and 1 mM of EDTA, and was left standing for 30 min. Subsequently, the filter paper was dipped in 1% Triton-X100 solution for 30 min. for bacteriolysis, and heat-treated at 60° C. for 1 hour to inactivate the enzymes derived from the host. The filter paper thus treated was then laid on an agar plate containing 0.2% of soluble starch to progress a reaction at 60° C., overnight. The plate subjected to the reaction was put under the iodine-vapor atmosphere to make the starch get color. The colonies which exhibit a halo was recognized as the colonies of positive clones. As a result, five positive clones were obtained from 6,000 transformants. According to analysis of the plasmids extracted from these clones, an insertional fragment of about 4.3 kbp was contained in a plasmid as the shortest insertional fragment.

Further, the insertional fragment was shortened by subjecting it to digestion with Bam HI and the same procedure as above. As a result, a transformant containing a plasmid which has an insertional fragment of about 3.5 kb was obtained. This plasmid was named as pKA1.

The restriction map of the insertional fragment of this plasmid is shown in FIG. 34.

EXAMPLE II-18

Determination of the Gene Coding for the Novel Amylase Derived from the *Sulfolobus solfataricus* Strain KM1

The base sequence of the insertional fragment in the plasmid, pKA1 obtained in Example II-17, (i.e. the DNA of the region corresponding to the plasmid, pKA2, described below) was determined.

At first, a deletion plasmid was prepared from the above plasmid DNA by using a deletion kit for kilo-sequencing which manufactured by Takara Shuzou Co. After that, the DNA sequence of the insertional fragment in the plasmid were determined by using a sequenase dye primer sequencing kit, PRISM, a terminator cycle sequencing kit, Tag Dye Deoxy™, both manufactured by Perkin Elmer Japan Co., and a DNA sequencer, GENESCAN Model 373A, manufactured by Applied Biosystems Co.

The base sequence, and the amino sequence anticipated therefrom are shown in Sequences No. 5 and No. 6, respectively.

Sequences corresponding to any of the partial amino acid sequences obtained in Example II-15, respectively, were recognized in the above amino acid sequence. This amino acid sequence was assumed to have 558 amino acid residues and code for a protein, the molecular weight of which estimated as 64.4 kDa. This molecular weight value almost equals the value, 61.0 kDa, obtained by SDS-PAGE analysis of the purified novel amylase derived from the *Sulfolobus solfataricus* strain KM1.

EXAMPLE II-19

Production of the Recombinant Novel Amylase in a Transformant

Figure 35:
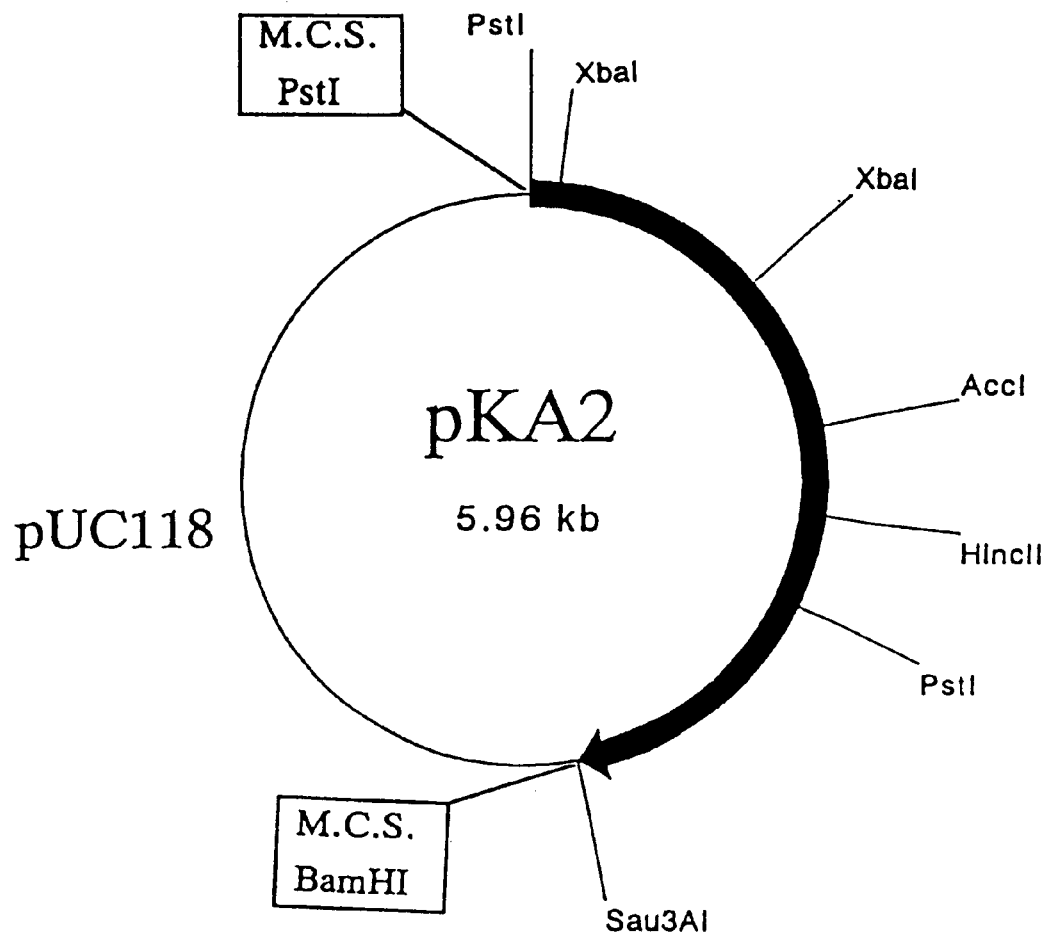
FIG. 35 is an illustration showing the restriction map of pKA2.

A plasmid, pKA2, was obtained by partially digesting the plasmid, pKA1, which was obtained in Example II-17, with a restriction enzyme, Pst I. FIG. 35 shows its restriction map. The enzymatic activity of the transformant which contains pKA2 was examined as follows. At first, the above transformant was cultivated overnight in a LB broth containing 100 µg/ml of ampicillin at 37° C. The cells collected by-centrifugation were suspended in 4 ml/g-cell of a 50 mM sodium acetate solution (pH 5.5), and subjected to ultrasonic crushing-treatment and centrifugation. The supernatant thus obtained was heat-treated at 70° C. for 1 hour to inactivate the amylase derived from the host cells. The precipitate was removed by centrifugation and the resultant was concentrated with an ultrafiltration membrane (critical molecular weight: 13,000) to obtain a crude enzyme solution which would be used in the following experiments.

(1) Substrate Specificity

The hydrolyzing properties and the hydrolyzed products were analyzed by allowing 35.2 Units/ml of the above crude enzyme solution to act on the various 10 mM substrates (except amylopectin and soluble starch were used as 3.0% solutions) listed in Table 39 below. Here, 1 Unit was defined as an enzymatic activity of producing 1 µmol of α,α-trehalose per hour from maltotriosyltrehalose used, as the substrate under the conditions based on those in Example II-1. The analysis was performed by TSK-gel Amide-80 HPLC described in Example II-1, wherein the index was the activity of producing both monosaccharide and disaccharide when the substrate was each of the various maltooligosaccharides, Amylose DP-17, amylopectin, soluble starch, various isomaltooligosaccharides, and panose; the activity of producing α,α-trehalose when the substrate was each of the various trehaloseoligosaccharides, and α-1,α-1-transferred isomer of Amylose DP-17 (the oligosaccharide derived from. Amylose DP-17 by transferring the linkage between the first and second glucose residues from the reducing end side into an α-1,α-1linkage); and the activity of producing glucose when the substrate was maltose or α,α-trehalose.

The results are as shown in Table 39 below.

Incidentally, each enzymatic activity value in the table is expressed with such a unit as 1 Unit equals the activity of liberating 1 µmol of each of the monosaccharide and disaccharide per hour.

TABLE 39

| Substrate | Liberated oligosaccharide | Production rate of mono- and disaccharides (units/ml) |
| --- | --- | --- |
| Maltose (G2) | Glucose | 0.15 |
| Maltotriose (G3) | Glucose + G2 | 0.27 |
| Maltotetraose (G4) | Glucose + G2 + G3 | 0.26 |
| Maltopentaose (G5) | Glucose + G2 + G3 + G4 | 2.12 |
| Amylose DP-17 | Glucose + G2 | 2.45 |
| Amylopectin | Glucose + G2 | 0.20 |
| Soluble starch | Glucose + G2 | 0.35 |
| α,α-Trehalose | not decomposed | 0 |
| Glucosyltrehalose | Glucose + Trehalose | 0.01 |
| Maltosyltrehalose | G2 + Trehalose | 4.52 |
| Maltotriosyltrehalose | G3 + Trehalose | 35.21 |
| Amylose DP-17, α-1, α-1-transferred isomer | Trehalose | 4.92 |
| Isomaltose | not decomposed | 0 |
| Isomaltotriose | not decomposed | 0 |
| Isomaltotetraose | not decomposed | 0 |
| Isomaltopentaose | not decomposed | 0 |
| Panose | not decomposed | 0 |

Figure 36A:
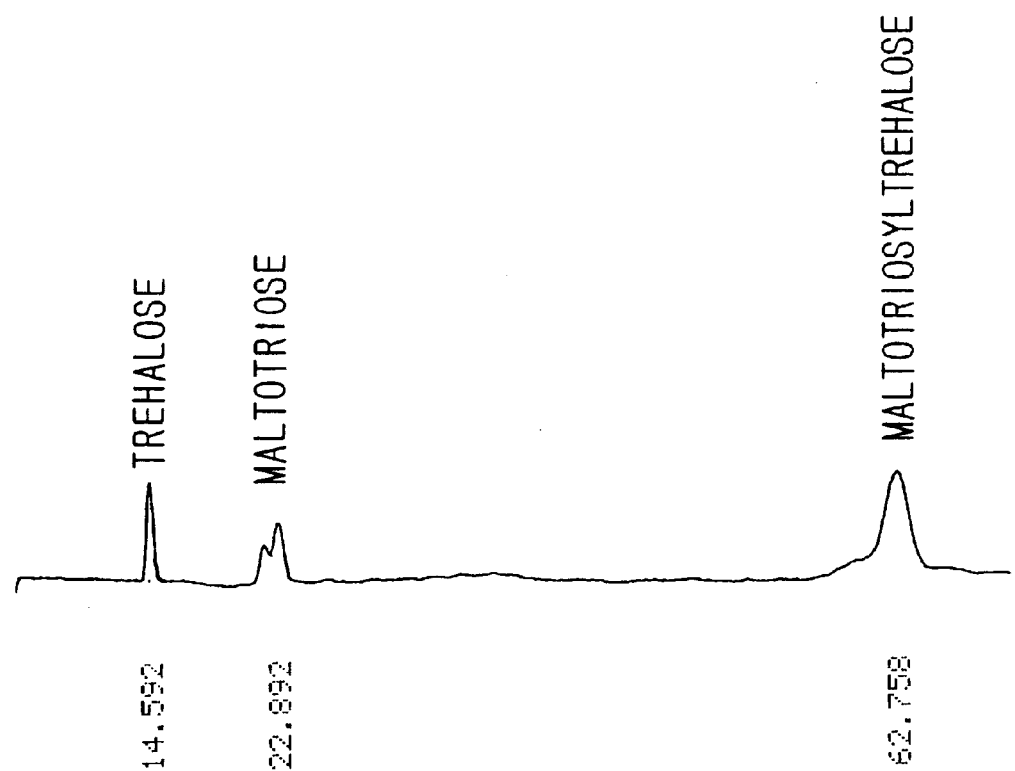
FIG. 36(A) is a graph showing the results of an analysis performed on the product derived from a maltotriosyltrehalose by using the recombinant novel amylase according to the present invention.
Figure 36B:
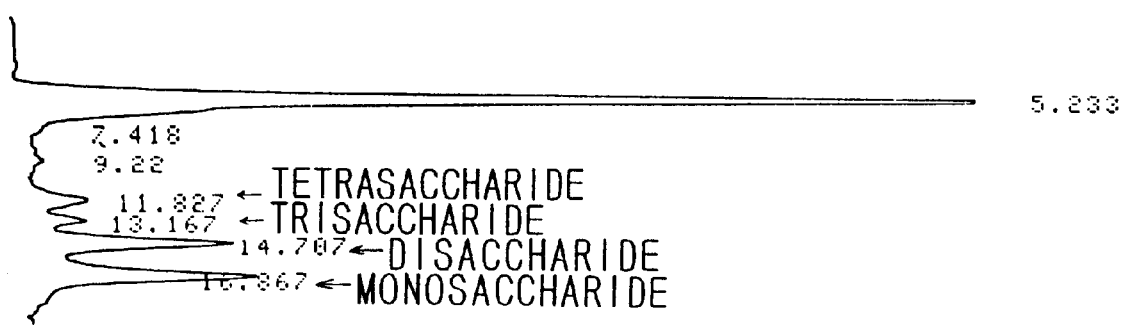
FIG. 36(B) is a graph showing the results of an analysis performed on the product derived from soluble starch by using the recombinant novel amylase according to the present invention.

Further, the analytic results of the reaction products from maltotriosyltrehalose by TSK-gel Amide-80 HPLC under the conditions based on those in Example II-1 are shown in FIG. 36(A). Moreover, the analytic results of the reaction products from soluble starch by AMINEX HPX-42A HPLC under the conditions described below are shown in FIG. 36(B).

Column: AMINEX HPX-42A (7.8×300 mm)
Solvent: Water
Flow rate: 0.6 ml/min.
Temperature: 85° C.
Detector: Refractive Index Detector From the above results, the present enzyme was confirmed to markedly effectively act on a trehaloseoligosaccharide, of which the glucose residue at the reducing end is α-1,α-1-linked, such as maltotoriosyltrehalose, to liberate α,α-trehalose and a corresponding maltooligosaccharide which has a polymerization degree reduced by two. Further, the present enzyme was confirmed to liberate principally glucose or maltose from maltose (G2)–maltopentaose (G5), amylose, and soluble starch. The present enzyme, however, did not act on α,α-trehalose, isomaltose, isomaltotriose, isomaltotetraose and isomaltopentaose, and panose.

(2) Endotype Amylase Activity

One hundred and fifty Units/ml [in terms of the same unit as that in the above (1)] of the above crude enzyme solution was allowed to act on soluble starch. The time-lapse change in the degree of coloring by the iodo-starch reaction was measured under the same conditions as the method for measuring starch-hydrolyzing activity in Example II-1. Further, produced amounts of monosaccharide and disaccharide were measured under the conditions based on those in the HPLC analysis method which is described in the above (1), namely, based on those for the above examination of substrate specificity. From the data thus obtained, a starch-hydrolyzing rate was estimated.

Figure 37:
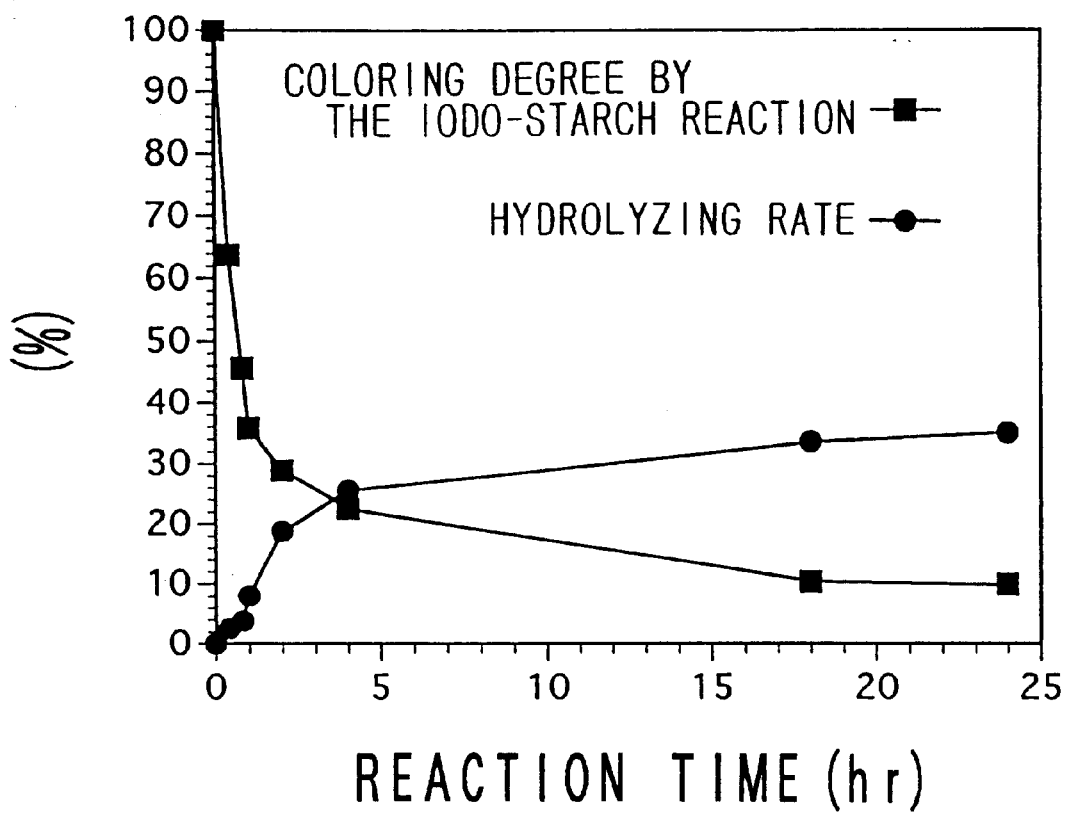
FIG. 37 is a graph showing time-course changes in disappearance of color generated by iodo, and starch-hydrolyzing percentage when the recombinant novel amylase according to the present invention is made to act on soluble starch.

The time-lapse change is shown in FIG. 37. As shown in the figure, the hydrolyzing rate at the point where the coloring degree by the iodo-starch reaction decreased to 50% was as low as 4.5%. Accordingly, the present crude enzyme was confirmed to have a property of an endotype amylase.

(3) Investigation of the Action Mechanism

Uridinediphosphoglucose [glucose-6-$^3$H] and maltotetraose were put into a reaction with glycogen synthase (derived from rabbit skeletal muscle, G-2259 manufactured by Sigma Co.) to synthesize maltopentaose, of which the glucose residue of the non-reducing end was radiolabeled with $^3$H, and the maltopentaose was isolated and purified. To 10 mM of this maltopentaose radiolabeled with $^3$H as a substrate, 10 Units/ml (in terms of the unit used in Example I-1) of the recombinant novel transferase obtained in Example I-20 above was added and put into a reaction at 60° C. for 3 hours. Maltotriosyltrehalose, of which the glucose residue of the non-reducing end was radiolabeled with $^3$H, was synthesized thereby, and the product was isolated and purified. Incidentally, it was confirmed by the following procedure that the glucose residue of the non-reducing end had been radiolabeled: The above product was completely decomposed into glucose and α,α-trehalose by glucoamylase (derived from Rhizopus, manufactured by Seikagaku Kougyou Co.); the resultants were sampled by thin-layer chromatography, and their radioactivities were measured by a liquid scintillation counter; as a result, radioactivity was not observed in the α,α-trehalose fraction but in the glucose fraction.

The above-prepared maltopentaose and maltotriosyltrehalose, of which the glucose residues of the non-reducing ends were radiolabeled with $^3$H, were used as substrates, and were put into reactions with 30 Units/ml and 10 Units/ml of the above crude enzyme solution, respectively. Sampling was performed before the reaction and 3 hours after the start of the reaction performed at 60° C. The reaction products were subjected to development by thin-layer chromatography (Kieselgel 60 manufactured by Merk Co.; solvent: butanol/ethanol/water=5/5/3). Each spot thus obtained and corresponding to each saccharide was collected, and its radiation was measured with a liquid scintillation counter. When maltopentaose was used as a substrate, radioactivity was not detected in the fractions of the hydrolysates, i.e. glucose and maltose, but in the fractions of maltotetraose and maltotriose. On the other hand, when maltotriosyltrehalose was used as a substrate, radioactivity was not detected in the fraction of the hydrolysate, i.e. α,α-trehalose, but in the fraction of maltotriose.

Consequently, as to the action mechanism, the recombinant novel amylase was found to have an amylase activity of the endotype function, and in addition, an activity of principally producing monosaccharide and disaccharide from the reducing end side.

Incidentally, the manufacturer of the reagents used in the above experiments are as follows.

α,α-trehalose: Sigma Co.
Maltose (G2): Wako Junyaku Co.
Maltotriose-Maltopentaose (G3–G5): Hayashibara Baiokemikaru Co.
Amylose DP-17: Hayashibara Biochemical Co.
Isomaltose: Wako pure chemical Co.
Isomaltotriose: Wako pure chemical Co.
Isomaltotetraose: Seikagaku Kougyou Co.
Isomaltopentaose: Seikagaku Kougyou Co.
Panose: Tokyo Kasei Kougyou Co.
Amylopectin: Nacalai tesque Co.

EXAMPLE II-20

Determination of Partial Amino Acid Sequences of the Novel Amylase Derived from the *Sulfolobus acidocaldarius* Strain ATCC 33909

The partial amino acid sequences of the purified enzyme obtained in Example II-4 were determined according to the process described in Example II-15.

The partial amino acid sequences are as follows.
AP-9: Leu Asp Tyr Leu Lys (Sequence No. 49)
AP-10: Lys Arg Glu Ile Pro Asp Pro Ala Ser Arg Tyr Gln Pro Leu Gly Val His (Sequence No. 50)
AP-11: Lys Asp Val Phe Val Tyr Asp Gly Lys (Sequence No. 51)
AP-12: His Ile Leu Gln Glu Ile Ala Glu Lys (Sequence No. 52)
AP-16: Lys Leu Trp Ala Pro Tyr Val Asn Ser Val (Sequence No. 53)
AP-17: Met Phe Ser Phe Gly Gly Asn (Sequence No. 54)
AP-18: Asp Tyr Tyr Tyr Gln Asp Phe Gly Arg Ile Glu Asp Ile Glu (Sequence No. 55)
AP-21: Lys Ile Asp Ala Gln Trp Val (Sequence No. 56)

EXAMPLE II-21
Preparation of DNA Probes Based on the Partial Amino Acid Sequences of the Novel Amylase Derived from the *Sulfolobus acidocaldarius* Strain ATCC 33909

According to information about the partial amino acid sequences determined in Example II-20, oligonucleotide DNA primers are prepared by using a DNA synthesizer (Model 381 manufactured by Applied Biosystems Co.). Their sequence were as follows.

After being stored at 4° C. for about 2 hours, DNA was adsorbed on a nylon membrane (Hybond N+, manufactured by Amersham Co. Baking was performed at 80° C. for 2 hours after brief washing with 2×SSPE. Using the PCR fragment obtained in Example II-21, the probe was labeled with $^{32}$P employing Megaprime DNA labeling system manufactured by Amersham Co.

Hybridization was performed overnight under the conditions of 65° C. with 6×SSPE containing 0.5% of SDS. Washing was performed by treating twice with 2×SSPE containing 0.1% of SDS at room temperature for 10 min.

Figure 39:
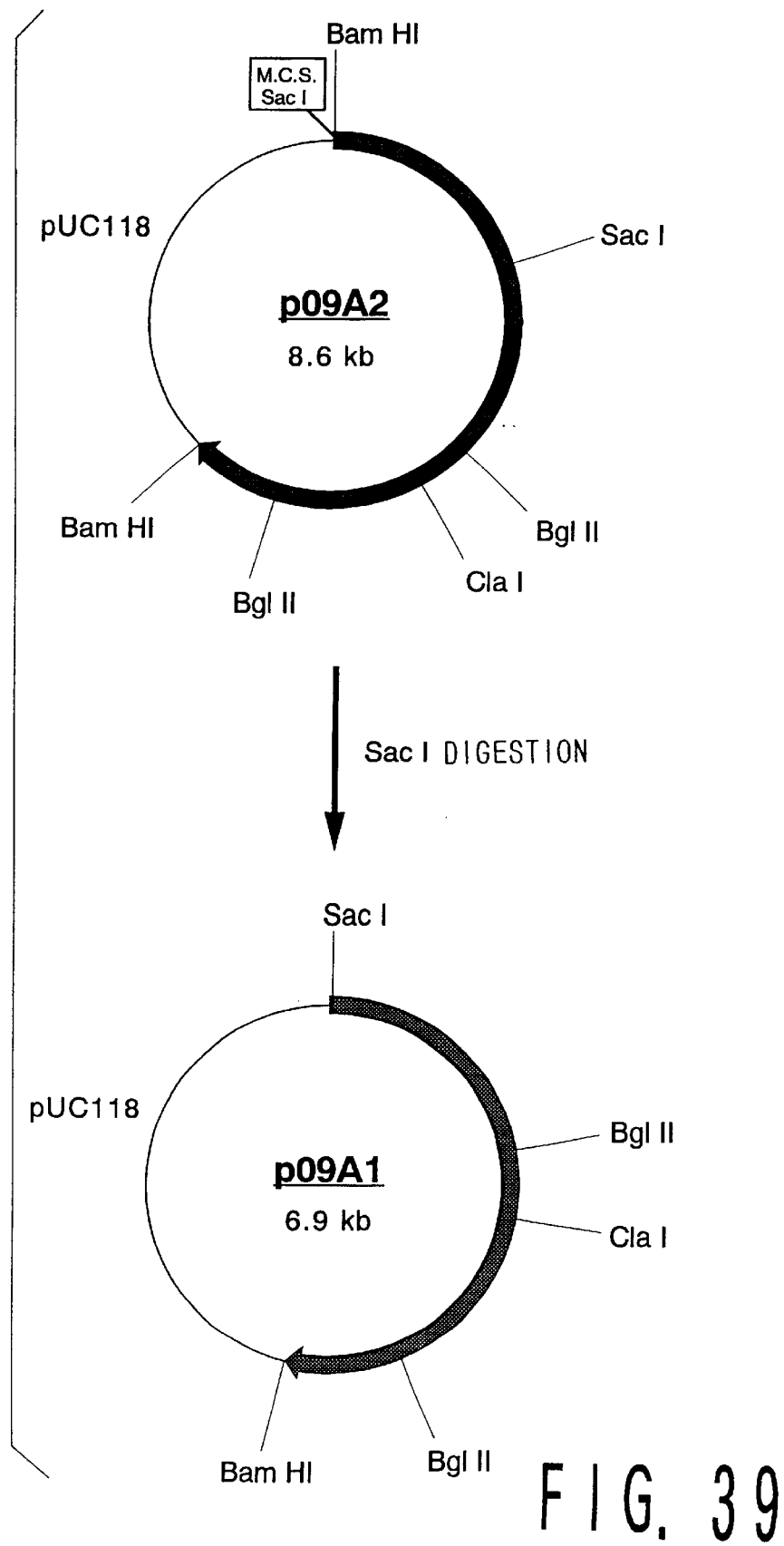
FIG. 39 is an illustration showing the process for producing p09A1 from p09A2.

Screening was started with 8,000 clones, approximately, and 17 positive clones were obtained. From these clones, a Bam HI fragment of about 5.4 kbp was obtained and the fragment was inserted into pUC118 at the corresponding restriction site. The plasmid thus obtained was named as p09A2. Further, the DNA of this plasmid was digested with Sau 3AI to obtain a plasmid named as p09A1. The restriction map of the insertional fragment in p09A1 is shown in FIG. 38, and the procedure for preparing p09A1 is shown in FIG. 39. As to the above plasmid, p09A1, a deletion plasmid was prepared using Double-standard Nested Delation Kit manufactured by Pharmacia Co. The base sequence, principally of the region corresponding to the structural gene of the novel

```
AP-10
Amino Acid Sequence
  N terminus              Pro Ala Ser Arg Tyr Gln Pro  C terminus
DNA Primer            5'AGCTAGTAGATATCAACC 3'          (Sequence No. 57)
Base Sequence              A   G   C   C   G
AP-11
(complementary strand)
Amino Acid Sequence
  N terminus          Asp Val Phe Val Tyr Asp Gly Lys C terminus
DNA Primer            5' TTTTCCATCATAAACAAAAACATC 3'  (Sequence No. 58)
Base Seqeunce              C  A       G   T   G   T
                                   C
```

PCR was performed using 100 pmol of each primer and about 100 µg of the chromosome DNA prepared in Example II-16 and derived from the *Sulfolobus acidocaldarius* strain ATCC 33909. The PCR apparatus used herein was Gene Amp PCR system Model 9600, manufactured by Perkin Elmer Co. In the reaction, 30 cycles of steps were carried out with 100 µl of the total reaction mixture, wherein the 1 cycle was composed of steps at 94° C. for 30 sec., at 54° C. for 30 sec., and at 72° C. for 30 sec. The amplified fragment of about 830 bp was subcloned into a plasmid, pT7 Blue T-Vector (manufactured by Novagen Co.). Determination of the base sequence of the insertional fragment in this plasmid was performed to find sequences corresponding to any of the amino acid sequences obtained in Example II-20.

EXAMPLE II-22
Cloning of a Gene Coding for the Novel Amylase Derived from the *Sulfolobus acidocaldarius* Strain ATCC 33909

The chromosome DNA of the *Sulfolobus acidocaldarius* strain ATCC 33909 was obtained according to the process described in Example II-16 from bacterial cells obtained according to the process described in Example II-4. The above chromosome DNA was partially digested with Sau 3AI, and subsequently, ligated to a Bam HI-restricted arm of EMBL3 (manufactured by STRATAGENE Co.) by using T4 DNA ligase. Packaging was carried out using Gigapack II Gold, manufactured by STRATAGENE Co. With the library obtained above, the *E. coli* strain LE392 was infected at 37° C. for 15 min., inoculated on NZY agar plates, and incubated at 37° C. for 8–12 hours, approximately, to form plaques.

amylase, was determined according to the process described in Example II-18. The base sequence thus determined and the amino acid sequence anticipated therefrom are shown in Sequences No. 7 and No. 8, respectively. Sequences corresponding to any of the partial amino acid sequences obtained in Example II-20, respectively, were recognized in this amino acid sequence. This amino acid sequence was assumed to have 556 amino acid residues and code for a protein, the molecular weight of which was estimated as 64.4 kDa. This molecular weight value almost equals the value obtained by SDS-PAGE analysis of the purified novel amylase derived from the *Sulfolobus solfataricus* strain ATCC 33909. Additionally, the existence of the activity of the novel amylase in a transformant containing the plasmid, p09A1 was confirmed according to the procedure described in Example II-19.

EXAMPLE II-23
Homology Between the Base Sequences and Between the Amino Acid Sequences of the Novel Amylases Derived from the Strain KM1 and the Strain ATCC 33909

Considering gapps and using sequence-analyzing software, GENETYX (produced by Software Development Co.), comparative analyses were carried out on the amino acid sequence of the novel amylase derived from the strain KM1, i.e. Sequence No. 6, and that derived from the strain ATCC 33909, i.e. Sequence No. 8; and on the base sequence coding for the novel amylase derived from the strain KM1, i.e. Sequence No. 5, and that derived from the strain ATCC 33909, i.e. Sequence No. 7. The results as to the amino acid sequences are shown in FIG. 40, and the results as to the base sequences are shown in FIG. 41. In each figure, the upper line indicates the sequence derived from the strain 33909, the lower line indicates the sequence derived from the strain KM1, and the symbol "*" in the middle line indicates the portions equal in both strains. Each of the couples indicated with symbol "." in FIG. 40 are a couple of amino acid residues which mutually have similar characteristics. The homology values are about 59% and 64% on the levels of the amino acid sequences and the base sequences, respectively.

EXAMPLE II-24

Hybridization Tests Between the Gene Coding for the Novel Amylase Derived from the *Sulfolobus solfataricus* strain KM1 or the *Sulfolobus acidocaldarius* Strain ATCC 33909 and Chromosome DNAs Derived from the Other Organisms Chromosome DNAs were obtained from the *Sulfolobus solfataricus* strain DSM 5833, the *Sulfolobus shibatae* strain DSM 5389, the *Acidianus brierleyi* strain DSM 1651, and the *E. coli* strain JM109, and digested with a restriction enzyme Hind III according to the procedure described in Example II-16.

These digested products were separated by 1% agarose gel electrophoresis, and transferred using the Southern blot technique to a Hybond-N membrane manufactured by Amersham Japan Co. The Pst I fragment of about 1.9 kbp (corresponding to the sequence from the 1st base to 1845th base of Sequence No. 5), which derived from pKA1 was labeled using a DIG system kit manufactured by Boehringer Mannheim Co., and the resultant was subjected to a hybridization test with the above-prepared membrane.

The hybridization was performed under the conditions of 40° C. for 3 hours with 5×SSC, and washing was performed by treating twice with 2×SSC containing 0.1% of SDS at 40° C. for 5 min., and twice with 0.1×SSC containing 0.1% of SDS at 40° C. for 5 min.

As a result, the Pst I fragment could hybridize with a fragment of about 13.0 kbp derived from the *Sulfolobus solfataricus* strain DSM 5833, a fragment of about 9.8 kbp derived from the *Sulfolobus shibatae* strain DSM 5389, and a fragment of about 1.9 kbp derived from the *Acidianus brierleyi* strain DSM 1651. On the other hand, no hybrid formation was observed in fragments derived from the *E. coli* strain JM109 which was used as a negative control.

Further, chromosome DNAs were obtained according to the procedure described in Example II-16 from the *Sulfolobus solfataricus* strains KM1, DSM 5354, DSM 5833, ATCC 35091, and ATCC 35092; the *Sulfolobus acidocaldarius* strains ATCC 33909, and ATCC 49426; the *Sulfolobus shibatae* strain DSM 5389; the *Acidianus brierleyi* strain DSM 1651; and the *E. coli* strain JM109, and digested with restriction enzymes, Xba I, Hind III, and Eco RV. These digested products were separated by 1% agarose gel electrophoresis and transferred using the Southern blot technique to a Hybond-N+ membrane manufactured by Amersham Japan Co. The region from the 1393th base to the 2121th base of Sequence No. 7 (obtained by digesting p09AI prepared in Example II-22 with restriction enzymes Eco T22I and Eco RV followed by separation in a gel) was labeled with $^{32}$P according to the procedure described in Example II-22 to make a probe, and this probe was subjected to a hybridization test with the above prepared membrane. The hybridization was performed overnight under the conditions of 60° C. with 6×SSPE containing 0.5% of SDS, and washing was performed by treating twice with 2×SSPE containing 0.1% of SDS at room temperature for 10 min. As a result, the following fragments were found to form hybrids: the fragments of about 3.6 kbp, about 1.0 kbp, about 0.9 kbp, about 0.9 kbp, and about 1.0 kbp derived from the *Sulfolobus solfataricus* strains KM1, DSM 5354, DSM 5833, ATCC 35091, and ATCC 35092, respectively; the fragments of about 0.9 kbp, and about 0.9 kbp derived from the *Sulfolobus acidocaldarius* strains ATCC 33909, and ATCC 49426, respectively; the fragment of about 1.4 kbp derived from the *Sulfolobus shibatae* strain DSM 5389; and the fragment of about 0.9 kbp derived from the *Acidianus brierleyi* strain DSM 1651. On the other hand, no hybrid formation was observed as to the chromosome DNA of the *E. coli* strain JM109. Moreover, it was confirmed, through data banks of amino acid sequences (Swiss prot and NBRF-PDB) and a data bank of base sequences (EMBL), and by using sequence-analyzing software, GENETYX (produced by Software Development Co.), that there is no sequence homologous to any of the amino acid sequences and base sequences within the scopes of Sequences No. 5, No. 6, No. 7, and No. 8. Consequently, the genes coding for the novel amylases were found to be highly conserved specifically in archaebacteria belonging to the order Sulfolobales.

EXAMPLE III-1

Production of α,α-Trehalose by Using the Recombinant Novel Amylase and the Recombinant Novel Transferase Production of α,α-trehalose was attempted by using the crude recombinant novel amylase obtained in Example II-19, the concentrated recombinant novel transferase obtained in Example I-20, and 10% soluble starch (manufactured by Nacalai tesque Co., special grade); and by supplementally adding pullulanase. The reaction was performed as follows.

At first, 10% soluble starch was treated with 0.5–50 Units/ml of pullulanase (derived from *Klebsiella pneumoniae*, and manufactured by Wako pure chemical Co.) at 40° C. for 1 hour. To the resultant, the above-mentioned recombinant novel transferase (10 Units/ml) and the above-mentioned recombinant novel amylase (150 Units/ml) were added, and the mixture was subjected to a reaction at pH 5.5 and 60° C. for 100 hours. The reaction was stopped by heat-treatment at 100° C. for 5 min., and the non-reacted substrate was hydrolyzed with glucoamylase. The reaction mixture was analyzed by an HPLC analyzing method under the conditions described in Example II-1.

Figure 42:
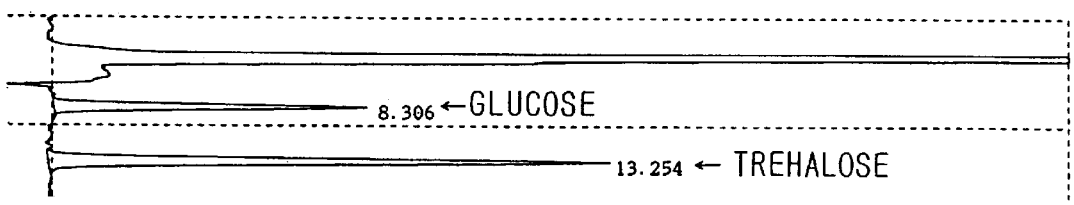
FIG. 42 is a graph showing the results of an analysis performed on the product derived from 10% soluble starch subjected to reaction with the recombinant novel amylase which is obtained in Example II-19, and the recombinant novel transferase which is obtained in Example I-20.

The analysis results by TSK-gel Amide-80 HPLC are shown in FIG. 42.

Here, as to enzymatic activity of the recombinant novel amylase, 1 Unit is defined as the activity of liberating 1 μmol of α,α-trehalose per hour from maltotriosyltrehalose. As to enzymatic activity of the recombinant novel transferase, 1 Unit is defined as the activity of producing 1 μmol of glucosyltrehalose per hour from maltotriose. As to enzymatic activity of pullulanase, 1 Unit is defined as the activity of producing 1 μmol of maltotriose per minute at pH 6.0 and 30° C. from pullulan.

The yield of α,α-trehalose was 67% when 50 Units/ml of pullulanase was added. This value suggests that the recombinant novel amylase can bring about almost the same yield as the purified novel amylase derived from the *Sulfolobus solfataricus* strain KM1 can under the above reaction condition.

Industrial Applicability

A novel, efficient and high-yield process for producing trehaloseoligosaccharide, such as glucosyltrehalose and maltooligosaccharide, and other saccharides from a raw material such as maltooligosaccharide can be provided by using a novel transferase which is obtained by an enzyme-producing process according to the novel purification process of the present invention, and which can act on saccharides, such as maltooligosaccharide, to produce trehaloseoligosaccharide, such as glucosyltrehalose and maltooligosyltrehalose, and other saccharides.

A novel, efficient and high-yield process for producing α,α-trehalose from a glucide raw material such as starch, starch hydrolysate and maltooligosaccharide can be provided by using the novel amylase of the present invention in combination with the novel transferase of the present invention.

What is claimed is:

1. A process for producing α,α-trehalose, comprising (a) subjecting a glucide raw material to endotype-hydrolysis, under conditions comprising a temperature range of about 50° C. to 80° C. and a pH range of about 3.5 to 8, to produce a substrate selected from amylose and maltooligosaccharide, (b) transforming, into an α-1, α-1 linkage, the first α-1,4 linkage from the reducing end of said substrate, and (c) hydrolyzing the α-1,4 linkage between the second and third glucose residues from the reducing end of the resultant substrate, to liberate α,α-trehalose therefrom.

2. The process of claim 1, wherein said hydrolyzing comprises exposing said glucide raw material to an amylase enzyme derived from the genus Sulfolobus.

3. The process of claim 2, wherein the concentration of said amylase enzyme is at least 1.5 Units/ml.

4. The process of claim 1, wherein said transforming is catalyzed by a transferase enzyme selected from the group consisting of a transferase derived from the genus Sulfolobus and a transferase derived from the genus Acidianus.

5. The process of claim 4, wherein said transferase is derived from *Sulfolobus solfataricus* strain KM1 (FERM BP-4626).

6. The process of claim 4, wherein said transferase is derived from *Sulfolobus acidocaldarius* strain ATCC 33909.

7. The process of claim 4, wherein said transferase is derived from *Acidianus brierleyi* strain DSM 1651.

8. The process of claim 4, wherein the concentration of said transferase enzyme is at least 0.1 Units/ml.

9. The process of claim 1, wherein said endotype-hydrolysis comprises subjecting said glucide raw material to an amylase enzyme derived from the genus Sulfolobus, and wherein said transforming is catalyzed by a transferase enzyme selected from the group consisting of a transferase derived from the genus Sulfolobus and a transferase derived from the genus Acidianus.

10. The process of claim 9, wherein said transferase is derived from *Sulfolobus solfataricus* strain KM1 (FERM BP-4626).

11. The process of claim 9, wherein said transferase is derived from *Sulfolobus acidocaldarius* strain ATCC 33909.

12. The process of claim 9, wherein said transferase is derived from *Acidianus brierleyi* strain DSM 1651.

13. The process of claim 9, wherein the concentration of said amylase enzyme is at least 1.5 Units/ml, and the concentration of said transferase enzyme is at least 0.1 Units/ml.

14. The process of claim 13, wherein the ratio of said amylase enzyme to said transferase enzyme is from about 0.075 to about 100.

15. The process of claim 9, wherein the concentration of said amylase enzyme is at least 15 Units/ml, and the concentration of said transferase enzyme is at least 1 Unit/ml, and the ratio of said amylase enzyme to said transferase enzyme is from about 3 to about 40.

16. The process of claim 1, wherein said glucide raw material is selected from the group consisting of starch, starch hydrolysate, and maltooligosaccharide.

17. The process of claim 16, wherein said starch hydrolysate is produced from starch by acidolysis or enzymatic hydrolysis.

18. The process of claim 16, wherein said starch hydrolysate is produced from starch by using a debranching enzyme.

19. The process of claim 18, wherein said debranching enzyme is selected from the group consisting of pullulanase and isoamylase.

20. The process of claim 1, wherein all glucose residues contained within said glucide raw material are α-1,4 linked.

21. The process of claim 1, further comprising exposing the glucide raw material to a debranching enzyme.

22. The process of claim 21, wherein said debranching enzyme is selected from the group consisting of pullulanase and isoamylase.

23. The process of claim 21, comprising multiple exposures of said glucide raw material to said debranching enzyme.

24. A process for producing α,α-trehalose, comprising: (a) subjecting a glucide raw material to endotype-hydrolysis that is catalyzed by an amylase enzyme derived from the genus Sulfolobus, under conditions comprising a temperature range of about 50° C. to about 80° C. and a pH range of about 3.5 to about 8, to produce a substrate selected from amylose and maltooligosaccharide; (b) transforming, into an α-1, α-1 linkage, the first α-1,4 linkage from the reducing end of said substrate, wherein said transformation is catalyzed by a transferase enzyme selected from the group consisting of a transferase derived from the genus Sulfolobus and a transferase derived from the genus Acidianus, and (c) hydrolyzing the α-1,4 linkage between the second and third glucose residues from the reducing end of the resultant substrate, to liberate α,α-trehalose therefrom, wherein said hydrolyzing comprises exposing said transformed substrate to an amylase enzyme that is derived from the genus Sulfolobus and that is present at a concentration of at least 1.5 units/ml.

25. The process of claim 24, wherein said transferase is derived from *Sulfolobus solfataricus* strain KM1 (FERM BP-4626).

26. The process of claim 24, wherein said transferase is derived from *Sulfolobus acidocaldarius* strain ATCC 33909.

27. The process of claim 24, wherein said transferase is derived from *Acidianus brierleyi* strain DSM 1651.

28. The process of claim 24, wherein the concentration of said transferase enzyme is at least 0.1 Units/ml.

29. The process of claim 28, wherein the ratio of said amylase enzyme to said transferase enzyme is from about 0.075 to about 100.

30. The process of claim 24, wherein the concentration of said amylase enzyme is at least 1.5 Units/ml, and the concentration of said transferase enzyme is at least 1.0 Unit/ml, and the ratio of said amylase enzyme to said transferase enzyme is from about 3 to about 40.

31. The process of claim 24, wherein said glucide raw material is selected from the group consisting of starch, starch hydrolysate, and maltooligosaccharide.

32. The process of claim 31, wherein said starch hydrolysate is produced from starch by acidolysis or enzymatic hydrolysis.

33. The process of claim 31, wherein said starch hydrolysate is produced from starch by using a debranching enzyme.

34. The process of claim 33, wherein said debranching enzyme is selected from the group consisting of pullulanase and isoamylase.

35. The process of claim 24, wherein all glucose residues contained within said glucide raw material are α-1,4 linked.

36. The process of claim 24, further comprising exposing the glucide raw material to a debranching enzyme.

37. The process of claim 36, wherein said debranching enzyme is selected from the group consisting of pullulanase and isoamylase.

38. The process of claim 36, comprising multiple exposures of said glucide raw material to said debranching enzyme.

* * * * *